US007208152B2

(12) United States Patent  
Briskin et al.

(10) Patent No.: US 7,208,152 B2
(45) Date of Patent: Apr. 24, 2007

(54) ANTIBODIES FOR "BONZO" CHEMOKINE RECEPTOR AND THERAPEUTIC USES THEREOF

(75) Inventors: Michael J. Briskin, Lexington, MA (US); Kristine E. Murphy, Malden, MA (US); Alyson M. Wilbanks, Chapel Hill, NC (US); Lijun Wu, Lexington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 478 days.

(21) Appl. No.: 10/174,293

(22) Filed: Jun. 17, 2002

(65) Prior Publication Data

US 2003/0165995 A1 Sep. 4, 2003

Related U.S. Application Data

(63) Continuation of application No. 09/722,064, filed on Nov. 22, 2000, now abandoned, which is a continuation-in-part of application No. 09/449,437, filed on Nov. 24, 1999, now Pat. No. 6,319,675.

(51) Int. Cl.
*A61K 39/395* (2006.01)
*A61K 39/00* (2006.01)
*C12P 21/08* (2006.01)
*C07K 16/28* (2006.01)

(52) U.S. Cl. .............................. 424/143.1; 424/130.1; 424/139.1; 435/7.1; 530/387.9; 530/388.22

(58) Field of Classification Search ................ 435/325, 435/326, 329, 331, 334, 343; 530/387.1, 530/387.3, 387.9, 388.1, 388.15
See application file for complete search history.

(56) References Cited

U.S. PATENT DOCUMENTS

| 5,739,103 | A | 4/1998 | Rollins et al. .................. 514/8 |
| 5,767,260 | A | 6/1998 | Whitlow et al. ............ 536/23.4 |
| 5,824,504 | A | 10/1998 | Elshourbagy et al. ....... 435/69.1 |
| 5,824,782 | A | 10/1998 | Hölzer et al. ............. 530/391.1 |
| 5,889,157 | A | 3/1999 | Pastan et al. ............. 530/387.1 |
| 5,948,647 | A | 9/1999 | Ring ......................... 435/69.6 |
| 5,985,276 | A | 11/1999 | Lindhofer et al. ........ 424/136.1 |
| 6,037,454 | A | 3/2000 | Jardieu et al. |
| 6,232,084 | B1 | 5/2001 | MacPhee et al. |
| 6,251,582 | B1 | 6/2001 | Littman et al. |
| 6,319,675 | B1 | 11/2001 | Briskin et al. ................ 435/7.1 |
| 2002/0076694 | A1 | 6/2002 | Littman et al. |

FOREIGN PATENT DOCUMENTS

| EP | 0834563 A2 | 4/1998 |
| WO | WO 98/44098 | * 10/1998 |
| WO | WO 99/03888 | 1/1999 |
| WO | WO 99/12968 | 3/1999 |
| WO | WO 99/27078 | 6/1999 |
| WO | WO 99/50670 | 10/1999 |
| WO | WO 01/64752 A2 | 9/2001 |

OTHER PUBLICATIONS

Yoshimura et al. (2003). Negative regulation of cytokine signaling influences inflammation. Current Opinion in Immunology. 15:704-708.*
Choy et al. (2001). Ctyokine pathways and joint inflammation in rheumatoid arthritis. N. Engl. J. Med. 344(12):907-916.*
Brussel, A., et al., "Sequences and Predicted Structures of Chimpanzee STRL33 (Bonzo) and gpr15 (BOB)," *Aids Res. Hum. Retroviruses* 15(14):1315-1319 (1999).
Lu, P.H. and R.S. Negrin, "A Novel Population of Expanded $CD3^+$ $CD56^+$ Cells Derived from T Cells with Potent *In Vivo* Antitumor Activity in Mice with Severe Combined Immunodeficiency," *J. Immunol.* 153(4) :1687-1696 (1994).
Liao, F. et al., "STRL33, a Novel Chemokine Receptor-like Protein, Functions as a Fusion Cofactor for Both Macrophage-tropic and T Cell Line-tropic HIV-1," *J. Exp. Med.* 185(11): 2015-2023 (1997).
Clapham, P.R. and R.A. Weiss, "Spoilt for Choice of Co-Receptors," *Nature 388*: 230-231 (1997).
Alkhatib, G. et al., "A New SIV Co-receptor, STRL33," *Nature 388*: 238 (1997).
Scarlatti, G. et al., "*In Vivo* Evolution of HIV-1 Co-receptor Usage and Sensitivity to Chemokine-Mediated Suppression," *Nature Medicine* 3(11): 1259-1265 (1997).
Edinger, A.L. et al., "CD4-independent, CCR5-dependent Infection of Brain Capillary Endothelial Cells by a Neurovirulent Simian Immunodeficiency Virus Strain," *Proc. Natl. Acad. Sci.*, USA 94: 14742-14747 (1997).

(Continued)

*Primary Examiner*—Christine J. Saoud
*Assistant Examiner*—Jon M Lockard
(74) *Attorney, Agent, or Firm*—Hamilton, Brook, Smith & Reynolds, P.C.

(57) ABSTRACT

The invention relates to an antibody or antigen-binding fragment thereof which binds to the CXC chemokine receptor Bonzo (also referred to as STRL33, TYMSTR, HBMBU14 and CXCR6) and blocks the binding of a ligand (e.g., SExCkine (also referred to as chemokine alpha-5 and CXCL16) to the receptor. The invention also relates to a method of identifying agents (molecules, compounds) which can bind to Bonzo and inhibit the binding of a ligand (e.g., SExCkine) and/or modulate a function of Bonzo. The invention relates to an antibody or antigen-binding fragment thereof which binds to the CXC chemokine SExCkine (also referred to as chemokine alpha-5) and inhibit binding of SExCkine to receptor (e.g., Bonzo). The invention also relates to targeting molecules which contain a first binding moiety which binds to mammalian Bonzo and a second binding moiety which binds to a molecule expressed on the surface of a target cell. The invention also relates to a method of promoting and/or effectuating the interaction of a $Bonzo^+$ cell and a target cell. The invention further relates to a method of modulating a function of Bonzo, and to the use of the antibodies, antigen-binding fragments, targeting molecules and agents identified by the method of the invention in research, therapeutic, prophylactic and diagnostic methods.

68 Claims, 66 Drawing Sheets

OTHER PUBLICATIONS

Edinger, A.L. et al., "Use of GPR1, GPR15, and STRL33 as Coreceptors by Diverse Human Immunodeficiency Virus Type 1 and Simian Immunodeficiency Virus Envelope Proteins," *Virology* 249(2): 367-378 (1998).

Mörner, A. et al., "Primary Human Immunodeficiency Virus Type 2 (HIV-2) Isolates, Like HIV-1 Isolates, Frequently Use CCR5 but Show Promiscuity in Coreceptor Usage," *J. Virol.* 73(3): 2343-2349 (1999).

Zhang, Y-J. and J.P. Moore, "Will Multiple Coreceptors Need to be Targeted by Inhibitors of Human Immunodeficiency Virus Type 1 Entry?," *J. Virol.* 73(4): 3443-3448 (1999).

Deng, H. et al., "Expression Cloning of New Receptors Used by Simian and Human Immunodeficiency Viruses," *Nature* 388: 296-300 (1997).

Zhang, Y-J. et al. "Use of Coreceptors Other than CCR5 by Non-Syncytium-Inducing Adult and Pediatric Isolates of Human Immunodeficiency Virus Type 1 is Rare In Vitro," *J. Virol.* 72(11): 9337-9344 (1998).

Littman, D.R., "Chemokine Receptors: Keys to AIDS Pathogenesis?," *Cell* 93: 677-680 (1998).

Owen, S.M. et al., "Genetically Divergent Strains of Human Immunodeficiency Virus Type 2 Use Multiple Coreceptors for Viral Entry," *J. Virol.* 72(7): 5425-5432 (1998).

Ponath, P.D. et al., "Molecular Cloning and Characterization of a Human Eotaxin Receptor Expressed Selectively on Eosinophils," *J. Exp. Med.* 183: 2437-2448 (1996).

Wu, L. et al., "Discrete Steps in Binding and Signaling of Interleukin-8 with Its Receptor," *J. Biol. Chem.* 271 (49): 31202-31209 (1996).

Wu, L. et al., "CD4-Induced Interaction of Primary HIV-1 gp120 Glycoproteins with the Chemokine Receptor CCR-5," *Nature* 384:179-183 (1996).

Loetscher, M. et al., "TYMSTR, A Putative Chemokine Receptor Selectively Expressed in Activated T Cells Exhibits HIV-1 Coreceptor Function," *Current Biology* 7(9):652-660 (1997).

Jin, Y. et al., "The Regulation of Phenotype and Function of Human Liver $CD3^+$ /$CD56^+$Lymphocytes, and Cells That Also Co-Express CD8 by IL-2, IL-12 and Anti-CD3 Monoclonal Antibody," *Human Immunology* 59: 352-362 (1998).

Goldman, L.A. et al., "Modifications of Vectors pEF-BOS, pcDNA1 and pcDNA3 Result in Improved Convenience and Expression," *Biotechniques* 21(6):1013-1015 (1996).

Sornasse, T. et al., "Differentiation and Stability of T Helper 1 and 2 Cells Derived from Naive Human Neonatal $CD4^+$ T Cells, Analyzed at the Single-cell Level," *J. Exp. Med.* 184:473-483 (1996).

Wu, L., et al. "CCR5 Levels and Expression Pattern Correlate with Infectability by Macrophage-tropic HIV-1, In Vitro," *J. Exp. Med.* 185 (9):1681-1691 (1997).

Yoshie, O., et al. "Novel Lymphocyte-Specific CC Chemokines and Their Receptors," *J. Leukoc. Biol.*, 62:634-644 (1997).

GenBank Accession No. AA290712, "zt18a10.r1 Soares Ovary Tumor NbHOT *Homo sapiens* cDNA Clone IMAGE:713466 5' , mRNA Sequence," (1997) [online], [retrieved on Jul. 14, 1999]. Retrieved from the Internet: <URL:http://www.ncbi.nlm.nih.gov>.

GenBank Accession No. AA283690, "zt18a10.s1 Soares Ovary Tumor NbHOT *Homo sapiens* cDNA Clone IMAGE:713466 3' Similar to Contains Element LTR8 Repetitive Element; mRNA Sequence," (1997) [online], [retrieved on Jul. 14, 1999]. Retrieved from the Internet: <URL:http://www.ncbi.nlm.nih.gov>.

GenBank Accession No. AI312518, "qp10a09.x1 NCI_CGAP_Kid5 *Homo sapiens* cDNA Clone IMAGE:1917592 3' Similar to Contains Alu Repetitive Element; Contains Element MSR1 Repetitive Element; mRNA Sequence," (1999) [online], [retrieved on Jul. 14, 1999]. Retrieved from the Internet: <URL:http://www.ncbi.nlm.nih.gov>.

GenBank Accession No. AA366329, "EST77447 Pancreas Tumor III *Homo sapiens* cDNA 5' End, mRNA Sequence," (1997) [online], [retrieved on Jul. 14, 1999]. Retrieved from the Internet: <URL:http://www.ncbi.nlm.nih.gov>.

GenBank Accession No. AA146672, "zo33b12.r1 Stratagene Colon (#937204) *Homo sapiens* cDNA Clone IMAGE:588671 5' mRNA Sequence," (1996) [online], [retrieved on Jul. 14, 1999]. Retrieved from the Internet: <URL:http://www.ncbi.nlm.nih.gov>.

GenBank Accession No. F14505, "SSC1C52 Porcine Small Intestine cDNA Library *Sus scrofa* cDNA, mRNA Sequence," (1996) [online], [retrieved on Jul. 14, 1999]. Retrieved from the Internet: <URL:http://www.ncbi.nlm.nih.gov>.

GenBank Accession No. F23105, "SSC21H07 Porcine Small Intestine cDNA Library *Sus scrofa* cDNA Clone c21h07 5' , mRNA Sequence," (1998) [online], [retrieved on Jul. 14, 1999]. Retrieved from the Internet: <URL:http://www.ncbi.nlm.nih.gov>.

GenBank Accession No. AI019535, "ua90a07.r1 Soares Mouse Mammary Gland NbMMG *Mus musculus* cDNA Clone IMAGE:1364724 5' , mRNA Sequence," (1998) [online], [retrieved on Jul. 14, 1999]. Retrieved from the Internet: <URL:http://www.ncbi.nlm.nih.gov>.

GenBank Accession No. AA121716, "zn95c09.r1 Stratagene Fetal Retina 937202 *Homo sapiens* cDNA Clone, IMAGE:565936 5' , mRNA Sequence" (1997) [online], [retrieved on Jul. 14, 1999]. Retrieved from the Internet: <URL:http://www.ncbi.nlm.nih.gov>.

GenBank Accession No. AA130776, "zo13d05.r1 Stratagene Colon (#937204) *Homo sapiens* cDNA Clone IMAGE:586761 5' , mRNA Sequence," (1997) [online], [retrieved on Jul. 14, 1999]. Retrieved from the Internet: <URL:http://www.ncbi.nlm/nih.gov>.

GenBank Accession No. AA130627, "zo13d05.s1 Stratagene Colon (#937204) *Homo sapiens* cDNA Clone IMAGE:586761 3' Similar to gb:M91159 !!!!ALU Class E Warning Entry !!!!(HUMAN); Contains Element PTR5 Repetitive Element; mRNA Sequence," (1997) [online], [retrieved on Jul. 14, 1999]. Retrieved from the Internet: <URL:http://www.ncbi.nlm.nih.gov>.

Chuntharapai, A. and Kim, K. J., "Generation of Monoclonal Antibodies to Chemokine Receptors," *Methods in Enzymology*, 288:15-27 (1997).

STRL 33/Bonzo Monoclonal Antibody MAB699, *de novo, New Products from R& D Systems*, p. 7 (1999).

Monoclonal Anti-human STRL 33/Bonzo Antibody, Technical Information, R&D Systems, Inc. (1999).

Shimaoka, T. et al., "Molecular Cloning of a Novel Scavenger Receptor for Oxidized Low Density Lipoprotein, SR-PSOX, on Macrophages," *J. Biol. Chem.* 275 (52) :40663-40666 (2000).

GenBank Accession No. AW347794, "32031 MARC 2PIG *Sus scrofa* cDNA 5', mRNA Sequence gi| 6845504|gb|AW347794. 1|AW347794 [6845504]," (2000) [online], [retrieved on Nov. 28, 2000]. Retrieved from the internet: <URL:http://www.ncbi.nlm.nih.gov>.

GenBank Accession No. AW261653, "um90c04.x1 Sugano Mouse Kidney mkia *Mus musculus* cDNA Clone IMAGE:2332038 3', mRNA Sequence gi|6638469|gb|AW261653 [6638469]," (2000) [online], [retrieved on Nov. 28, 2000]. Retrieved from the internet: <URL:http://www.ncbi.nlm.nih.gov>.

Matloubian M. et al., "A Transmembrane CXC Chemokine is a Ligand for HIV-Coreceptor Bonzo," *Nature Immunol.* 1(4):298-304 (2000).

Sharron, M. et al., "Expression and Coreceptor Activity of STRL33/ Bonzo on Primary Peripheral Blood Lymphocytes," *Blood* 96(1):41-49 (2000).

Unutmaz, D. et al., "The Primate Lentiviral Receptor Bonzo/ STRL33 is Coordinately Regulated with CCR5 and its Expression Pattern is Conserved Between Human and Mouse," *J. Immunol.* 165(6):3284-3292 (2000).

Ignatius, R. et al., "The Immunodeficiency Virus Coreceptor, Bonzo/STRL33/TYMSTR, is Expressed by Macaque and Human Skin- and Blood-Derived Dendritic Cells," *AIDS Research and Human Retroviruses* 16(11) :1055-1059 (2000).

U.S. Appl. No. 60/066,369 entitled "Chemokine Alpha-5", by Wei, Y-F. et al., filed Nov. 21, 1997.

GenBank Accession No. M25897, "Human Platelet Factor 4 (PF4) mRNA, Complete Cds," (1995) [online], [retrieved on Mar. 30, 2001]. Retrieved from the internet: <URL:http://www.ncbi.nlm.nih.gov>.

GenBank Accession No. AF007545, "*Homo sapiens* SIV/HIV Receptor Bonzo (Bonzo) mRNA, Complete Cds," (1997) [online],

[retrieved on Mar. 30, 2001]. Retrieved from the internet: <URL:http://www.ncbi.nlm.nih.gov>.

GenBank Accession No. U73531, "Human G Protein-Coupled Receptor STRL33.3 (STRL33) mRNA, Complete Cds," (1997) [online], [retrieved on Nov. 24, 1999]. Retrieved from the internet: <URL:http://www.ncbi.nlm.nih.gov>. Liao et al.

GenBank Accession No. NM_006564, "*Homo sapiens* G Protein-Coupled Receptor (TYMSTR) mRNA," (1999) [online], [retrieved on Nov. 24, 1999]. Retrieved from the internet: <URL:http://www.ncbi.nlm.nih.gov>, Liao et al.

GenBank Accession No. U73529, "Human G Protein-Coupled Receptor STRL33.3 (STRL33) mRNA, Complete Cds," (1997) [online], [retrieved on Nov. 24, 1999]. Retrieved from the internet: <URL:http://www.ncbi.nlm.nih.gov>. Liao et al.

Tabata, S., et al., "Distribution and Kinetics of SR-PSOX/CXCL16 and CXCR6 Expression on Human Dendritic Cell Subsets and $CD4^+$ T Cells," *J. Leukoc. Biol.*, 77:777-786 (2005).

van der Voort, R., et al., "Elevated CXCL16 Expression by Synovial Macrophages Recruits Memory T Cells Into Rheumatoid Joints," *Arthritis Rheum.*, 52(5):1381-1391 (2005).

Kim., C. H., et al., "Bonzo/CXCR6 Expression Defines Type 1-Polarized T-Cell Subsets with Extralymphoid Tissue Homing Potential," *J. Clin. Invest.*, 107(5):595-601 (2001).

Heydtmann, M., et al., "CXC Chemokine Ligand 16 Promotes Integrin-Mediated Adhesion of Liver-Infiltrating Lymphocytes to Cholangiocytes and Hepatocytes Within the Inflamed Human Liver," *J. Immunol.*, 174(2):1055-1062 (2005).

Geissman, F., et al., "Intravascular Immune Surveillance by $CXCR6^+$ NKT Cells Patrolling Liver Sinusoids," *PLoS Biol.*, 3(4)e113:650-661 (2005).

Sato, T., et al., "Role for CXCR6 in Recruitment of Activated $CD8^+$ Lymphocytes to Inflamed Liver," *J. Immunol.*, 174(1):277-283 (2005).

Calabresi, P. A., et al., "Chemokine Receptor Expression on MBP-Reactive T Cells: CXCR6 is a Marker of IFNµ-Producing Effector Cells," *J. Neuroimmunol.*, 127:96-105 (2002).

Lee, B., et al., "Epitope Mapping of CCR5 Reveals Multiple Conformational States and Distinct but Overlapping Structures Involved in Chemokine and Coreceptor Function," *J. Biol. Chem.*, 274(14):9617-9626 (1999).

Wu, L., et al., "Interaction of Chemokine Receptor CCR5 with its Ligands: Multiple Domains for HIV-1 gp120 Binding and a Single Domain for Chemokine Binding," *J. Exp. Med.*, 186(8):1373-1381 (1997).

Doranz, B. J., et al., "Identification of CXCR4 Domains That Support Coreceptor and Chemokine Receptor Functions," *J. Virol.*, 73(4):2752-2761 (1999).

Karpus, W. J., et al., "An Important Role for the Chemokine Macrophage Inflammatory Protein-1α in the Pathogenesis of the T Cell-Mediated Autoimmune Disease, Experimental Autoimmune Encephalomyelitis" *J. of Immunol.*, 155:5003-5010 (1995).

Hesselgesser J., et al., "Identification and Characterization of Small Molecule Functional Antagonists of the CCR1 Chemokine Receptor," *J. Biol. Chem.*, 273(25):15687-15692 (1998).

Taub, D. D., et al., "T Lymphocyte Recruitment by Interleukin-8 (IL-8)," *J. Clin. Invest.*, 97(8):1931-1941 (1996).

Fuentes, M. E., et al., "Controlled Recruitment of Monocytes and Macrophages to Specific Organs Through Transgenic Expression of Monocyte Chemoattractant Protein-1," *J. of Immunol.*, 155:5769-5776 (1995).

Zogorski, J. and Wahl S. M., "Inhibition of Acute Peritoneal Inflammation in Rats by a Cytokine-Induced Neutrophil Chemoattractant Receptor Antagonist," *J. of Immunol.*, 159:1059-1062 (1997).

Chen, S., et al., "In Vivo Inhibition of CC and $CX_3C$ Chemokine-induced Leukocyte Inflitration and Attenuation of Glomerulonephritis in Wistar-Kyoto (WKY) Rats by vMIP-II" *J. Exp. Med.*, 188(1):193-198 (1998).

\* cited by examiner

FIG. 1

```
   1 atggcagagc atgattacca tgaagactat gggttcagca gtttcaatga cagcagccag
  61 gaggagcatc aagacttcct gcagttcagc aaggtctttc tgccctgcat gtacctggtg
 121 gtgtttgtct gtggtctggt ggggaactct ctggtgctgg tcatatccat cttctaccat
 181 aagttgcaga gcctgacgga tgtgttcctg gtgaacctac cctgctga cctggtgttt
 241 gtctgcactc tgccccttctg ggcctatgca ggcatccatg aatgggtgtt tggccaggtc
 301 atgtgcaaga gcctactggg catctacact attaacttct acacgtccat gctcatcctc
 361 acctgcatca ctgtggatcg tttcattgta gtggttaagg ccaccaaggc ctacaaccag
 421 caagccaaga ggatgaccctg gggcaaggtc accagcttgc tcatctgggt gatatcctg
 481 ctggtttcct tgcccaaaat tatctatgc aatgtcttta atctcgacaa gctcatatgt
 541 ggttaccatg acgaggcaat ttccactgtg gttcttgcc cccagatgac actggggttc
 601 ttcttgccac tgctcaccat gattgtctgc tattcagtca taatcaaaac actgcttcat
 661 gctggaggct tccagaagca cagatctcta aagatcatct tcctggtgat ggctgtgttc
 721 ctgctgacccc agatgccctt caacctcatg aagttcatcc gcagcacaca ctgggaatac
 781 tatgccatga ccagctttca ctacaccatc atggtgacag aggccatcgc agtttcgagg
 841 gcctgcctta accctgtgct ctatgccttt gtcagcctga gtttcgaaa gaacttctgg
 901 aaacttgtga aggacattgg ttgcctccct tacctgggg tctcacatca atggaaatct
 961 tctgaggaca attccaagac ttttctgcc tcccacaatg tggaggccac cagcatgttc
1021 cagttatag
```

FIG. 2

```
MAEHDYHEDY GFSSFNDSSQ EEHQDFLQFS KVFLPCMYLV VFVCGLVGNS LVLVISIFYH KLQSLTDVFL
VNLPLADLVF VCTLPFWAYA GIHEWVFGQV MCKSLLGIYT INFYTSMLIL TCITVDRFIV VVKATKAYNQ
QAKRMTWGKV TSLLIWVISL LVSLPQIIYG NVFNLDKLIC GYHDEAISTV VLATQMTLGF FLPLLTMIVC
YSVIIKTLLH AGGFQKHRSL KIIFLVMAVF LLTQMPFNLM KFIRSTHWEY YAMTSFHYTI MVTEAIAYLR
ACLNPVLYAF VSLKFRKNFW KLVKDIGCLP YLGVSHQWKS SEDNSKTFSA SHNVEATSMF QL
```

```
1.
    CGGCGACTCTCTCCACCGGGCCGCCCGGGAGGCTCATGCAGCGCGGCTGGGTCCCGCGGC
61
    GCCCGGATCGGGGAAGTGAAAGTGCCTCGGAGGAGGAGGGCCGGTCCGGCAGTGCAGCCG
121
    CCTCACAGGTCGGCGGACGGGCCAGGCGGGCGGCCTCCTGAACCGAACCGAATCGGCTCC
181
    TCGGGCCGTCGTCCTCCCGCCCCTCCTCGCCCGCCGCCGGAGTTTTCTTTCGGTTTCTTC
241
    CAAGATTCCTGGCCTTCCCTCGACGGAGCCGGGCCCAGTGCGGGGGCGCAGGGCGCGGGA
301
    GCTCCACCTCCTCGGCTTTCCCTGCGTCCAGAGGCTGGCATGGCGCGGGCCGAGTACTGA
361
    GCGCACGGTCGGGGCACAGCAGGGCCGGTGGGTGCAGCTGGCTCGCGCCTCCTCTCCGGC
421
    CGCCGTCTCCTCCGGTCCCCGGCGAAAGCCATTGAGACACCAGCTGGACGTCACGCGCCG
481
    GAGCATGTCTGGGAGTCAGAGCGAGGTGGCTCCATCCCCGCAGAGTCCGCGGAGCCCCGA
541
    GATGGGACGGGACTTGCGGCCCGGGTCCCGCGTGCTCCTGCTCCTGCTTCTGCTCCTGCT
    M  G  R  D  L  R  P  G  S  R  V  L  L  L  L  L  L  L  L  L        20
601
    GGTGTACCTGACTCAGCCAGGCAATGGCAACGAGGGCAGCGTCACTGGAAGTTGTTATTG
    V  Y  L  T  Q  P  G  N  G  N  E  G  S  V  T  G  S  C  Y  C        40
661
    TGGTAAAAGAATTTCTTCCGACTCCCCGCCATCGGTTCAGTTCATGAATCGTCTCCGGAA
       G  K  R  I  S  S  D  S  P  P  S  V  Q  F  M  N  R  L  R  K     60
721
    ACACCTGAGAGCTTACCATCGGTGTCTATACTACACGAGGTTCCAGCTCCTTTCCTGGAG
       H  L  R  A  Y  H  R  C  L  Y  Y  T  R  F  Q  L  L  S  W  S     80
781
    CGTGTGTGGAGGCAACAAGGACCCATGGGTTCAGGAATTGATGAGCTGTCTTGATCTCAA
       V  C  G  G  N  K  D  P  W  V  Q  E  L  M  S  C  L  D  L  K    100
```

FIG. 4B

```
841
    AGAATGTGGACATGCTTACTCGGGGATTGTGGCCCACCAGAAGCATTTACTTCCTACCAG
     E  C  G  H  A  Y  S  G  I  V  A  H  Q  K  H  L  L  P  T  S    120

901
    CCCCCCAACTTCTCAGGCCTCAGAGGGGGCATCTTCAGATATCCACACCCCTGCCCAGAT
     P  P  T  S  Q  A  S  E  G  A  S  S  D  I  H  T  P  A  Q  M    140

961
    GCTCCTGTCCACCTTGCAGTCCACTCAGCGCCCCACCCTCCCAGTAGGATCACTGTCCTC
     L  L  S  T  L  Q  S  T  Q  R  P  T  L  P  V  G  S  L  S  S    160

1021
    GGACAAAGAGCTCACTCGTCCCAATGAAACCACCATTCACACTGCGGGCCACAGTCTGGC
     D  K  E  L  T  R  P  N  E  T  T  I  H  T  A  G  H  S  L  A    180

1081
    AGTTGGGCCTGAGGCTGGGGAGAACCAGAAGCAGCCGGAAAAAAATGCTGGTCCCACAGC
     V  G  P  E  A  G  E  N  Q  K  Q  P  E  K  N  A  G  P  T  A    200

1141
    CAGGACATCAGCCACAGTGCCGGTCCTGTGCCTCCTGGCCATCATCTTCATCCTCACCGC
     R  T  S  A  T  V  P  V  L  C  L  L  A  I  I  F  I  L  T  A    220

1201
    AGCCCTTTCCTATGTGCTGTGCAAGAGGAGGAGGGGGCAGTCACCGCAGTCCTCTCCAGA
     A  L  S  Y  V  L  C  K  R  R  R  G  Q  S  P  Q  S  S  P  D    240

1261
    TCTGCCGGTTCATTATATACCTGTGGCACCTGACTCTAATACCTGAGCCAAGAATGGAAG
     L  P  V  H  Y  I  P  V  A  P  D  S  N  T  *                   254

1321
    CTTGTGAGGAGACGGACTCTATGTTGCCCAGGCTGTTATGGAACTCCTGAGTCAAGTGAT
1381
    CCTCCCACCTTGGCCTCTGAAGGTGCGAGGATTATAGGCGTCACCTACCACATCCAGCCT
1441
    ACACGTATTTGTTAATATCTAACATAGGACTAACCAGCCACTGCCCTCTCTTAGGCCCCT
```

FIG. 4C

```
1501
        CATTTAAAAACGGTTATACTATAAAATCTGCTTTTCACACTGGGTGATAATAACTTGGAC
1561
        AAATTCTATGTGTATTTTGTTTTGTTTTGCTTTGCTTTGTTTTGAGACGGAGTCTCGCTC
1621
        TGTCATCCAGGCTGGAGTGCAGTGGCATGATCTCGGCTCACTGCAACCCCCATCTCCCAG
1681
        GTTCAAGCGATTCTCCTGCCTCCTCCTAAGTAGCTGGGACTACAGGTGCTCACCACCACA
1741
        CCCGGCTAATTTTTTGTATTTTTAGTAGAGACGGGGTTTCACCATGTTGACCAGGCTGGT
1801
        CTCGAACTCCTGACCTGGTGATCTGCCCACCCAGGCCTCCCAAAGTGCTGGGATTAAAGG
1861
        TGTGAGCCACCATGCCTGGCCCTATGTGTGTTTTTTAACTACTAAAAATTATTTTTGTAA
1921
        TGATTGAGTCTTCTTTATGGAAACAACTGGCCTCAGCCCTTGCGCCCTTACTGTGATTCC
1981
        TGGCTTCATTTTTTGCTGATGGTTCCCCCTCGTCCCAAATCTCTCTCCCAGTACACCAGT
2041
        TGTTCCTCCCCCACCTCAGCCCTCTCCTGCATCCTCCTGTACCCGCAACGAAGGCCTGGG
2101
        CTTTCCCACCCTCCCTCCTTAGCAGGTGCCGTGCTGGGACACCATACGGGTTGGTTTCAC
2161
        CTCCTCAGTCCCTTGCCTACCCCAGTGAGAGTCTGATCTTGTTTTTATTGTTATTGCTTT
2221
        TATTATTATTGCTTTTATTATCATTAAAACTCTAGTTCTTGTTTTGTCTCTCAAAAAAAA
2281
        AAAAAAAAAAAAAAAAAAAAAAAAAAAAA
```

FIG. 5

```
  1  ccgcagcatg agctccgcag ccgggttctg cgcctcacgc cccgggctgc tgttcctggg
 61  gttgctgctc ctgccacttg tggtcgcctt cgccagcgct gaagctgaag aagatgggga
121  cctgcagtgc ctgtgtgtga agaccacctc ccaggtccgt cccaggcaca tcaccagcct
181  ggaggtgatc aaggccggac cccactgccc cactgcccaa ctgatagcca cgctgaagaa
241  tggaaggaaa atttgcttgg acctgcaagc cccgctgtac aagaaaataa ttaagaaact
301  tttggagagt tagctactag ctgcctacgt gtgtgcattt gctatatagc atacttcttt
361  tttccagttt caatctaact gtgaaagaaa cttctgatat ttgtgttatc cttatgattt
421  taaataaaca aaataaatc
```

FIG. 6

MSSAAGFCAS RPGLLFLGLL LLPLVVAFAS AEAEEDGDLQ CLCVKTTSQV RPRHITSLEV IKAGPHCPTA
QLIATLKNGR KICLDLQAPL YKKIIKKLLE S

4A11
(IgG2b)

7A2
(IgG2a)

7F3
(IgG2a)

9G2
(IgM)

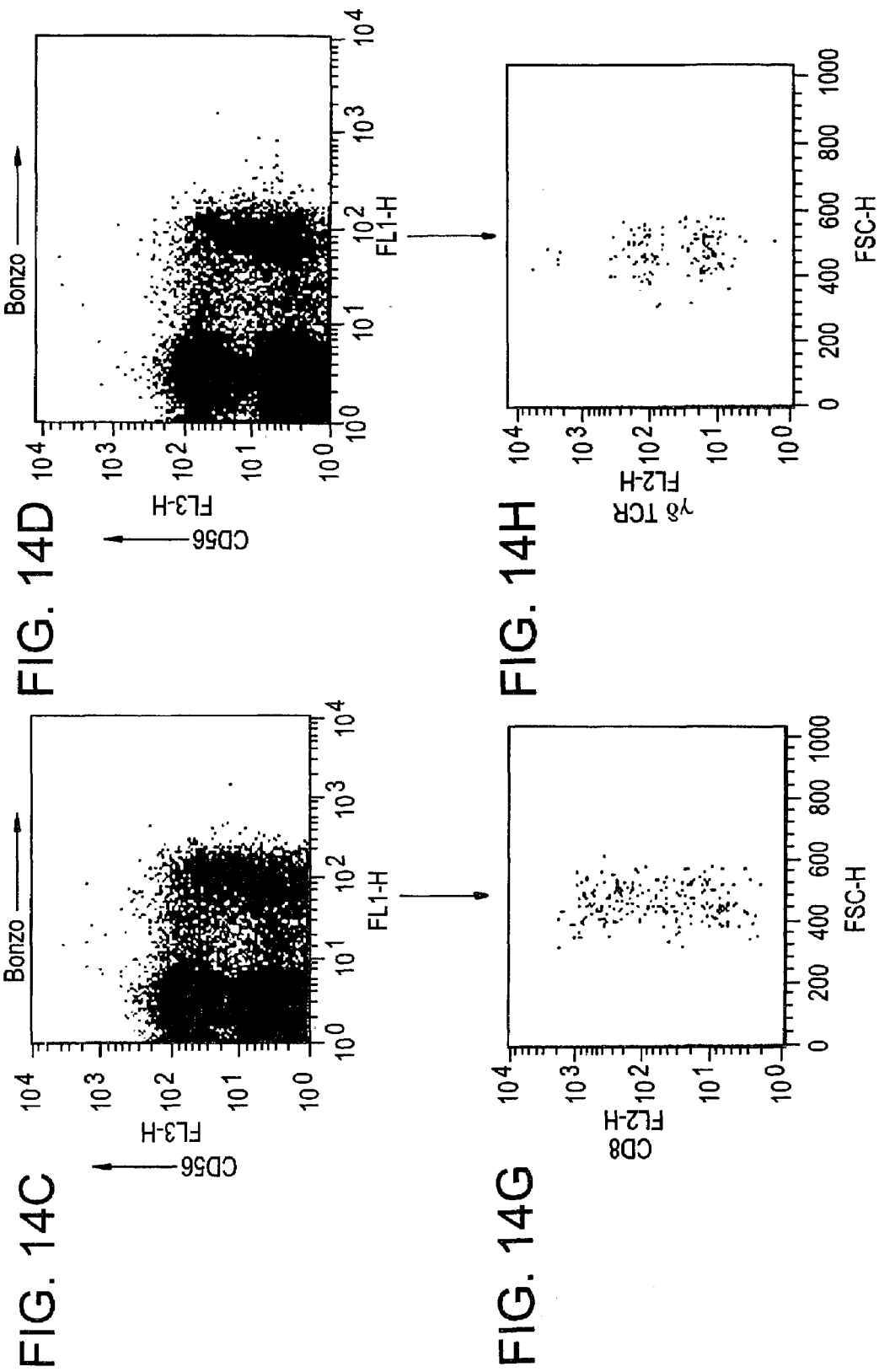

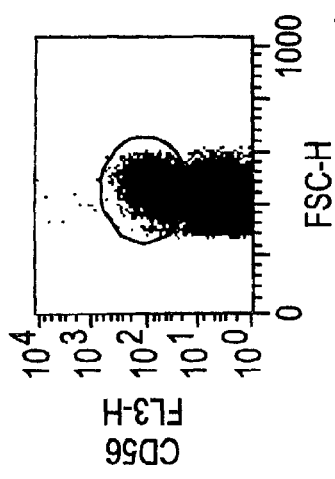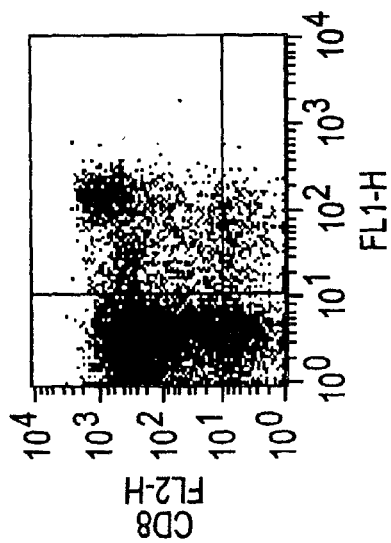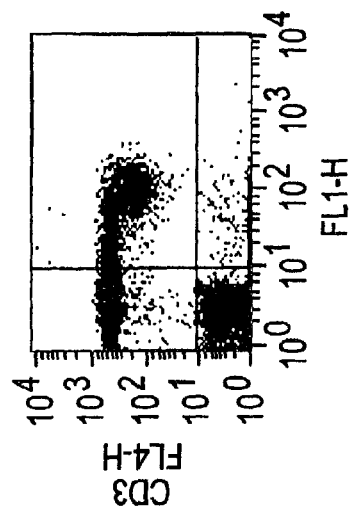
FIG. 15A
FIG. 15B
FIG. 15C

4A11-30-8
anti-Bonzo
(IgG2b)

7F3-8-1
anti-Bonzo
(IgG2a)

7A2-32-1
anti-Bonzo
(IgG2a)

7H12-12-2
anti-CCR7
(IgG2b)

CD3 Blasts

LAK Cells

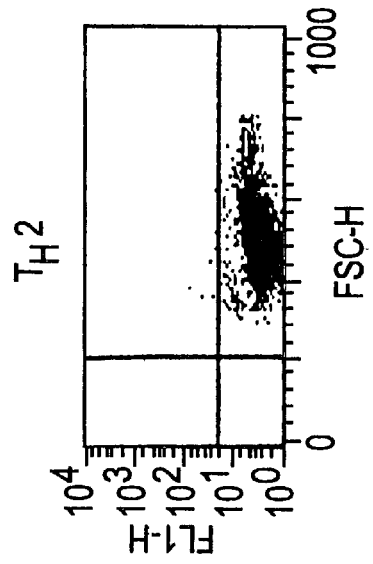
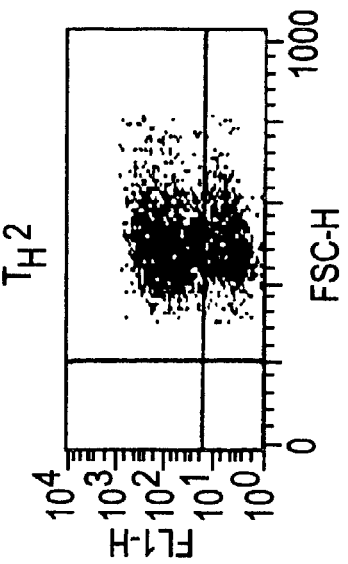
MOPC
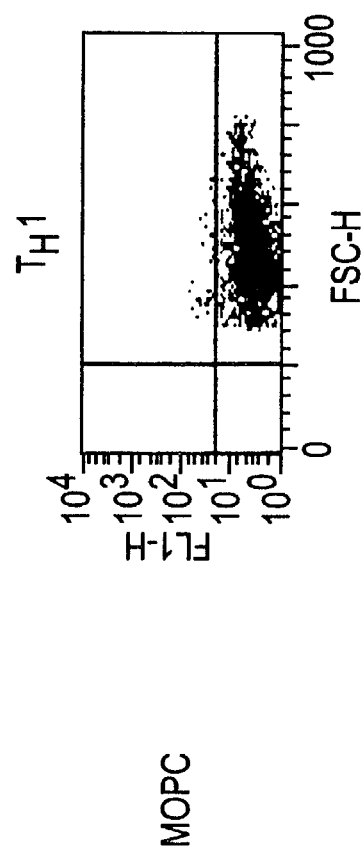
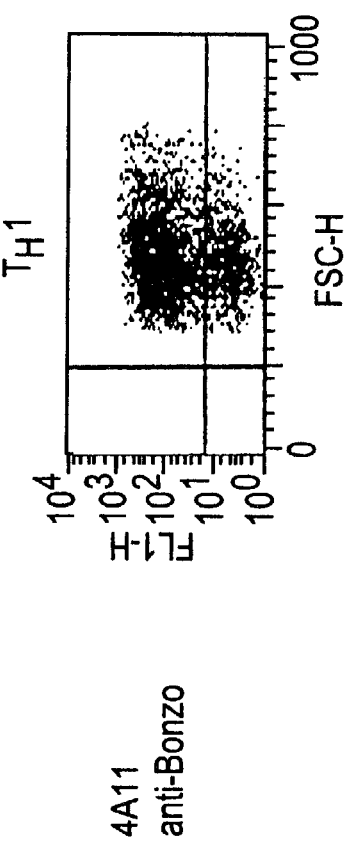
4A11
anti-Bonzo

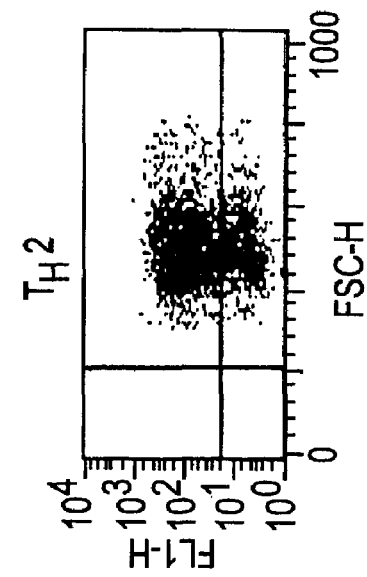
FIG. 23F
FIG. 23E
7F3
anti-Bonzo
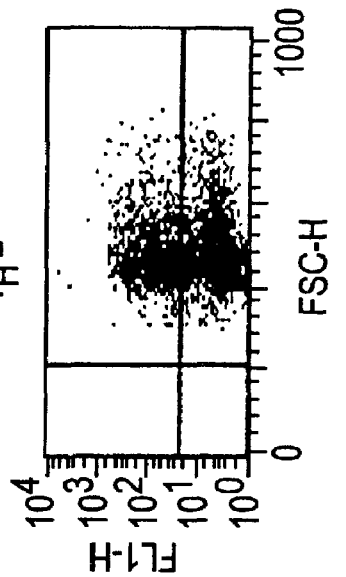
FIG. 23H
FIG. 23G
1G1
anti-CCR4

$T_H1$

CCR4

$T_H1$

CCR4

$T_H1$

Bonzo $T_H1$

Bonzo $T_H1$

CCR7

$T_H1$

CCR7

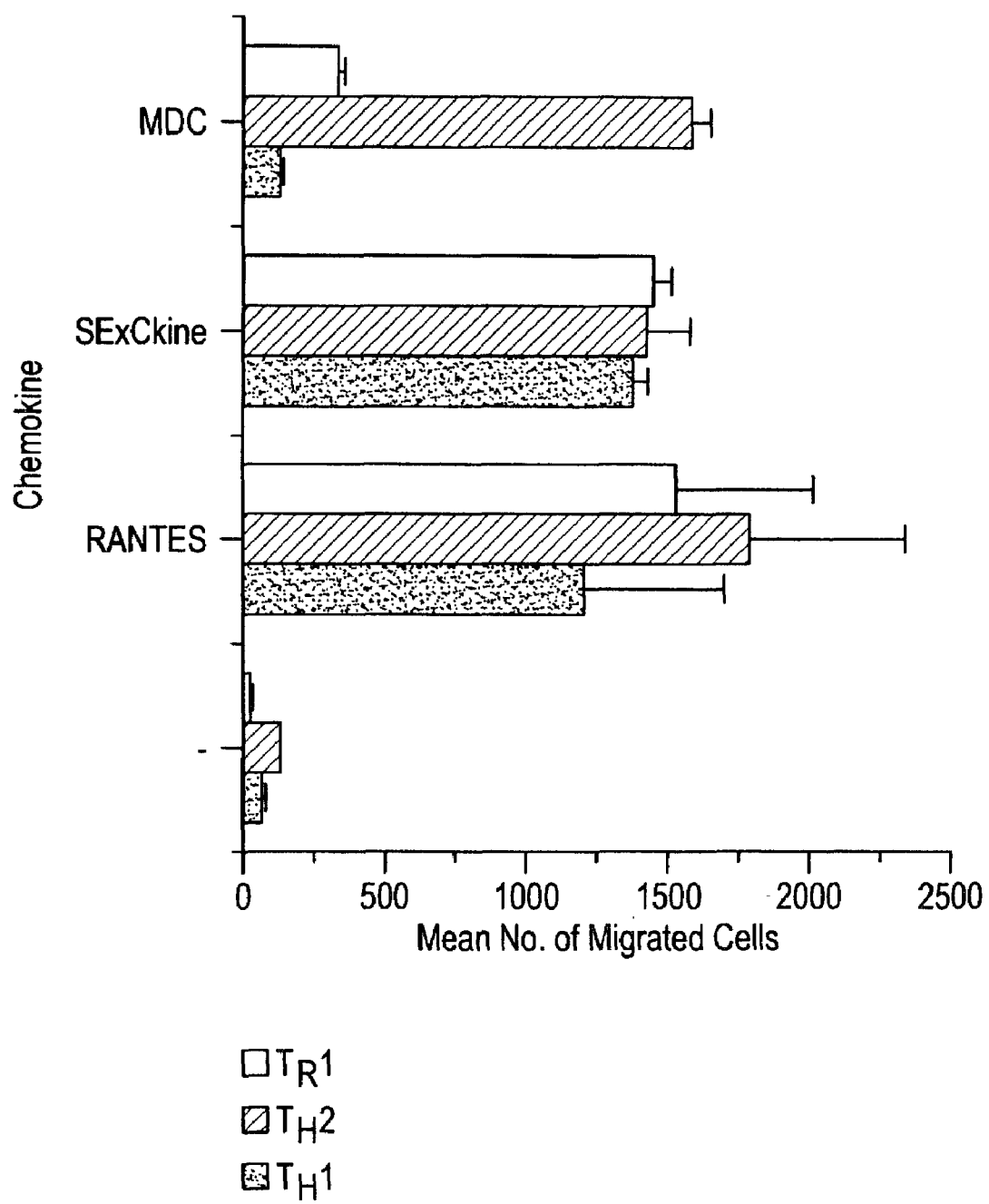

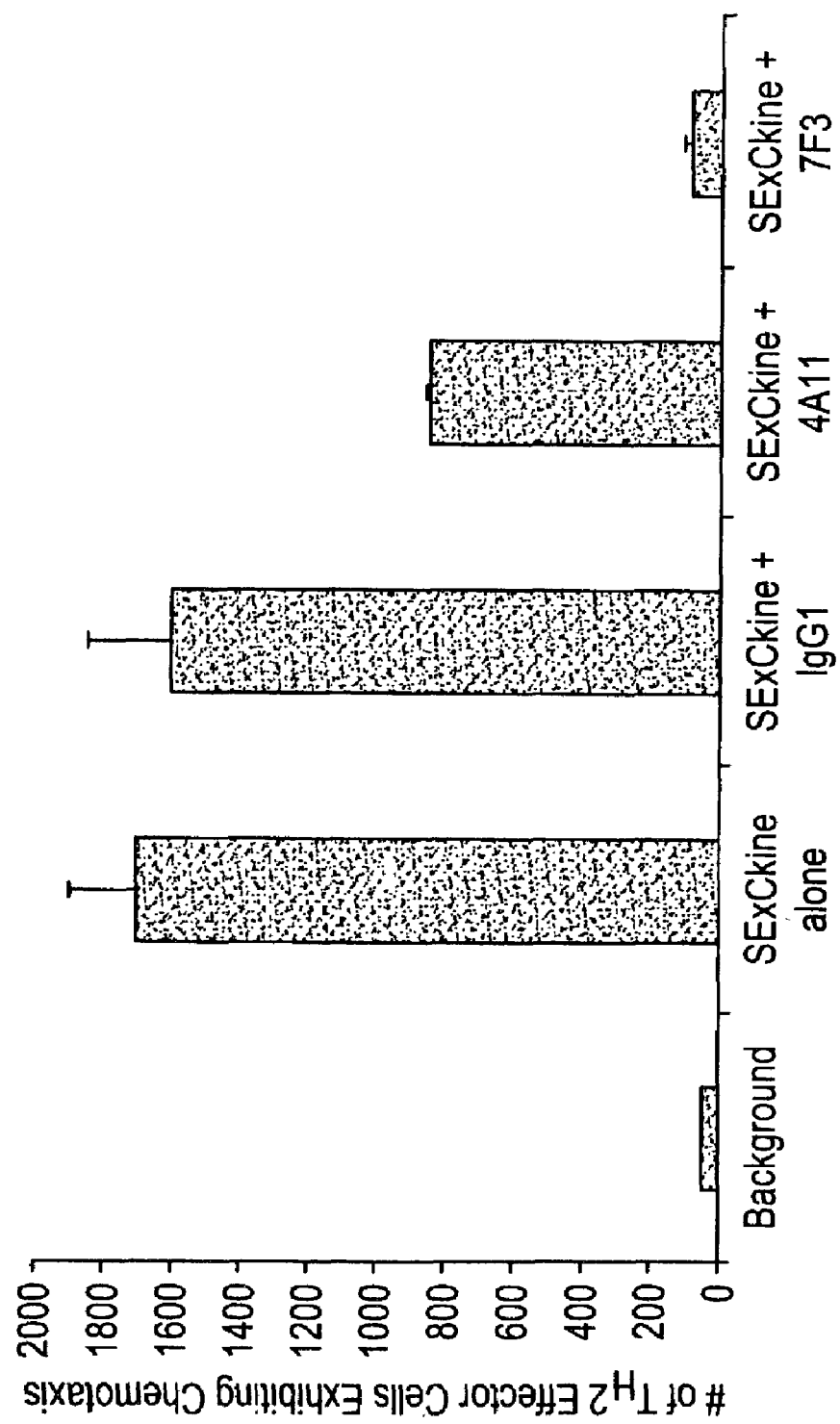

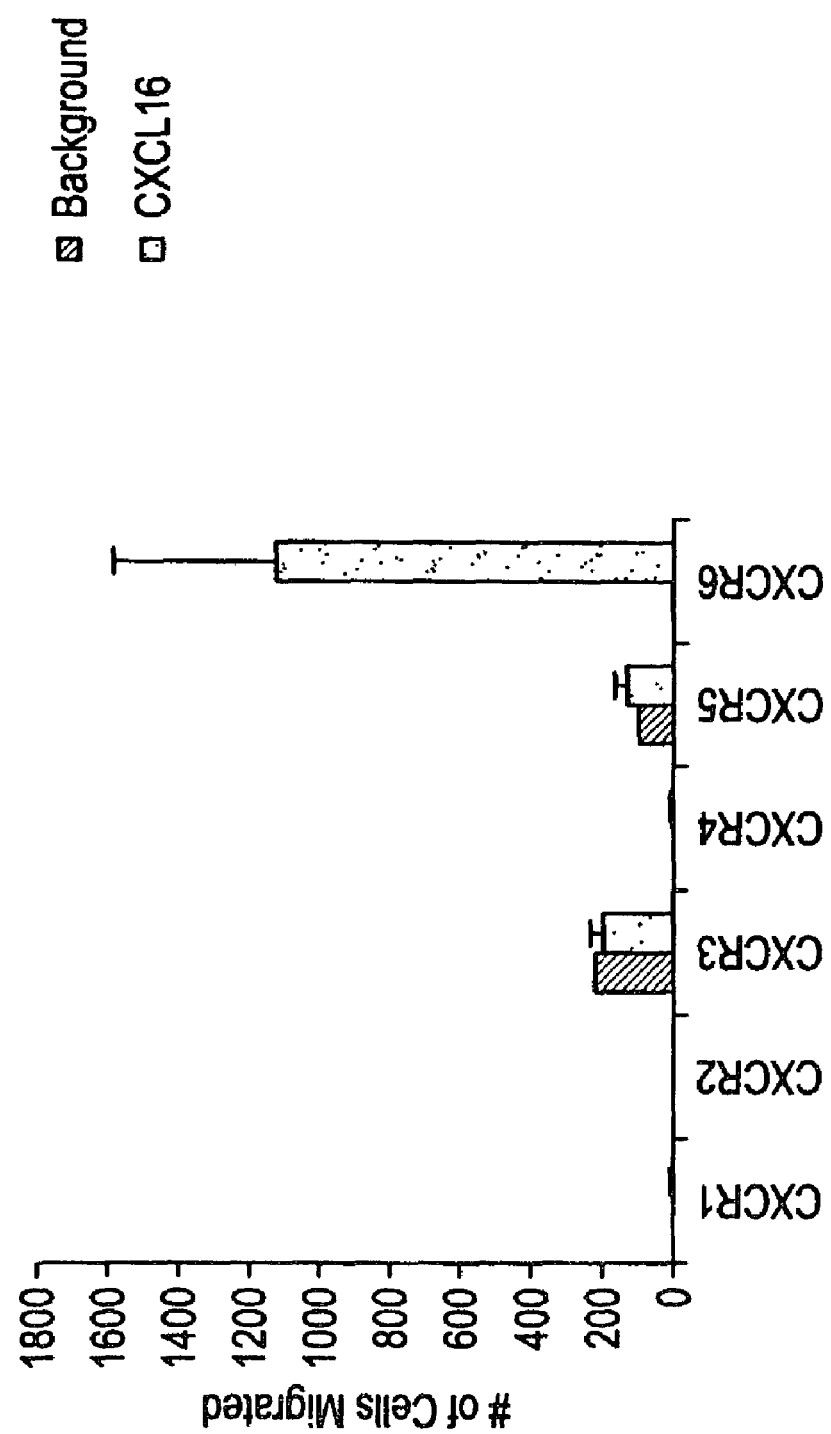

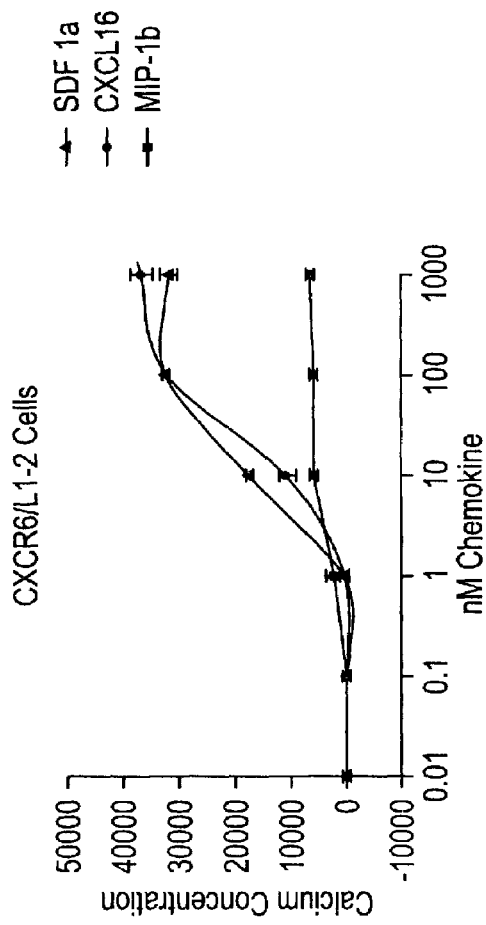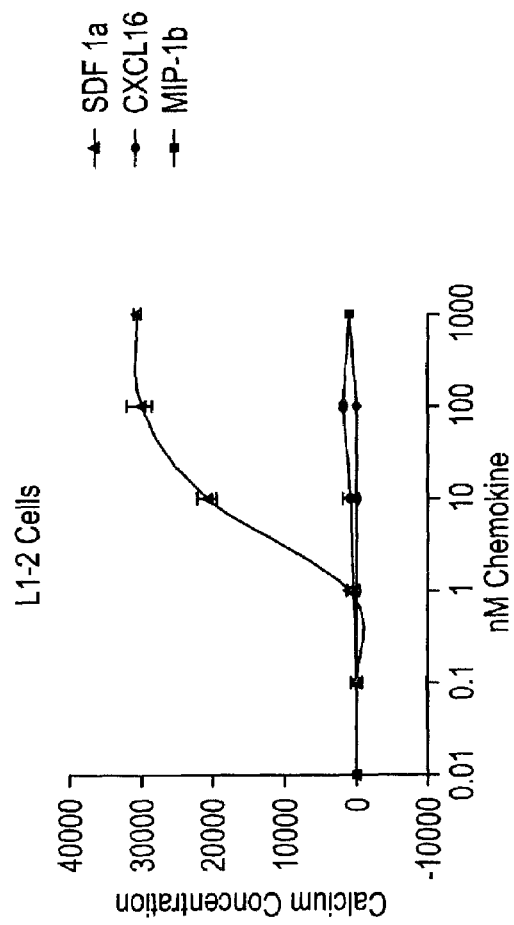
FIG. 42A
FIG. 42B

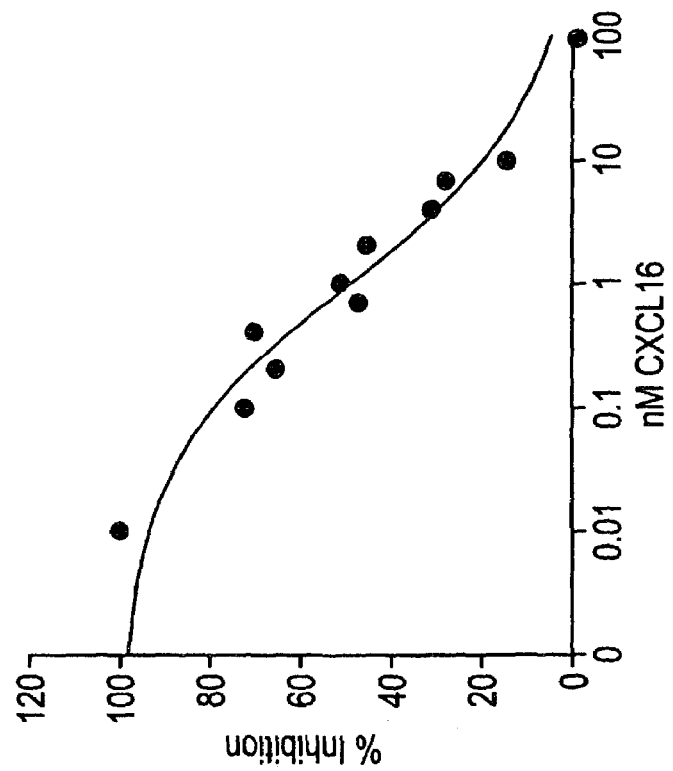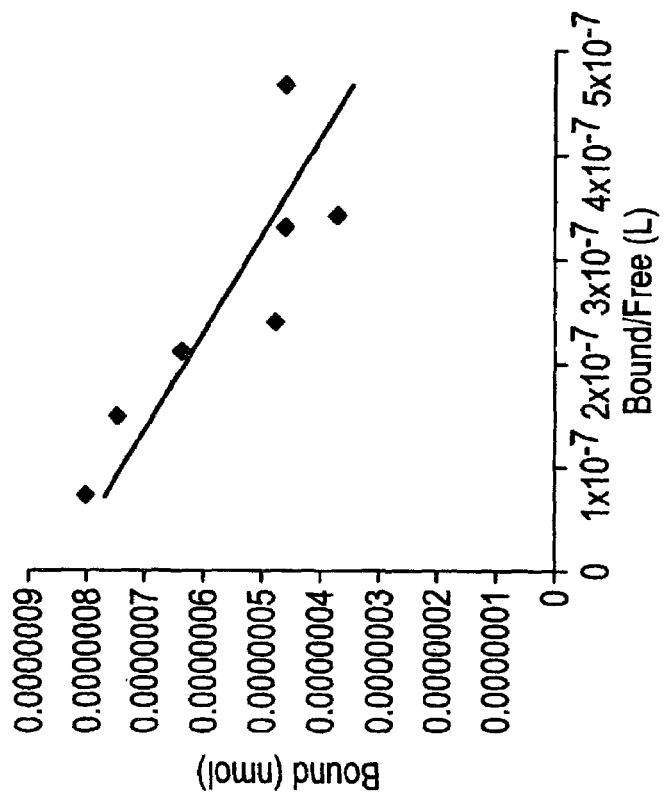
FIG. 43A
FIG. 43B

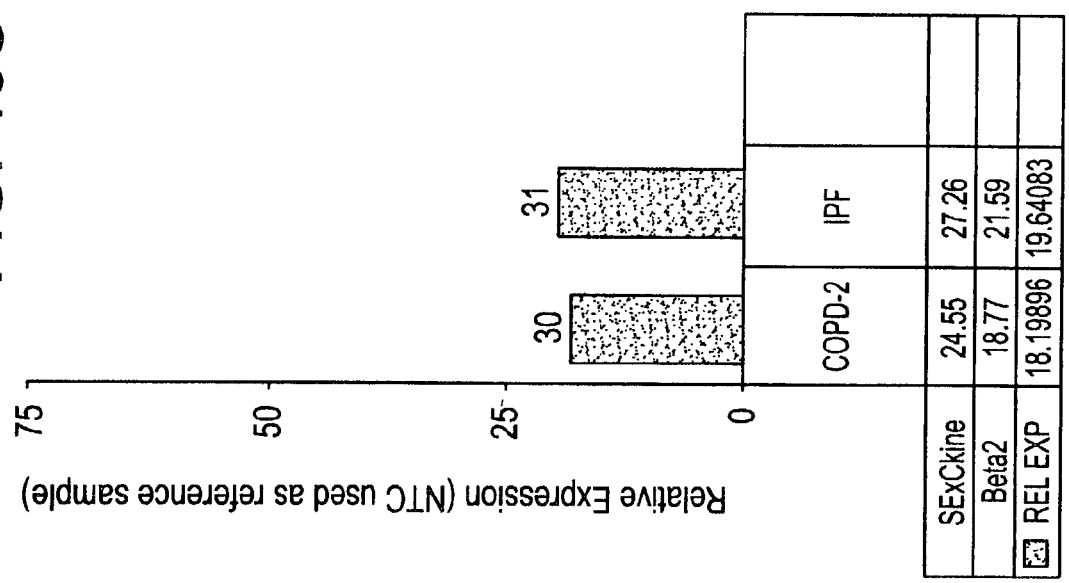

SEQUENCE LISTING

<160> NUMBER OF SEQ ID NOS: 27

<210> SEQ ID NO 1
<211> LENGTH: 1029
<212> TYPE: DNA
<213> ORGANISM: Homo Sapiens

<400> SEQUENCE: 1

```
atggcagagc atgattacca tgaagactat gggttcagca gtttcaatga cagcagccag      60
gaggagcatc aagacttcct gcagttcagc aaggtctttc tgccctgcat gtacctggtg     120
gtgtttgtct gtggtctggt ggggaactct ctggtgctgg tcatatccat cttctaccat     180
aagttgcaga gcctgacgga tgtgttcctg gtgaacctac ccctggctga cctggtgttt     240
gtctgcactc tgcccttctg ggcctatgca ggcatccatg aatgggtgtt tggccaggtc     300
atgtgcaaga gcctactggg catctacact attaacttct acacgtccat gctcatcctc     360
acctgcatca ctgtggatcg tttcattgta gtggttaagg ccaccaaggc ctacaaccag     420
caagccaaga ggatgacctg gggcaaggtc accagcttgc tcatctgggt gatatccctg     480
ctggtttcct tgcccaaat tatctatggc aatgtctttta atctcgacaa gctcatatgt     540
ggttaccatg acgaggcaat ttccactgtg gttcttgcca cccagatgac actggggttc     600
ttcttgccac tgctcaccat gattgtctgc tattcagtca taatcaaaac actgcttcat     660
gctggaggct ccagaagca cagatctcta aagatcatct tcctggtgat ggctgtgttc     720 ctgctgacc agatgccctt caacctcatg aagttcatcc gcagcacaca ctgggaatac     780
tatgccatga ccagctttca ctacaccatc atggtgacag aggccatcgc ataccctgagg     840 gcctgcctta accctgtgct ctatgccttt gtcagcctga gtttcgaaa gaacttctgg     900 aaacttgtga aggacattgg ttgcctccct taccttgggg tctcacatca atggaaatct     960
tctgaggaca attccaagac tttttctgcc tcccacaatg tggaggccac cagcatgttc    1020
cagttatag                                                           1029
```

<210> SEQ ID NO 2
<211> LENGTH: 342
<212> TYPE: PRT
<213> ORGANISM: Homo Sapiens

<400> SEQUENCE: 2

```
Met Ala Glu His Asp Tyr His Glu Asp Tyr Gly Phe Ser Ser Phe Asn
 1               5                  10                  15

Asp Ser Ser Gln Glu Glu His Gln Asp Phe Leu Gln Phe Ser Lys Val
            20                  25                  30
```

```
Phe Leu Pro Cys Met Tyr Leu Val Val Phe Cys Gly Leu Val Gly
         35                  40                  45

Asn Ser Leu Val Leu Val Ile Ser Ile Phe Tyr His Lys Leu Gln Ser
     50                  55                  60

Leu Thr Asp Val Phe Leu Val Asn Leu Pro Leu Ala Asp Leu Val Phe
 65                  70                  75                  80

Val Cys Thr Leu Pro Phe Trp Ala Tyr Ala Gly Ile His Glu Trp Val
                 85                  90                  95

Phe Gly Gln Val Met Cys Lys Ser Leu Leu Gly Ile Tyr Thr Ile Asn
             100                 105                 110

Phe Tyr Thr Ser Met Leu Ile Leu Thr Cys Ile Thr Val Asp Arg Phe
         115                 120                 125

Ile Val Val Val Lys Ala Thr Lys Ala Tyr Asn Gln Gln Ala Lys Arg
130                 135                 140

Met Thr Trp Gly Lys Val Thr Ser Leu Leu Ile Trp Val Ile Ser Leu
145                 150                 155                 160

Leu Val Ser Leu Pro Gln Ile Ile Tyr Gly Asn Val Phe Asn Leu Asp
                 165                 170                 175

Lys Leu Ile Cys Gly Tyr His Asp Glu Ala Ile Ser Thr Val Val Leu
             180                 185                 190

Ala Thr Gln Met Thr Leu Gly Phe Phe Leu Pro Leu Leu Thr Met Ile
         195                 200                 205

Val Cys Tyr Ser Val Ile Ile Lys Thr Leu Leu His Ala Gly Gly Phe
210                 215                 220

Gln Lys His Arg Ser Leu Lys Ile Ile Phe Leu Val Met Ala Val Phe
225                 230                 235                 240

Leu Leu Thr Gln Met Pro Phe Asn Leu Met Lys Phe Ile Arg Ser Thr
                 245                 250                 255

His Trp Glu Tyr Tyr Ala Met Thr Ser Phe His Tyr Thr Ile Met Val
             260                 265                 270

Thr Glu Ala Ile Ala Tyr Leu Arg Ala Cys Leu Asn Pro Val Leu Tyr
         275                 280                 285

Ala Phe Val Ser Leu Lys Phe Arg Lys Asn Phe Trp Lys Leu Val Lys
290                 295                 300

Asp Ile Gly Cys Leu Pro Tyr Leu Gly Val Ser His Gln Trp Lys Ser
305                 310                 315                 320

Ser Glu Asp Asn Ser Lys Thr Phe Ser Ala Ser His Asn Val Glu Ala
                 325                 330                 335

Thr Ser Met Phe Gln Leu
             340

<210> SEQ ID NO 3
<211> LENGTH: 1763
<212> TYPE: DNA
<213> ORGANISM: Homo Sapiens

<400> SEQUENCE: 3
ggcacgaggc cgagatggga cgggacttgc ggcccgggtc ccgcgtgctc ctgctcctgc      60
ttctgctcct gctggtgtac ctgactcagc caggcaatgg caacgagggc agcgtcactg     120
gaagttgtta ttgtggtaaa agaatttctt ccgactcccc gccatcggtt cagttcatga     180
atcgtctccg gaaacaccct agagcttacc atcggtgtct atactacacg aggttccagc     240
tcctttcctg gagcgtgtgt ggaggcaaca aggacccatg ggttcaggaa ttgatgagct     300
gtcttgatct caaagaatgt ggacatgctt actcggggat tgtggcccac cagaagcatt     360
```

-continued

```
tacttcctac cagcccccca atttctcagg cctcagaggg ggcatcttca gatatccaca    420
cccctgccca gatgctcctg tccaccttgc agtccactca gcgccccacc ctcccagtag    480
gatcactgtc ctcggacaaa gagctcactc gtcccaatga accaccatt cacactgcgg     540
gccacagtct ggcagttggg cctgaggctg gggagaacca gaagcagccg gaaaaaaatg    600
ctggtcccac agccaggaca tcagccacag tgccggtcct gtgcctcctg gccatcatct    660
tcatcctcac cgcagcccct tcctatgtgc tgtgcaagag gaggaggggg cagtcaccgc    720
agtcctctcc agatctgccg gttcattata tacctgtggc acctgactct aatacctgag    780
ccaagaatgg aagcttgtga ggagacggac tctatgttgc ccaggctgtt atggaactcc    840
tgagtcaagt gatcctccca ccttggcctc tgaaggtgcg aggattatag gcgtcaccta    900
ccacatccag cctacacgta tttgttaata tctaacatag gactaaccag ccactgccct    960
ctcttaggcc cctcatttaa aaacggttat actataaaat ctgcttttca cactgggtga   1020
taataacttg gacaaattct atgtgtattt tgttttgttt tgctttgctt tgttttgaga   1080
cggagtctcg ctctgtcatc caggctggag tgcagtggca tgatctcggc tcactgcaac   1140
ccccatctcc caggttcaag cgattctcct gcctcctcct gagtagctgg gactacaggt   1200
gctcaccacc acacccggct aatttttttgt attttttagta gagaccgggg tttcaccatg   1260
ttgaccaggc tggtctcgaa ctcctgacct ggtgatctgc ccacccaggc ctcccaaagt   1320
gctgggatta aggtgtgag ccaccatgcc tggccctatg tgtgtttttt aactactaaa    1380
aattattttt gtaatgattg agtcttcttt atggaaacaa ctggcctcag cccttgcgcc   1440
cttactgtga ttcctggctt catttttttgc tgatggttcc ccctcgtccc aaatctctct   1500
cccagtacac cagttgttcc tcccccacct cagccctctc ctgcatcctc ctgtacccgc   1560
aacgaaggcc tgggctttcc caccctccct ccttagcagg tgccgtgctg ggacaccata   1620
cgggttggtt tcacctcctc agtcccttgc ctacccagt gagagtctga tcttgttttt    1680
attgttattg cttttattat tattgctttt attatcatta aaactctagt tcttgttttg   1740
tctctccgaa aaaaaaaaa aaa                                              1763
```

<210> SEQ ID NO 4
<211> LENGTH: 254
<212> TYPE: PRT
<213> ORGANISM: Homo Sapiens

<400> SEQUENCE: 4

```
Met Gly Arg Asp Leu Arg Pro Gly Ser Arg Val Leu Leu Leu Leu
 1               5                  10                  15

Leu Leu Leu Leu Val Tyr Leu Thr Gln Pro Gly Asn Gly Asn Glu Gly
             20                  25                  30

Ser Val Thr Gly Ser Cys Tyr Cys Gly Lys Arg Ile Ser Ser Asp Ser
         35                  40                  45

Pro Pro Ser Val Gln Phe Met Asn Arg Leu Arg Lys His Leu Arg Ala
     50                  55                  60

Tyr His Arg Cys Leu Tyr Tyr Thr Arg Phe Gln Leu Leu Ser Trp Ser
 65                  70                  75                  80

Val Cys Gly Gly Asn Lys Asp Pro Trp Val Gln Glu Leu Met Ser Cys
                 85                  90                  95

Leu Asp Leu Lys Glu Cys Gly His Ala Tyr Ser Gly Ile Val Ala His
            100                 105                 110

Gln Lys His Leu Leu Pro Thr Ser Pro Pro Ile Ser Gln Ala Ser Glu
        115                 120                 125
```

Gly Ala Ser Ser Asp Ile His Thr Pro Ala Gln Met Leu Leu Ser Thr
                130                 135                 140

Leu Gln Ser Thr Gln Arg Pro Thr Leu Pro Val Gly Ser Leu Ser Ser
145                 150                 155                 160

Asp Lys Glu Leu Thr Arg Pro Asn Glu Thr Thr Ile His Thr Ala Gly
                165                 170                 175

His Ser Leu Ala Val Gly Pro Glu Ala Gly Glu Asn Gln Lys Gln Pro
            180                 185                 190

Glu Lys Asn Ala Gly Pro Thr Ala Arg Thr Ser Ala Thr Val Pro Val
        195                 200                 205

Leu Cys Leu Leu Ala Ile Ile Phe Ile Leu Thr Ala Ala Pro Ser Tyr
210                 215                 220

Val Leu Cys Lys Arg Arg Arg Gly Gln Ser Pro Gln Ser Ser Pro Asp
225                 230                 235                 240

Leu Pro Val His Tyr Ile Pro Val Ala Pro Asp Ser Asn Thr
                245                 250

<210> SEQ ID NO 5
<211> LENGTH: 2309
<212> TYPE: DNA
<213> ORGANISM: Homo Sapiens

<400> SEQUENCE: 5

```
cggcgactct ctccaccggg ccgcccggga ggctcatgca gcgcggctgg gtcccgcggc        60
gcccggatcg gggaagtgaa agtgcctcgg aggaggaggg ccggtccggc agtgcagccg       120
cctcacaggt cggcggacgg gccaggcggg cggcctcctg aaccgaaccg aatcggctcc       180
tcgggccgtc gtcctcccgc ccctcctcgc ccgccgccgg agttttcttt cggtttcttc       240
caagattcct ggccttccct cgacggagcc gggcccagtg cgggggcgca gggcgcggga       300
gctccacctc ctcggctttc cctgcgtcca gaggctggca tggcgcgggc cgagtactga       360
gcgcacggtc ggggcacagc agggccggtg ggtgcagctg gctcgcgcct cctctccggc       420
cgccgtctcc tccggtcccc ggcgaaagcc attgagacac cagctggacg tcacgcgccg       480
gagcatgtct gggagtcaga gcgaggtggc tccatccccg cagagtccgc ggagccccga       540
gatgggacgg gacttgcggc ccgggtcccg cgtgctcctg ctcctgcttc tgctcctgct       600
ggtgtacctg actcagccag gcaatggcaa cgagggcagc gtcactggaa gttgttattg       660
tggtaaaaga atttcttccg actccccgcc atcggttcag ttcatgaatc gtctccggaa       720
acacctgaga gcttaccatc ggtgtctata ctacacgagg ttccagctcc tttcctggag       780
cgtgtgtgga ggcaacaagg acccatgggt tcaggaattg atgagctgtc ttgatctcaa       840
agaatgtgga catgcttact cggggattgt ggcccaccaa agcatttac ttcctaccag       900 cccccccaact tctcaggcct cagaggggc atcttcagat atccacaccc ctgcccagat       960
gctcctgtcc accttgcagt ccactcagcg ccccacccctc ccagtaggat cactgtcctc      1020
ggacaaagag ctcactcgtc ccaatgaaac caccattcac actgcgggcc acagtctggc      1080
agttgggcct gaggctgggg agaaccagaa gcagccggaa aaaaatgctg gtcccacagc      1140
caggacatca gccacagtgc cggtcctgtg cctcctggcc atcatcttca tcctcaccgc      1200
agccctttcc tatgtgctgt gcaagaggag gaggggggcag tcaccgcagt cctctccaga      1260
tctgccggtt cattatatac ctgtggcacc tgactctaat acctgagcca agaatggaag      1320
cttgtgagga gacggactct atgttgccca ggctgttatg gaactcctga gtcaagtgat      1380
cctcccacct tggcctctga aggtgcgagg attataggcg tcacctacca catccagcct      1440
```

```
                                                              -continued acacgtattt gttaatatct aacataggac taaccagcca ctgccctctc ttaggcccct    1500
catttaaaaa cggttatact ataaaatctg cttttcacac tgggtgataa taacttggac    1560
aaattctatg tgtattttgt tttgttttgc tttgctttgt tttgagacgg agtctcgctc    1620
tgtcatccag gctggagtgc agtggcatga tctcggctca ctgcaacccc catctcccag    1680
gttcaagcga ttctcctgcc tcctcctaag tagctgggac tacaggtgct caccaccaca    1740
cccggctaat ttttgtatt tttagtagag acggggtttc accatgttga ccaggctggt    1800
ctcgaactcc tgacctggtg atctgcccac ccaggcctcc caaagtgctg ggattaaagg    1860
tgtgagccac catgcctggc cctatgtgtg ttttttaact actaaaaatt atttttgtaa    1920
tgattgagtc ttctttatgg aaacaactgg cctcagccct tgcgcccta ctgtgattcc     1980 tggcttcatt ttttgctgat ggttccccct cgtcccaaat ctctctccca gtacaccagt    2040
tgttcctccc ccacctcagc cctctcctgc atcctcctgt acccgcaacg aaggcctggg    2100 cttcccacc ctccctcctt agcaggtgcc gtgctgggac accatacggg ttggtttcac     2160
ctcctcagtc ccttgcctac cccagtgaga gtctgatctt gttttattg ttattgcttt     2220 tattattatt gcttttatta tcattaaaac tctagttctt gttttgtctc tcaaaaaaaa    2280
aaaaaaaaaa aaaaaaaaa aaaaaaaaa                                       2309

<210> SEQ ID NO 6
<211> LENGTH: 254
<212> TYPE: PRT
<213> ORGANISM: Homo Sapiens

<400> SEQUENCE: 6

Met Gly Arg Asp Leu Arg Pro Gly Ser Arg Val Leu Leu Leu Leu
  1               5                  10                  15

Leu Leu Leu Leu Val Tyr Leu Thr Gln Pro Gly Asn Gly Asn Glu Gly
                 20                  25                  30

Ser Val Thr Gly Ser Cys Tyr Cys Gly Lys Arg Ile Ser Ser Asp Ser
             35                  40                  45

Pro Pro Ser Val Gln Phe Met Asn Arg Leu Arg Lys His Leu Arg Ala
         50                  55                  60

Tyr His Arg Cys Leu Tyr Tyr Thr Arg Phe Gln Leu Leu Ser Trp Ser
 65                  70                  75                  80

Val Cys Gly Gly Asn Lys Asp Pro Trp Val Gln Glu Leu Met Ser Cys
                 85                  90                  95

Leu Asp Leu Lys Glu Cys Gly His Ala Tyr Ser Gly Ile Val Ala His
            100                 105                 110

Gln Lys His Leu Leu Pro Thr Ser Pro Pro Thr Ser Gln Ala Ser Glu
        115                 120                 125

Gly Ala Ser Ser Asp Ile His Thr Pro Ala Gln Met Leu Leu Ser Thr
    130                 135                 140

Leu Gln Ser Thr Gln Arg Pro Thr Leu Pro Val Gly Ser Leu Ser Ser
145                 150                 155                 160

Asp Lys Glu Leu Thr Arg Pro Asn Glu Thr Thr Ile His Thr Ala Gly
                165                 170                 175

His Ser Leu Ala Val Gly Pro Glu Ala Gly Glu Asn Gln Lys Gln Pro
            180                 185                 190

Glu Lys Asn Ala Gly Pro Thr Ala Arg Thr Ser Ala Thr Val Pro Val
        195                 200                 205

Leu Cys Leu Leu Ala Ile Ile Phe Ile Leu Thr Ala Ala Leu Ser Tyr
    210                 215                 220
```

```
Val Leu Cys Lys Arg Arg Arg Gly Gln Ser Pro Gln Ser Ser Pro Asp
225                 230                 235                 240

Leu Pro Val His Tyr Ile Pro Val Ala Pro Asp Ser Asn Thr
                245                 250

<210> SEQ ID NO 7
<211> LENGTH: 439
<212> TYPE: DNA
<213> ORGANISM: Homo Sapiens

<400> SEQUENCE: 7
ccgcagcatg agctccgcag ccgggttctg cgcctcacgc cccgggctgc tgttcctggg      60
gttgctgctc ctgccacttg tggtcgcctt cgccagcgct gaagctgaag aagatgggga     120
cctgcagtgc ctgtgtgtga agaccacctc ccaggtccgt cccaggcaca tcaccagcct    180
ggaggtgatc aaggccggac cccactgccc cactgcccaa ctgatagcca cgctgaagaa    240
tggaaggaaa atttgcttgg acctgcaagc cccgctgtac aagaaaataa ttaagaaact    300
tttggagagt tagctactag ctgcctacgt gtgtgcattt gctatatagc atacttcttt    360
tttccagttt caatctaact gtgaaagaaa cttctgatat ttgtgttatc cttatgattt    420
taaataaaca aataaatc                                                  439

<210> SEQ ID NO 8
<211> LENGTH: 101
<212> TYPE: PRT
<213> ORGANISM: Homo Sapiens

<400> SEQUENCE: 8

Met Ser Ser Ala Ala Gly Phe Cys Ala Ser Arg Pro Gly Leu Leu Phe
1               5                   10                  15

Leu Gly Leu Leu Leu Pro Leu Val Val Ala Phe Ala Ser Ala Glu
                20                  25                  30

Ala Glu Glu Asp Gly Asp Leu Gln Cys Leu Cys Val Lys Thr Thr Ser
        35                  40                  45

Gln Val Arg Pro Arg His Ile Thr Ser Leu Glu Val Ile Lys Ala Gly
    50                  55                  60

Pro His Cys Pro Thr Ala Gln Leu Ile Ala Thr Leu Lys Asn Gly Arg
65                  70                  75                  80

Lys Ile Cys Leu Asp Leu Gln Ala Pro Leu Tyr Lys Lys Ile Ile Lys
                85                  90                  95

Lys Leu Leu Glu Ser
            100

<210> SEQ ID NO 9
<211> LENGTH: 69
<212> TYPE: DNA
<213> ORGANISM: Homo Sapiens

<400> SEQUENCE: 9
tttggatcca tgtatcccta tgacgtgccc gactatgctg cagagcatga ttaccatgaa     60
gactatggg                                                            69

<210> SEQ ID NO 10
<211> LENGTH: 38
<212> TYPE: DNA
<213> ORGANISM: Homo Sapiens
```

```
<400> SEQUENCE: 10
tttgcggccg cctataactg aacatgctg gtggcctc                              38

<210> SEQ ID NO 11
<211> LENGTH: 12
<212> TYPE: PRT
<213> ORGANISM: Homo Sapiens

<400> SEQUENCE: 11

Cys Tyr Pro Tyr Asp Val Pro Asp Tyr Ala Ser Leu
 1               5                  10

<210> SEQ ID NO 12
<211> LENGTH: 31
<212> TYPE: DNA
<213> ORGANISM: Homo Sapiens

<400> SEQUENCE: 12
cgcgtcgaca gccgagatgg gacgggactt g                                    31

<210> SEQ ID NO 13
<211> LENGTH: 27
<212> TYPE: DNA
<213> ORGANISM: Homo Sapiens

<400> SEQUENCE: 13
ggtctagatg tcctggctgt gggacca                                         27

<210> SEQ ID NO 14
<211> LENGTH: 23
<212> TYPE: DNA
<213> ORGANISM: Homo Sapiens

<400> SEQUENCE: 14
gaggatccat gggacgggac ttg                                             23

<210> SEQ ID NO 15
<211> LENGTH: 28
<212> TYPE: DNA
<213> ORGANISM: Homo Sapiens

<400> SEQUENCE: 15
cctctagatg atgtcctggc tgtgggac                                        28

<210> SEQ ID NO 16
<211> LENGTH: 29
<212> TYPE: DNA
<213> ORGANISM: Homo Sapiens

<400> SEQUENCE: 16
ggtctagaaa gtaaatgctt ctggtgggc                                       29

<210> SEQ ID NO 17
<211> LENGTH: 28
<212> TYPE: DNA
<213> ORGANISM: Homo Sapiens

<400> SEQUENCE: 17
cctctagagc tcatcaattc ctgaaccc                                        28
```

```
<210> SEQ ID NO 18
<211> LENGTH: 29
<212> TYPE: DNA
<213> ORGANISM: Homo Sapiens

<400> SEQUENCE: 18
ggtctagact gggagggtgg ggcgctgag                                29

<210> SEQ ID NO 19
<211> LENGTH: 25
<212> TYPE: DNA
<213> ORGANISM: Homo Sapiens

<400> SEQUENCE: 19
attgtggtaa aagaatttct tccga                                   25

<210> SEQ ID NO 20
<211> LENGTH: 20
<212> TYPE: DNA
<213> ORGANISM: Homo Sapiens

<400> SEQUENCE: 20
caggtgtttc cggagacgat                                         20

<210> SEQ ID NO 21
<211> LENGTH: 23
<212> TYPE: DNA
<213> ORGANISM: Homo Sapiens

<400> SEQUENCE: 21
tccccgccat cggttcagtt cat                                     23

<210> SEQ ID NO 22
<211> LENGTH: 21
<212> TYPE: DNA
<213> ORGANISM: Homo Sapiens

<400> SEQUENCE: 22 caccccact gaaaaagatg a                                        21

<210> SEQ ID NO 23
<211> LENGTH: 26
<212> TYPE: DNA
<213> ORGANISM: Homo Sapiens

<400> SEQUENCE: 23
cttaactatc ttgggctgtg acaaag                                  26

<210> SEQ ID NO 24
<211> LENGTH: 23
<212> TYPE: DNA
<213> ORGANISM: Homo Sapiens

<400> SEQUENCE: 24
atgcctgccg tgtgaaccac gtg                                     23

<210> SEQ ID NO 25
<211> LENGTH: 22
<212> TYPE: DNA
<213> ORGANISM: Homo Sapiens

<400> SEQUENCE: 25
atgccatgac cagcttctcac ta                                     22
```

```
<210> SEQ ID NO 26
<211> LENGTH: 19
<212> TYPE: DNA
<213> ORGANISM: Homo Sapiens

<400> SEQUENCE: 26
ttaaggcagg ccctcaggt                                                19

<210> SEQ ID NO 27
<211> LENGTH: 23
<212> TYPE: DNA
<213> ORGANISM: Homo Sapiens

<400> SEQUENCE: 27
tcatggtgac agaggccatc gca                                           23
```

ANTIBODIES FOR "BONZO" CHEMOKINE RECEPTOR AND THERAPEUTIC USES THEREOF

RELATED APPLICATIONS

This application is a continuation of U.S. Ser. No. 09/722,064, filed Nov. 22, 2000, now abandoned which is a continuation-in-part of U.S. Ser. No. 09/449,437 (now U.S. Pat. No. 6,319,675 B1), filed Nov. 24, 1999. The entire teachings of both of these applications are incorporated herein by reference.

BACKGROUND OF THE INVENTION

Chemokines are a large and growing family of 6–14 kD (non-glycosylated) proteins that mediate a wide range of biological functions (Taub, D. D. and Openheim, J. J., *Ther. Immunol.*, 1:229–246 (1994)). The chemokines can be divided into families based on the position of four cysteine residues that form two disulfide bonds (Kelner, G. S., et al., *Science*, 266:12395–1399 (1994); Bazan, J. F., et al., *Nature*, 385:640–644 (1997); Pin, Y., et al., *Nature*, 385:611–617 (1997)). Chemokine receptors can also be divided into families based on the type of chemokine they bind, although, no clear structural differences have been identified that distinguish the receptor sub-families (Mackay, C. R., *J. Exp. Med.*, 184:799–802 (1996)). In addition, there are a number of so-called "orphan" chemokine receptors (e.g., Bonzo) which share sequence homology with well-characterized chemokine receptors, but for which the biological functions and specific receptor agonists remain unknown.

Chemokines play a vital role in leukocyte adhesion and extravasation. For example, in various in vitro assays, chemokines can induce the chemotaxis or transendothelial migration of leukocytes (Taub, D. D. and Oppenheim, J. J., *Ther. Immunol.*, 1:229–246 (1994)), while in vivo injection (Taub, D. D., et al., *J. Clin. Invest.*, 97:1931–1941 (1996)) or over-expression of chemokines (Fuentes, M. E., et al., *J. Immunol.*, 155:5769–5776 (1995)) can result in leukocyte accumulation at the site of chemokine injection or expression. Antagonists of chemokines can prevent leukocyte trafficking (Bargatze, R. F. and Butcher, E. C., *J. Exp. Med.*, 178:367–372 (1993)) and may have beneficial effects in several models of acute and chronic inflammation (Sekido, N., et al., *Nature*, 365:654–657 (1993); Karpus, W. J., et al., *J. Immunol.*, 155:5003–5010 (1995)). Chemokines have also been reported to modulate angiogenesis (Gupta, S. K., et al., *Proc. Natl. Acad. Sci. USA*, 92:7799–7803 (1995) and hematopoiesis (Taub, D. D. and Openheim, J. J., *Ther. Immunol.*, 1:229–246 (1994)), as well as T lymphocyte activation (Zhou, Z., et al., *J. Immunol.* 151:4333–4341 (1993); Taub, D. D., et al., *J. Immunol.*, 156:2095–2103 (1996)). In addition, several chemokine receptors act as co-receptors, along with CD4, for entry of M tropic and T tropic HIV-1 (Choe, H., et al., *Cell*, 85:1135–1148 (1996); Feng, Y., et al., *Science*, 272:872–877 (1996)).

Leukocyte adhesion to endothelium is thought to involve several overlapping steps including rolling, activation and arrest. Rolling leukocytes are exposed to factors expressed at the adhesion site resulting in activation of the leukocyte and up-regulation of integrin-mediated adhesion. As a consequence of such integrin-mediated interactions, leukocytes arrest on the endothelium (Bargatze, R. F. and Butcher, E. C., *J. Exp. Med.*, 178:367–372 (1993); Bargatze, R. F., et al., *Immunity*, 3:99–108 (1995)). Leukocyte activation and up-regulation of integrin molecules occurs via a pertussis toxin-sensitive mechanism that is thought to involve chemokine receptors (Bargatze, R. F. and Butcher, E. C., *J. Exp. Med.*, 178:367–372 (1993); Campbell, J. J., et al., *Science*, 279:381–383 (1998)).

Memory CD4$^+$ lymphocytes can be grouped based upon the expression of certain chemokine receptors. For example, CXCR3, CCR2 and CCR5 (Qin, S., et al., *Eur. J. Immunol.*, 26:640–647 (1996); Qin, S., et al., *J. Clin. Invest.*, 101:746–754 (1998); Liao, F., et al., *J. Immunol.*, 162:186–194 (1999)) are all expressed on subsets of memory CD4 lymphocytes, and certain chemokines act selectively on naive T cells (Adema, G. J., et al., *Nature*, 387:713–717 (1997)). Furthermore, several chemokines which are ligands for such receptors have been shown to be expressed in inflammatory sites (Gonzalo, J. A., et al., *J. Clin. Invest.*, 98:2332–2345 (1996)) and in some cases in lymph nodes draining a challenged site (Tedla, N., et al., *J. Immunol.*, 161:5663–5672 (1998)). In vitro-derived $T_H1/TH_H2$ lymphocyte lines have also been shown to differentially express chemokine receptors. Specifically, $T_H1$ lymphocytes have been shown to selectively express CXCR3 and CCR5, while $T_H2$ lymphocytes selectively express CCR4, CCR8 and CCR3 (Bonecchi, R. G., et al., *J. Exp. Med.*, 187:129–134 (1998); Sallusto, F. D., et al., *J. Exp. Med.*, 187:875–883 (1998); Sallusto, F., *Science*, 277:2005–2007 (1997); Andrew, D. P., et al., *J. Immunol* 161:5027–5038 (1998); Zingoni, A., et al., *J. Immunol.*, 161:547–555 (1998)). Interestingly, in some cases the chemokines for these respective chemokine receptors, such as MDC for CCR4 and IP-10 for CXCR3, are induced by cytokines associated with a $T_H1/T_H2$ environment (Andrew, D. P., et al., *J. Immunol* 161:5027–5038(1998); Luster, A. D., et al., *Nature*, 315:672–676 (1985)).

SUMMARY OF THE INVENTION

The invention relates to antibodies (immunoglobulins) and antigen-binding fragments thereof which bind mammalian Bonzo (also known as CXCR6) or portion of the receptor. In one embodiment, the antibody or antigen-binding fragment thereof binds human Bonzo. In another embodiment, the antibody or antigen-binding fragment thereof can inhibit the binding of ligand (e.g., SExCkine (Spleen Extracted Chemokine) also referred to as chemokine alpha-5 (WO 99/27078) or CXCL16) to a mammalian Bonzo. In a preferred embodiment, the antibody or antibody-binding fragment can bind human Bonzo and inhibit the binding of SExCkine to the receptor. In another embodiment, the antibody or antigen-binding fragment can bind Bonzo expressed on the membrane of a cell and inhibit a cellular response to binding of ligand to Bonzo.

In another embodiment, the antibody or antigen-binding fragment of the invention binds to an epitope which is the same as or is similar to the epitope recognized by mAb 4A11, mAb 7A2, mAb 7F3, mAb 9G2 or an antigen-binding fragment of any of the foregoing. In another embodiment, the binding of the antibody or antigen-binding fragment of the invention to human Bonzo can be inhibited by mAb 4A11, mAb 7A2 or mAb 7F3. In another embodiment, the antibody is mAb 4A11, mAb 7A2, mAb 7F3, mAb 9G2 or an antigen-binding fragment of any of the foregoing.

The invention also relates to an isolated cell that produces an antibody or antigen-binding fragment of the present invention, including those which bind to mammalian Bonzo and inhibit the binding of a ligand to the receptor. In one embodiment, the isolated cell is murine hybridoma 4A11 (also referred to as murine hybridoma LS212-4A11-30-8)

deposited under ATCC Accession No. PTA-991. In another embodiment, the isolated cell is murine hybridoma 7A2 (also referred to as murine hybridoma LS212-7A2-32-1) deposited under ATCC Accession No. PTA-992. In another embodiment, the isolated cell is murine hybridoma 7F3 (also referred to as murine hybridoma LS212-7F3-8-7) deposited under ATCC Accession No. PTA-990. In another embodiment, the isolated cell is murine hybridoma 9G2 (also referred to as murine hybridoma LS212-9G2-7-2).

The invention also relates to antibodies (immunoglobulin) and antigen-binding fragments thereof (e.g., an antigen-binding fragment) which bind mammalian SExCkine. In one embodiment, the antibody or antigen-binding fragment thereof binds human SExCkine. In another embodiment, the antibody or antigen-binding fragment thereof can inhibit the binding of SExCkine to receptor (e.g., Bonzo). In a preferred embodiment, the antibody or antibody-binding fragment can bind human SExCkine and inhibit the binding of SExCkine to Bonzo.

In another embodiment, the antibody or antigen-binding fragment of the invention recognizes mammalian SExCkine and binds to an epitope which is the same as or is similar to the epitope recognized by mAb 9B10, mAb 10B12 or mAb SD7 or an antigen-binding fragment of any of the foregoing. In another embodiment, the binding of the antibody or antigen-binding fragment of the invention to human SExCkine (CXCL16) can be inhibited by mAb 9B10, mAb 10B12 or mAb SD7. In another embodiment, the antibody is mAb 9B10, mAb 10B12 or mAb SD7 or an antigen-binding fragment of any of the foregoing.

The invention also relates to an isolated cell that produces an antibody or antigen-binding fragment of the present invention, including those which bind to mammalian SExCkine and inhibit the binding of SExCkine to receptor. In one embodiment, the isolated cell is murine hybridoma 9B10, deposited under ATCC Accession No. PTA-2628. In another embodiment, the isolated cell is murine hybridoma 10B12, deposited under ATCC Accession No. PTA-2629. In another embodiment, the isolated cell is murine hybridoma SD7, deposited under ATCC Accession No. PTA-2630.

The invention also relates to a method of detecting or identifying an agent (i.e., molecule or compound) which binds to mammalian Bonzo. In one embodiment, an agent which can bind to mammalian Bonzo and inhibit (reduce or prevent) the binding of a ligand (e.g., SExCkine) to Bonzo is identified in a competitive binding assay. In other embodiments, agents for use in therapy are identified in a direct binding assay. Thus, the invention encompasses methods of identifying agents which modulate Bonzo function, such as ligands or other substances which bind a mammalian Bonzo, including inhibitors (e.g., antagonists) or promoters (e.g., agonists) of receptor function. A suitable source of a mammalian Bonzo or a ligand-binding variant thereof can be used to identify a Bonzo binding agent in accordance with the method of the invention. In one embodiment, a cell (e.g., cell line, recombinant cell) that expresses a mammalian Bonzo or a ligand binding variant thereof is used. In another embodiment, a membrane preparation of a cell that expresses a mammalian Bonzo or a ligand binding variant thereof is used.

The invention also relates to a method of detecting or identifying an agent (i.e., molecule or compound) which binds mammalian SExCkine. In one embodiment, an agent which can bind mammalian SExCkine and inhibit (reduce or prevent) the binding of SExCkine to a receptor (e.g., Bonzo) is identified in a competitive binding assay. In other embodiments, agents for use in therapy are identified in a direct binding assay. Thus, the invention encompasses methods of identifying agents which modulate SExCkine function, such as receptors or other substances which bind a mammalian SExCkine. These agents can include inhibitors (e.g., antagonists) or promoters (e.g., agonists) of SExCkine function. A suitable source of a mammalian SExCkine or a receptor-binding variant thereof can be used to identify a SExCkine-binding agent in accordance with the method of the invention. In one embodiment, a cell (e.g., cell line, recombinant cell) that expresses a mammalian SExCkine or a receptor-binding variant thereof is used. In another embodiment, a membrane preparation which expresses cell surface SExCkine or a receptor-binding variant thereof is used. In another embodiment, soluble SExCkine (e.g., recombinant, synthetic) or a receptor-binding variant thereof is used.

The invention also relates to therapeutic methods in which agents which can bind to a mammalian Bonzo and modulate (inhibit or promote) a Bonzo function are administered to a subject in need of such therapy. In one embodiment, the therapeutic method is a method of treating a subject having an inflammatory disease. In another embodiment, the subject has a cancer or an infection (e.g., viral, bacterial, fungal). In another embodiment, the therapeutic method is a method of inhibiting a cellular response (e.g., $Ca^{2+}$ flux, chemotaxis, exocytosis, respiratory burst). In another embodiment, the method is a method of modulating a Bonzo function. In another embodiment, SExCkine is locally administered to a subject to recruit Bonzo$^+$ cells to the area of administration.

The invention also relates to therapeutic methods in which antibodies or antigen-binding fragments thereof which bind to SExCkine and inhibit binding of SExCkine to receptor are administered to a subject in need of such therapy. In one embodiment, the therapeutic method is a method of treating a subject having an inflammatory disease. In a particular embodiment, the therapeutic method is a method of treating a subject with inflammatory arthritis (e.g., rheumatoid arthritis). In another embodiment, the therapeutic method is a method of inhibiting a cellular response to the binding of SExCkine to a receptor (e.g., $Ca^{2+}$ flux, chemotaxis, exocytosis, respiratory burst). In another embodiment, the method is a method of modulating a SExCkine function (e.g., receptor binding, signaling, induction of a cellular response). In another embodiment, an effective amount of anti-SExCkine antibody or antigen-binding fragment thereof is administered to a subject to modulate the recruitment of Bonzo$^+$ cells. In a particular embodiment, an effective amount of anti-SExCkine antibody or antigen-binding fragment thereof is administered to a subject to inhibit the recruitment of Bonzo$^+$ cells.

The invention also relates to targeting molecules that can effectuate the interaction of a Bonzo$^+$ cell or a SExCkine$^+$ cell with a target cell. The targeting molecule can include a first binding moiety which binds Bonzo or SExCkine expressed on the surface of a cell and a second binding moiety which binds an antigen expressed on the surface of a target cell. In one embodiment, the first binding moiety is SExCkine or a receptor-binding variant thereof, and the second binding moiety is an antibody or antigen-binding fragment thereof which binds a tumor antigen or a viral antigen.

The invention also relates to therapeutic methods in which targeting molecules are administered to a subject in need of such therapy. In one embodiment, the therapeutic method is a method of treating a subject having a tumor or a viral infection.

The invention further relates to a method for detecting or quantifying a mammalian Bonzo or a portion thereof in a biological sample. The method comprises combining a biological sample and an agent which binds mammalian Bonzo (e.g., SExCkine, anti-Bonzo antibody or antigen-binding fragment of the invention) under conditions suitable for binding, and detecting a complex formed between Bonzo and the agent. In one embodiment, the biological sample comprises human cells or a fraction of said cells (e.g., membrane preparation).

The invention further relates to a method for detecting or quantifying a mammalian SExCkine or portion thereof in a biological sample. The method comprises contacting a biological sample and an agent which binds mammalian SExCkine (e.g., a receptor such as Bonzo, an antibody or antigen-binding fragment that binds SExCkine) under conditions suitable for binding, and detecting a complex formed between SExCkine and the agent.

The invention also relates to a test kit for identifying or quantifying a mammalian Bonzo or a portion thereof in a biological sample. In one embodiment, the kit comprises an antibody of the invention and suitable ancillary reagents.

The invention also relates to a test kit for identifying or quantifying a mammalian SExCkine or a portion thereof in a biological sample. In one embodiment, the kit comprises an antibody of the invention and suitable ancillary reagents.

The present invention further relates to an antibody, antigen-binding fragment, targeting molecule or agent as described herein for use in therapy (including prophylaxis) or diagnosis, and to the use of such an antibody, antigen-binding fragment, targeting molecule or agent for the manufacture of a medicament for the treatment of a particular disease or condition as described herein (e.g., an inflammatory disease, cancer, infection (e.g., viral, bacterial, fungal)).

The invention further relates to isolated nucleic acids encoding the antibodies and targeting molecules of the invention, and to recombinant constructs and host cells comprising nucleic acids encoding the antibodies and targeting molecules of the invention.

BRIEF DESCRIPTION OF THE DRAWINGS

FIG. 1 illustrates the nucleic acid sequence of a cDNA encoding human (*Homo sapiens*) Bonzo (SEQ ID NO:1) deposited in GenBank under Accession Number AF007545, having an open-reading frame beginning at position 1.

FIG. 2 illustrates the amino acid sequence of human Bonzo polypeptide (SEQ ID NO:2) encoded by the DNA sequence shown in FIG. 1 (SEQ ID NO:1).

FIG. 3 illustrates the nucleic acid sequence of a cDNA encoding human SExCkine (SEQ ID NO:3) and the amino acid sequence of the encoded human SExCkine polypeptide (SEQ ID NO:4). The cloned cDNA consists of 1763 nucleotides with an open reading frame encoding 254 amino acids. The open reading frame includes a predicted signal peptide of 29 amino acids (amino acid residues 1–29 of SEQ ID NO: 4, underlined), a predicted membrane proximal mucin domain (amino acid residues 118–201 of SEQ ID NO: 4, boxed), a predicted transmembrane segment (amino acid residues 202–226 of SEQ ID NO: 4, underlined) and a cytoplasmic tail (amino acid residues 227–254 of SEQ ID NO: 4).

FIGS. 4A–4C illustrate the nucleic acid sequence of a cDNA encoding human chemokine alpha-5 (SEQ ID NO:5) (WO 99/27078) and the amino acid sequence (FIGS. 4A and 4B) of the encoded human chemokine alpha-5 polypeptide (SEQ ID NO:6).

FIG. 5 illustrates the nucleic acid sequence of a cDNA encoding human platelet factor-4 (SEQ ID NO:7) deposited in GenBank under Accession Number M25897, having an open-reading frame beginning at position 8.

FIG. 6 illustrates the amino acid sequence of human platelet factor-4 precursor polypeptide (SEQ ID NO:8) encoded by the DNA sequence shown in FIG. 5 (SEQ ID NO:7). Mature human platelet factor-4 consists of amino acid residues 32–101 (Poncz, M., et al., *Blood,* 69:219–223 (1987)).

FIGS. 14A–14H are fluorescence plots showing expression of lymphocyte subset markers on Bonzo$^+$CD56$^+$ lymphocytes. Expression was analyzed in a three color study gating on Bonzo$^+$CD56$^+$ cells (FIGS. 14A–14D). The gated cells were analyzed for expression of CD3 (FIG. 14E), CD4 (FIG. 14F), CD8 (FIG. 14G) or γδ T cell receptor (TCR) (FIG. 14H).

FIGS. 15A–15C are fluorescence plots showing Bonzo expression on CD3$^+$CD56$^+$ and on CD8$^+$CD56$^+$ human cytotoxic effector cells from peripheral blood. Expression of Bonzo and CD56, CD3 and CD8 was analyzed in a four-color study, gating on CD56$^+$ cells. FIG. 15A is a fluorescence plot showing the population of CD56$^+$ cells which were gated on. The gated CD56$^+$ cells were analyzed for the expression of Bonzo (x-axis) and CD3 (y-axis, FIG. 15B) or CD8 (y-axis, FIG. 15C). Quadrants were set according to staining of isotype control mAbs (lgG2a). The data are representative of multiple donors analyzed.

FIGS. 19A and 19B are fluorescence plots showing the gated CD3$^+$CD56$^+$ cells. FIGS. 19C and 19D are fluorescence plots showing the expression of Bonzo on the gated cells. Bonzo expression was detected by staining with hybridoma culture supernatant containing mAb 7F3.

FIGS. 23A–23H are fluorescence plots showing Bonzo expression on in vitro-derived $T_H1$ and $T_H2$ cells. Chronically-activated $T_H1$ and $T_H2$ cells were generated from human CD4$^+$ umbilical vein lymphocytes by two cycles of in vitro activation with appropriate cytokines. The cells were analyzed by staining with isotype control mAb MOPC (IgG2b) (FIGS. 23A and 23B), mAb 4A11 (FIGS. 23C and 23D), mAb 7F3 (FIGS. 23E and 23F) or mAb 1G1, which binds the $T_H2$ subset marker CCR4 (FIGS. 23G and 23H).

FIG. 27 is a histogram showing that chemotaxis of in vitro-derived $T_H1$, $T_H2$ and $T_R1$ cells was induced by SExCkine. Chemotaxis of the $T_H1$, $T_H2$ and $T_R1$ cells was also induced by RANTES. However, only $T_H2$ cells migrated significantly in cultures containing MDC. No chemotaxis was observed in cultures that did not contain chemokine (−).

FIG. 28 is a histogram showing that SExCkine-induced chemotaxis of $T_H2$ cells was inhibited by mAb 7F3 or mAb 4A11. $T_H2$ cells were incubated with concentrated supernatant from murine hybridoma 7F3 which produces mAb 7F3, from murine hybridoma 4A11 which produces mAb 4A11, or from a murine hybridoma which produces an isotype control antibody (IgG1), prior to exposure to SExCkine. Background is the number of cells that migrated in wells containing assay media without chemokine.

FIG. 41 is a histogram showing that purified recombinant SExCkine (CXCL16) selectively induces chemotaxis of L1.2 cells that express Bonzo (CXCR6) (L1.2/Bonzo transfectants). Chemotaxis of L1.2 cells that were transfected with CXCR1, CXCR2, CXCR3, CXCR4, CXCR5 or CXCR6 (Bonzo) was assessed in in vitro chemotaxis assays using purified recombinant SExCkine (CXCL16; 10 nM). Background measurements were obtained from assays in which no SExCkine (CXCL16) was added. SExCkine (CXCL16) did not induce chemotaxis of L1.2 cells that expressed CCR1, CCR2, CCR3, CCR4, CCR5, CCR6, CCR7, CCR8 or CCR9 under the conditions tested.

FIGS. 42A and 42B are graphs showing that recombinant purified SExCkine (CXCL16; -●-) induced a dose-dependent increase in intracellular free calcium (calcium flux) in Bonzo-transfected L1.2 cells (CXCR6/L1-2 Cells) (FIG. 42A) but not in non-transfected control L1.2 cells (FIG. 42B). CXCR4, a receptor for SDF-1α, is expressed on L1.2 cells and SDF-1α (SDF 1a; -▲-)) induced dose-dependent calcium flux in both CXCR6-transfected and control L1.2 cells, indicating a response mediated through endogenously-expressed CXCR4. MIP 1β (MIP 1b; -■-) did not induce calcium flux in either the parental L1.2 or Bonzo/L1.2 transfected cells.

FIGS. 43A and 43B are graphs showing the binding of purified recombinant SExCkine (CXCL16) to Bonzo/L1.2 transfectants. FIG. 43A shows that binding of $^{125}$H-labeled purified recombinant SExCkine (CXCL16) to Bonzo-transfected L1.2 cells was competitively inhibited by unlabeled SExCkine (nM CXCL16). Binding assays contained about 1.25×10$^5$ Bonzo/L1.2 transfectants, 1 nM $^{125}$H-labeled SExCkine (CXCL16) and various concentrations of unlabeled SExCkine (CXCL16). The amount of $^{125}$I-labeled SExCkine (CXCL16) that bound to Bonzo/L1.2 cells was determined by scintillation counting, and % inhibition of binding (0% inhibition is the amount of binding in the absence of unlabeled SExCkine (CXCL16)) was calculated. The calculated value of 50% inhibition was 1 nM of SExCkine (CXCL16). FIG. 43B depicts the Scatchard analysis of the binding data. The results shown are the average of two experiments and the calculated Kd for the binding of SExCkine (CXCL16) to Bonzo is 1 nM.

FIGS. 46A, 46B and 46C are histograms depicting the results of TaqMan® (Roche Molecular Systems, Inc., Basel, Switzerland) quantitative PCR analysis of the expression of SExCkine (CXCL16) in a variety of cell types and tissues. The values plotted correspond to the relative expression (REL EXP), which takes into consideration expression of a control gene, β-2 microglobulin, as well as a no-template control reaction (NTC). The cell types that were examined are T effector cells $T_H0$ (RL6 Th0) (bar 1), $T_H1$ (RL6 Th1) (bar 2) and $T_H2$ (RL6 Th2) (bar3), dendritic cells stimulated with LPS+IL-1β+TNF-α+IFN-γ (Kaps DCs C) (bar 4), normal human lung fibroblasts (NHLF) (bars 5–6), normal human dermal fibroblasts (NHDF) (bars 7–12), rheumatoid arthritis synovial cells (RA synovio type B) (bars 13–16), cells isolated from normal synoviums (bar 17), cells isolated from diseased synoviums (bar 18), cells isolated from a normal colon (normal colon (CHT 439)) (bar 19), cells isolated from a colitis colon (bar 20), cells isolated from a normal brain (normal brain (NDR 169)) (bar 21), cells isolated from normal hearts (bar 22), cells isolated form normal kidneys (bar 23), cells isolated from normal spleens (bar 24), cells isolated from normal tonsils (bar 25), cells isolated form normal lymph nodes (bar 26), cells isolated from normal livers (Liver Pool Pit 260/CHT 339) (bar 27), cells isolated from normal lung (Lung CUT 811) (bar 28), lung cells isolated from patients with chronic obstructive pulmonary disease (COPD-l and COPD-2) (bar 29 and 30) and lung cells isolated from patients with interstitial pulmonary fibrosis (IPF) (bar 31). In certain cases, the cells were stimulated with one or more of the following agents: TNF-α (TNFa), TGF-β (TGFb), IL-1, IFN-γ (IFNg). Stimulated cell were produced by culturing the cells in media that contained the indicated agent for 4 hours or for 24 hours. RNA was isolated from the cells, the isolated RNAs were pooled (4/24 hr), and cDNA was produced and used as template in the TaqMan® (Roche Molecular Systems, Inc., Basel, Switzerland) quantitative PCR reactions.

DETAILED DESCRIPTION OF THE INVENTION

Figure 7:
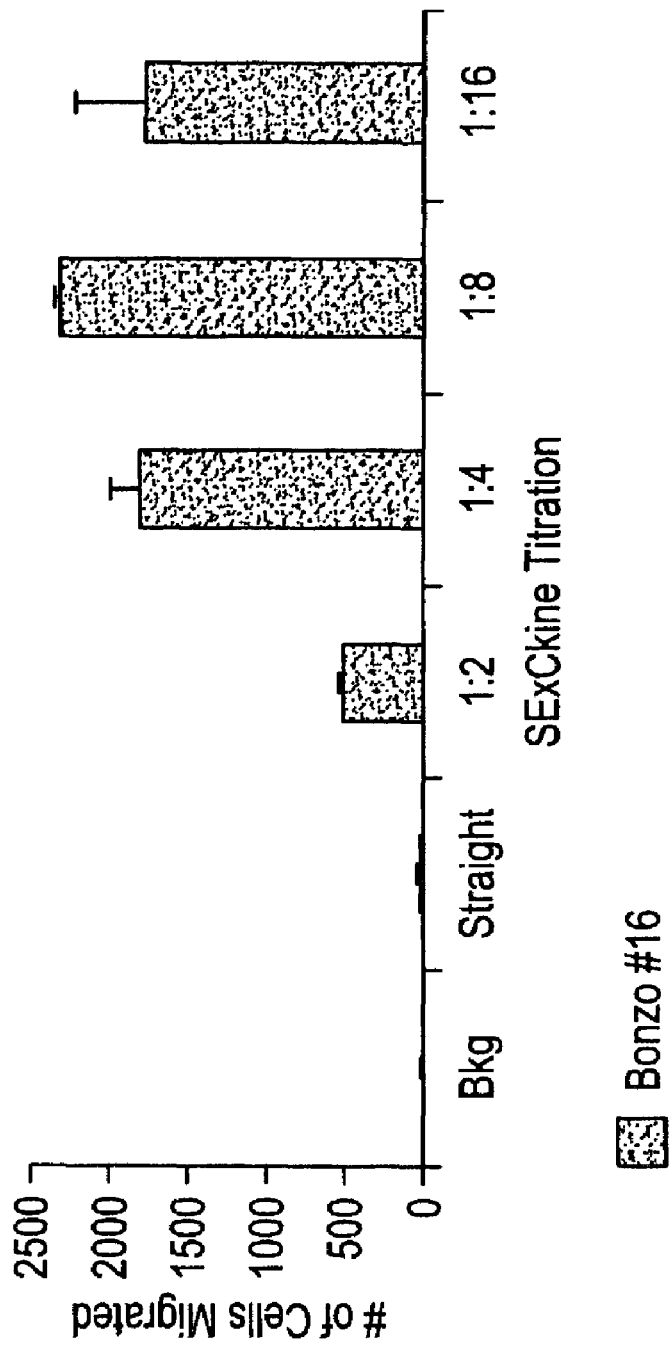
FIG. 7 is a histogram showing that transfected L1.2 cells which express Bonzo (Bonzo/L1.2) undergo SExCkine-induced chemotaxis. Bonzo/L1.2 cells were assayed for chemotactic response to undiluted culture supernatant of 293T cells transiently transfected with SExCkine (Straight) or to various dilutions of the supernatant (1:2, 1:4, 1:8 and 1:16). Bkg:chemotaxis in the presence of assay media without chemokine.
Figure 8A:
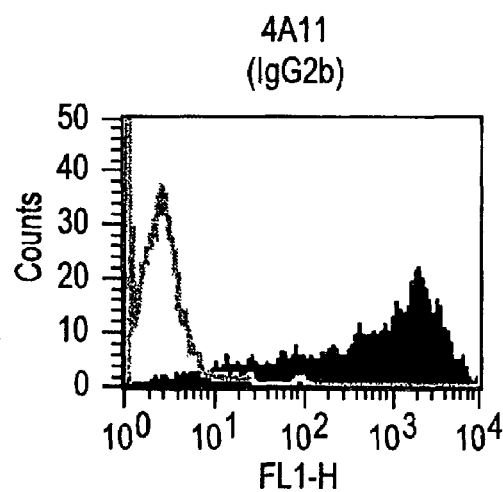
FIGS. 8A–8D are fluorescence plots showing that mAb 4A11 (IgG2b, FIG. 8A), mAb 7A2 (IgG2a, FIG. 8B), mAb 7F3 (IgG2a, FIG. 8C) and mAb 9G2 (IgM, FIG. 8D) each bind to Bonzo/L1.2 cells.
Figure 8B:
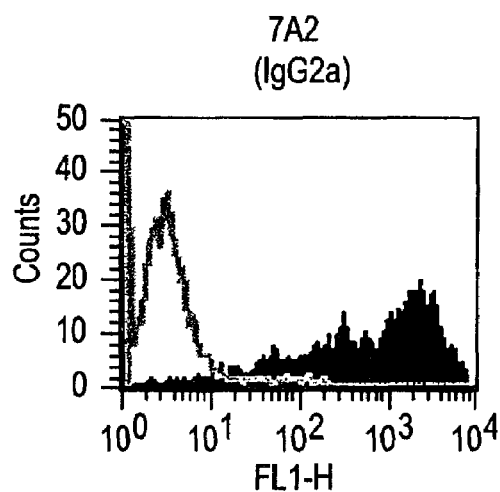
Figure 8C:
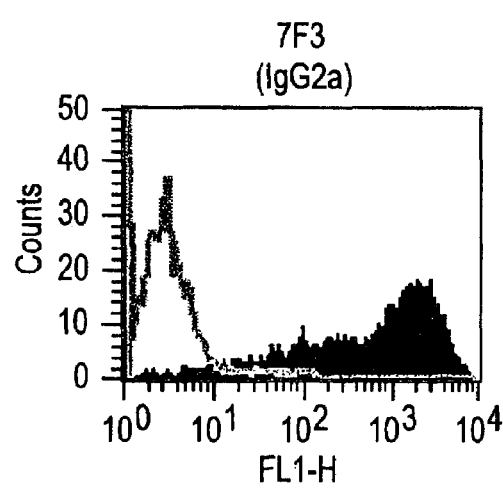
Figure 8D:
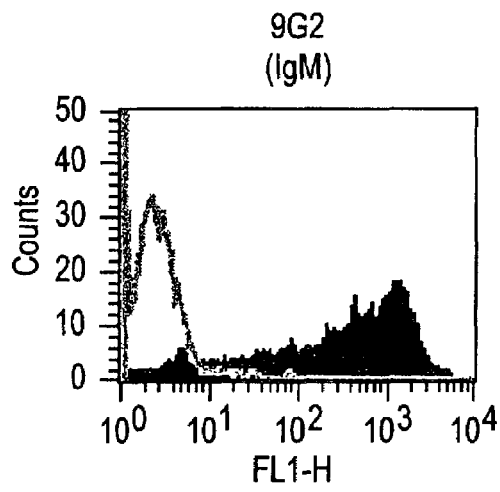
Figure 9A:
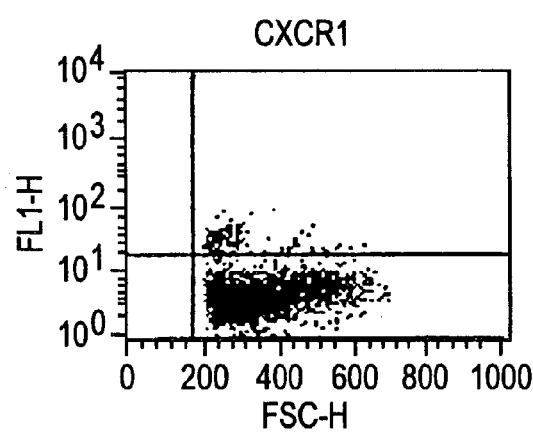
FIGS. 9A–9G are fluorescence plots showing that mAb 7F3 binds to Bonzo/L1.2 cells (FIG. 9F) but not to L1.2 cells that express CXCR1 (FIG. 9A), CXCR2 (FIG. 9B), CXCR3 (FIG. 9C), CXCR4 (FIG. 9D), CXCR5 (FIG. 9E) or to untransfected L1.2 cells (FIG. 9G). No binding was detected in further staining studies using transfected L1.2 cells which expressed CCR1, CCR2, CCR3, CCR4, CCR5, CCR6, CCR7, CCR8, CCR9, hemagglutinin-tagged (Ha-) Bob, Ha-LyGpr, Ha-AJP, Ha-RDC, V28, GPR5, GPR-9–6 or Ha-Af.
Figure 9C:
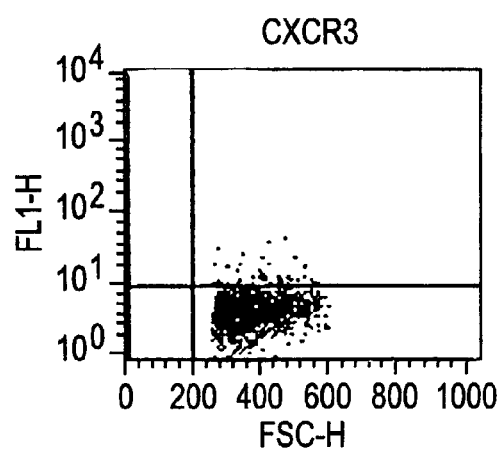
Figure 9B:
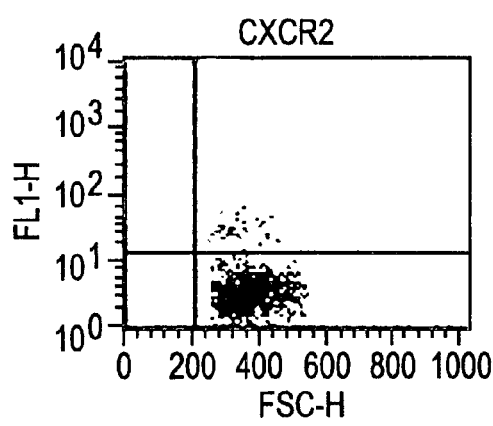
Figure 9D:
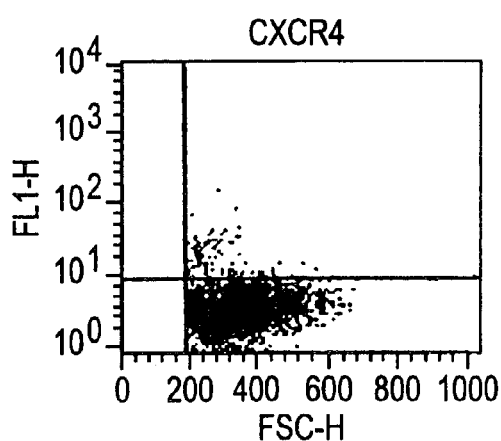
Figure 9E:
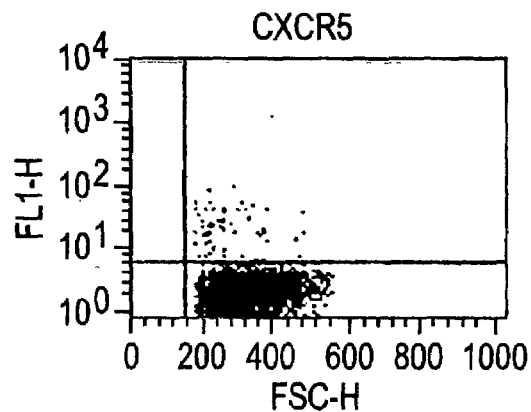
Figure 9F:
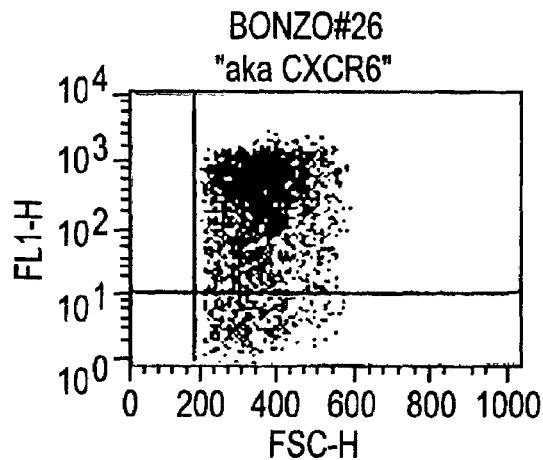
Figure 9G:
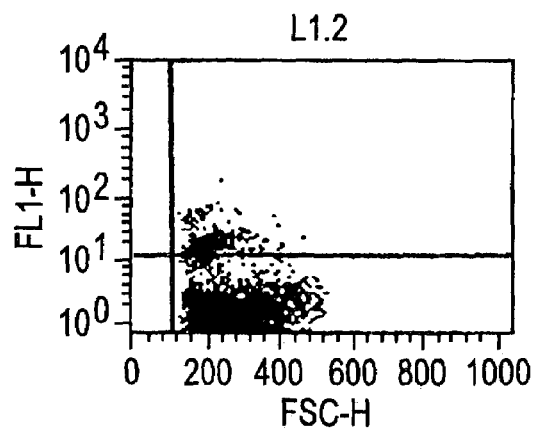

Chemokines and their receptors constitute an important component in the regulation of directed leukocyte migration. Chemokines are produced at sites of inflammation and attract various leukocytes bearing the corresponding receptors. While the spectrum of chemokines expressed at the inflammatory site can differentially attract certain inflammatory cells, selectivity and variation in chemokine receptor expression on leukocytes provides further regulation to ensure appropriate cell recruitment in response to particular inflammatory stimuli. As the number of identified and characterized chemokine receptors continues to grow, it is becoming increasingly clear that cells selectively express several receptors which may identify, mark, or otherwise characterize functional subsets of leukocytes such as $T_H1$, $T_H2$ and $T_R1$, naive and memory, activated and quiescent T cells. Because several characterized and/or orphan chemokine receptors can be co-expressed on individual cells, it has been difficult to validate the role of specific receptors in the initiation and progression of disease or, for that matter, in normal immune function.

As described herein, a study of the orphan chemokine receptor Bonzo (also referred to as STRL33 (Liao, F. et al., *J. Exp. Med.,* 185:2015–2023 (1997), TYMSTR (Loetscher, M. et al., *Current Biology,* 7:652–660 (1997), HBMBU14 (Elshourbagy et al., U.S. Pat. No. 5,824,504; EP 0 834 563 A2) and CXCR6) was conducted. In the course of the study, a chemokine which binds and activates Bonzo was isolated. This chemokine is referred to herein as SExCkine (also referred to as chemokine alpha-5 (WO 99/27078) and CXCL16). Antibodies which bind human Bonzo (e.g., mAb 4A11, mAb 7A2, mAb 7F3, mAb 9G2) were produced and used to analyze the expression and function of the receptor on various types of leukocytes. The receptor was found to be expressed on small populations of both $CD4^+$ and $CD8^+$ T cells and on $CD16^+/CD56^+$ NK cells, but was not found on $CD19^+/CD20^+$ B cells or $CD14^+$ monocytes. The receptor is expressed by both skin homing ($CLA^+$) and mucosal homing ($\alpha4\beta7^{hi}$ and $\alpha E^+$) $CD4^+$ lymphocytes. Bonzo is expressed predominantly on the memory subset of lymphocytes ($CD45RO^{hi}$), however, some expression was detected on naive ($CD45RA^{hi}$) cells. Bonzo expression was increased on activated cells (e.g., in vitro-derived CD3 blasts, $T_H1$, $T_H2$, $T_R1$ and lymphokine-activated killer cells (LAK)).

Antibodies which bind human SExCkine (e.g., mAb 9B10, mAb10B12, mAb SD7) were also produced and used to analyze the expression and function of this chemokine. SExCkine was found to be highly expressed on subsets of $CD14^+$ and $CD19^+$ peripheral blood leukocytes, indicating that primary antigen presenting cells including B lymphocytes and monocyte/macrophages could present this chemokine as a cell-surface (i.e., transmembrane) protein. SExCkine was also expressed on the surface of granulocytes and dendritic cells.

The invention relates to the chemokine receptor Bonzo and to agents (e.g., ligands, antibodies, antagonists, agonists) which bind to the receptor. In one aspect, the invention relates to methods for detecting or identifying an agent (i.e., molecule or compound) which can bind to a mammalian Bonzo or a ligand-binding variant thereof.

The invention also relates to the chemokine SExCkine and to agents (e.g., receptors, antibodies, antagonists, agonists) which bind to SExCkine. In one aspect, the invention relates to methods of detecting or identifying an agent (i.e., molecule or compound) which can bind to a mammalian SExCkine or a receptor-binding variant thereof.

Binding Assays

As used herein "mammalian Bonzo" refers to naturally-occurring or endogenous mammalian Bonzo proteins and to proteins having an amino acid sequence which is the same as that of a naturally-occurring or endogenous corresponding mammalian Bonzo protein (e.g., recombinant proteins, synthetic proteins (i.e., produced using the methods of synthetic organic chemistry)). Accordingly, as defined herein, the term includes mature receptor protein, polymorphic or allelic variants, and other isoforms of a mammalian Bonzo (e.g., produced by alternative splicing or other cellular processes), and modified or unmodified forms of the foregoing (e.g., lipidated, glycosylated, unglycosylated). Naturally-occurring or endogenous mammalian Bonzo proteins include wild type proteins such as mature Bonzo, polymorphic or allelic variants and other isoforms which occur naturally in mammals (e.g., humans, non-human primates). Such proteins can be recovered or isolated from a source which naturally produces mammalian Bonzo, for example. These proteins and mammalian Bonzo proteins having the same amino acid sequence as a naturally-occurring or endogenous corresponding mammalian Bonzo, are referred to by the name of the corresponding mammal. For example, where the corresponding mammal is a human, the protein is designated as a human Bonzo protein (e.g., a recombinant human Bonzo produced in a suitable host cell).

"Functional variants" of mammalian Bonzo proteins include functional fragments, functional mutant proteins, and/or functional fusion proteins which can be produced using suitable methods (e.g., mutagenesis (e.g., chemical mutagenesis, radiation mutagenesis), recombinant DNA techniques). A "functional variant" is a protein or polypeptide which has at least one function characteristic of a mammalian Bonzo protein as described herein, such as a binding activity, a signaling activity and/or ability to stimulate a cellular response. Preferred functional variants can bind a ligand (i.e., one or more ligands, such as SExCkine).

Generally, fragments or portions of mammalian Bonzo proteins include those having a deletion (i.e., one or more deletions) of an amino acid (i.e., one or more amino acids) relative to the mature mammalian Bonzo protein (such as N-terminal, C-terminal or internal deletions). Fragments or portions in which only contiguous amino acids have been deleted or in which non-contiguous amino acids have been deleted relative to mature mammalian Bonzo protein are also envisioned.

Mutant mammalian Bonzo proteins include natural or artificial variants of a mammalian Bonzo protein differing by the addition, deletion and/or substitution of one or more contiguous or non-contiguous amino acid residues (e.g., receptor chimeras). Such mutations can occur at one or more sites on a protein, for example, a conserved region or nonconserved region (compared to other chemokine receptors or G protein-coupled receptors), extracellular region, cytoplasmic region or transmembrane region.

Fusion proteins encompass polypeptides comprising a mammalian Bonzo (e.g., human Bonzo) or a variant thereof as a first moiety, linked via a covalent bond (e.g., a peptide bond) to a second moiety not occurring in the mammalian Bonzo as found in nature. Thus, the second moiety can be an amino acid, oligopeptide or polypeptide. The second moiety can be linked to the first moiety at a suitable position, for example, the N-terminus, the C-terminus or internally. In one embodiment, the fusion protein comprises an affinity ligand (e.g., an enzyme, an antigen, epitope tag (e.g., hemagglutinin (HA)), a binding domain) as the first moiety, and a second moiety comprising a linker sequence and human Bonzo or a portion thereof. Additional (e.g., third, fourth) moieties can be present as appropriate.

In one embodiment, a functional variant of mammalian Bonzo (e.g., a ligand binding variant) shares at least about 80% amino acid sequence similarity with said mammalian Bonzo, preferably at least about 90% amino acid sequence similarity, and more preferably at least about 95% amino acid sequence similarity with said mammalian Bonzo. In another embodiment, a functional fusion protein comprises a first moiety which shares at least about 85% sequence similarity with a mammalian Bonzo, preferably at least about 90% sequence similarity, and more preferably at least about 95% sequence similarity with a mammalian Bonzo (e.g., a human Bonzo (e.g., SEQ ID NO:2)). In another embodiment, a functional mammalian Bonzo protein or functional variant of a mammalian Bonzo protein shares at least about 80% amino acid sequence similarity, preferably at least about 90% amino acid sequence similarity, and more preferably at least about 95% amino acid sequence similarity with a naturally-occurring human Bonzo (e.g., SEQ ID NO:2). Amino acid sequence similarity can be determined using, a suitable sequence alignment algorithm, such as the Lasergene system (DNASTAR, Inc., Madison, Wis.), using the Clustal method with the PAM 250 residue weight table, a gap penalty of 10, a gap length penalty of 10 and default parameters (pairwise alignment parameters: ktuple=1, gap penalty=3, window=4 and diagonals saved=5). In one embodiment, a mammalian Bonzo or portion thereof is encoded by a nucleic acid sequence which is different from a naturally-occurring nucleic acid sequence, but which, due to the degeneracy of the genetic code, encodes mammalian Bonzo or a portion thereof.

A composition comprising a mammalian Bonzo or functional variant thereof can be used in a binding assay to detect and/or identify agents that can bind to the receptor. Compositions suitable for use in a binding assay include, for example, cells which naturally express a mammalian Bonzo or functional variant thereof, such as Bonzo$^+$ memory lymphocytes, CD3$^+$CD56$^+$CD8$^+$Bonzo$^+$ cytotoxic effector cells, lymphokine-activated killer (LAK) cells, cytokine-induced killer (CIK) cells anti-CD3 generated lymphoblasts, cell lines and recombinant cells comprising an exogenous nucleic acid sequence which encodes a mammalian Bonzo or functional variant thereof. Compositions suitable for use in a binding assay also include, membrane preparations which comprise a mammalian Bonzo or functional variant thereof. Such membrane preparations can contain natural (e.g., plasma membrane) or synthetic membranes. Preferably, the membrane preparation is a membrane fraction of a cell that expresses a mammalian Bonzo or a functional variant thereof.

In one embodiment, the method of detecting or identifying an agent that binds to a mammalian Bonzo is a competitive binding assay in which the ability of a test agent to inhibit the binding of a reference agent (e.g., a ligand, an antibody) is assessed. For example, the reference agent can be labeled with a suitable label as described herein, and the amount of labeled reference agent required to saturate the Bonzo present in the assay can be determined. A saturating amount of labeled reference agent and various amounts of a test agent can be contacted with a composition comprising a mammalian Bonzo or functional variant thereof under conditions suitable for binding, and complex formation determined. In this type of assay, a decrease in the amount of complex formed between the labeled reference agent and Bonzo or functional variant thereof indicates that the test agent binds to Bonzo.

The formation of a complex between the reference agent and Bonzo or functional variant thereof can be detected or measured directly or indirectly using any suitable method. For example, the reference agent can be labeled with a suitable label and the formation of a complex can be determined by detection of the label. The specificity of the complex can be determined using a suitable control such as excess unlabeled reference agent or label alone. Labels suitable for use in detection of a complex between an agent and a mammalian Bonzo or functional variant thereof include, for example, a radioisotope, an epitope label (tag), an affinity label (e.g., biotin, avidin), a spin label, an enzyme, a fluorescent group or a chemiluminescent group. When labels are not employed, complex formation can be determined by surface plasmon resonance or other suitable methods.

The capacity of the test agent to inhibit the formation of a complex between the reference agent and a mammalian Bonzo can be reported as the concentration of test agent required for 50% inhibition (IC$_{50}$ values) of specific binding of labeled reference agent. Specific binding is preferably defined as the total binding (e.g., total label in complex) minus the non-specific binding. Non-specific binding is preferably defined as the amount of label still detected in complexes formed in the presence of excess unlabeled reference agent. Reference agents which are suitable for use in the method include molecules and compounds which specifically bind to a mammalian Bonzo or a functional variant thereof, for example, a chemokine ligand of Bonzo or an antibody. In one embodiment, neither the reference agent nor the test agent is platelet factor 4 or a Bonzo-binding variant (e.g., fragment) thereof. In a preferred embodiment, the reference agent is a mammalian SExCkine or a receptor-binding variant thereof.

As used herein "mammalian SExCkine" refers to naturally-occurring or endogenous mammalian SExCkine proteins (e.g., SEQ ID NO:4, SEQ ID NO:6) and to proteins having an amino acid sequence which is the same as that of a naturally-occurring or endogenous corresponding mammalian SExCkine protein (e.g., recombinant proteins, synthetic proteins (i.e., produced using the methods of synthetic organic chemistry)). Accordingly, as defined herein, the term includes mature protein, polymorphic or allelic variants, and other isoforms of a mammalian SExCkine (e.g., produced by alternative splicing, proteolytic processing or other cellular processes), and modified or unmodified forms of the foregoing (e.g., lipidated, glycosylated (e.g., with glycosaminoglycans), unglycosylated,). Naturally-occurring or endogenous mammalian SExCkine proteins include wild type proteins such as transmembrane SExCkine and soluble SExCkine, polymorphic or allelic variants and other isoforms which occur naturally in mammals (e.g., humans, non-human primates). Such proteins can be recovered or isolated from a source which naturally produces mammalian SExCkine, for example. These proteins and mammalian SExCkine proteins having the same amino acid sequence as a naturally-occurring or endogenous corresponding mammalian SExCkine, are referred to by the name of the corresponding mammal. For example, where the corresponding mammal is a human, the protein is designated as a human SExCkine protein (e.g., a recombinant human SExCkine produced in a suitable host cell).

"Functional variants" of mammalian SExCkine proteins include functional fragments, functional mutant proteins, and/or functional fusion proteins which can be produced using suitable methods (e.g., mutagenesis (e.g., chemical mutagenesis, radiation mutagenesis), recombinant DNA techniques). A "functional variant" is a protein or polypeptide which has at least one function characteristic of a mammalian SExCkine protein as described herein, such as receptor-binding activity, SExCkine-induced or mediated signaling activity and/or SExCkine-induced or mediated ability to stimulate a cellular response. Preferred functional variants can bind receptor (i.e., one or more receptors, such as Bonzo). The functional variant can be a cell surface (i.e., transmembrane) SExCkine that can transduce signals (SExCkine-mediated signaling) or stimulate a cellular response (SexCkine-mediated cellular response).

Generally, fragments or portions of mammalian SExCkine proteins include those having a deletion (i.e., one or more deletions) of an amino acid (i.e., one or more amino acids) relative to the mature mammalian SExCkine protein (such as N-terminal, C-terminal or internal deletions). Fragments or portions in which only contiguous amino acids have been deleted or in which non-contiguous amino acids have been deleted relative to mature mammalian SExCkine protein are also envisioned.

Mutant mammalian SExCkine proteins include natural or artificial variants of a mammalian SExCkine protein differing by the addition, deletion and/or substitution of one or more contiguous or non-contiguous amino acid residues (e.g., receptor chimeras). Such mutations can occur at one or more sites on a protein, for example a conserved region or nonconserved region (compared to other chemokines), extracellular region, cytoplasmic region, or transmembrane region.

Fusion proteins encompass polypeptides comprising a mammalian SExCkine (e.g., human SExCkine) or a receptor-binding variant thereof as a first moiety, linked via a covalent bond (e.g., a peptide bond) to a second moiety not occurring in the mammalian SExCkine or variant as found in nature. Thus, the second moiety can be an amino acid, oligopeptide or polypeptide. The second moiety can be linked to the first moiety at a suitable position, for example, the N-terminus, the C-terminus or internally. In one embodiment, the fusion protein comprises an affinity ligand (e.g., an enzyme, an antigen, epitope tag, a binding domain) as the first moiety, and a second moiety comprising a linker sequence and human SExCkine or a portion thereof. Additional (e.g., third, fourth) moieties can be present as appropriate.

"Receptor-binding variants" of mammalian SExCkine proteins include receptor-binding fragments (e.g., proteolytic fragments), receptor-binding mutant proteins and receptor-binding fusion proteins which can be produced using suitable methods (e.g., mutagenesis (e.g., chemical mutagenesis, radiation mutagenesis), recombinant DNA techniques). A "receptor-binding variant" can be identified using a suitable receptor-receptor binding assay such as a Bonzo-binding assay described herein.

Receptor-binding variants of SExCkine include, for example, polypeptides which have the amino acid sequence of residues 1–202, 30–202, 1–155, 30–155, 1–117 or 30–117 of human SExCkine (e.g., SEQ ID NO:4). Additional receptor-binding variants of mammalian SExCkine (e.g., human SExCkine) can be polypeptides of from about 10 to about 128 amino acid residues or from about 40 to about 80 amino acid residues which comprise the amino acid sequence of a portion of the extracellular region of mammalian SExCkine (e.g., residues 30–202 of SEQ ID NO:4). For example, a synthetic peptide consisting of amino acid residues 30 (Asn) to 95 (Ser) of human SExCkine (SEQ ID NO:4) has been synthesized. This sixty-six amino acid peptide bound Bonzo and induced migration of Bonzo/L1.2 cells in a chemotaxis assay.

Receptor-binding variants of mammalian SExCkine also include proteins and polypeptides in which one or more naturally-occurring amino acid residues are conservatively substituted. A conservative amino acid substitution refers to the replacement of a first amino acid by a second amino acid that has chemical and/or physical properties (e.g., charge, structure, polarity, hydrophobicity/hydrophilicity) which are similar to those of the first amino acid. Groups of amino acids with similar chemical and/or physical properties include, for example, those with hydrophilic side chains (e.g., asparagine, glutamine, serine, threonine, tyrosine, lysine, arginine, histidine, aspartate, glutamate), hydrophobic side chains (e.g., alanine, valine, leucine, isoleucine, proline, phenylalanine, tryptophan, methionine, cysteine, glycine), acidic side chains (e.g., aspartate, glutamate), basic side chains (e.g., lysine, arginine, histidine), aromatic side chains (e.g., phenylalanine, tryptophan, histidine, tyrosine) and nucleophilic side chains (e.g., cysteine, serine, threonine).

In one embodiment, the receptor-binding variant of mammalian SExCkine shares at least about 85% amino acid sequence similarity with a corresponding portion of a naturally-occurring mammalian SExCkine (e.g., SEQ ID NO:4, SEQ ID NO:6), preferably at least about 90% amino acid sequence similarity, and more preferably at least about 95% amino acid sequence similarity with a corresponding portion of a naturally-occurring mammalian SExCkine. Amino acid sequence similarity can be identified by aligning the amino acid sequence of the receptor binding variant with the amino acid sequence of mammalian SExCkine (e.g., SEQ ID NO:4, SEQ ID NO:6) using a suitable sequence alignmnent algorithm, such as the Lasergene system (DNASTAR, Inc., Madison, Wis.), as described herein. Variants can be prepared using any suitable methods, (e.g., solid phase peptide synthesis, by expression of nucleic acids encoding the variant), and tested for receptor binding.

A composition comprising a mammalian SExCkine or functional variant thereof can be used in a binding assay to detect and/or identify agents that can bind to SExCkine. Compositions suitable for use in a binding assay include, for example, cells which naturally express a mammalian SExCkine or functional variant thereof (e.g., CD19$^+$ B lymphocytes, CD14$^+$ monocytes/macrophages, granulocytes, dendritic cells). Additional compositions which are suitable for use in a binding assay include cell lines and recombinant cells which comprise an exogenous nucleic acid sequence encoding a mammalian SExCkine or functional variant thereof.

As described herein, SExCkine can be expressed as a cell surface protein (i.e., transmembrane protein, integral membrane protein). Accordingly, compositions which are suitable for use in a binding assay also include membrane preparations which comprise a mammalian cell-surface SExCkine or functional variant thereof. Such membrane preparations can contain natural (e.g., plasma membrane) or synthetic membranes. Preferably, the membrane preparation is a membrane fraction of a cell that expresses a mammalian cell-surface SExCkine or functional variant thereof. SExCkine can also be isolated as a soluble protein. Therefore, supernatants isolated from cultures of cells that express soluble SExCkine are also suitable compositions for use in a binding assay.

In one embodiment, the method of detecting or identifying an agent that binds to a mammalian SExCkine is a competitive binding assay in which the ability of a test agent to inhibit the binding of a reference agent (e.g., a receptor, an antibody) is assessed. For example, the reference agent can be labeled with a suitable label as described herein, and the amount of labeled reference agent required to saturate the SExCkine present in the assay can be determined. A saturating amount of labeled reference agent and various amounts of a test agent can be contacted with a composition comprising a mammalian SExCkine or functional variant thereof under conditions suitable for binding, and complex formation determined. In this type of assay, a decrease in the amount of complex formed between the labeled reference agent and SExCkine or functional variant thereof indicates that the test agent binds to SExCkine.

The formation of a complex between the reference agent and SExCkine or functional variant thereof can be detected or measured directly or indirectly using any suitable method. For example, the reference agent can be labeled with a suitable label and the formation of a complex can be determined by detection of the label. The specificity of the complex can be determined using a suitable control such as excess unlabeled reference agent or label alone. Labels suitable for use in detection of a complex between an agent and a mammalian SExCkine or functional valiant thereof include, for example, a radioisotope, an epitope label (tag), an affinity label (e.g., biotin, avidin), a spin label, an enzyme, a fluorescent group or a chemiluminescent group. When labels are not employed, complex formation can be determined by surface plasmon resonance or other suitable methods.

The capacity of the test agent to inhibit the formation of a complex between the reference agent and a mammalian SExCkine can be reported as the concentration of test agent required for 50% inhibition (IC$_{50}$ values) of specific binding of labeled reference agent. Specific binding is preferably defined as the total binding (e.g., total label in complex) minus the non-specific binding. Non-specific binding is preferably defined as the amount of label still detected in complexes formed in the presence of excess unlabeled reference agent. Reference agents which are suitable for use in the method include molecules and compounds which specifically bind to a mammalian SExCkine (e.g., human SExCkine) or a functional variant thereof, for example, a chemokine receptor of SExCkine or an anti-SExCkine antibody. In a preferred embodiment, the reference agent is the chemokine receptor Bonzo. In another preferred embodiment, the reference agent is an anti-SExCkine antibody or antigen-binding fragment thereof, as described herein.

The invention also relates to a method of identifying or isolating an agent (i.e., molecule or compound) which can be used in therapy, as described herein. In one embodiment, the agent is identified or isolated in a competitive binding assay as described above. In certain embodiments, cells which express a mammalian Bonzo or a functional variant thereof are maintained under conditions appropriate for expression of receptor. The cells are contacted with an agent (e.g., ligand, antagonist, agonist) under conditions suitable for binding (e.g., in a suitable binding buffer), and the formation of a complex between the agent and said mammalian Bonzo or functional variant thereof is detected or measured using suitable techniques. For example, the agent can be labeled as described herein and the amount of label present in an agent-Bonzo complex can be determined. The extent of complex formation can be determined relative to a suitable control (e.g., compared with background determined in the absence of agent, compared with binding of a second agent (i.e., a standard, an isotype control), compared with binding of agent to cells that do not express Bonzo).

In other embodiments, cells which express mammalian cell surface SExCkine or functional variant thereof are maintained under conditions appropriate for expression of said SExCkine. The cells are contacted with an agent (e.g., receptor, antagonist, agonist, antibody) under conditions suitable for binding (e.g., in a suitable binding buffer), and the formation of a complex between the agent and said mammalian SExCkine or functional variant thereof is detected or measured using suitable techniques. For example, the agent can be labeled as described herein and the amount of label present in an agent-SExCkine complex can be determined. The extent of complex formation can be determined relative to a suitable control (e.g., compared with background determined in the absence of agent, compared with binding of a second agent (e.g., a standard, an isotype control), compared with binding of agent to cells that do not express SExCkine).

The invention also relates to a method of identifying or isolating an agent for use in treating a subject having an inflammatory disease. In one embodiment, the method is a method of identifying or isolating an agent for use in inhibiting a cellular response to ligand binding to Bonzo+ leukocytes. In another embodiment, the method is a method of identifying or isolating an agent for use in inhibiting a signaling activity or cellular response induced upon SExCkine binding to receptor. In a particular embodiment, the method is a method of identifying or isolating an agent for use in modulating a Bonzo-mediated function in a subject. In another embodiment, the method is a method of identifying or isolating an agent for use in modulating a SExCkine-mediated or SExCkine-induced function in a subject.

A variety of agents, such as proteins (e.g., antibodies), peptides, peptidomimetics, small organic molecules, nucleic acids and the like, can be tested for binding to Bonzo or SExCkine. According to the method of the present invention, agents can be individually screened or one or more agents can be tested simultaneously. Where a mixture of compounds is tested, the compounds selected by the processes described can be separated (as appropriate) and identified using suitable methods (e.g., sequencing, chromatography). The presence of one or more compounds (e.g., a ligand, inhibitor, promoter) in a test sample call also be determined according to these methods.

Agents which bind to a mammalian Bonzo or a mammalian SExCkine and which are useful in the therapeutic methods described herein can be identified, for example, by screening libraries or collections of molecules, such as, the Chemical Repository of the National Cancer Institute, in assays described herein or using other suitable methods. Libraries, such as combinatorial libraries, of compounds (e.g., organic compounds, recombinant or synthetic peptides, "peptoids", nucleic acids) produced by combinatorial chemical synthesis or other methods can be tested (see e.g., Zuckerman, R. N. et al., *J. Med. Chem.*, 37: 2678–2685 (1994) and references cited therein; see also, Ohlmeyer, M. H. J. et al., *Proc. Natl. Acad. Sci. USA* 90:10922–10926 (1993) and DeWitt, S. H. et al., *Proc. Natl. Acad. Sci. USA* 90:6909–6913 (1993), relating to tagged compounds; Rutter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a library carry unique tags, identification of individual compounds by chromatographic methods is possible.

In one embodiment, the reference and test agents employed in the method are not viruses or viral proteins (e.g., viral envelope proteins). In another embodiment, the collection of agents tested according to the methods of the invention does not comprise chemokines, or mutants or analogues thereof. In yet another embodiment, the collection of agents tested according to the methods of the invention does not comprise chemokine receptors or mutants or analogues thereof.

Functional Assays

Functional assays can be used to detect and identify agonists (promoters) and antagonists (inhibitors) of a mammalian Bonzo receptor. An agent can be studied in one or more suitable functional assays to determine if said agent can modulate (inhibit (reduce or prevent) or promote) one or more functions of Bonzo. For example, an agent can be tested in an extracellular acidification assay, calcium flux assay, ligand binding assay, chemotaxis assay or assay which monitors degranulation or inflammatory mediator release (see, for example, Hesselgesser et al., *J. Biol. Chem.* 273(25): 15687–15692 (1998) and WO 98/02151).

For example, an agent which binds to a mammalian Bonzo or functional variant thereof can be tested in a leukocyte chemotaxis assay using suitable cells. Suitable cells include, for example, cell lines, recombinant cells or isolated cells which express a mammalian Bonzo and undergo Bonzo ligand-induced (e.g., SExCkine-induced) chemotaxis. In one example, Bonzo-expressing recombinant L1.2 cells (see Campbell, et al. *J. Cell Biol,* 134:255–266 (1996) regarding L1.2 cells), can be used in a modification of a transendothelial migration assay (Ponath, P. D. et al., *J. Exp. Med.,* 183:2437–2448 (1996), Carr, M. W., et al. T. A., *Proc. Natl Acad Sci, USA,* (91):3652 (1994)). The endothelial cells used in this assay are preferably the endothelial cell line, ECV 304 (Takahashi, K. et al., *In Vitro Cell Dev. Biol.,* 26(3 Pt 1):265–274 (1990)), which can be obtained from the American Type Culture Collection (Manassas, Va.) or the European Collection of Animal Cell Cultures (Reference No: 92091712), Salisbury, United Kingdom). Endothelial cells can be cultured on 6.5 mm diameter TRANSWELL culture inserts (Costar Corp., Cambridge, Mass.) with 3.0 μm pore size. Culture media for the ECV 304 cells can consist of M199+10% FCS, L-glutamine, and antibiotics. The assay media can consist of equal parts RPMI 1640 and M199 with 0.5% BSA (bovine serum albumin). Two hours before the assay, $2\times10^5$ ECV 304 cells can be plated onto each insert of the 24 well TRANSWELL chemotaxis plate and incubated at 37° C. Chemotactic factor such as SExCkine can be added to the 24-well tissue culture plates in a final volume of 600 μL. Endothelial-coated TRANSWELL plates can be inserted into each well and $10^6$ cells of the leukocyte type being studied can be added to the top chamber in a final volume of 100 μL of assay medium. The plate can then be incubated at 37° C. in 5% $CO_2$/95% air for 1–2 hours. The cells that migrate to the bottom chamber during incubation can be counted, for example using flow cytometry. To count cells by flow cytometry, 500 μL of the cell suspension from the lower chamber can be placed in a tube and relative counts can obtained for a set period of time, for example, 30 seconds. This counting method is highly reproducible and allows gating on the leukocytes and the exclusion of debris or other cell types from the analysis. Alternatively, cells can be counted with a microscope. Assays to evaluate agents that can inhibit or promote chemotaxis can be performed in the same way as control experiment described above, except that agent solutions, in assay media containing up to 1% of DMSO co-solvent, can be added to both the top and bottom chambers prior to addition of the cells. The capacity of an agent to inhibit or promote chemotaxis can be determined by comparing the number of cell that migrate to the bottom chamber in wells which contain the agent, to the number of cells which migrate to the bottom chamber in control wells. Control wells can contain equivalent amounts of DMSO, but no agent. If desired, the endothelial cells can be omitted from the described chemotaxis assay and ligand-induced migration across the TRANSWELL insert can be measured.

An agent can also be assessed by monitoring cellular responses induced by active receptor, using suitable cells which express a mammalian Bonzo or a functional variant thereof. For instance, exocytosis (e.g., degranulation of cells leading to release of one or more enzymes or other granule components, such as esterases (e.g., serine esterases), perforin, and/or granzymes), inflammatory mediator release (such as release of bioactive lipids such as leukotrienes (e.g., leukotriene $C_4$)), and respiratory burst, can be monitored by methods known in the art or other suitable methods (see e.g., Taub, D. D. et al., *J. Immunol.*, 155: 3877–3888 (1995), regarding assays for release of granule-derived serine esterases; Loetscher et al., *J. Immunol.*, 156: 322–327 (1996), regarding assays for enzyme and granzyme release; Rot, A. et al., *J. Exp. Med.*, 176: 1489–1495 (1992) regarding respiratory burst; Bischoff, S. C. et al., *Eur. J. Immunol.*, 23: 761–767 (1993) and Baggliolini, M. and C. A. Dahinden, *Immunology Today*, 15: 127–133 (1994)). A variety of functional assays which employ recombinant cells which express a mammalian Bonzo or functional variant thereof can be employed. For example, assays in which expression of an endogenous or exogenous reporter gene (e.g., β-galactosidase, green fluorescent protein) is induced upon ligand binding to a mammalian Bonzo or variant expressed by recombinant cells (e.g., recombinant bacteria, recombinant yeast, recombinant mammalian cells) can be used.

In one embodiment, an agent that can inhibit or promote a function of Bonzo is identified by monitoring the release of an enzyme upon degranulation or exocytosis by a cell capable of this function. Cells expressing a mammalian Bonzo or a functional variant thereof can be maintained in a suitable medium under suitable conditions, and degranulation can be induced. The cells are contacted with an agent to be tested, and enzyme release can be assessed. The release of an enzyme into the medium can be detected or measured using a suitable assay, such as an immunological assay, or biochemical assay for enzyme activity.

The medium can be assayed directly, by introducing components of the assay (e.g., substrate, co-factors, antibody) into the medium (e.g., before, simultaneous with or after the cells and agent are combined). The assay can also be performed on medium which has been separated from the cells or further processed (e.g., fractionated) prior to assay. For example, convenient assays are available for enzymes, such as serine esterases (see e.g., Taub, D. D. et al., *J. Immunol.*, 155: 3877–3888 (1995) regarding release of granule-derived serine esterases).

In another embodiment, cells expressing a mammalian Bonzo or a functional variant thereof are combined with a ligand of Bonzo (e.g., SExCkine), an agent to be tested is added before, after or simultaneous therewith, and $Ca^{2+}$ flux (a transient increase in the concentration of intracellular free calcium ions $[Ca^{2+}]_i$) is assessed. Inhibition of ligand-induced $Ca^{2+}$ flux is indicative that the agent is an inhibitor or antagonist of mammalian Bonzo function. Calcium mobilization can be monitored using a fluorometric imaging plate reader (FLIPR) (see, for example, Coward, P., et al., *Anal. Biochem.*, 270:242–248 (1999)). Other suitable assays can monitor complex formation between Bonzo and ligand (e.g., SExCkine), for example, using time-resolved fluorescence or fluorometric microvolume assay technology (FMAT) (see, for example, Kane, S. A. et al., *Anal Biochem.*, 278 (1):29–38 (2000), Degan, P. et al., *Mol. Biotechnol*, 13(3): 215–222 (1999) and Saarinen, K. et al., *J. Immunol. Methods*, 236(1–2):19–26 (2000) regarding time-resolved fluorescence; Miraglia S. et al., *J. Biomol. Screen*, 4(4): 193–204 (1999), regarding FMAT).

Engagement of the chemokine receptors of a lymphocyte can cause integrin activation, and induction of adherence to adhesion molecules expressed in vasculature or the perivascular space. Cellular adherence can be monitored by methods known in the art or other suitable methods. In one embodiment, a ligand, inhibitor and/or promoter of Bonzo function is identified by monitoring cellular adherence by a cell capable of adhesion. For example, an agent to be tested can be combined with (a) cells expressing a mammalian Bonzo or a functional variant thereof (preferably non-adherent cells which when transfected with receptor and stimulated with agonists (e.g., ligand) acquire adhesive ability), (b) a composition comprising a suitable adhesion molecule (e.g., a substrate such as a culture well coated with an adhesion molecule, such as fibronectin), and (c) a ligand or promoter (e.g., SExCkine), and maintained under conditions suitable for ligand- or promoter-induced adhesion. Labeling of cells with a fluorescent dye provides a convenient means of detecting adherent cells. Nonadherent cells can be removed (e.g., by washing) and the number of adherent cells determined. The effect of the agent in inhibiting or enhancing ligand- or promoter-induced adhesion can be indicative of inhibitor or promoter activity, respectively. Agents active in the assay include inhibitors and promoters of binding, signaling, and/or cellular responses. In another embodiment, an agent to be tested can be combined with cells expressing a mammalian Bonzo or a functional variant thereof and a composition comprising a suitable adhesion molecule under conditions suitable for ligand- or promoter-induced adhesion, and adhesion is monitored. Increased adhesion relative to a suitable control is indicative of the presence of a ligand and/or promoter.

The binding assays and functional assays described above can be used, alone or in combination with each other or other suitable methods, to detect or identify agents which bind a mammalian Bonzo protein and/or modulators (antagonists, agonists) of a Bonzo protein function. The in vitro methods of the present invention can be adapted for high-throughput screening in which large numbers of samples are processed (e.g., a 96-well format). Cells expressing a mammalian Bonzo (e.g., human Bonzo) or a functional variant thereof at levels suitable for high-throughput screening can be used, and thus, are particularly valuable in the identification and/or isolation of agents which bind Bonzo, and modulators of Bonzo function. Expression of Bonzo or a variant thereof can be monitored in a variety of ways. For instance, expression can be monitored using antibodies of the present invention which bind receptor or a portion thereof or using a Bonzo ligand (e.g., SExCkine, platelet factor 4). Also, commercially available antibodies can be used to detect expression of an antigen- or epitope-tagged fusion protein comprising a receptor protein or polypeptide (e.g., FLAG-tagged receptors), and cells expressing the Bonzo or functional variant at the desired level can be selected (e.g., by flow cytometry).

Functional assays can also be used to detect agonists (promoters) and antagonists (inhibitors) of a mammalian SExCkine or functional variant thereof. An agent can be studied in one or more suitable functional assays to determine if said agent can modulate (inhibit (reduce or prevent) or promote) one or more functions of SExCkine, including functions resulting from SExCkine-induced activation (e.g., through Bonzo), SExCkine-mediated signaling (signaling through SExCkine) and SExCkine-mediated cellular response. For example, an agent can be tested in an extracellular acidification assay, calcium flux assay, receptor binding assay, chemotaxis assay or assay which monitors degranulation or inflammatory mediator release (see, for example, Hesselgesseretal., *J. Biol. Chem.* 273(25):15687–15692 (1998) and WO 98/02151).

In one embodiment, an agent which binds to a mammalian SExCkine or functional variant thereof can be tested in a leukocyte chemotaxis assay using suitable cells. Suitable cells include, for example, cell lines, recombinant cells or isolated cells which express a receptor for mammalian SExCkine (e.g., Bonzo) and undergo SExCkine-induced chemotaxis. In a particular embodiment, Bonzo-expressing recombinant L1.2 cells (see Campbell, et al. *J Cell Biol*, 134:255–266 (1996) regarding L1.2 cells) can be used in a modification of a transendothelial migration assay.

Agents can also be assessed for SExCkine agonist (promoter) or antagonist (inhibitor) activity by monitoring other cellular responses of SExCkine-induced receptor (e.g., Bonzo) activation. Using suitable cells which express a mammalian receptor for SExCkine (e.g., Bonzo), a number of functional assays, such as those described herein, can be performed.

The binding assays and functional assays described herein can be used, alone or in combination with each other or other suitable methods, to detect or identify agents which bind a mammalian SExCkine protein and/or modulators (antagonists, agonists) of a SExCkine protein function (e.g., receptor binding, signaling, induction of a cellular response). The in vitro methods of the present invention can be adapted for high-throughput screening in which large numbers of samples are processed (e.g., a 96-well format). Cells expressing a mammalian SExCkine (e.g., human SExCkine) or a functional variant thereof at levels suitable for high-throughput screening can be used, and thus, are particularly valuable in the identification and/or isolation of agents which bind SExCkine, and modulators of SExCkine function. Expression of SExCkine or a variant thereof can be monitored in a variety of ways. For instance, expression can be monitored using antibodies of the present invention which bind SExCkine or a portion thereof (e.g., anti-SExCkine antibodies mAb 9B10, mAb 10B12, mAb SD7) or expression can be monitored using a receptor which binds SExCkine (e.g., Bonzo). In addition, commercially available antibodies can be used to detect expression of an antigen- or epitope-tagged fusion protein comprising a receptor protein or polypeptide (e.g., FLAG-tagged receptors), and cells expressing the receptor (e.g., Bonzo) at the desired level can be selected (e.g., by flow cytometry).

Antibodies and Antibody Producing Cells

The invention relates to antibodies which bind to mammalian Bonzo and to antibodies which bind to mammalian SExCkine. Preferred antibodies of the invention can bind to Bonzo or SExCkine and thereby inhibit the binding of ligand to receptor. The antibody of the invention can be polyclonal or monoclonal, and the term "antibody" is intended to encompass both polyclonal and monoclonal antibodies. The terms polyclonal and monoclonal refer to the degree of homogeneity of an antibody preparation, and are not intended to be limited to particular methods of production. The term "antibody" as used herein also encompasses functional fragments of antibodies, including fragments of chimeric, humanized, primatized, veneered or single chain antibodies. Functional fragments include antigen-binding fragments of antibodies which bind to a mammalian Bonzo, and antigen-binding fragments of antibodies which bind to a mammalian SExCkine. For example, antibody fragments capable of binding to a mammalian Bonzo or SExCkine or portions thereof, including, but not limited to Fv, Fab, Fab' and F(ab')$_2$ fragments are encompassed by the invention. Such fragments can be produced by enzymatic cleavage or by recombinant techniques. For example, papain or pepsin cleavage can generate Fab or F(ab')$_2$ fragments, respectively. Other proteases with the requisite substrate specificity can also be used to generate Fab or F(ab')$_2$ fragments. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

Single chain antibodies, and chimeric, humanized or primatized (CDR-grafted), or veneered antibodies, as well as chimeric, CDR-grafted or veneered single chain antibodies, comprising portions derived from different species, and the like are also encompassed by the present invention and the term "antibody". The various portions of these antibodies can be joined together chemically by conventional techniques, or can be prepared as a contiguous protein using genetic engineering techniques. For example. nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., *BioTechnology*, 10: 1455–1460 (1992), regarding primatized antibody, and Ladner et al., U.S. Pat. No. 4,946,778 and Bird, R. E. et al., *Science*, 242: 423–426 (1988)) regarding single chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, M., et al., *Nucl. Acids Res.*, 17: 5404 (1989)); Sato, K., et al., *Cancer Research*, 53: 851–856 (1993); Daugherty, B. L. et al., *Nucleic Acids Res.*, 19(9). 2471–2476 (1991); and Lewis, A. P. and J. S. Crowe, *Gene*, 101: 297–302 (1991)). Using these or other suitable methods, variants can also be readily produced. In one embodiment. cloned variable regions can be mutated, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993).

The antibody can be a humanized antibody comprising one or more Immunoglobulin chains, said antibody comprising a CDR of nonhuman origin (e.g., one or more CDRs derived from an antibody of nonhuman origin) and a framework region derived from a light and/or heavy chain of human origin (e.g., CDR-grafted antibodies with or without framework changes). In one aspect of this embodiment, the antibody comprises the light chain CDRs (CDR1, CDR2 and CDR3) and heavy chain CDRs (CDR1, CDR2 and CDR3) of a nonhuman immunoglobulin.

The antibodies described herein can also be conjugated to an agent. In one embodiment, the agent is a label, for example, a radioisotope, an epitope label (tag), an affinity label (e.g., biotin, avidin), a spin label, an enzyme, a fluorescent group or a chemiluminescent group. In another embodiment, the antibody is conjugated to a drug or toxin. Drugs and toxins which can be conjugated to the antibodies of the present invention include, for example, chemotherapeutic agents (e.g., mitomycin C, paxlitaxol, methotrexate, 5-fluorouracil, cisplatin, cyclohexamide) and toxins (e.g., ricin, gelonin).

Antibodies which are specific for mammalian (e.g., human) Bonzo or mammalian (e.g., human) SExCkine can be raised against an appropriate immunogen, such as isolated and/or recombinant human Bonzo or portions thereof (including synthetic molecules, such as synthetic peptides) or isolated and/or recombinant human SExCkine or portions thereof (including synthetic molecules, such as synthetic peptides). Antibodies can also be raised by immunizing a suitable host (e.g., mouse) with cells that express Bonzo, such as activated T cells, or with cells that express SExCkine, such as CD19$^+$ B lymphocytes, CD14$^+$ monocytes/macrophages, dendritic cells or granulocytes. In addition, cells expressing a recombinant mammalian Bonzo or SExCkine, such as transfected cells, can be used as immunogens or in a screen for antibody which binds thereto (See e.g., Chuntharapai et al., J. Immunol., 152: 1783–1789 (1994); Chuntharapai et al., U.S. Pat. No. 5,440,021).

Preparation of immunizing antigen, and polyclonal and monoclonal antibody production can be performed using any suitable technique. A variety of methods have been described (see e.g., Kohler et al., Nature, 256: 495–497 (1975) and Eur. J. Immunol. 6: 511–519 (1976); Milstein et al., Nature 266: 550–552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 97, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line such as SP2/0, P3X63Ag8.653 or a heteromyloma) with antibody-producing cells. Antibody-producing cells can be obtained from the peripheral blood or, preferably the spleen or lymph nodes, of humans or other suitable animals immunized with the antigen of interest. The fused cells (hybridoinas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity (e.g., human antibodies or antigen-binding fragments) can be used, including, for example, methods which select recombinant antibody from a library (e.g., a phage display library). Transgenic animals capable of producing a repertoire of human antibodies (e.g., Xenomouse® (Abgenix, Fremont, Calif.)) can be produced using suitable methods (see e.g., Jakobovits et al., Proc. Natl. Acad. Sci. USA, 90: 2551–2555 (1993); Jakobovits et al., Nature, 362: 255–258 (1993)). Additional methods which are suitable for production of transgenic animals capable of producing a repertoire of human antibodies have been described (e.g., Lonberg et al., U.S. Pat. No. 5,545,806; Surani et al., U.S. Pat. No. 5,545,807; Lonberg et al., WO97/13852).

Anti-Bonzo Antibodies

In one embodiment, the antibody or antigen-binding fragment thereof has specificity for a mammalian Bonzo, preferably a naturally-occurring or endogenous human Bonzo. In another embodiment, the antibody is an IgG or antigen-binding fragment of an IgG. In another embodiment, the antibody or antigen-binding fragment can bind to a mammalian Bonzo and inhibit (reduce or prevent) one or more functions of the receptor. In another embodiment, the antibody is a human antibody or an antigen-binding fragment thereof. In another embodiment, the antibody is a humanized antibody or an antigen-binding fragment thereof. In a preferred embodiment, the antibody or antigen-bindinig fragment can inhibit binding of a ligand (i.e., one or more ligands) to the receptor, and/or one or more functions mediated by Bonzo in response to ligand binding.

In a particular embodiment, an antibody or antigen-binding fragment of the invention can inhibit the binding of a mammalian ligand (e.g., human SExCkine) to mammalian (e.g., human) Bonzo and/or one or more functions (e.g., cellular response) mediated by Bonzo in response to ligand binding. Inhibition of a cellular response to binding of ligand to Bonzo can be assessed in a suitable in vitro assay. Preferably, the antibody or antigen-binding fragment of the invention can inhibit a cellular response to binding of ligand to Bonzo in an in vitro assay with an $IC_{50}$ of less than about 10 μg/mL. Also preferred are antibodies and antigen-binding fragments which inhibit a ligand-induced (e.g., SExCkine-induced) cellular response in an in vitro chemotaxis assay with an $IC_{50}$ of less than about 8 μg/mL, or less than about 7 μg/mL, or less than about 5 μg/mL, or less than about 1 μg/mL. Particularly preferred antibodies and antigen-binding fragments are those which inhibit a ligand-induced (e.g., SExCkine-induced) cellular response in an in vitro assay with an $IC_{50}$ of less than about 0.5 μg/mL or less than about 0.1 μg/mL. In one embodiment, the antibody or antigen-binding fragment can inhibit ligand-induced (e.g., SExCkine-induced) chemotaxis of Bonzo$^+$ cells (e.g., Bonzo/L1.2 cells) in an in vitro chemotaxis assay, such as the assay described herein. In another embodiment, the antibody or antigen-binding fragment can inhibit a ligand-induced (e.g., SExCkine-induced) cellular response in an in vitro assay (e.g., chemotaxis assay) with an $IC_{50}$ that is lower than the $IC_{50}$ of the anti-human STRL33/Bonzo monoclonal antibody available from R&D Systems, Minneapolis, Minn. (catalogue number MAB699). In one embodiment, the $IC_{50}$ of the antibody or antigen-binding fragment of the invention is lower than the $IC_{50}$ of the anti-human STRL33/Bonzo monoclonal antibody available from R&D Systems (catalogue number MAB699) by a factor of about 2 or more. For example, the $IC_{50}$ of the antibody or antigen-binding fragment of the invention can be lower than the $IC_{50}$ of the anti-human STRL33/Bonzo monoclonal antibody available from R&D Systems (catalogue number MAB699) by a factor of about 2, 3, 4, 5, 8,10, 50, 100, 500, or 1000.

Other functions which can be mediated by Bonzo in response to ligand binding (e.g., SExCkine) include, for example, signal transduction (e.g., GDP/GTP exchange by Bonzo-associated G proteins, transient increase in the concentration of cytosolic free calcium $[Ca^{2+}]_i$) and Bonzo-mediated processes and cellular responses (e.g., proliferation, migration, chemotaxis, secretion, degranulation, inflammatory mediator release (such as release of bioactive lipids such as leukotrienes (e.g., leukotriene $C_4$)), respiratory burst).

As described herein, antibodies designated "mAb 4A11", "mAb 7A2", "mAb 7F3" and "mAb 9G2" which bind human Bonzo have been produced.

mAb 4A11 can be produced by murine hybridoma 4A11, also referred to as murine hybridoma LS212–4A11–30–8, which was deposited on Nov. 24, 1999, on behalf of LeukoSite, Inc., 215 First Street, Cambridge, Mass. 02142, U.S.A. (now Millennium Pharmaceuticals Inc., 75 Sidney Street, Cambridge, Mass., 02139, USA), at the American Type Culture Collection, 10801 University Boulevard, Manassas, Va. 20110, U.S.A., under Accession No. PTA-991. The invention relates to murine hybridoma 4A11, to the antibody it produces and to nucleic acids encoding the antibody.

mAb 7A2 can be produced by murine hybridoma 7A2, also referred to as murine hybridoma LS212–7A2–32–1, which was deposited on Nov. 24, 1999, on behalf of LeukoSite, Inc., 215 First Street, Cambridge, Mass. 02142, U.S.A. (now Millennium Pharmaceuticals Inc., 75 Sidney Street, Cambridge, Mass., 02139, USA), at the American Type Culture Collection, 10801 University Boulevard, Manassas, Va. 20110, U.S.A., under Accession No. PTA-992. The invention relates to murine hybridoma 7A2, to the antibody it produces, and to nucleic acids encoding the antibody.

mAb 7F3 can be produced by murine hybridoma 7F3, also referred to as murine hybridoma LS212–7F3–8–7, which was deposited on Nov. 24, 1999, on behalf of LeukoSite, Inc., 215 First Street, Cambridge, Mass. 02142, U.S.A. (now Millennium Pharmaceuticals Inc., 75 Sidney Street, Cambridge, Mass., 02139, USA), at the American Type Culture Collection, 10801 University Boulevard, Manassas, Va. 20110, U.S.A., under Accession No. PTA-990. The invention relates to murine hybridoma 7F3, to the antibody it produces, and to nucleic acids encoding the antibody.

mAb 9G2 can be produced by murine hybridoma 9G2, also referred to as murine hybridoma LS212–9G2–7–2. The invention relates to murine hybridoma 9G2, to the antibody it produces, and to nucleic acids encoding the antibody.

In another embodiment, the anti-Bonzo antibody of the invention is mAb 4A11, mAb 7A2, mAb 7F3, mAb 9G2 or an antigen-binding fragment of any of the forgoing. Preferred among these are mAb 4A11, mAb 7A2, mAb 7F3 or antigen-binding fragments thereof. In another embodiment, the binding of the antibody or antigen-binding fragment to mammalian (e.g., human) Bonzo can be inhibited by mAb 4A11, mAb 7A2 or mAb 7F3. Such inhibition can be the result of competition for the same or similar epitope or steric interference (e.g., where antibodies bind overlapping epitopes or adjacent epitopes). Inhibition by mAb 4A11, mAb 7A2 or mAb 7F3 can also be due to a change in the conformation of Bonzo that is induced upon antibody binding to the receptor.

In still another embodiment, the antibody or antigen-binding fragment of the invention has the same or similar epitopic specificity as mAb 4A11, mAb 7A2, mAb 7F3 or mAb 9G2. Antibodies with an epitopic specificity which is the same as or similar to that of mAb 4A11, mAb 7A2, mAb 7F3 or mAb 9G2 can be identified by a variety of suitable methods. For example, an antibody with the same or similar epitopic specificity as e.g., mAb 4A11 can be identified based upon the ability to compete with mAb 4A11 for binding to human Bonzo. In another example, the binding of e.g., 4A11 and the binding of an antibody with the same or similar epitopic specificity for human Bonzo can be inhibited by a single peptide (e.g., natural peptide, synthetic peptide). The peptide can comprise about nine to about fifty amino acids. Preferably, the peptide comprises about nine to about twenty-six amino acids. In still another example, an antibody with the same or similar epitopic specificity as mAb 4A11, mAb 7A2, mAb 7F3 or mAb 9G2 can be identified using chimeric receptors (see e.g., Rucker et al., *Cell* 87:437–446 (1996)).

In additional embodiments, the antibody is a humanized antibody comprising the six CDRs (light chain CDRs (CDR1, CDR2 and CDR3) and heavy chain CDRs (CDR1, CDR2 and CDR3)) of mAb 4A11, mAb 7A2, mAb 7F3 or mAb 9G2. In one embodiment, the antibody is a humanized antibody comprising the light chain CDRs (CDR1, CDR2 and CDR3) and heavy chain CDRs (CDR1, CDR2 and CDR3) of mAb 4A11, mAb 7A2 or mAb 7F3. In a preferred embodiment, the antibody is a humanized antibody comprising the light chain CDRs (CDR1, CDR2 and CDR3) and heavy chain CDRs (CDR1, CDR2 and CDR3) of mAb 7F3.

The invention also relates to a bispecific antibody, or functional fragment thereof (e.g., F(ab')$_2$), which binds to a mammalian Bonzo and at least one other antigen (e.g., tumor antigen, viral antigen). In a particular embodiment, the bispecific antibody, or functional fragment thereof, has the same or similar epitopic specificity as mAb 4A11, mAb 7A2, mAb 7F3 or mAb 9G2 and at least one other antibody. Bispecific antibodies can be secreted by triomas and hybrid hybridomas. Generally, triomas are formed by fusion of a hybridoma and a lymphocyte (e.g., antibody-secreting B cell) and hybrid hybridomas are formed by fusion of two hybridomas. Each of the fused cells (i.e., hybridomas, lymphocytes) produces a monospecific antibody. However, triomas and hybrid hybridomas can produce an antibody containing antigen-binding sites which recognize different antigens. The supernatants of triomas and hybrid hybridomas can be assayed for bispecific antibody using a suitable assay (e.g., ELISA), and bispecific antibodies can be purified using conventional methods. (see, e.g., U.S. Pat. No. 5,959,084 (Ring et al.), U.S. Pat. No. 5,141,736 (Iwasa et al.), U.S. Pat. Nos. 4,444,878, 5,292,668, 5,523,210 (all to Paulus et al.) and U.S. Pat. No. 5,496,549 (Yamazaki et al.)).

Anti-SExCkine Antibodies

In another embodiment, the antibody or antigen-binding fragment thereof has specificity for a mammalian SExCkine, preferably a naturally-occurring or endogenous human SExCkine. Such antibodies and antigen-binding fragments can be produced by a variety of suitable methods, such as those described herein. In one embodiment, the anti-SExCkine antibody can be raised against an appropriate immunogen, such as an isolated soluble and/or recombinant SExCkine or portions thereof (including synthetic molecules, such as synthetic peptides). Antibodies can also be raised by immunizing a suitable animal (e.g., mouse) with cells which express the transmembrane form of SExCkine, such as CD14$^+$ B lymphocytes and CD19$^+$ monocytes/macrophages. In another embodiment, the antibody is an IgG or antigen-binding fragment of an IgG. In another embodiment, the antibody is a human antibody or an antigen-binding fragment thereof. In another embodiment, the antibody is a humanized antibody or an antigen-binding fragment thereof. In a preferred embodiment, the antibody or antigen-binding fragment can bind to a mammalian SExCkine and inhibit (reduce or prevent) the binding of the chemokine to a receptor (e.g., Bonzo), and thereby inhibit one or more functions mediated by the receptor in response to SExCkine binding. For example, the anti-SExCkine antibody can inhibit SExCkine-induced chemotaxis of Bonzo$^+$ cells. Other functions which can be mediated by SExCkine binding to receptor (e.g., Bonzo) include, for example, signal transduction (e.g., GDP/GTP exchange by receptor-associated G proteins, transient increase in the concentration of cytosolic free calcium $[Ca^{2+}]_i$) and receptor-mediated processes and cellular responses (e.g., proliferation, migration, chemotaxis, secretion, degranulation, inflammatory mediator release (such as release of bioactive lipids such as leukotrienes (e.g., leukotriene $C_4$)), respiratory burst).

In one embodiment, the antibody or antigen-binding fragment can bind to a mammalian transmembrane (i.e., cell surface) SExCkine and modulate signaling through SExCkine (SExCkine-mediated signaling). In another embodiment, the antibody or antigen-binding fragment can bind to a mammalian transmembrane SExCkine and inhibit (reduce or prevent) signaling through SExCkine.

As described herein, antibodies designated "mAb 9B10", "mAb 10B12" and "mAb SD7 (also referred to as mAb 2D7)" which bind human SExCkine have been produced.

mAb 9B10 can be produced by murine hybridoma 9B10, which was deposited on Oct. 20, 2000, on behalf of Millennium Pharmaceuticals, Inc., 75 Sidney Street, Cambridge, Mass. 02139, U.S.A., at the American Type Culture Collection, 10801 University Boulevard, Manassas, Va. 20110, U.S.A., under Accession No. PTA-2628. The invention relates to murine hybridoma 9B10, to the antibody it produces and to nucleic acids encoding the antibody.

mAb 10B12 can be produced by murine hybridoma 10B12, which was deposited on Oct. 20, 2000, on behalf of Millennium Pharmaceuticals, Inc., 75 Sidney Street, Cambridge, Mass. 02139, U.S.A., at the American Type Culture Collection, 10801 University Boulevard, Manassas, Va. 20110, U.S.A., under Accession No. PTA-2629. The invention relates to murine hybridoma 10B12, to the antibody it produces and to nucleic acids encoding the antibody.

mAb SD7 can be produced by murine hybridoma SD7, which was deposited on Oct. 20, 2000, on behalf of Millennium Pharmaceuticals, Inc., 75 Sidney Street, Cambridge, Mass. 02139, U.S.A., at the American Type Culture Collection, 10801 University Boulevard, Manassas, Va. 20110, U.S.A., under Accession No. PTA-2630. The invention relates to murine hybridoma SD7, to the antibody it produces and to nucleic acids encoding the antibody.

In one embodiment, the anti-SExCkine antibody of the invention is mAb 9B10, mAb 10B12, mAb SD7 or an antigen-binding fragment of any of the foregoing. Preferred among these is mAb SD7 or antigen-binding fragments thereof. In another embodiment, the binding of the antibody or antigen-binding fragment to mammalian (e.g., human) SExCkine can be inhibited by mAb 9B10, mAb 10B12 or mAb SD7. Such inhibition can be the result of competition for the same or similar epitope or steric interference (e.g., where antibodies bind overlapping epitopes or adjacent epitopes). Inhibition by mAb 9B10, mAb 10B12 or mAb SD7 can also be due to a change in the conformation of SExCkine that is induced upon antibody binding to the receptor.

In still another embodiment, the antibody or antigen-binding fragment of the invention has the same or similar epitopic specificity as mAb 9B10, mAb 10B12 or mAb SD7. Antibodies with an epitopic specificity which is the same as or similar to that of mAb 9B10, mAb 10B12 or mAb SD7 can be identified by a variety of suitable methods. For example, an antibody with the same or similar epitopic specificity as e.g., mAb SD7 can be identified based upon the ability to compete with mAb SD7 for binding to human SExCkine. In another example, the binding of e.g., SD7 and the binding of an antibody with the same or similar epitopic specificity for human SExCkine can be inhibited by a single peptide (e.g., natural peptide, synthetic peptide). The peptide can comprise about nine to about fifty amino acids. Preferably, the peptide comprises about nine to about twenty-six amino acids. In still another example, an antibody with the same or similar epitopic specificity as mAb 9B10, mAb 10B12 or mAb SD7 can be identified using chimeric receptors (see e.g., Rucker et al., *Cell* 87:437–446 (1996)).

In additional embodiments, the antibody is a humanized antibody comprising the six CDRs (light chain CDRs (CDR1, CDR2 and CDR3) and heavy chain CDRs (CDR1, CDR2 and CDR3)) of mAb 9B10, mAb 10B12 or mAb SD7. In a preferred embodiment, the antibody is a humanized antibody comprising the light chain CDRs (CDR1, CDR2 and CDR3) and heavy chain CDRs (CDR1, CDR2 and CDR3) of mAb SD7.

The invention also relates to a bispecific antibody, or functional fragment thereof (e.g., $F(ab')_2$), which binds to a mammalian SExCkine and at least one other antigen (e.g., tumor antigen, viral antigen). In a particular embodiment, the bispecific antibody, or functional fragment thereof, has the same or similar epitopic specificity as mAb 9B10, mAb 10B12 or mAb SD7 and at least one other antibody. Bispecific antibodies can be prepared using suitable methods, such as those described herein.

As used herein the term "specific antibody" or "specific" when referring to an antibody-antigen interaction is used to indicate that the antibody can selectively bind to a mammalian Bonzo or a mammalian SExCkine, rather than to indicate that the antibody can bind to only one antigen. For example, an antibody may bind to one or several antigens with low affinity and bind to human Bonzo with a higher affinity. Such an antibody is considered to be specific for human Bonzo because when used (e.g., in therapeutic or diagnostic application) at a suitable concentration, the antibody can selectively bind to human Bonzo. The concentration of antibody required to provide selectivity for mammalian Bonzo or mammalian SExCkine (e.g., a concentration which reduces or eliminates low affinity binding) can be readily determined by suitable methods, such as titration.

In another aspect, the invention relates to an isolated cell which produces an antibody or an antigen-binding fragment of the invention. In a preferred embodiment, the isolated antibody-producing cell of the invention is an immortalized cell, such as a hybridoma, heterohybridoma, lymphoblastoid cell or a recombinant cell. The antibody-producing cells of the present invention have uses other than for the production of antibodies. For example, the cell of the present invention can be fused with other cells (such as suitably drug-marked human myeloma, mouse myeloma, human-mouse heteromyeloma or human lymphoblastoid cells) to produce, for example, additional hybridomas, and thus provide for the transfer of the genes encoding the antibody. In addition, the cell can be used as a source of nucleic acids encoding the anti-Bonzo or anti-SExCkine immunoglobulin chains, which can be isolated and expressed (e.g., upon transfer to other cells using any suitable technique (see e.g., Cabilly et al., U.S. Pat. No. 4,816,567, Winter, U.S. Pat. No. 5,225,539)). For instance, clones comprising a sequence encoding a rearranged anti-Bonzo light and/or heavy chain or rearranged anti-SExCkine light and/or heavy chain can be isolated (e.g., by PCR). In addition, cDNA libraries can be prepared from mRNA isolated from an appropriate cell line, and cDNA clones encoding an anti-Bonzo immunoglobulin chain(s) or an anti-SExCkine immunoglobulin chain(s) can be isolated. Thus, nucleic acids encoding the heavy and/or light chains of the antibodies, or portions thereof, can be obtained and used for the production of the specific immunoglobulin, immunoglobulin chain, or variants thereof (e.g., humanized immunoglobulins) in a variety of host cells or in an in vitro translation system. For example, the nucleic acids, including cDNAs, or derivatives thereof encoding variants such as a humanized immunoglobulin or immunoglobulin chain, can be placed into suitable prokaryotic or eukaryotic vectors (e.g., expression vectors) and introduced into a suitable host cell by an appropriate method (e.g., transformation, transfection, electroporation, infection), such that the nucleic acid is operably linked to one or more expression control elements (e.g., in the vector or integrated into the host cell genome), to produce a recombinant antibody-producing cell.

The antibody of the invention can be produced by any suitable method, for example, by collecting serum from an animal (e.g., mouse, human, transgenic mouse) which has been immunized with a mammalian Bonzo or a mammalian SExCkine. In another example, a suitable antibody-producing cell (e.g., hybridoma, heterohybridoma, lymphoblastoid cell, recombinant cell) can be maintained, either in vitro or in vivo, under conditions suitable for expression (e.g., in the presence of inducer, suitable media supplemented with appropriate salts, growth factors, antibiotic, nutritional supplements), whereby the antibody or antigen-binding fragment is produced. If desired, the antibody or antigen-binding fragment can be recovered and/or isolated (e.g., from the host cells, culture medium) and purified to the desired degree. Recovery and purification of the antibody can be achieved using suitable methods, such as, centrifugation, filtration, column chromatography (e.g., ion-exchange, gel filtration, hydrophobic-interaction, affinity), preparative native electrophoresis, precipitation and ultrafiltration. It will be appreciated that the method of production encompasses expression in a host cell of a transgenic animal (see e.g., WO 92/03918, GenPharm International, published Mar. 19, 1992).

As described herein, preferred antibodies of the invention can bind to mammalian Bonzo or mammalian SExCkine and thereby inhibit the binding of ligand to receptor. A variety of suitable methods, such as the assays described herein, can be used to assess inhibition of binding of a ligand (e.g., SExCkine) to a receptor (e.g., Bonzo) and/or function associated with binding of ligand to receptor.

The invention also includes antibodies and antigen-binding fragments thereof which can bind to mammalian Bonzo or SExCkine but which do not inhibit the binding of ligand to receptor.

Targeting Molecules

The invention also relates to targeting molecules which can effectuate the interaction of a Bonzo$^+$ cell with a target cell. The targeting molecule includes a first binding moiety which can bind mammalian Bonzo, and a second binding moiety which can bind a molecule expressed on the surface of a target cell. Preferred target cells include tumor cells and virus-infected cells. A variety of molecules which are expressed at higher levels or uniquely on tumor cells (e.g., tumor antigens, such as Lewis Y. HER-2/neu, disialoganglioside G3, carcinoembrionic antigen, CD30) and/or virus-infected cells (e.g., viral antigens, such as influenza virus hemagglutinin, Epstein-Barr virus LMP-1, hepatitis C virus E2 glycoprotein, HIV gp160, HIV gp 120) are known in the art. The targeting molecule can contain any suitable second binding moiety which binds to a molecule expressed on a desired target cell (see for example, Ring, U.S. Pat. No. 5,948,647, the entire teachings of which are incorporated herein by reference). Suitable binding moieties include, for example, proteins and peptides (including post-translationally modified forms, e.g., glycosylated, phosphorylated, lipidated), sugars, lipids, peptidomimetics, small organic molecules, nucleic acids and other agents which bind mammalian Bonzo or a molecule expressed on the surface of a target cell. Suitable binding moieties can be identified using any suitable method, such as the binding assays described herein.

The first binding moiety can be, for example, an antibody which binds mammalian Bonzo or antigen-binding fragment thereof (e.g., Fab, Fv, Fab', F(ab)'$_2$), a Bonzo ligand (e.g., mammalian SExCkine, mammalian platelet factor 4) or Bonzo-binding variant of a ligand. The second binding moiety can be, for example, an antibody or antigen-binding fragment thereof which binds to a molecule expressed on the target cell or antigen-binding fragment thereof. Where the targeting molecule comprises a first binding moiety which is an anti-Bonzo antibody or antigen-binding fragment thereof, it is preferred that said anti-Bonzo antibody does not inhibit binding of ligand to Bonzo.

In another embodiment, the first binding moiety is an antibody which binds mammalian SExCkine or antigen-binding fragment thereof (e.g., Fab, Fv, Fab', F(ab)'$_2$), The second binding moiety can be, for example, an antibody or antigen-binding fragment thereof which binds to a molecule expressed on the target cell or antigen-binding fragment thereof. Where the targeting molecule comprises a first binding moiety which is an anti-SExCkine antibody or antigen-binding fragment thereof, it is preferred that said anti-SExCkine antibody does not inhibit binding of SExCkine to receptor.

The first binding moiety can be directly or indirectly bonded to the second binding moiety through a variety of suitable linkages. For example, when the first binding moiety and the second binding moiety are both proteins or peptides, the moieties can be part of a contiguous polypeptide (i.e., a fusion protein). Where the targeting molecule is a fusion protein, the first and second binding moieties can be arranged on the polypeptide in any suitable configuration. The first and second binding moieties can be indirectly bonded through a (i.e., one or more) peptide linker, or bonded directly to each other through a peptide bond. For example, when the targeting molecule comprises an Fv and a Bonzo ligand, the amino acid sequence of the ligand can be fused to the amino-terminus or the carboxyl-terminus of the Fv. The sequence encoding the ligand can also serve as a spacer or be inserted into a spacer which connects the variable regions (heavy chain variable region, light chain variable region) of the Fv.

Where the binding moieties are not part of a contiguous polypeptide they can be directly bonded by a chemical bond formed by reaction of a functional group (or activated derivative thereof) on the first moiety with a second functional group (or activated derivative thereof) on the second moiety. For example, two thiols can react to form a disulfide bond and an amine can react with a carboxylic acid or acyl halide to form an amide. A variety of other suitable reactions which can be used are known in the art (see, for example, Hermanson, G. T., *Bioconjugate Techniques*, Academic Press: San Diego, Calif. (1996)). The binding moieties can be indirectly bonded through a suitable linker (e.g., a peptide linker). Generally, a linker contains two reactive groups which can react to form bonds with the first binding moiety and/or the second binding moiety. Linkers which contain two different reactive groups (e.g., a heterobifunctional linker) can be used to selectively conjugate the first binding moiety to the second binding moiety. Many linkers which are suitable for forming conjugates between proteins, nucleic acids, peptides, vitamins, sugars, lipids, small organic molecules and other suitable agents are known (see, for example, U.S. Pat. Nos. 5,856,571, 5,880,270; Hermanson, G. T., *Bioconjugate Techniques*, Academic Press: San Diego, Calif. (1996)).

Preferably, the independent activities of the binding moieties (e.g., binding activities, chemoattractant activity) of the targeting molecule are not significantly different from the activities of the binding moieties as separate molecular entities. For example, where the first binding moiety is an antibody or antigen-binding fragment that binds Bonzo, the targeting molecule can bind to Bonzo with an affinity which is within a factor of about 1000, preferably within a factor of 100, more preferably within a factor of 10 or substantially the same as the affinity of the free antibody or antigen-binding fragment. Similarly, where the first binding moiety is a Bonzo ligand (e.g., human SExCkine, human platelet factor 4), the targeting molecule can induce chemotaxis of Bonzo$^+$ cells (e.g., Bonzo/L1.2 cells) with an effective dose 50 ($EC_{50}$) that is within a factor of about 1000, preferably within a factor of 100, more preferably within a factor of 10 or substantially the same as the $EC_{50}$ of the free ligand (e.g. human SExCkine, human platelet factor 4). Target molecules with these preferred characteristics can be prepared using any suitable method. For example, a variety of linkers of differing length and with different reactive groups can be bonded to mammalian SExCkine and the resulting products can be assayed in a chemotaxis assay as described herein. Compounds which display a suitable amount of chemoattractant activity can then be reacted with, for example, an antibody or antigen-binding fragment thereof which binds a tumor antigen (e.g., HER-2/neu). The resulting targeting molecule can then be assayed for binding to tumor antigen (e.g., by ELISA) and for chemoattractant activity. In one embodiment, the targeting molecule is a bispecific antibody or bispecific antigen-binding fragment thereof (e.g., F(ab')$_2$) which has specificity for mammalian Bonzo and a molecule expressed on a target cell (e.g., tumor antigen, viral antigen).

In another embodiment, the targeting molecule is an immunoconjugate wherein a Bonzo ligand (e.g., mammalian SExCkine, mammalian platelet factor 4) or receptor-binding variant thereof is bonded to an antibody or antigen-binding fragment thereof which binds to a target cell (e.g., a tumor antigen expressed on target cell, a viral antigen expressed on target cell) through a linker. The linker can form a bond with specific sites on the antibody and/or ligand, for example, the linker can be bonded to the side chain of cysteinyl residues, the side chain of lysyl residues, the side chains of aspartyl or glutamyl residues.

In another embodiment, the targeting molecule is a fusion protein comprising a Bonzo ligand (e.g., mammalian SExCkine, mammalian platelet factor 4) or receptor-binding variant thereof and an antibody or antigen-binding fragment thereof (e.g., Fab, Fab', F(ab')$_2$, Fv) which binds to a target cell (e.g., a tumor antigen expressed on target cell, a viral antigen expressed on target cell). Preferably, the Bonzo ligand is the extracellular region of mammalian SExCkine (e.g., human SExCkine) or a receptor-binding variant thereof. Several suitable methods for preparing fusion proteins are known in the art, for example, the fusion protein can be prepared using the methods described in U.S. Pat. Nos. 5,767,260, 5,824,782 and 5,889,157, or other suitable methods. The entire teachings of U.S. Pat. Nos. 5,767,260, 5,824,782 and 5,889,157 are incorporated herein by reference.

In one embodiment, the targeting molecule is a fusion protein comprising a first moiety which shares at least about 85% sequence similarity with a corresponding portion of a naturally-occurring mammalian Bonzo ligand (e.g. human SExCkine (e.g., SEQ ID NO:4, SEQ ID NO:6), human platelet factor 4 (e.g., amino acid residues 32–100 of SEQ ID NO:8)), preferably at least about 90% sequence similarity, and more preferably at least about 95% sequence similarity with a corresponding portion of a naturally-occurring mammalian Bonzo ligand. Amino acid sequence similarity can be identified using a suitable sequence alignment algorithm, such as the Lasergene system (DNASTAR, Inc., Madison, Wis.), as described herein. Variants can be prepared using any suitable methods (e.g., solid phase peptide synthesis, by expression of nucleic acids encoding the variant), and tested for receptor binding.

Nucleic Acids, Constructs and Vectors

The invention also relates to isolated and/or recombinant nucleic acids which encode a targeting molecule of the invention. Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

In one embodiment, the nucleic acid encodes a fusion protein wherein a Bonzo ligand (e.g., mammalian SExCkine, mammalian platelet factor 4) or a receptor-binding variant thereof is bonded (directly or through a peptide linker) to an antibody or antigen-binding fragment thereof which binds a target cell. Preferably, the nucleic acid encodes a fusion protein wherein the extracellular domain of human SExCkine or a receptor-binding variant thereof is bonded (directly or through a peptide linker) to an antibody or antigen-binding fragment thereof which binds a tumor antigen expressed on the surface of a human cell or a viral antigen expressed on the surface of a human cell.

The invention also relates to recombinant cells which can produce a targeting molecule (e.g., fusion protein). Recombinant cells can be produced using a variety of suitable methods. For example, a nucleic acid encoding all or part of the coding sequence for the desired fusion protein can be inserted into a nucleic acid vector (e.g., a DNA vector, such as a plasmid, virus or other suitable replicon for expression). A variety of vectors are available, including vectors which are maintained in single copy or multiple copy, or which become integrated into the host cell chromosome. Suitable expression vectors for the expression of a nucleic acid encoding all or part of the coding sequence of the desired fusion protein are also available. Suitable expression vectors can contain a number of components, including, but not limited to one or more of the following: an origin of replication; a selectable marker gene; one or more expression control elements, such as a transcriptional control element (e.g., a promoter, an enhancer, a terminator), and/or one or more translation signals; a signal sequence or leader sequence for targeting to the secretory pathway in a selected host cell (e.g., of mammalian origin or from a heterologous mammalian or non-mammalian species). In a construct, a signal sequence can be provided by the vector, the insert nucleic acid, or other source. Sequences present at a site of integration can also provide these elements.

A promoter can be provided for expression in a suitable host cell. Promoters can be constitutive or inducible. For example, a promoter can be operably linked to a nucleic acid encoding the fusion protein, such that it directs expression of the encoded polypeptide. A variety of suitable promoters for prokaryotic (e.g., lac, tac, T3, T7 promoters for *E. coli*) and eukaryotic (e.g., yeast alcohol dehydrogenase (ADH1), SV40, CMV) hosts are available.

In addition, the expression vectors typically comprise a selectable marker for selection of host cells carrying the vector, and, in the case of replicable expression vector, an origin or replication. Genes encoding products which confer antibiotic or drug resistance are common selectable markers and may be used in prokaryotic (e.g., β-lactamase gene (ampicillin resistance), Tet gene for tetracycline resistance) and eukaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated. The present invention also relates to cells carrying these expression vectors.

The invention also relates to a method of producing a targeting molecule. For example, a nucleic acid encoding a targeting molecule fusion protein, or a construct comprising such nucleic acid, can be introduced into a suitable host cell by a method appropriate to the host cell selected (e.g., transformation, transfection, electroporation, infection), such that the nucleic acid is operably linked to one or more expression control elements (e.g., in a vector, in a construct created by processes in the cell, integrated into the host cell genome). Host cells can be maintained under conditions suitable for expression (e.g., in the presence of inducer, suitable media supplemented with appropriate salts, growth factors, antibiotic, nutritional supplements, etc.), whereby the encoded polypeptide is produced. If desired, the encoded targeting molecule can be isolated (e.g., from the host cells, medium, milk). It will be appreciated that the method encompasses expression in a host cell of a transgenic animal (see e.g., WO 92/03918, GenPharm International, published Mar. 19, 1992).

Models of Inflammation

In vivo models of inflammation are available which can be used to assess the efficacy of antibodies (anti-Bonzo, anti-SExCkine), antigen-binding fragments and targeting molecules of the invention, as well as agents identified by the methods described herein as in vivo therapeutics. For example, leukocyte infiltration upon intradermal injection of a Bonzo ligand (e.g., SExCkine, platelet factor 4) and an antibody or antigen-binding fragment thereof reactive with mammalian Bonzo into a suitable animal, such as rabbit, mouse, rat, guinea pig or primate (e.g., rhesus macaque) can be monitored (see e.g., Van Damme, J. et al., *J. Exp. Med.*, 176: 59–65 (1992); Zachariae, C. O. C. et al., *J. Exp. Med.* 171: 2177–2182 (1990); Jose, P. J. et al., *J. Exp. Med.* 179: 881–887 (1994)). In one embodiment, skin biopsies are assessed histologically for infiltration of leukocytes (e.g., Bonzo+ T cells). In another embodiment, labeled cells (e.g., stably transfected cells expressing a mammalian Bonzo, labeled with $^{111}$In for example) capable of chemotaxis and extravasation are administered to the animal. For example, an antibody or agent to be assessed which binds a mammalian Bonzo can be administered, either before, simultaneously with or after a Bonzo ligand or agonist (e.g., SExCkine) is administered to the test animal. A decrease of the extent of infiltration in the presence of antibody or agent as compared with the extent of infiltration in the absence of said antibody or agent is indicative of inhibition.

As described herein, Bonzo is expressed on chronically-stimulated lymphocytes (e.g., chronically-stimulated T cell subsets (e.g., $T_H1$, $T_H2$, $T_R1$, LAK, CIK)) and SExCkine is expressed on antigen-presenting cells (e.g., CD14+ monocyte/macrophages and CD19+ B lymphocytes). Thus, animal models of inflammatory diseases can be used to assess the therapeutic efficacy of Bonzo-modulating or SExCkine-modulating agents. A variety of in vivo models of inflammatory diseases are available, which can be used to assess the in vivo effects of ligands, inhibitors, promoters or targeting molecules as therapeutic agents, including a sheep model for asthma (see e.g., Weg, V. B. et al., *J. Exp. Med.*, 177: 561 (1993), the teachings of which are incorporated herein by reference), a rat delayed type hypersensitivity model (Rand, M. L. et al., *Am. J. Pathol.*, 148: 855–864 (1996), the teachings of which are incorporated herein by reference), or other suitable models. Additional suitable models include, models of mucosal inflammatory diseases (e.g., respiratory tract, urogenital tract, alimentary canal and associated organs and tissues (e.g., pancreas, liver, gall bladder)). For example, the antibodies and antigen-binding fragments of the invention, as well as agents identified by the methods described herein, can be studied in the cotton-top tamarin model of inflammatory bowel disease (Podolsky, D. K., et al., *J. Clin. Invest.* 92:372–380 (1993)). The CD45RB$^{Hi}$/SCID model provides a mouse model with similarity to both Crohn's disease and ulcerative colitis (Powrie, F. et al., *Immunity*, 1: 553–562 (1994)). Therapeutic efficacy in this model can be assessed, for example, by using parameters such as inhibition of recruitment of $^{111}$In-labeled cells to the colon and reduction in the number of CD4+ T lymphocytes in the lamina propria of the large intestine after administration (e.g., intravenous (i.v.), intraperitoneally (i.p.), per oral (p.o.)) of an agent. Knockout mice which develop intestinal lesions similar to those of human inflammatory bowel disease have also been described (Strober, W. and Ehrhardt, R. O., *Cell*, 75: 203–205 (1993)), and NOD mice provide an animal model of insulin-dependent diabetes mellitus.

Well established animal models for multiple sclerosis (e.g., experimental autoimmune encephalitis in rodents (e.g., mice, rats)), cancers and infectious diseases which can be used to assess the therapeutic efficacy of targeting molecules and Bonzo-modulating agents are available. For example, anti-tumor activity of targeting molecules and Bonzo agonists can be evaluated in a MCA26 colon carcinoma liver tumor model, in SCID mice injected with human gastric tumor cell line MKN-45, in mice (C3H/HeN) injected with CL-62 melanoma cells, in mice injected with HOPE2 metastatic melanoma cells or other suitable models (see, for example, Pham-Nguyen, K. B., et al., *Int. J. Cancer,* 81:813–819 (1999); Senba, T., et al., *Anticancer Res.,* 18:17–24 (1 998), Thibault, C., et al., *Int. J. Cancer,* 67: 232–237 (1996), Hariharan, K., et al., *Int. J. Oncol.,* 12:1229–1235 (1998)). Animal models which closely resemble human disease, such as viral infection (HIV, EBV, hepatitis C virus) and cancer (e.g., lymphoid tumors) in SCID-hu mice can be used (see, for example, Seydel K. B. et al., *Gastroenterolog,* 115:1446–1453 (1998), Bristol, G. C. et al., *Methods,* 12:343–347 (1997), Jansen, B. et al., *Int.*

*J. Cancer*, 67:821–825 (1996), McCune, J. M., et al., *Curr. Top. Microbiol. Immunol.*, 152:183–193 (1989)).

Diagnostic Applications

The Bonzo-binding agents described herein (e.g., antibodies of the present invention, SExCkine) have application in procedures in which Bonzo can be detected on the surface of cells. The receptor provides a marker of the leukocyte cell types in which it is expressed. For example, antibodies raised against a mammalian Bonzo protein or peptide, such as the anti-Bonzo antibodies described herein (e.g., mAb 4A11, mAb 7A2, mAb 7F3, mAb 9G2), can be used to detect and/or quantify cells expressing a mammalian Bonzo. In one embodiment, the antibodies can be used to sort cells which express Bonzo from among a mixture of cells (e.g., to isolate cytotoxic "anti-tumor" cells, such as Bonzo$^+$CD3$^+$CD56$^+$ T cells). Suitable methods for counting and/or sorting cells can be used for this purpose (e.g., flow cytometry, fluorescence-activated cell sorting). If desired, sorted cells can be expanded by culture under conditions suitable for expansion of cytotoxic effector cells. Culture conditions which are suitable for expanding cytotoxic effector cells, including CD3$^+$CD56$^+$ cells, are known in the art (see, for example, Lu, P. H. et al., *J Immunol.*, 153:1687–1696 (1994); Jin, Y. et al., *Human Immunology*, 59:352–362 (1998)). In another embodiment, Bonzo$^+$ cells are identified by the ability to bind SExCkine or a receptor-binding valiant thereof. Cell counts can be used in the diagnosis of diseases or conditions in which an increase or decrease in leukocyte cell types (e.g., leukocytes which home to the mucosa) is observed.

Furthermore, Bonzo-binding agents described herein (e.g., antibodies of the present invention, SExCkine) can be used to detect or measure expression of Bonzo. For example, antibodies of the present invention can be used to detect or measure a mammalian Bonzo in a biological sample (e.g., cells, tissues or body fluids from an individual such as blood, serum, leukocytes (e.g., activated T lymphocytes), bronchoalveolar lavage fluid, saliva, bowel fluid, biopsy specimens). For example, a sample (e.g., tissue and/or fluid) can be obtained from an individual and a suitable assay can be used to assess the presence or amount of Bonzo protein. Suitable assays include immunological and immunochemical methods such as flow cytometry (e.g., FACS analysis) and immunosorbent assays, including enzyme-linked immunosorbent assays (ELISA), radioimmunoassay (RIA), chemiluminescence assays, immuno-blot (e.g., western blot), immunocytochemistry and immunohistology. Generally, a sample and antibody or antigen-binding fragment of the present invention are combined under conditions suitable for the formation of a complex between Bonzo and the antibody or antigen-binding fragment thereof, and the formation of said complex is assessed (directly or indirectly).

The presence of an increased level of Bonzo reactivity in a sample (e.g., a tissue sample) obtained from an individual can be indicative of inflammation and/or leukocyte (e.g., activated T cell) infiltration and/or accumulation associated with an inflammatory disease or condition, such as inflammatory arthritis (e.g., rheumatoid arthritis), an inflammatory bowel disease, allograft rejection, delayed type hypersensitivity reaction, or an infection such as a viral or bacterial infection. The presence of a decreased level of Bonzo reactivity in the circulation (e.g., on the surface of circulating lymphocytes) can also be indicative of leukocyte infiltration and/or accumulation at inflammatory sites. The level of expression of a mammalian Bonzo protein or variant can also be used to correlate increased or decreased expression of a mammalian Bonzo protein with a particular disease or condition, and in the diagnosis of a disease or condition in which increased or decreased expression of a mammalian Bonzo protein occurs (e.g., increased or decreased relative to a suitable control, such as the level of expression in a normal individual). Similarly, the course of therapy can be monitored by assessing Bonzo immunoreactivity in a sample from a subject. For example, antibodies of the present invention can be used to monitor the number of cells expressing Bonzo in a sample (e.g., blood, tissue) from a subject being treated with an anti-inflammatory or immunomodulating agent (e.g., immunosuppressive agent, such as cyclosporin A; immunostimulant, such as IL-2).

Kits for use in detecting the presence of a mammalian Bonzo protein in a biological sample can also be prepared. Such kits can include an agent which binds to a mammalian Bonzo receptor or portion of said receptor (e.g., antibody or functional fragment thereof, ligand (e.g., SExCkine)), as well as one or more ancillary reagents suitable for detecting the presence of a complex between the antibody or fragment and Bonzo or portion thereof. The antibody compositions of the present invention can be provided in lyophilized form, either alone or in combination with additional antibodies specific for other epitopes. The antibodies or antigen-binding fragments thereof, which can be labeled or unlabeled, can be included in the kits with adjunct ingredients (e.g., buffers, such as Tris (Tris(hydroxymethyl)aminomethane), phosphate and carbonate, stabilizers, excipients, biocides and/or inert proteins, e.g., bovine serum albumin). For example, the antibodies or antigen-binding fragments can be provided as a lyophilized mixture with the adjunct ingredients, or the adjunct ingredients can be separately provided for combination by the user. Generally these adjunct materials will be present in less than about 5% by weight based on the amount of active antibody, and usually will be present in a total amount of at least about 0.001% by weight based on antibody concentration. Where a second antibody or antigen-binding fragment capable of binding to the anti-Bonzo antibody or antigen-binding fragment is employed, such antibody or fragment can be provided in the kit, for instance in a separate vial or container. The second antibody or antigen-binding fragment, if present, is typically labeled, and can be formulated in an analogous manner with the antibody formulations described above. The components (e.g., anti-Bonzo antibody or antigen-binding fragment thereof, ancillary reagent) of the kit can be packaged separately or together within suitable containment means (e.g., bottle, box, envelope, tube). When the kit comprises a plurality of individually packaged components, the individual packages can be contained within a single larger containment means (e.g., bottle, box, envelope, tube).

Similarly, the present invention also relates to a method of detecting and/or quantifying expression of a mammalian Bonzo receptor or a portion of the receptor by a cell, in which a composition comprising a cell or fraction thereof (e.g., membrane fraction) is contacted with an antibody or functional fragment thereof (e.g., mAb 4A11, mAb 7A2, mAb 7F3, mAb 9G2) which binds to a mammalian Bonzo or portion of the receptor under conditions appropriate for binding of the antibody or fragment thereto. and binding is monitored. Detection of the antibody or antigen-binding fragment, indicative of the formation of a complex between said antibody or fragment and a mammalian Bonzo or a portion thereof, indicates the presence of the receptor. Binding of antibody to the cell can be determined using any suitable method. The method can be used to detect expression of Bonzo on cells from a subject (e.g., in a sample, such as a body fluid, such as blood, saliva or other suitable sample). The level of expression of Bonzo on the surface of cells (e.g., leukocytes) can also be determined, for instance, by flow cytometry, and the level of expression (e.g., staining intensity) can be correlated with disease susceptibility, progression or risk.

The SExCkine-binding agents described herein (e.g., anti-SExCkine antibodies and antigen-binding fragments thereof, SExCkine-binding receptors such as Bonzo) have application in procedures in which SExCkine can be detected on the surface of cells or in solution (e.g., in plasma, serum, culture supernatant). The protein provides a marker for cell types in which SExCkine is expressed. For example, antibodies raised against a mammalian SExCkine protein or peptide (e.g., mAb 9B12, mAb 10B12, mAb SD7) can be used to detect and/or quantify cells expressing a mammalian SExCkine. In one embodiment, the antibodies can be used to isolate cells (e.g., sort) which express cell-surface (i.e., transmembrane) SExCkine from among a mixture of cells (e.g., to isolate SExCkine$^+$CD19$^+$ B lymphocytes, SExCkine$^+$CD14$^+$ monocyte/macrophages and/or SExCkine$^+$ dendritic cells, cells expressing transmembrane SExCkine, cells expressing intracellular SExCkine). Suitable methods for counting and/or sorting cells can be used for this purpose (e.g., flow cytometry, fluorescence-activated cell sorting). If desired, sorted cells can be expanded by culture under conditions suitable for expansion. Cell counts can be used in the diagnosis of diseases or conditions in which an increase or decrease in SExCkine expression is observed.

Furthermore, SExCkine-binding agents described herein (e.g., anti-SExCkine antibodies and antigen-binding fragments thereof, SExCkine-binding receptors such as Bonzo) can be used to detect or measure expression of SExCkine. For example, anti-SExCkine antibodies of the present invention (e.g., mAb 9B10, mAb 10B12, mAb SD7) can be used to detect or measure a mammalian SExCkine in a biological sample (e.g., cells, tissues or body fluids from an individual such as blood, serum, leukocytes (e.g., activated T lymphocytes), bronchoalveolar lavage fluid, saliva, bowel fluid, biopsy specimens). For example, a sample (e.g., tissue and/or fluid) can be obtained from an individual and a suitable assay can be used to assess the presence or amount of SExCkine protein. Suitable assays include immunological and immunochemical methods such as flow cytometry (e.g., FACS analysis) and immunosorbent assays, including enzyme-linked immunosorbent assays (ELISA), radioimmunoassay (RIA), chemiluminescence assays, immuno-blot (e.g., western blot), immunocytochemistry and immunohistology. Generally, a sample and antibody or antigen-binding fragment of the present invention are combined under conditions suitable for the formation of a complex between SExCkine and said antibody or fragment, and the formation of said complex is assessed (directly or indirectly).

The presence of an increased level of SExCIcine reactivity in a sample (e.g., blood, serum, tissue) obtained from an individual can be indicative of inflammation and/or leukocyte (e.g., activated T cell) infiltration and/or accumulation associated with an inflammatory disease or condition, such as inflammatory arthritis (e.g., rheumatoid arthritis), an inflammatory bowel disease, allograft rejection, delayed type hypersensitivity reaction, or an infection such as a viral or bacterial infection. The level of expression of a mammalian SExCkine protein or variant can also be used to correlate increased or decreased expression of a mammalian SExCkine protein with a particular disease or condition, and in the diagnosis of a disease or condition in which increased or decreased expression of a mammalian SExCkine protein occurs (e.g., increased or decreased relative to a suitable control, such as the level of expression in a normal individual). Similarly, the course of therapy can be monitored by assessing SExCkine immunoreactivity in a sample from a subject. For example, antibodies of the present invention can be used to monitor the amount of SExCkine in a sample (e.g., blood, serum, tissue) from a subject being treated with an anti-inflammatory or immunomodulating agent (e.g., immunosuppressive agent, such as cyclosporin A; immunostimulant, such as IL-2).

Kits for use in detecting the presence of a mammalian SExCkine protein in a biological sample can also be prepared. Such kits can include an antibody or functional fragment thereof which binds to a mammalian SExCkine or portion thereof, as well as one or more ancillary reagents suitable for detecting the presence of a complex between the antibody or fragment and SExCkine or portion thereof. The antibody compositions of the present invention can be provided in lyophilized form, either alone or in combination with additional antibodies specific for other epitopes. The antibodies or antigen-binding fragments, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the antibodies or antigen-binding fragments can be provided as a lyophilized mixture with the adjunct ingredients, or the adjunct ingredients can be separately provided for combination by the user. Generally these adjunct materials will be present in less than about 5% by weight based on the amount of active antibody, and usually will be present in a total amount of at least about 0.001% by weight based on antibody concentration. Where a second antibody or antigen-binding fragment capable of binding to the anti-SExCkine antibody or antigen-binding fragment is employed, such antibody or fragment can be provided in the kit, for instance in a separate vial or container. The second antibody or antigen-binding fragment, if present, is typically labeled, and can be formulated in an analogous manner with the antibody formulations described above. The components (e.g., anti-SExCkine antibody or antigen-binding, fragment thereof, ancillary reagent) of the kit can be packaged separately or together within suitable containment means (e.g., bottle, box, envelope, tube). When the kit comprises a plurality of individually packaged components, the individual packages can be contained within a single larger containment means (e.g., bottle, box, envelope tube).

Similarly, the present invention also relates to a method of detecting and/or quantifying expression of a mammalian SExCkine or a portion thereof by a cell, in which a composition comprising a cell or fraction thereof (e.g., membrane fraction, saponin-permeabilized cell) is contacted with an antibody or functional fragment thereof (e.g., mAb 9B10, mAb 10B12, mAb SD7) which binds to a mammalian SExCkine or portion thereof under conditions appropriate for binding of the antibody or fragment thereto, and binding is monitored. Detection of the antibody or antigen-binding fragment, indicative of the formation of a complex between said antibody or fragment and a mammalian SExCkine or a portion thereof, indicates the presence of the receptor. Binding of antibody to SExCkine can be determined using any suitable method. The method can be used to detect cell surface (e.g., on the plasma membrane) SExCkine expression or intracellular (e.g., soluble) SExCkine expression by cells from a subject (e.g., in a sample, such as a body fluid, such as blood, saliva or other suitable sample) (see, for example, Kallas, E. G., et al., *J. Infect. Dis.*, 179:1124–1131 (1999), regarding intracellular staining of cells to detect secreted proteins.) The level of expression of SExCkine (e.g., staining intensity) can be correlated with disease susceptibility, progression or risk.

Methods of Therapy

Modulation of mammalian Bonzo function according to the present invention, through the inhibition or promotion of at least one function characteristic of a mammalian Bonzo protein, provides an effective and selective way of inhibiting or promoting receptor-mediated functions. Similarly, modulation of mammalian SExCkine function according to the present invention, through the inhibition or promotion of at least one function characteristic of a mammalian SExCkine protein, provides an effective and selective way of inhibiting or promoting SEcCkine-mediated or induced functions. Once lymphocytes are recruited to a site, other leukocyte types, such as monocytes, may be recruited by secondary signals. Thus, agents which can modulate Bonzo function, including ligands, inhibitors and/or promoters, such as those identified as described herein, can be used to modulate leukocyte function (e.g., leukocyte infiltration including recruitment and/or accumulation). Similarly, agents which can modulate SExCkine function, including, inhibitors and/or promoters, such as those identified as described herein, can also be used to modulate leukocyte function (e.g., leukocyte infiltration including recruitment and/or accumulation).

In one aspect, the present invention provides a method of modulating (inhibiting or promoting) an inflammatory response in a subject in need of such therapy, comprising administering an effective amount of an agent which inhibits or promotes mammalian Bonzo function to an individual in need of such therapy. In another aspect, the present invention provides a method of modulating (inhibiting or promoting) an inflammatory response in a subject in need of such therapy, comprising administering an effective amount of an agent which inhibits or promotes mammalian SExCkine function to an individual in need of such therapy. In one embodiment, an effective amount of an agent which inhibits one or more functions of a mammalian Bonzo protein (e.g., a human Bonzo) or inhibits one or more functions of a mammalian SExCkine protein (e.g., a human SExCkine), is administered to a subject to inhibit (i.e., reduce or prevent) inflammation. For example, antibodies of the present invention, including antibodies and antigen-binding fragments thereof which bind Bonzo and inhibit binding of ligand to receptor (e.g., mAb 4A11, mAb 7A2, mAb 7F3), and antibodies and antigen-binding fragments thereof which bind SExCkine and inhibit binding of SExCkine to Bonzo (e.g., mAb SD7), can be used in the method. As a result, one or more inflammatory processes, such as leukocyte emigration, chemotaxis, exocytosis (e.g., of enzymes) or inflammatory mediator release, is inhibited. For example, leukocytic infiltration of inflammatory sites (e.g., in an inflamed mucous membrane (e.g., colon, small intestine)) can be inhibited according to the present method. In another embodiment, an effective amount of an agent which inhibits one or more functions of a mammalian Bonzo protein (e.g., a human Bonzo) is administered to a subject to inhibit (i.e., reduce or prevent) Bonzo-mediated homing of leukocytes. In yet another embodiment, an effective amount of an agent which inhibits one or more functions of a mammalian SExCkine protein (e.g., a human SExCkine) is administered to a subject to inhibit (i.e., reduce or prevent) SExCkine-induced Bonzo-mediated homing of leukocytes.

Thus, the invention relates to a method of treating a subject having an inflammatory disease, comprising administering an effective amount of an antagonist of Bonzo and/or SExCkine function. In a particular embodiment, the subject has an inflammatory bowel disease, such as Crohn's disease or colitis. In another particular embodiment, the subject has inflammatory arthritis (e.g., rheumatoid arthritis).

The invention also relates to a method of inhibiting Bonzo-mediated homing of leukocytes in a subject, comprising administering an effective amount of an antagonist of Bonzo function and/or SExCkine function. For example, the homing of leukocytes to mucosal sites can be inhibited using this method.

In one embodiment, an agent (e.g., receptor agonist) which promotes one or more functions of a mammalian Bonzo protein (e.g., a human Bonzo) is administered to induce (trigger or enhance) the recruitment of cells to a desired site or to induce an inflammatory response, such as leukocyte emigration, chemotaxis, exocytosis (e.g., of enzymes) or inflammatory mediator release, resulting in the beneficial stimulation of inflammatory processes. For example, T cells including $CD3^+CD56^+$ cells can be recruited to combat infections (e.g., viral, bacterial, fungal) or tumors (e.g., breast tumors, ovarian tumors, lung tumors, colon tumors, liver tumors, prostate tumors, brain tumors).

In another embodiment, a targeting molecule, as described herein, is administered to effectuate or promote the interaction of a $Bonzo^+$ cell (e.g., $Bonzo^+$ CIK cell) with a target cell (e.g., a cell infected with a virus, tumor cell). For example, a targeting molecule can be administered to promote the interaction of $Bonzo^+$ cytotoxic/cytolytic cells (e.g., cytotoxic T cells, $CD3^+CD56^+$ cells, NK cells, CIK, LAK) with tumor cells and/or virus-infected cells, resulting in the beneficial targeting of cytotoxic/cytolytic activity. Accordingly, a targeting molecule (e.g., a bispecific anti-Bonzo X anti-tumor antigen antibody) can be administered to treat a subject having a tumor or infection (e.g., viral infection). Targeting molecules can also be administered to recruit $Bonzo^+$ cytotoxic/cytolytic cells and/or augment cytotoxic/cytolytic effector function in a subject, for example, as a component of a vaccine.

In another embodiment, the invention is drawn to a method of delivering a desired agent (for example, a drug, such as a chemotherapeutic agent, a toxin) to a $SExCkine^+$ cell. In one embodiment, the method comprises administering an effective amount of an anti-SExCkine antibody or antigen-binding fragment thereof that is conjugated to a chemotherapeutic agent or toxin.

In another embodiment, the invention relates to a method of promoting Bonzo-mediated homing of leukocytes in a subject, comprising administering an effective amount of a promoter (e.g., agonist) of Bonzo function and/or SExCkine function.

Agents which can inhibit the binding of SExCkine to receptor (e.g., Bonzo), including anti-SExCkine antibodies, such as those identified as described herein, can be used to modulate leukocyte function (e.g., leukocyte infiltration including recruitment and/or accumulation). In a particular embodiment, mAb SD7, or an antibody having the epitopic specificity of mAb SD7, can be used to inhibit $Bonzo^+$ leukocyte function (e.g., leukocyte infiltration of $Bonzo^+$ cells including recruitment and/or accumulation).

In one aspect, the present invention provides a method of modulating (inhibiting or promoting) an inflammatory response in a subject in need of such therapy, comprising administering an effective amount of an antibody which inhibits binding of SExCkine to receptor (e.g., Bonzo) to an individual in need of such therapy. In one embodiment, an effective amount of an antibody which inhibits binding of mammalian SExCkine to mammalian Bonzo protein (e.g., a human Bonzo) is administered to a subject to inhibit (i.e., reduce or prevent) inflammation. As a result, one or more inflammatory processes, such as leukocyte emigration, chemotaxis, exocytosis (e.g., of enzymes) or inflammatory mediator release, is inhibited. For example, leukocytic infiltration of inflammatory sites (e.g., in an inflamed mucus membrane (e.g., colon, small intestine)) can be inhibited according to the present method. In another embodiment, an effective amount of an antibody which inhibits binding of mammalian SExCkine to mammalian Bonzo protein (e.g., a human Bonzo) is administered to a subject to inhibit (i.e., reduce or prevent) SExCkine-induced homing of leukocytes.

In another embodiment, Bonzo$^+$ cells are sorted (e.g., from the peripheral blood isolated from a subject) to prepare a population of cells enriched in cytotoxic effector cells (e.g., Bonzo$^+$CD3$^+$CD56$^+$ cells, Bonzo$^+$CD56$^+$ NK cells). For example, peripheral blood cells can be contacted with an anti-Bonzo antibody under conditions suitable for binding of antibody to Bonzo expressed on the surface of cells. The cells to which the anti-Bonzo antibody is bound can be isolated using any suitable method. For example, direct or indirect fluorescence-activated cell sorting or direct or indirect magnetic sorting can be used. The sorted cells can be administered to a subject in need thereof, or the population of sorted cells can be expanded and/or differentiated by culture under suitable conditions. For example, LAK cells or CIK cells can be generated and/or expanded. The expanded cells can also be administered to a subject in need of cytotoxic effector cells (e.g., a subject which has a tumor, a subject which has a viral infection). Preferably, autologous cytotoxic effector cells are administered. Culture conditions which are suitable for expanding cytotoxic effector cells, including CD3$^+$CD56$^+$ cells, CIK and LAK cells, are known in the art (see, for example, Lu, P. H. et al., *J. Immunol.*, 153:1687–1696 (1994); Jin, Y. et al., *Human Immunology*, 59:352–362 (1998)).

In another embodiment, cells which express cell-surface SExCkine are sorted (e.g., from the peripheral blood isolated from a subject) to prepare a population of cells enriched in SExCkine$^+$CD19$^+$ cells, SExCkine$^+$CD14$^+$ monocyte/macrophages and/or SExCkine$^+$dendritic cells. For example, peripheral blood cells can be contacted with an anti-SExCkine antibody under conditions suitable for binding of antibody to SExCkine expressed on the surface of cells. The cells to which the anti-SExCkine antibody is bound can be isolated using the methods described above (e.g., direct or indirect fluorescence-activated cell sorting, direct or indirect magnetic sorting) or other suitable methods. The isolated cells can be administered to a subject in need thereof, or the population of isolated cells can be expanded and/or differentiated by culture under suitable conditions.

The term "subject" is defined herein to include animals such as mammals, including, but not limited to, primates (e.g., humans), cows, sheep, goats, horses, dogs, cats, rabbits, guinea pigs, rats, mice or other bovine, ovine, equine, canine, feline, rodent or murine species.

Diseases and conditions associated with inflammation, infection, and cancer can be treated using the method. In a preferred embodiment, the disease or condition is one in which the actions of lymphocytes, particularly effector cells such as activated or stimulated T lymphocytes and natural killer (NK) cells, are to be inhibited or promoted for therapeutic (including prophylactic) purposes. In a particularly preferred embodiment, the inflammatory disease or condition is a T cell-mediated disease or condition.

Diseases or conditions, including chronic diseases, of humans or other species which can be treated with inhibitors of Bonzo and/or SExCkine function, include, but are not limited to:

inflammatory or allergic diseases and conditions, including systemic anaphylaxis or hypersensitivity responses, drug allergies (e.g., to penicillin, cephalosporins), insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis (e.g., necrotizing, cutaneous, and hypersensitivity vasculitis); spondyloarthropathies; scleroderma; respiratory allergic diseases such as asthma, chronic obstructive pulmonary disease, allergic rhinitis, hypersensitivity lung diseases, hypersensitivity pneumonitis, interstitial lung diseases (ILD) (e.g., idiopathic pulmonary fibrosis, or ILD associated with rheumatoid arthritis, or other autoimmune conditions);

autoimmune diseases, such as arthritis (e.g., rheumatoid arthritis, psoriatic arthritis), multiple sclerosis, systemic lupus erythematosus, myasthenia gravis, diabetes, including diabetes mellitus and juvenile onset diabetes, glomerulonephritis and other nepliritides, autoimmune thyroiditis, Behcet's disease;

graft rejection (e.g., in transplantation), including allograft rejection or graft-versus-host disease;

viral infection, particularly infection by simian immunodeficiency virus (SIV) or human immunodeficiency virus (HIV);

other diseases or conditions in which undesirable inflammatory responses are to be inhibited can be treated, including, but not limited to, atherosclerosis (e.g., transplant-accelerated atherosclerosis), restenosis, cytokine-induced toxicity, myositis (including polymyositis, dermatomyositis).

Diseases or conditions of humans or other species which can be treated with promoters (e.g., an agonist) of Bonzo and/or SExCkine function or targeting molecules, include, but are not limited to:

cancers, for example, solid tumors and/or those with leukocytic infiltration of the skin or organs such as cutaneous T cell lymphoma (e.g., mycosis fungoides);

diseases in which angiogenesis or neovascularization plays a role, including neoplastic disease, retinopathy (e.g., diabetic retinopathy), and macular degeneration;

infectious diseases, such as bacterial infections and tuberculoid leprosy, and especially viral infections;

immunosuppression, such as that in individuals with immunodeficiency syndromes such as AIDS, individuals undergoing radiation therapy, chemotherapy, or other therapy which causes immunosuppression; immunosuppression due to congenital deficiency in receptor function or other causes.

Modes of Administration

According to the method, one or more agents can be administered to the subject by an appropriate route, either alone or in combination with another drug. An effective amount of an agent (e.g., a molecule which inhibits ligand binding, an anti-Bonzo antibody or antigen-binding fragment thereof, an anti-SExCkine antibody or antigen-binding fragment thereof, a targeting molecule) is administered. An effective amount is an amount sufficient to achieve the desired therapeutic or prophylactic effect, under the conditions of administration, such as an amount sufficient to promote the interaction of a Bonzo⁺ cell with a target cell. For example, an effective amount can be an amount that is sufficient for inhibition or promotion of Bonzo receptor function, and thereby, inhibition or promotion, respectively, of a Bonzo-mediated process (e.g., an inflammatory response). An effective amount can also be an amount that is sufficient for inhibition or promotion of SExCkine ligand function, and thereby, inhibition or promotion, respectively, of a SExCkine-mediated process (e.g., an inflammatory response). The agents can be administered in a single dose or multiple doses. The dosage can be determined by methods known in the art and is dependent, for example, upon the agent chosen, the subject's age, sensitivity and tolerance to drugs, and overall well-being. Typically, an effective amount can range from about 0.01 mg per day to about 100 mg per day for an adult. Preferably, the dosage ranges from about 1 mg per day to about 100 mg per day or from about 1 mg per day to about 10 mg per day. Antibodies and antigen-binding fragments thereof, such as human, humanized and chimeric antibodies and antigen-binding fragments can often be administered with less frequency than other types of therapeutics. For example, an effective amount of an antibody can range from about 0.01 mg/kg to about 5 or 10 mg/kg administered daily, weekly, biweekly or monthly.

A variety of routes of administration are possible including, for example, oral, dietary, topical, transdermal, rectal, parenteral (e.g., intravenous, intraarterial, intramuscular, subcutaneous, intradermal injection), and inhalation (e.g., intrabronchial, intranasal or oral inhalation, intranasal drops) routes of administration, depending on the agent and disease or condition to be treated. Administration can be local or systemic as indicated. The preferred mode of administration can vary depending upon the particular agent (e.g., Bonzo antagonist) chosen, and the particular condition (e.g., disease) being treated, however, oral or parenteral administration is generally preferred.

The agent can be administered as a neutral compound or as a salt. Salts of compounds containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium and the like.

The agent can be administered to the individual as part of a pharmaceutical composition for modulation of Bonzo function comprising an inhibitor or promoter of Bonzo function and a pharmaceutically-acceptable carrier. In another embodiment, the agent is administered to the individual as part of a pharmaceutical composition for modulation of SExCkine function comprising an inhibitor or promoter of SExCkine function and a pharmaceutically-acceptable carrier. Formulation will vary according to the route of administration selected (e.g., solution, emulsion, capsule). Suitable pharmaceutical carriers can contain inert ingredients which do not interact with the promoter (agonist) or inhibitor (antagonist) of Bonzo and/or SExCkine function. Standard pharmaceutical formulation techniques can be employed, such as those described in Remington's Pharmaceutical Sciences, Mack Publishing Company, Easton, Pa.

Suitable pharmaceutical carriers for parenteral administration include, for example, sterile water, physiological saline, bacteriostatic saline (saline containing about 0.9% mg/mL benzyl alcohol), phosphate-buffered saline (referred to herein as PBS), Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986). For inhalation, the agent can be solubilized and loaded into a suitable dispenser for administration (e.g., an atomizer, nebulizer or pressurized aerosol dispenser).

Furthermore, where the agent is a protein or peptide, the agent can be administered via in vivo expression of the recombinant protein. In vivo expression can be accomplished via somatic cell expression according to suitable methods (see, e.g., U.S. Pat. No. 5,399,346). In this embodiment, a nucleic acid encoding the protein can be incorporated into a retroviral, adenoviral or other suitable vector (preferably, a replication-deficient infectious vector) for delivery, or can be introduced into a transfected or transformed host cell capable of expressing the protein for delivery. In the latter embodiment, the cells can be implanted (alone or in a barrier device), injected or otherwise introduced in an amount effective to express the protein in a therapeutically-effective amount.

The present invention will now be illustrated by the following Examples, which are not intended to be limiting in any way.

EXAMPLE 1

Methods and Materials

Construction of Recombinant Cells Expressing Bonzo

DNA encoding Bonzo was obtained by polymerase chain reaction (PCR) using human genomic DNA as template with a synthetic 5'-olignucleotide primer (ttt gga tcc atg tat ccc tat gac gtg ccc gac tat gct gca gag cat gat tac cat gaa gac tat ggg, SEQ ID NO: 9) and a 3'-oligonucleotide primer (ttt gcg gcc gcc tat aac tgg aac atg ctg gtg gcc tc, SEQ ID NO: 10) which contained flanking BamHI and NotI restriction sites, respectively. The 5'-oligonucleotide primer was designed to produce a DNA encoding Bonzo that contains an N-terminal Hemagglutinin (HA) epitope (CYPYDVPDYASL; SEQ ID NO: 11). The PCR contained 0.2 µM primers (total), 0.39 µg human genomic DNA, 0.2 mM dNTPs, 3.75 U PFU polymerase. Cycling parameters were: 95° C. for 5 minutes, followed by 30 cycles of 95° C. for 30 seconds, 55° C. for 1 minute and 72° C. for 1.5 minutes, then 72° C. for 10 minutes. The PCR fragment was subcloned into the BamHI and NotI sites of pCDEF/IRES. pCDEF/IRES was prepared by inserting the MluI-NotI fragment from pCDEF3 (Goldman, L. A., et al., *Biotechniques*, 21:1013–1015 (1996)) into the MluI-NotI sites of pIRESneo (Clontech) which contains a bicistronic fragment to facilitate the selection of high expressors. An EF1 promoter drove expression of the cDNA inserted into pCDEF/IRES. The resulting construct was transfected into the L1.2 cell line (a murine pre-B lymphoma).

The murine pre-B lymphoma cell line L1.2 was obtained from Dr. Eugene Butcher (Stanford University) and maintained in RPMI-1640 supplemented with 10% bovine serum. 20 µg of linearized plasmid was used to transfect the cell line as follows. L1.2 cells were washed twice in HBSS and resuspended in 0.8 mL of the same. The plasmid DNA was mixed with the cells and incubated for 10 minutes at room temperature and then transferred to a 0.4 cm electroporation cuvette and a single pulse applied at 250 V, 960 µF. The electroporation was followed by a 10 minute incubation at room temperature. G418 was added to a final concentration of 0.8 mg/mL 48 hr post-transfection and the cells plated in 96 well plates at 25,000 cells/well. After 2–3 weeks under drug selection, cells expressing high levels of Bonzo were selected by staining with anti-HA.11 mAb (Babco, Berkely, Calif.) and subcloned. The resulting stable transfectants were used to immunize mice.

Generation of Anti-Bonzo Hybridomas

MAbs reactive with Bonzo were generated by immunizing mice with L1.2 cells expressing high levels of transfected Bonzo (Bonzo/L1.2 cells). Six female mice (C57BL6) were immunized by intraperitoneal injection of about $10^7$ cells in phosphate-buffered saline (PBS). The mice received six injections at three week intervals. The Bonzo/L1.2 cells used for the first 2–3 injections were treated with mitomycin C to prevent tumor growth. A final (seventh) injection was administered intravenously. Four days after the final injection, the animals were sacrificed, the spleens were removed, and splenocytes were fused with SP2/0 cells and selected in media containing hypoxanthine, aminopterine and thymine (HAT media) as described (Coligan, J. E. et al., *Current Protocols in Immunology*, John Wiley and Sons, New York (1992)). About 3000 to about 5000 hybridomas were screened for each fusion. Four hybridomas that secreted anti-Bonzo mAbs were isolated and are presented in Table 1. The hybridomas can be maintained under standard culture conditions (humidified incubator, 37° C., 5% $CO_2$) in the following culture media: Dulbecco's modified Eagle medium (DMEM) containing 10% fetal bovine serum, 2 mM L-glutamine, 1 mM sodium pyruvate and 100 ng/mL interleukin 6. Penicillin (50 U/mL) and streptomycin (50 µg/mL) can be added to the culture media if desired.

TABLE 1

| hybridoma | antibody | isotype | inhibited binding of SExCkine to Bonzo |
|---|---|---|---|
| Murine hybridoma 4A11 | mAb 4A11 | IgG2b | yes |
| Murine hybridoma 7A2 | mAb 7A2 | IgG2a | yes |
| Murine hybridoma 7F3 | mAb 7F3 | IgG2a | yes |
| Murine hybridoma 9G2 | mAb 9G2 | IgM | partial | mAb Specificity and Immunofluorescent Staining

The reactivity of the mAbs was assessed by staining (indirect immunofluorescence and flow cytometry) human peripheral blood mononuclear cells (PBMCs), isolated by Lymphoprep™ (Nycomed Pharma AS, Oslo Norway) density gradient centrifugation of venous blood collected from volunteer donors, and numerous transfected L1.2 cells that expressed chemokine receptors (CCR1, CCR2, CCR3, CCR4, CCR5, CCR6, CCR7, CCR8, CXCR1, CXCR2, CXCR3, CXCR4, CXCR5, GPR5, V28 and GPR9-6) or orphan G protein-coupled receptors (Bob, LyGPR, AF014958 (AF, CRAM), APJ and RDC). Nucleotide sequences encoding these receptors are deposited in Genbank under the accession numbers presented in Table 2. For staining, transfected cells or PBMCs were washed once with phosphate-buffered saline (PBS) and resuspended in PBS containing 5% human serum and 0.1% sodium azide (staining buffer). Cells were then incubated with 50 µL of hybridoma culture supernatant or isotype-matched control mAbs MOPC 141 (IgG2b), UPC 10 (IgG2a) or TEPC 183 (IgM) (isotype control mAbs were used at 1 µg/mL and were purchased from Sigma Chemical Co., St. Louis, Mo.) for 20 minutes at 4° C. Then, the cells were washed with staining buffer and resuspended in 50 µL FITC-conjugated, affinity purified F(ab')₂ goat anti-mouse IgG (Jackson ImmunoResearch Laboratories, West Grove, Pa.) diluted 1:200 in staining buffer. The resuspended cells were incubated for 20 minutes at 4° C., and then washed once in staining buffer and analyzed on the FACScan® (Becton-Dickinson, Franklin Lakes, N.J.).

TABLE 2

| Receptor | Accession number |
|---|---|
| CCR1 | L09230 |
| CCR2 | U03882 |
| CCR3 | U49727 |
| CCR4 | X85740 |
| CCR5 | X91492 |
| CCR6 | U45984 |
| CCR7 | L31581 |
| CCR8 | U62556 |
| GPR-9-6 (CCR9) | U45982 |
| CXCR1 | M68932 |
| CXCR2 | M73969 |
| CXCR3 | X95876 |
| CXCR4 | A45747 |
| CXCR5 | X68149 |
| Bob (GPR15) | U34806 |
| LyGPR | X98510 |
| AF014958 (CRAM) | AF014958 |
| V28 (Cx3CR1) | U20350 |
| APJ | U03462 |
| GPR5 | P46094 |
| RDC | M64749 |

Chemotaxis Assay

Primary cells (in vitro-derived TH cells, LAK cells, CIK cells or Bonzo/L1.2 cells were used in chemotaxis assays.

Assays Using CIK Cells, $T_H1$ Cells or $T_H2$ Cells:

Endothelial cells (ECV 304, American Type Culture Collection, Manassas, Va. or the European Collection of Animal Cell Cultures (Reference No: 92091712), Salisbury, United Kingdom) were cultured on 6.5 mm diameter TRANSWELL culture inserts (Costar Corp., Cambridge, Mass.) with 3.0 µm pore size. The culture media consisted of M199+10% FCS, L-glutamine, and antibiotics. The assay media consisted of equal parts RPMI 1640 and M199 with 0.5% BSA. The day before the assay, $2 \times 10^5$ ECV 304 cells were plated onto each insert of the 24 well TRANSWELL chemotaxis plate and the plate was incubated at 37° C. (In some instances, ECV 304 cells were plated on the inserts up to a week before the assay.) SExCkine was added to the 24-well tissue culture plates in a final volume of 600 µL. Endothelial-coated TRANSWELLs were then inserted into each well and $10^6$ cells of the leukocyte type being studied were added to the top chamber in a final volume of 100 µL of assay medium. The plate was incubated at 37° C. in 5% $CO_2$/95% air for 1–2 hours. The cells that migrated to the lower chamber were then removed, placed in FACS tubes and counted on a FACScan (Becton-Dickinson, Franklin Lakes, N.J.) using the acquisition phase at 30 second intervals. Forward angle and side scatter gates were set to exclude debris. Where indicated, the data points were the result of duplicate wells, with the mean value shown and the error bars representing the standard deviation.

For antibody-inhibition studies, the leukocytes being studied were incubated with concentrated hybridoma supernatant containing anti-Bonzo mAbs, purified anti-Bonzo mAbs at varying concentrations or isotype-matched control antibodies for about 20 minutes at 37° C. prior to being added to the top chamber of the TRANSWELL.

Assays Using Bonzo/L1.2 Cells:

Two days prior to the assay, the Bonzo/L1.2 cells were split to a density of $0.3 \times 10^6$/mL. On the day of the assay the transfected Bonzo/L1.2 cells were centrifuged and resuspended at a density of $1 \times 10^7$/mL in an assay buffer which consisted of DMEM supplemented with 10% bovine calf serum. The assay was conducted essentially as described above, except that no endothelial cells were used.

Preparation of Chronically-Activated $T_H 1$ and $T_H 2$ Lymphocytes

As previously described (Sornasse, T., et al., *J. Exp. Med.*, 184:473–483 (1996)), six-well Falcon plates were coated overnight with 10 µg/mL anti-CD28 and 2 µg/mL OKT3, and then washed twice with PBS. Umbilical cord blood CD4+ lymphocytes (Poietic Systems, German Town, Md.) were cultured at $10^5 – 10^6$ cells/mL in DMEM with 10% FCS and IL-2 (4 ng/mL). IL-12 (5 ng/mL) and anti-IL-4 (1 µg/mL) were used to direct to $T_H 1$, while IL-4 (5 ng/mL) and anti-IFN gamma (1 µg/mL) were used to direct to $T_H 2$. After 4–5 days, the activated $T_H 1$ and $T_H 2$ lymphocytes were washed once in DMEM and cultured for 4–7 days in DMEM with 10% FCS and IL-2 (1 ng/mL). Following this, the activated $T_H 1$ and $T_H 2$ lymphocytes were re-stimulated for 5 days with anti-CD28/OKT3 and cytokines as described above, but with the addition of anti-CD95L (1 µg/mL) to prevent apoptosis. After 4–5 days the $T_H 1$ and $T_H 2$ lymphocytes were washed and then cultured again with IL-2 for 4 days. Activated $T_H 1$ and $T_H 2$ lymphocytes were maintained in this way for a maximum of three cycles.

Preparation of CD3 Blasts

CD3 blasts were generated using anti-CD3 antibody (OKT3, Pharmingen, San Diego, Calif.) and maintained in medium supplemented with recombinant human IL-2 as described (Wu, L., et al., *J. Exp. Med.*, 185:1681–1692 (1997)). Briefly, $2 \times 10^6$ PBMCs/mL in RPMI-1640 plus 10% FCS were added to tissue culture plates coated with OKT3 (5 µg/mL). After 4–6 days of culture, blasts were removed to fresh media supplemented with recombinant human IL-2 (100 U/mL, Hoffman-LaRoche, Nutley, N.J.).

Preparation of LAK and CIK Cells

PBMCs were resuspended in complete RPMI (cRPMI) containing 10% FCS (Hyclone Labs, Logan, Utah), penicillin (50 U/mL), streptomycin (50 µg/mL), L-glutamine (2 mM ), 2-mercaptoethanol (50 µM). Adherent cells were removed using two rounds of adherence to plastic at 37° C. LAK cells were prepared by culturing the resulting non-adherent cells in cRPMI supplemented with IL-2 (5 ng/mL) for 3–6 days. CIK cells were prepared by culturing the resulting non-adherent cells in cRPMI supplemented with IFN-γ (1000 U/mL) for 24 hours. Then, IL-2 (final concentration 5 ng/mL) and anti-CD3 mAb OKT3 (final concentration 25 ng/mL) were added, and the cells were cultured for an additional 2–3 weeks. The resulting CIK cells were subcultured every 3 days in fresh cRPMI supplemented with IL-2 (5 ng/mL).

Preparation of $T_R 1$ Cells $T_R 1$ cells were prepared by stimulating umbilical cord blood CD4+ lymphocytes in the presence of IL-10 (see, for example, Groux, et al., *Nature,*, 389:737–742 (1997)).

Northern Blot Analysis

Human multiple tissue northern blots I and II and a cancer cell line blot (Clontech, Palo Alto, Calif.) were used to analyze the expression of the gene encoding the Bonzo ligand. cDNA probes were labeled with $\alpha^{32}$P-dCTP by priming with random hexamers. A 400 bp fragment representing most of the chemokine domain of SExCkine cDNA cloned in pCDEF3 (from the 5' EcoR1 site (within vector pCDEF3) to an EcoRV site of a cDNA encoding human SExCkine (SEQ ID NO: 3)) was used as the hybridization probe for all blots. Hybridization was performed at 68° C. for 1 hour in ExpressHyb (Clontech) with denatured probe at a concentration of $1 \times 10^6$ CPM/mL. Blots were then washed for 20 minutes in 2×SSC/0.05% SDS at room temperature followed by high stringency washes at 50° C., 60° C., or 65° C. in 0.1×SSC/0.1% SDS for 20 minutes per wash and exposed to Kodak XAR film with an intensifying screen.

Construction of Recombinant SExCkine His-Tagged and Alkaline Phosphatase Expression Plasmids Fusion proteins consisting of amino-terminal regions of SExCkine fused to a C-terminal Histadine (His) tag were made in pEF-His or pEF1/V5-His A vector from Invitrogen (Carlsbad, Calif.) and fusion proteins consisting of N-terminal SExCkine regions fused to human alkaline phosphatase with a C-terminal His tag were made in the pDERF-SEAP vector (Yoshie, O., et al., *J. Leukoc. Biol.*, 62(5): 634–644 (1997)).

The alkaline phosphatase fusion was produced by amplifying human SExCkine cDNA (SEQ ID NO:3) by PCR using a 5' synthetic oligonucleotide primer that contained a SalI site (5' cgc gtc gac age cga gat ggg acg gga ctt g 3', SEQ ID NO:12) and a 3' synthetic oligonucleotide primer that contained a XbaI site (5' ggt cta gat gtc ctg gct gtg gga cca 3', SEQ ID NO:13). The 5' primer (SEQ ID NO:12) annealed to nucleotides 15–29 of SEQ ID NO:3 and the 3' primer (SEQ ID NO:13) annealed to nucleotides 602–622 of SEQ ID NO:3. The DNA product from this reaction encodes for a protein which begins at the initiating Met (amino acid residue 1 of SEQ ID NO:4. The PCR was run for 30 cycles (95° C. (30 seconds), 55° C. (30 seconds), 72° C. (1 minute)).

Similarly, a region encoding the entire extracellular domain of SExCkine was made by PCR using a synthetic 5' primer that contained a Bam-HI site (5' gag gat cca tgg gac ggg act tg 3', SEQ ID NO:14) and a synthetic 3' primer that contained an XbaI site (5' cct eta gat gat gtc ctg gct gtg gga c 3', SEQ ID NO:15). The 5' primer (SEQ ID NO:14) annealed to nucleotides 15–29 of SEQ ID NO:3 and the 3' primer (SEQ ID NO:15) annealed to nucleotides 604–622 of SEQ ID NO:3. The DNA product of this reaction, which encodes a protein beginning at the initiating Met, was subcloned into the pEF-His vector as described below.

Additional constructs encoding fragments of the extracellular domain of SExCkine were made by PCR using a 5' primer (SEQ ID NO:14) and synthetic primer KHLL 3' (5' ggt cta gaa agt aaa tgc ttc tgg tgg gc 3', SEQ ID NO:16) or synthetic primer LMS 3' (5' cct cta gag ctc atc aat tcc tga acc c 3', SEQ ID NO:17) or synthetic primer 155 3' (5' ggt cta gac tgg gag ggt ggg gcg ctg ag 3', SEQ ID NO:18). Primer KHLL 3' annealed to nucleotides 345–364 of SEQ ID NO:3, and the product of the amplification reaction encoded residues 1 to 117 of SExCkine (SEQ ID NO:4). Primer LMS 3' annealed to nucleotides 280–300 of SEQ ID NO:3, and the product of the amplification reaction encoded residues 1 to 95 of SExCkine (SEQ ID NO:4). Primer 155 3' annealed to nucleotides 457–477 of SEQ ID NO:3, and the product of the amplification reaction encoded residues 1 to 155 of SExCkine (SEQ ID NO:4). Primers KHLL 3', LMS 3' and 155 3' each contained an XbaI restriction site.

The PCR inserts were purified using a Qiagen PCR purification kit (Qiagen, Valencia, Calif.), run on a 1% agarose gel and the fragment sizes were confirmed next to a 1 kb ladder. The PCR inserts and vectors (pDREF-SEAP, pEF-His, pEF1/V5-His A) were cut with the appropriate enzymes (SalI and XbaI, BamHI and XbaI). The inserts were ligated to the appropriate vector using 25 ng cut vector, 75 ng cut insert, 2 μL ligase buffer, 1 μL ligase and 5 μL $H_2O$ for a final volume of 10 μL. The ligation reaction was incubated at 15° C. overnight (about 14 hours). The ligation was transformed into DH10B cells which were plated on selective media (LB amp). Plasmids were purified from transformants and constructs containing the inserted PCR fragment were identified by restriction analysis.

Transfection and Assays of Recombinant SExCkine Proteins

Thirty 10 cm plates (Becton-Dickinson, Franklin Lakes, N.J.) were seeded with $1 \times 10^6$ 293T cells in DMEM+10% FCS. The next day the 293T cells were transfected by adding 10 μg SExCkine/SEAP DNA to 790 μL opti-MEM (800 μL total) and mixing it with a solution of 60 μL LipofectAMINE™ 2000 (Gibco/BRL, Rockville, Md.) in 740 μL opti-MEM (800 μL total). The mixture was incubated at room temperature for 30 min, an additional 6.4 mL of opti-MEM was added to the mixture, and the mixture was added to the plates containing 293T cells. The plates were incubated at 37° C. for 3 hours, then 8.0 mL DMEM+20% FCS was added. After 24 hours, the transfection mixture was removed, the plates were washed with 1× PBS, and 10 mL of serum-free DMEM was added. The plates were then incubated for 3 days. The media (culture supernatant) was removed and filtered (500 mL filter bottle) to remove cellular debris. The harvested media was assayed for chemotactic activity using Bonzo/L1.2 cells essentially as described above. In addition, dilution curves were generated using supernatant diluted in media in a range of undiluted to 1:16 to assess general activity.

Purification of Recombinant SExCkine-Alkaline Phosphatase Fusion Protein

A 0.79 $cm^2 \times 5$ cm column (Biorad, Hercules, Calif.) was packed with 1 mL of anti-alkaline phosphatase agarose (Sigma #A2080). The agarose was washed with 10 mL 1× PBS and the protein eluted with 10 mL 50 mM sodium citrate, pH 3.2 (elution buffer was allowed to settle at the bottom of the column for 1 hour before elution). 10×1 mL elution fractions were collected and the protein concentration of each was determined using the Bradford assay (10 μL of each elution fraction was assayed). 50 μL of Tris base (pH 10.8) was added to each elution to neutralize the elution buffer. Elution fractions containing the fusion protein were identified by Western blot (4–20% Tris glycine gel, blocked with 5% milk) using an anti-His antibody (Qiagen, Valencia, Calif.).

Alkaline phosphatase activity in the elution fractions was determined by spotting a nitrocellulose blot with 5 μL of elution fractions 1 and 2, 5 μL of Tris buffer as a negative control, and 5 μL of original culture supernatant as a positive control. The blot was blocked for 2 hours in 5% milk and developed using an alkaline phosphatase detection kit (10 mL buffer, 100 μL reagent A, 100 μL reagent B; BioRad).

Chemotactic activity was determined as described using $1 \times 10^6$ transfected L1.2 cells expressing Bonzo (Bonzo/L1.2 cells) and 0.5 nM, 5 nM, and 25 nM of purified SExCkine/SEAP (concentrations based on the results of a Bradford assay).

Results and Discussion

Figure 3:
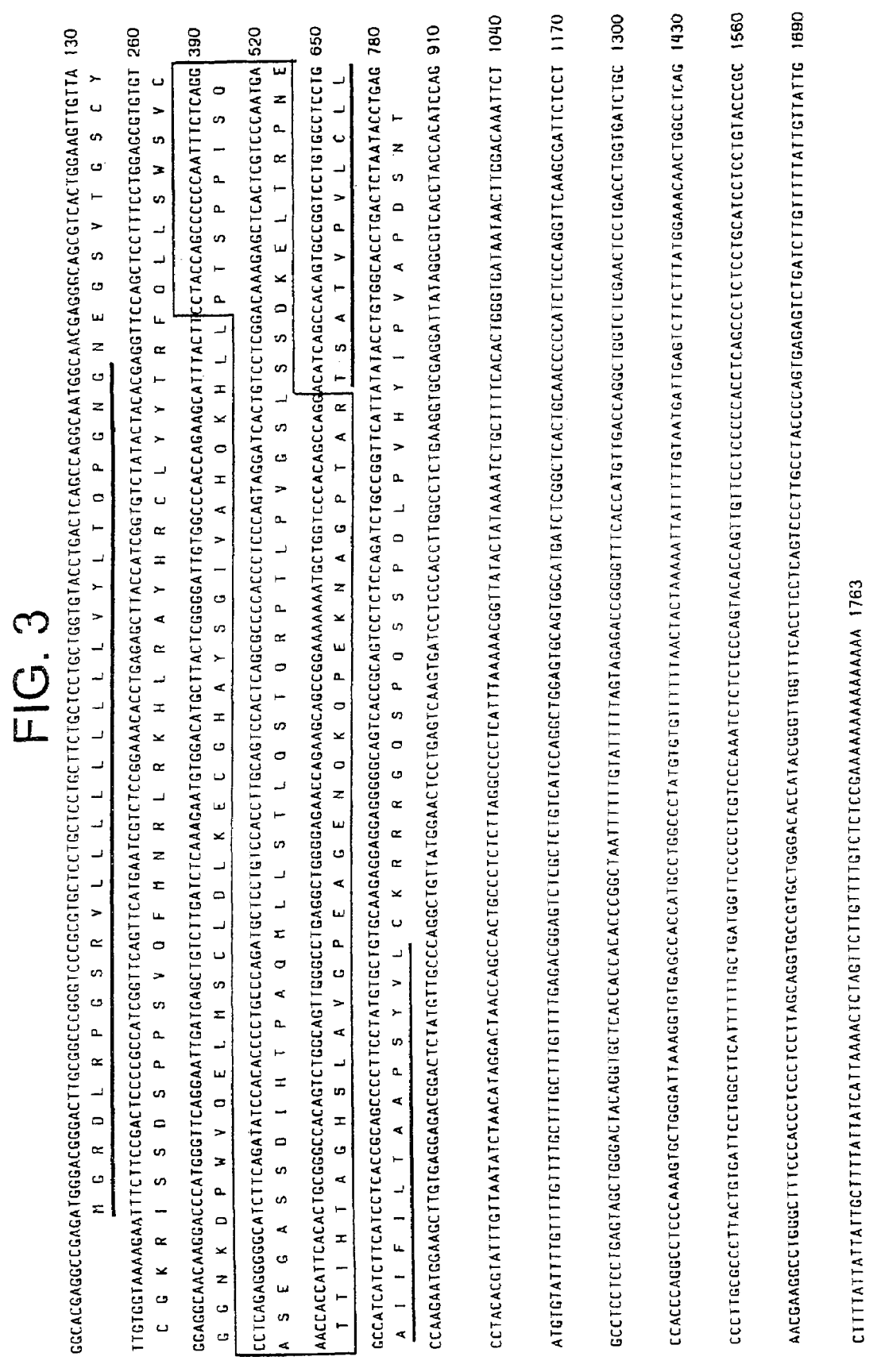
Figure 30:
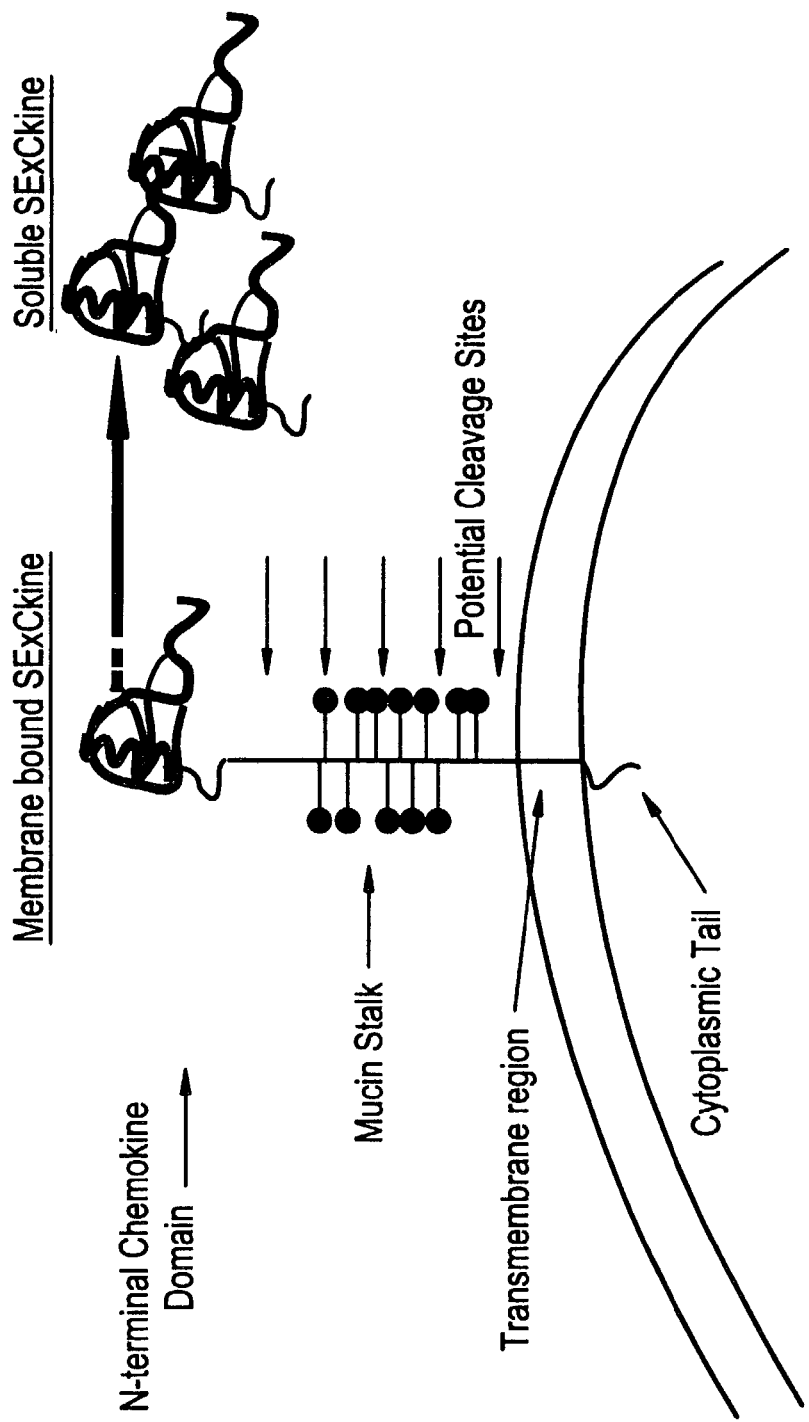
FIG. 30 illustrates the predicted structure of the transmembrane form of human SExCkine.

During the course of this study a natural ligand for Bonzo, that induced chemotaxis of Bonzo/L1.2 cells, was identified. This ligand is referred to herein as SExCkine (Spleen Extracted Chemokine, SEQ ID NO:4). SExCkine is a CXC chemokine based upon the positions of conserved cysteine residues. However, the SExCkine protein includes an N-terminal chemokine domain, a membrane-proximal mucin domain, a transmembrane region and a cytoplasmic tail (FIG. 3, FIG. 30). Thus, SExCkine is structurally similar to the CX3C chemokine fractalkine (Bazan, J. F., et al., Nature 385(6617):640–644 (1997)). The primary structure indicates that SExCkine can be expressed on the cell membrane (as an integral membrane protein). Chemoattractant activity was found in the supernatant of 293T cells transfected with a cDNA (SEQ ID NO:3) encoding the full length protein (FIG. 7). Thus, at least some portion of SExCkine is processed (e.g., by cleavage) to form a soluble chemokine.

Northern blot analysis revealed that multiple transcripts which hybridized with a SExCkine cDNA probe were detected in many tissues, including, spleen, thymus, prostate, testis, ovary, small intestine, colon, peripheral blood leukocytes, pancreas, kidney, liver, lung, placenta, brain and heart, and several cancer cell lines, including melanoma, lung carcinoma, colorectal adenocarcinoma, Burkitt's Lymphoma, lymphoblastic leukemia, Hela cells and promelocytic leukemia HL60. High expression of a 1.8 kb transcript which corresponds in size to isolated cDNA encoding human SExCkine (SEQ ID NO:3) was seen in spleen, peripheral blood leukocytes, prostate, testis and ovary. The nature of other hybridizing transcripts, which can be partially processed molecules or molecules with a similar nucleotide sequence, is under investigation.

Additional Northern blot analysis using a fragment encompassing the entire chemokine domain of SExCkine as a probe revealed that a band of approximately 2.4 kb was observed in lung, liver, fetal liver, spleen and peripheral blood leukocytes. Lower levels of expression were also seen in kidney, pancreas, lymph nodes and placenta. Multiple bands were also detected using the full-length SExCkine cDNA and were most likely due to the repeat sequences found in the 3' end of the cDNA and parts of the mucin domain. In addition, exposure of the blot prior to more stringent washes revealed the presence of other sized RNA species in certain tissues, indicating that related genes may be expressed in some of the examined tissues.

Figure 10:
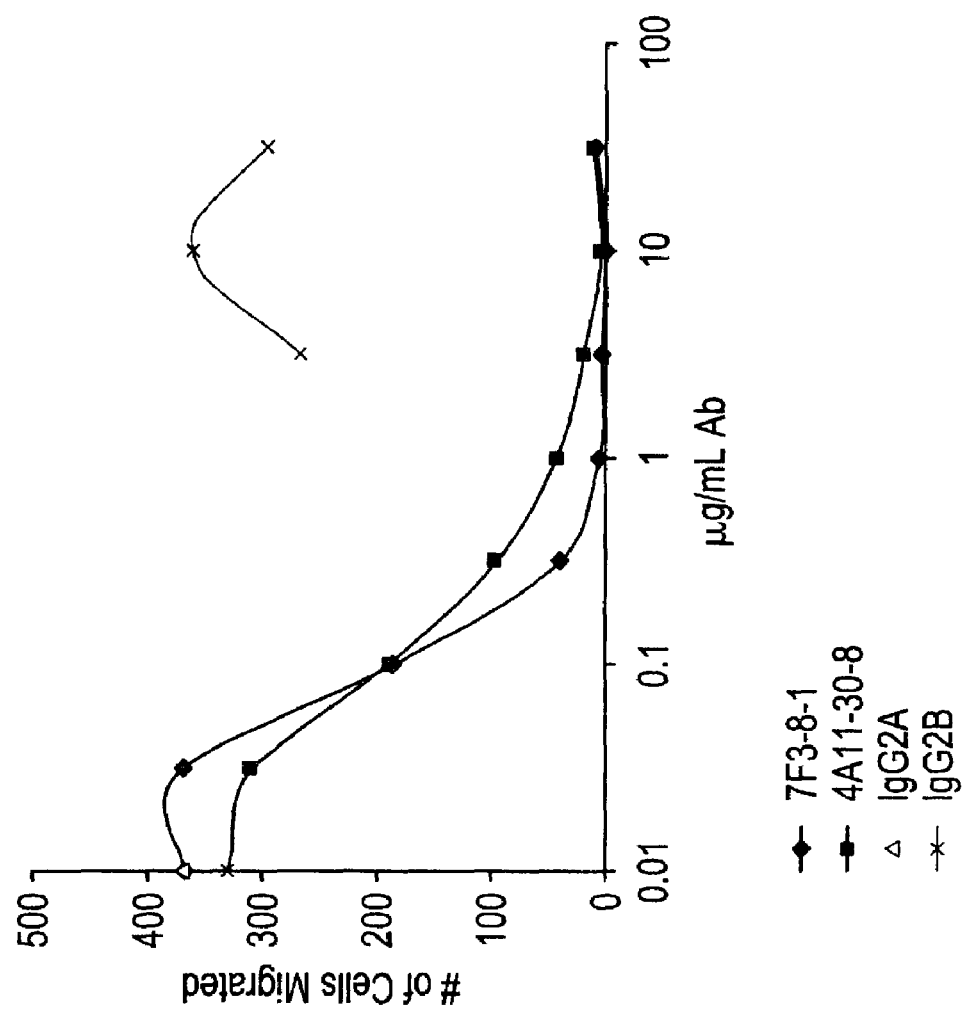
FIG. 10 is a graph showing dose dependent inhibition of SExCkine-induced chemotaxis of Bonzo/L1.2 cells by mAb 7F3 or mAb 4A11. Bonzo/L1.2 cells were incubated with concentrated supernatant from murine hybridoma 7F3 which produces mAb 7F3, from murine hybridoma 4A11 which produces mAb 4A11, or from a murine hybridoma which produces an isotype control antibody (IgG2a or IgG2b), prior to exposure to SExCkine.
Figure 11A:
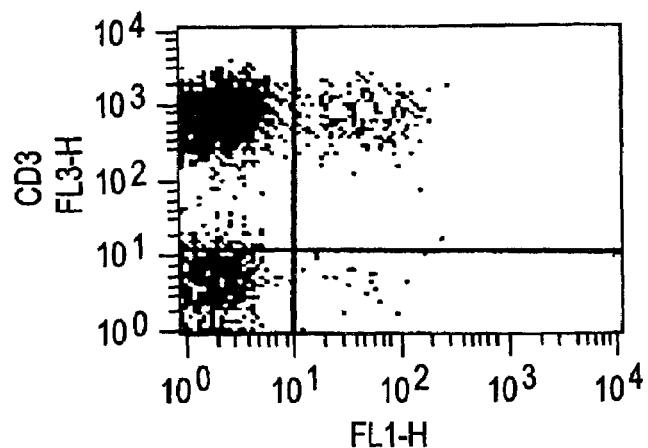
FIGS. 11A–11H are fluorescence plots showing Bonzo expression on various populations of human peripheral blood mononuclear lymphocytes. Expression of Bonzo (x-axis) and lymphocyte subset markers (y-axes) CD3 (FIG. 11A), CD4 (FIG. 11B), CD8 (FIG. 11C), CD56 (FIG. 11D), CD45RO (FIG. 11E), CD45RA (FIG. 11F), CD20 (FIG. 11G) and CD14 (FIG. 11H) on human peripheral blood lymphocytes were assessed by two-color staining. Quadrants were set according to staining of isotype control mAbs (IgG2a). The data are representative of multiple donors analyzed.
Figure 11B:
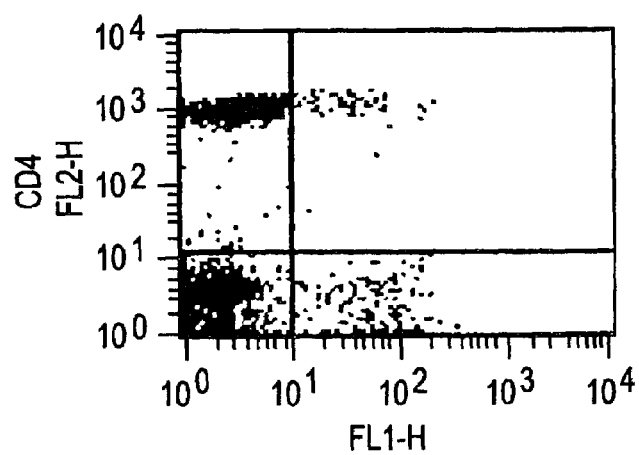
Figure 11C:
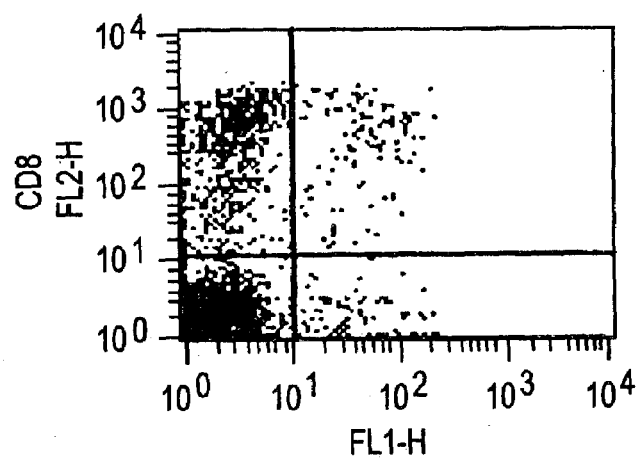
Figure 11D:
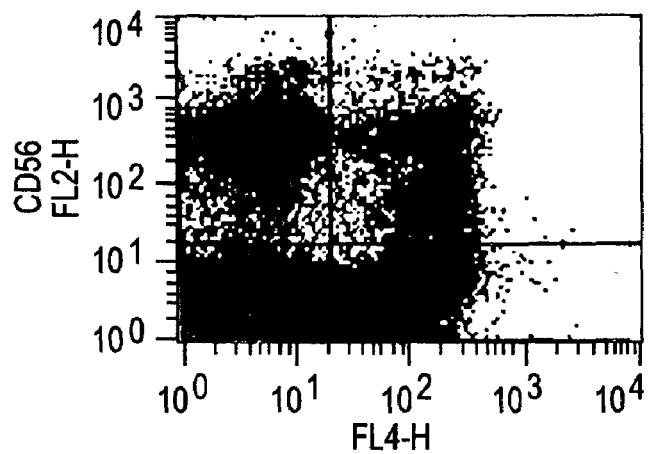
Figure 11E:
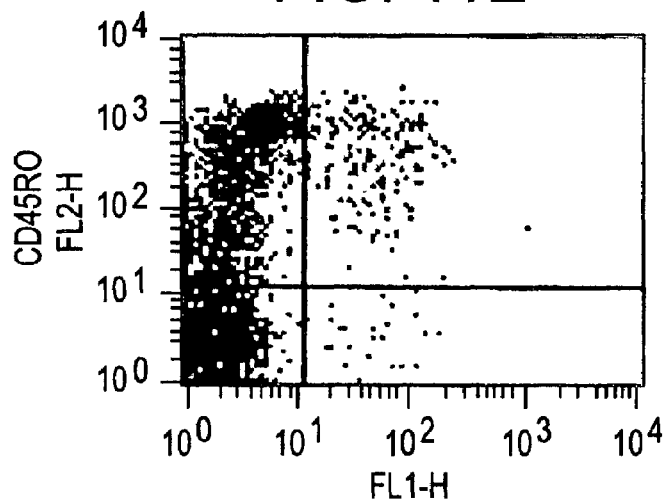
Figure 11F:
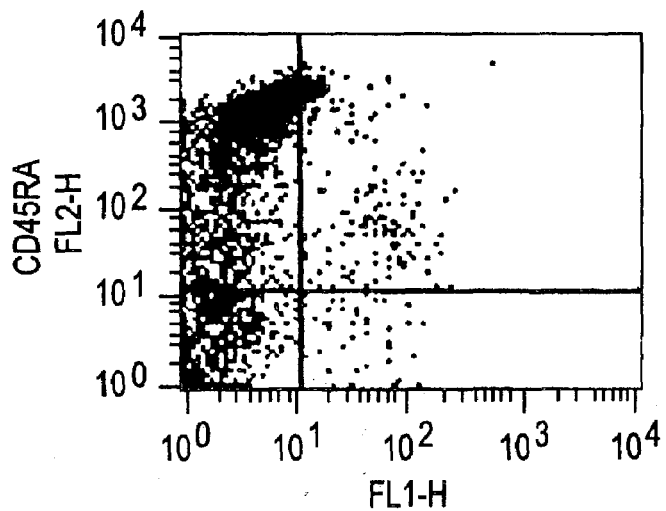
Figure 11G:
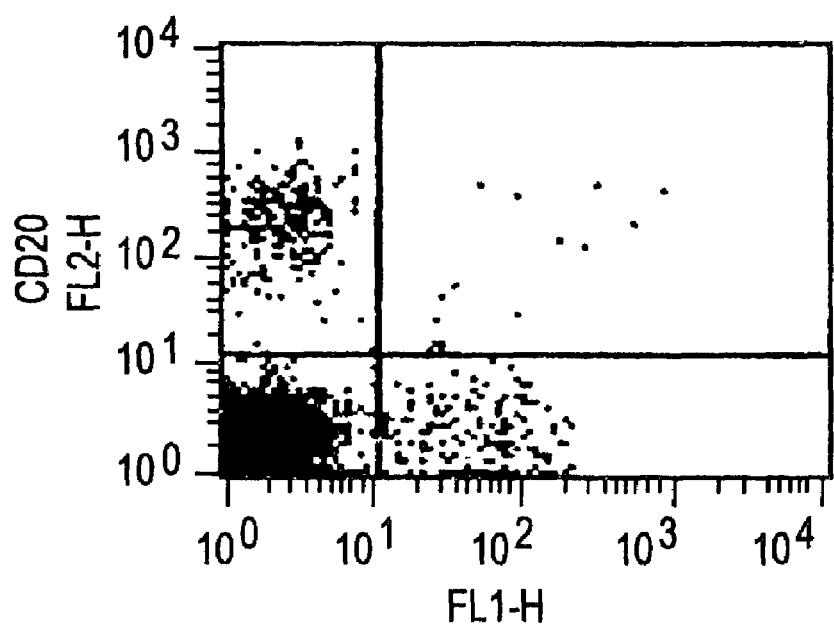
Figure 11H:
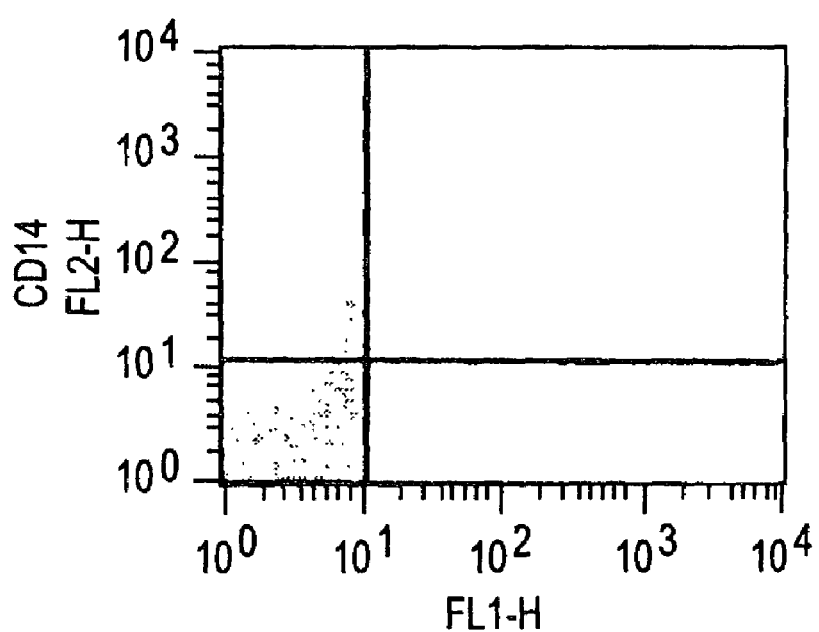
Figure 12A:
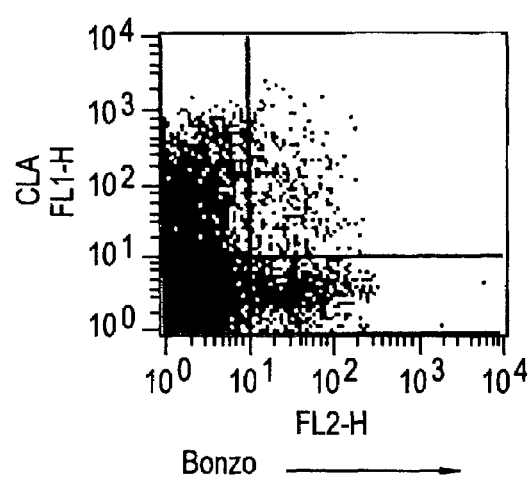
FIGS. 12A–12D are fluorescence plots showing Bonzo expression on subsets of human peripheral blood CD4$^+$ T lymphocytes. Expression of Bonzo (x-axis) and lymphocyte subset markers (y-axes) CLA (FIG. 12A), CD49d ($\alpha$4 integrin, FIG. 12B), $\beta$7 integrin (FIG. 12C) and CD103 ($\alpha$E integrin, FIG. 12D) on human peripheral blood CD4$^+$ T lymphocytes were assessed by three-color staining, gating on CD4$^+$ cells. Quadrants were set according to staining of isotype control mAbs (IgG2a). The data are representative of multiple donors analyzed.
Figure 12B:
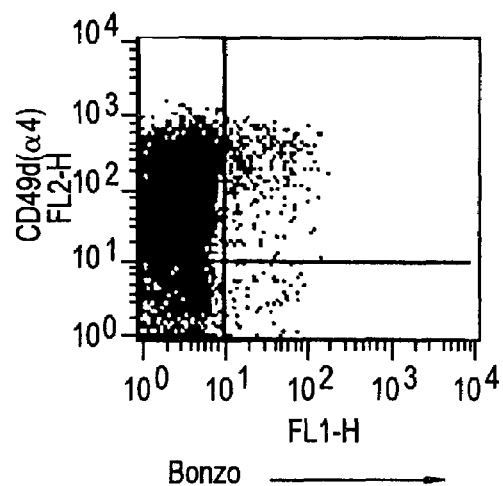
Figure 12C:
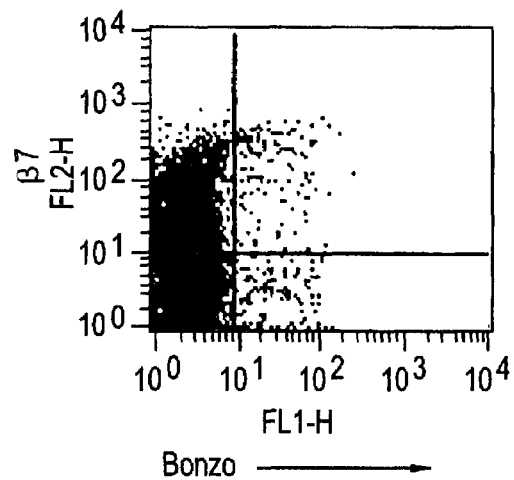
Figure 12D:
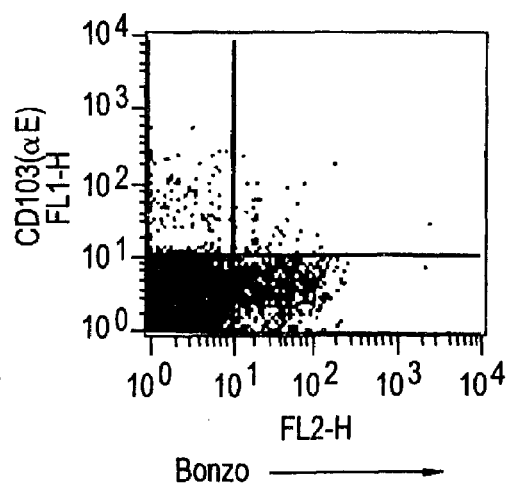
Figure 13A:
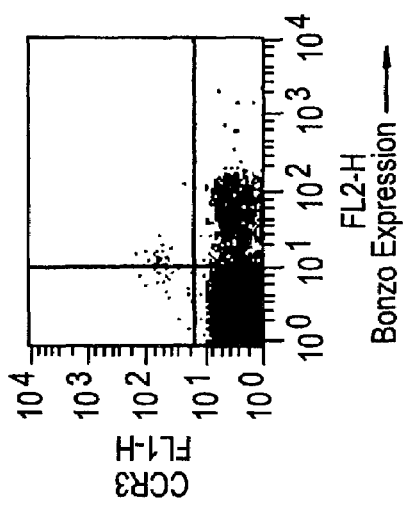
FIGS. 13A–13J are fluorescence plots showing co-expression of Bonzo and other CC or CXC chemokine receptors on human peripheral blood lymphocytes. Expression of Bonzo (x-axis) and CC or CXC chemokine receptors (y-axes) CCR1 (FIG. 13A), CCR2 (FIG. 13B), CCR3 (FIG. 13C), CCR5 (FIG. 13D)), CCR6 (FIG. 13E)), CXCR1 (FIG. 13F), CXCR2 (FIG. 13G), CXCR3 (FIG. 13H), CXCR4 (FIG. 13I) and CXCR5 (FIG. 13J) on human peripheral blood lymphocytes were assessed by two-color staining. Quadrants were set according to staining of isotype control mAbs (IgG2a). The data are representative of multiple donors analyzed.
Figure 13B:
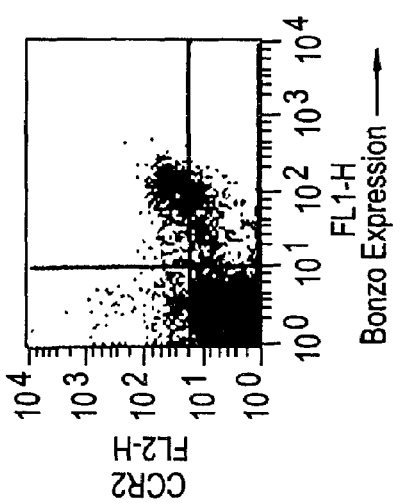
Figure 13C:
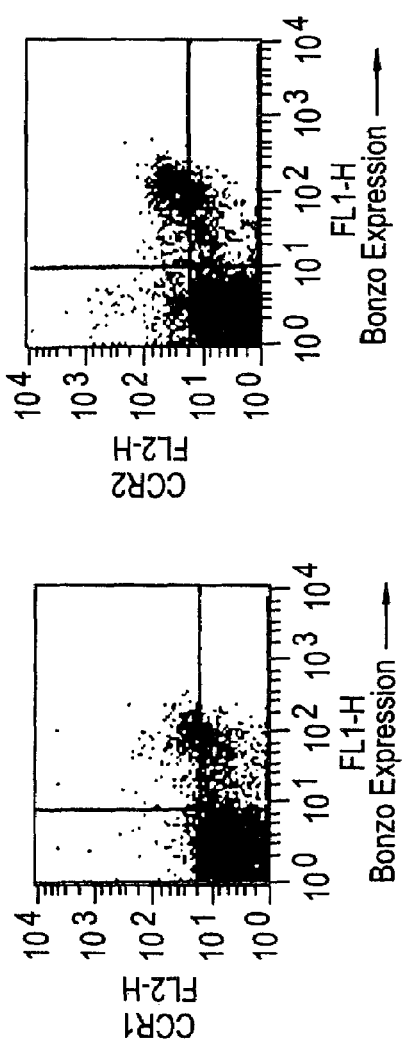
Figure 13D:
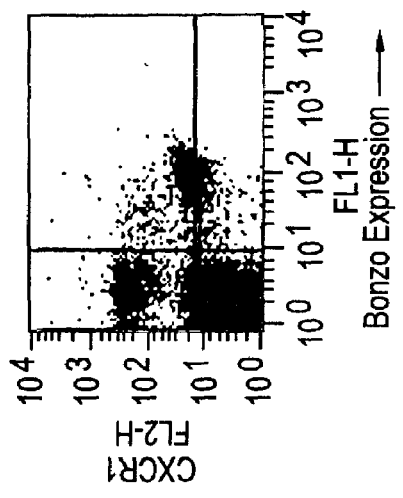
Figure 13E:
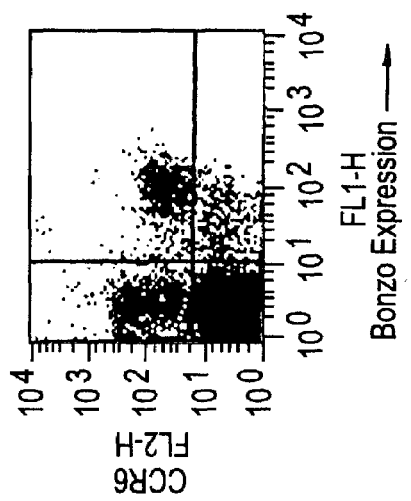
Figure 13F:
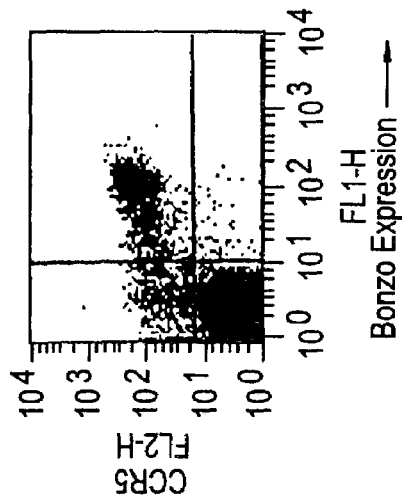
Figure 13G:
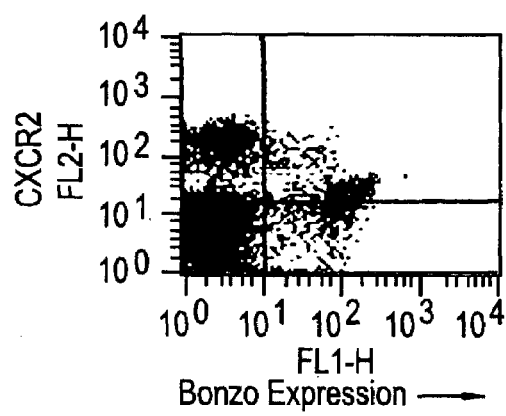
Figure 13H:
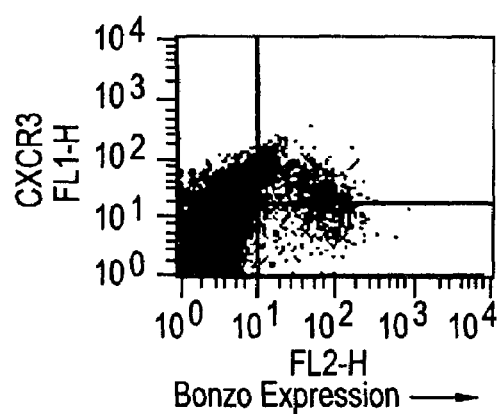
Figure 13I:
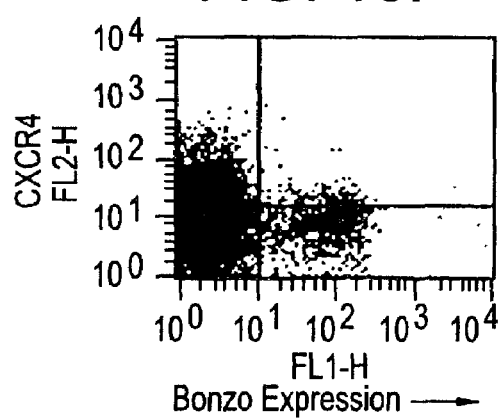
Figure 13J:
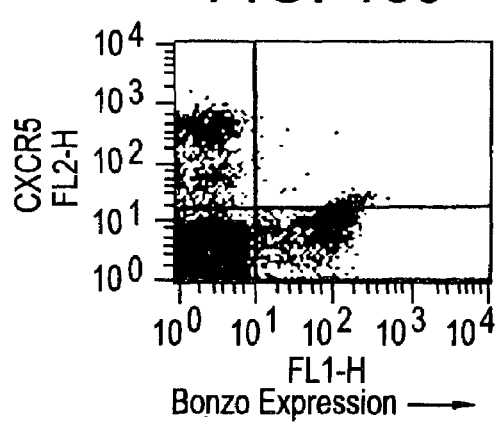
Figure 14A:
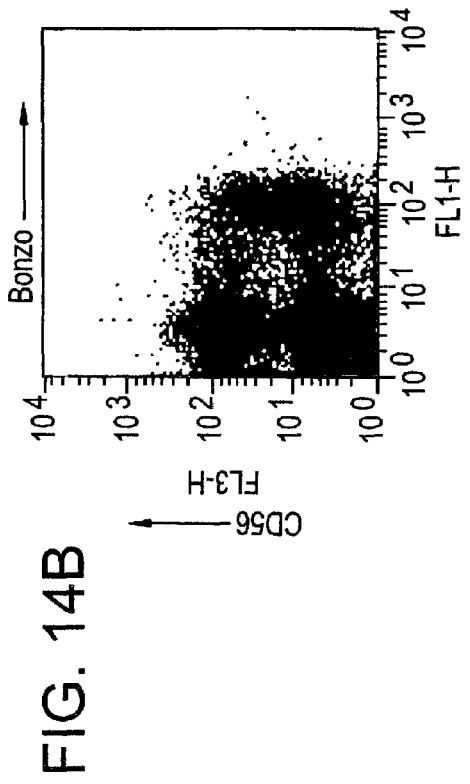
Figure 14B:
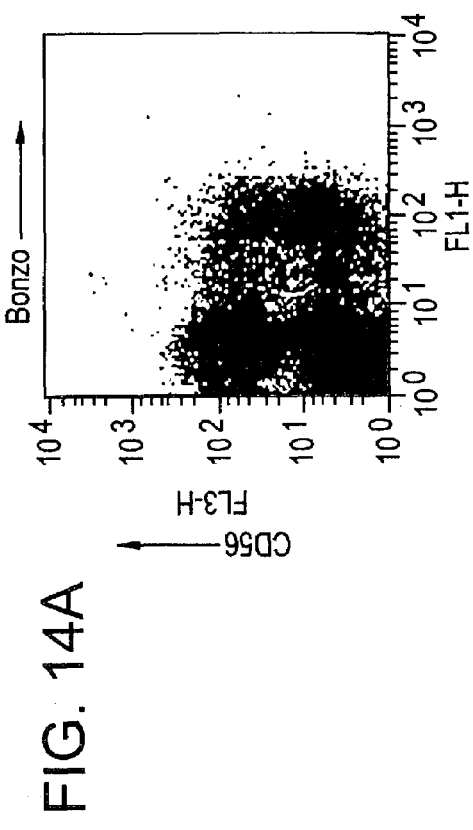
Figure 14E:
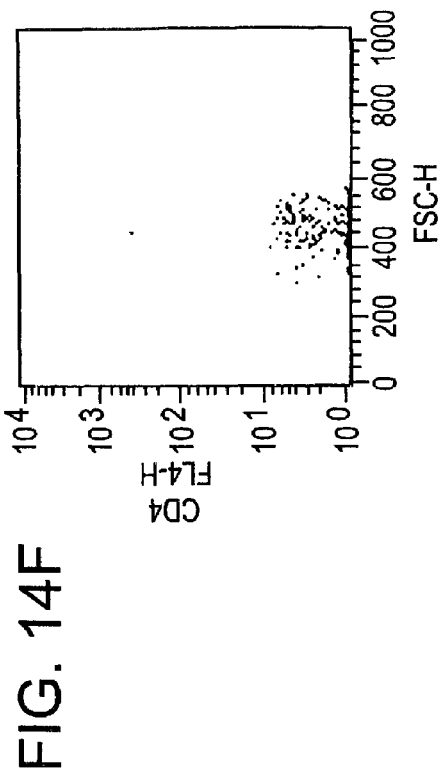
Figure 14F:
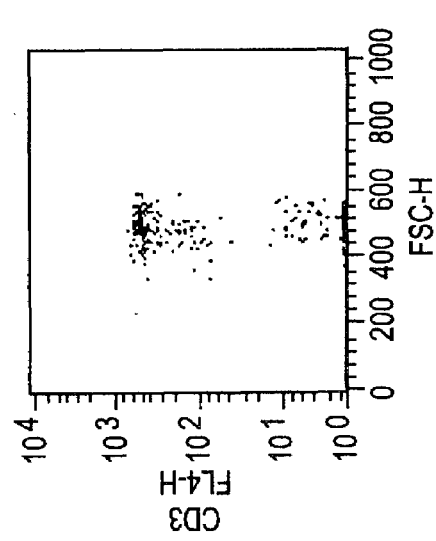
Figure 16A:
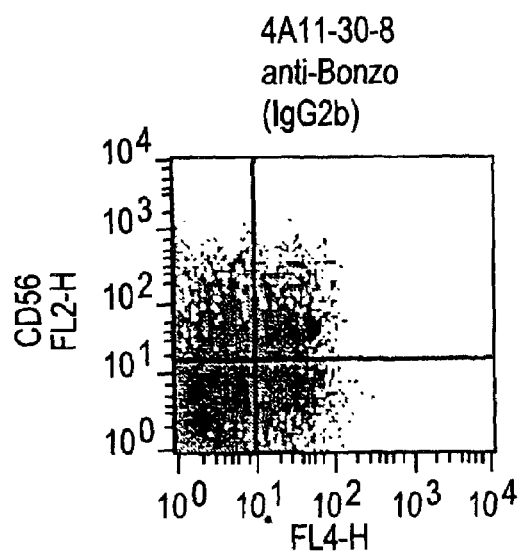
FIGS. 16A–16D are fluorescence plots showing Bonzo expression on CD8$^{hi}$, CD45RA$^{lo}$, CD56$^+$ human peripheral blood T cells (an anti-tumorigenic cell population). Expression was analyzed in a four-color study gating on CD8$^{hi}$CD45RA$^{lo}$ cells. The gated cells were analyzed for expression of CD56 (y-axis) and Bonzo (x-axis) using mAb 4A11 (FIG. 16A), mAb 7F3 (FIG. 16B) and mAb 7A2 (FIG. 16C). mAb 7H12, which binds CCR7, served as a negative control (FIG. 16D).
Figure 16B:
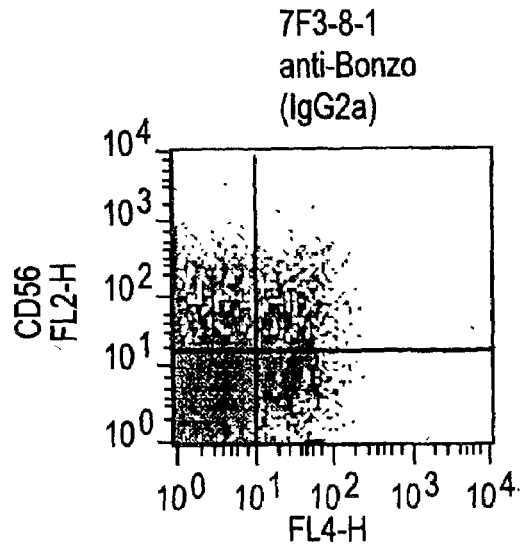
Figure 16C:
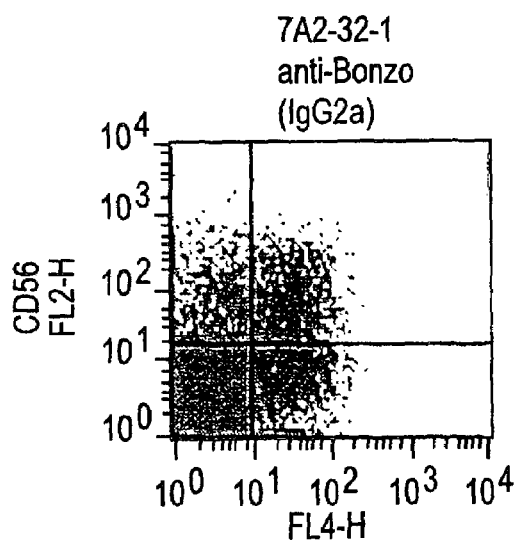
Figure 16D:
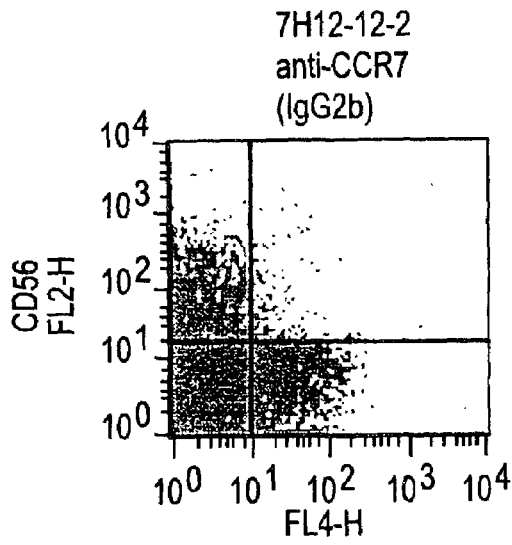
Figure 17A:
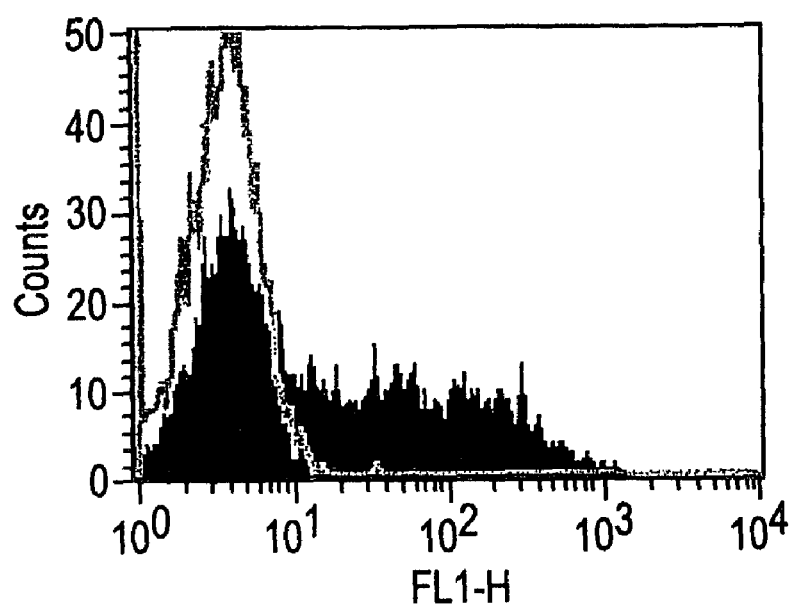
FIGS. 17A and 17B are fluorescence histograms showing that Bonzo is expressed on activated T cells (CD3 blasts, FIG. 17A) and NK cells (LAK cells, FIG. 17B). Bonzo expression was detected by staining with hybridoma culture supernatant containing mAb 7F3. The CD3 Blasts were activated with anti-CD3 antibody and were maintained in IL2 for 9 days prior to staining. The LAK cells were activated with IL12 for 6 days.
Figure 17B:
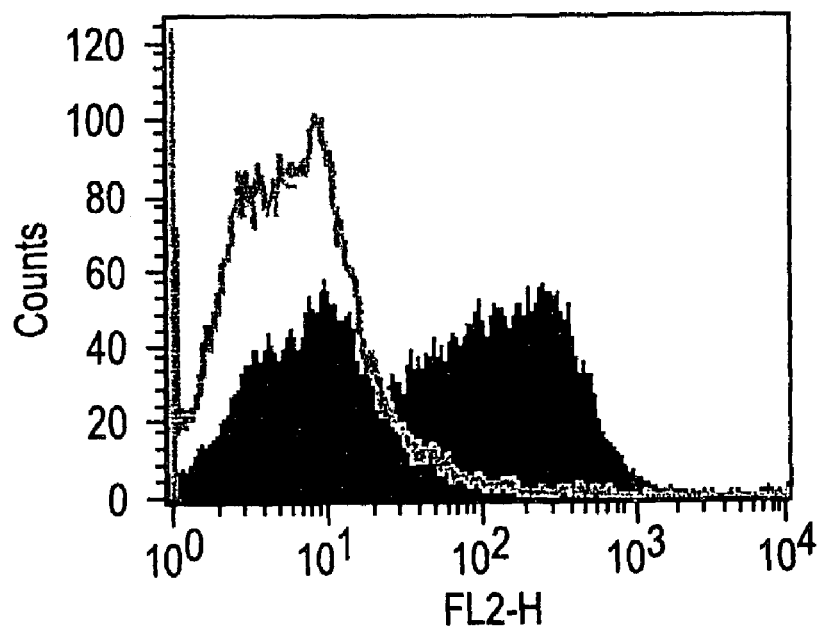
Figure 31:
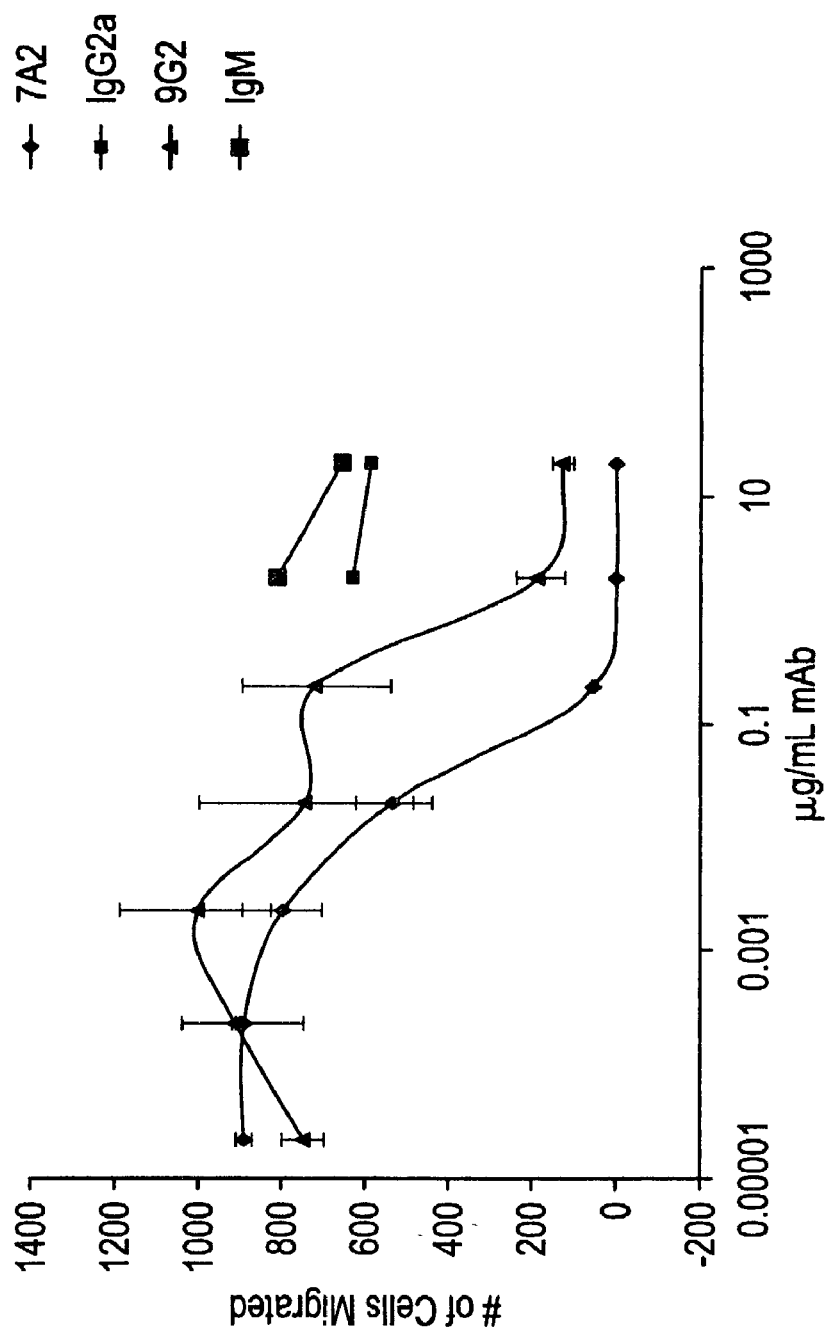
FIG. 31 is a graph showing dose-dependent inhibition of SExCkine-induced chemotaxis of Bonzo/L1.2 cells by mAb 7A2 or mAb 9G2. Bonzo/L1.2 cells were incubated with concentrated supernatant from murine hybridoma 7A2 which produces mAb 7A2, from murine hybridoma 9G2 which produces mAb 9G2, or from a murine hybridoma which produces an isotype control antibody (IgG2a or IgM), prior to exposure to SExCkine.
Figure 32:
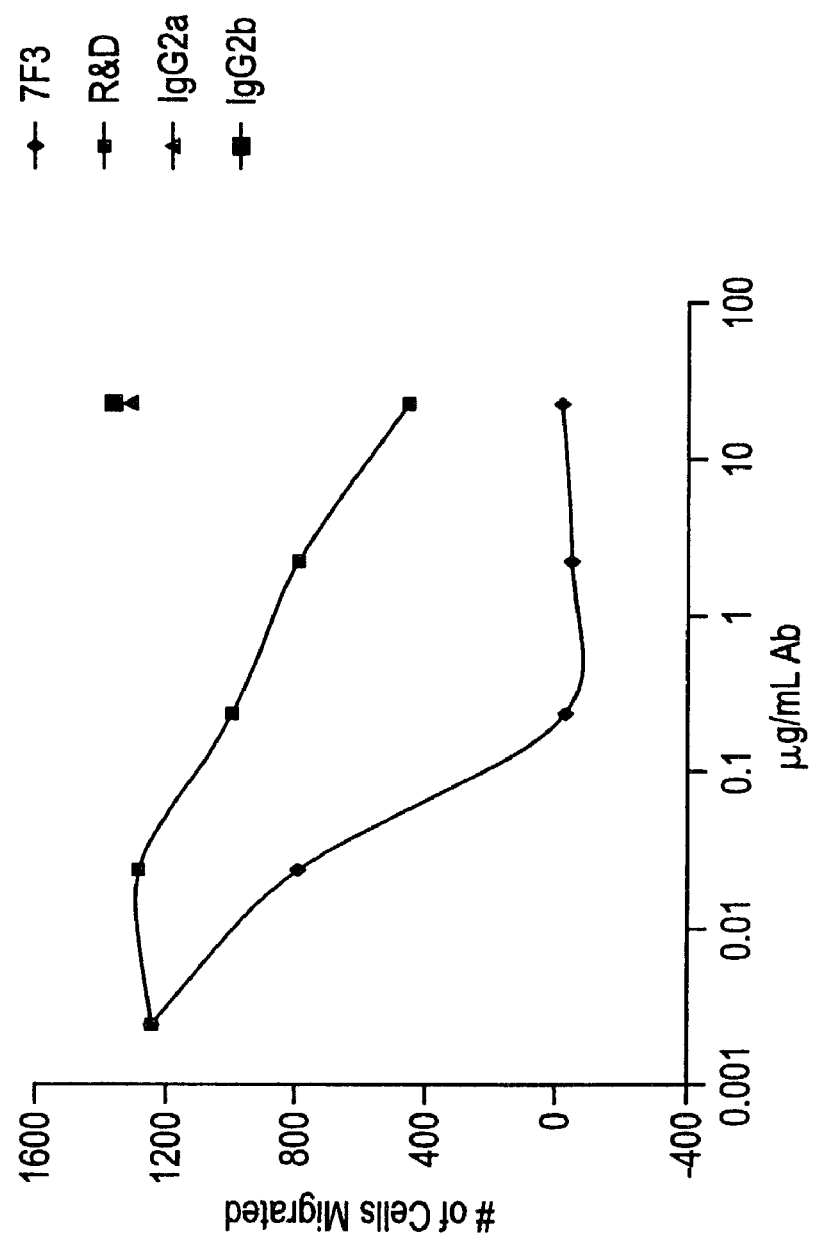
FIG. 32 is a graph illustrating dose dependent inhibition of SExCkine-induced chemotaxis of Bonzo/L1.2 cells by anti-Bonzo antibodies in an in vitro chemotaxis assay. Bonzo/L1.2 cells were incubated with purified mAb 7F3, with anti-human STRL33/Bonzo monoclonal antibody from R&D Systems, Minneapolis, Minn. (catalogue number MAB699) or isotype control antibodies (IgG2a or IgG2b), prior to exposure to SExCkine. The $IC_{50}$ for mAb 7F3 was determined to be 0.025 μg/mL, and the $IC_{50}$ for the antibody from R&D systems was determined to be 7.97 μg/mL.
Figure 33A:
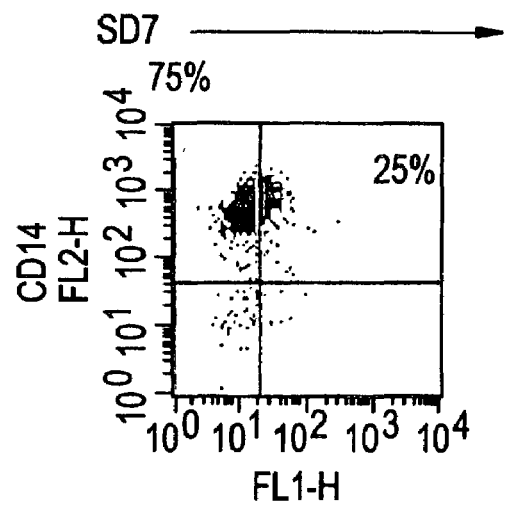
FIGS. 33A–33D are fluorescence plots showing that SExCkine (CXCL16) is expressed on the surface of human $CD14^+$ monocytes and human $CD19^+$ B cells. Peripheral blood mononuclear cells (PBMC) were stained using an anti-CD14 (FIGS. 33A and 33B) or anti-CD19 antibody (FIGS. 33C and 33D) and anti-SExCkine (CXCL16) monoclonal antibody mAb SD7 (FIGS. 33A and 33C). Expression was assessed by two-color flow cytometry using an IgG1 antibody (IgG1) as an isotype control (FIGS. 33B and 33D). These data are representative of multiple donors analyzed.
Figure 33C:
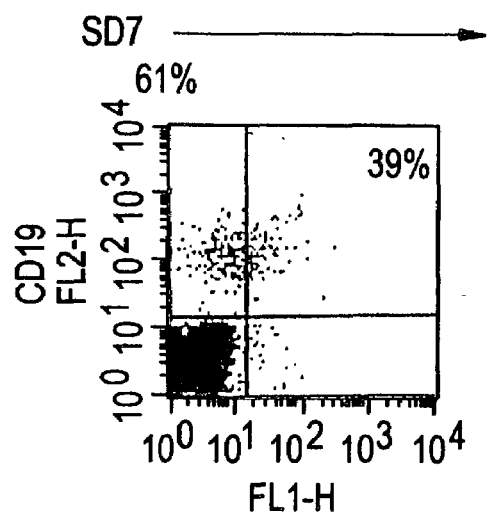
Figure 33B:
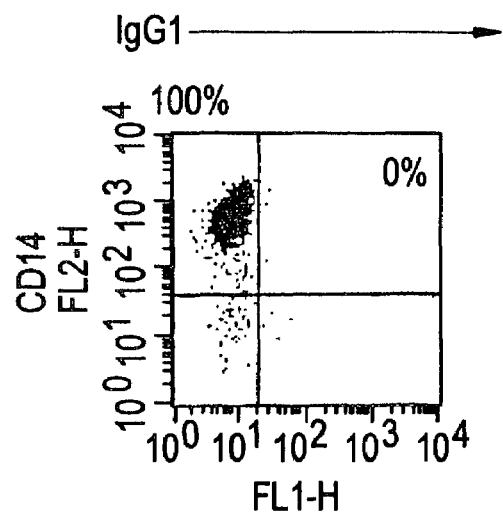
Figure 33D:
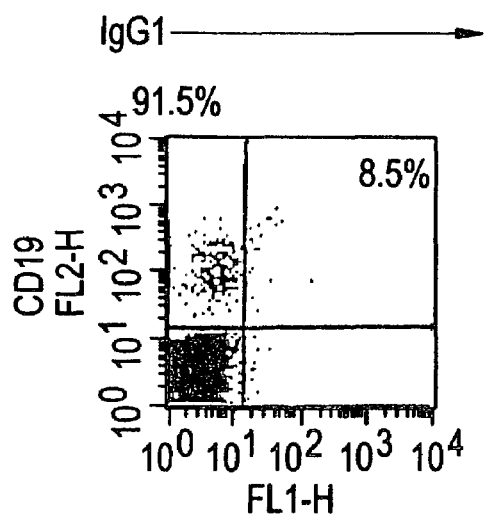

A panel of antibodies which bind human Bonzo were produced by immunizing mice with transfected L1.2 cells that expressed high levels of Bonzo. The antibodies specifically bound to Bonzo expressed on the surface of Bonzo/L1.2 cells (FIGS. 8A–8D) but did not bind to transfected L1.2 cells which expressed CCR1, CCR2, CCR3, CCR4, CCR5, CCR6, CCR7, CCR8, CXCR1, CXCR2, CXCR3, CXCR4, CXCR5, GPR5, V28, GPR9-6, Bob, LyGPR, AF, APJ or RDC (FIGS. 9A–9G). The antibodies, (e.g., mAbs 4A11, 7A2 and 7F3) inhibited the binding of SExCkine to Bonzo (FIG. 10, FIG. 31, Table 1). Staining studies revealed that Bonzo is expressed on small populations of $CD4^+$ and $CD8^+$ T cells as well as on $CD16^+/CD56^+$ NK cells. However, no expression of Bonzo was observed on $CD19^+/CD20^+$ B cells or on $CD14^+$ monocytes (FIGS. 11A–11H). Multi-color staining studies were performed to analyze the co-expression of Bonzo and other cell surface proteins (FIGS. 12A–12D, 13A–13J, 14A–14H, 15A–15C, 16A–16D). These studies revealed that Bonzo is expressed predominantly on $CD45RO^{hi}$ memory lymphocytes. Furthermore, Bonzo expression was detected on both skin homing ($CLA^+$) and gut homing ($\alpha 4\beta 7^+$ and $\alpha E^+$) $CD4^+$ lymphocytes (FIGS. 12A–12D). Bonzo was co-expressed with CCR1, CCR2, CCR5, CCR6, CXCR1, CXCR2 or CXCR3 on lymphocytes (FIGS. 13A–13J).

Figure 18:
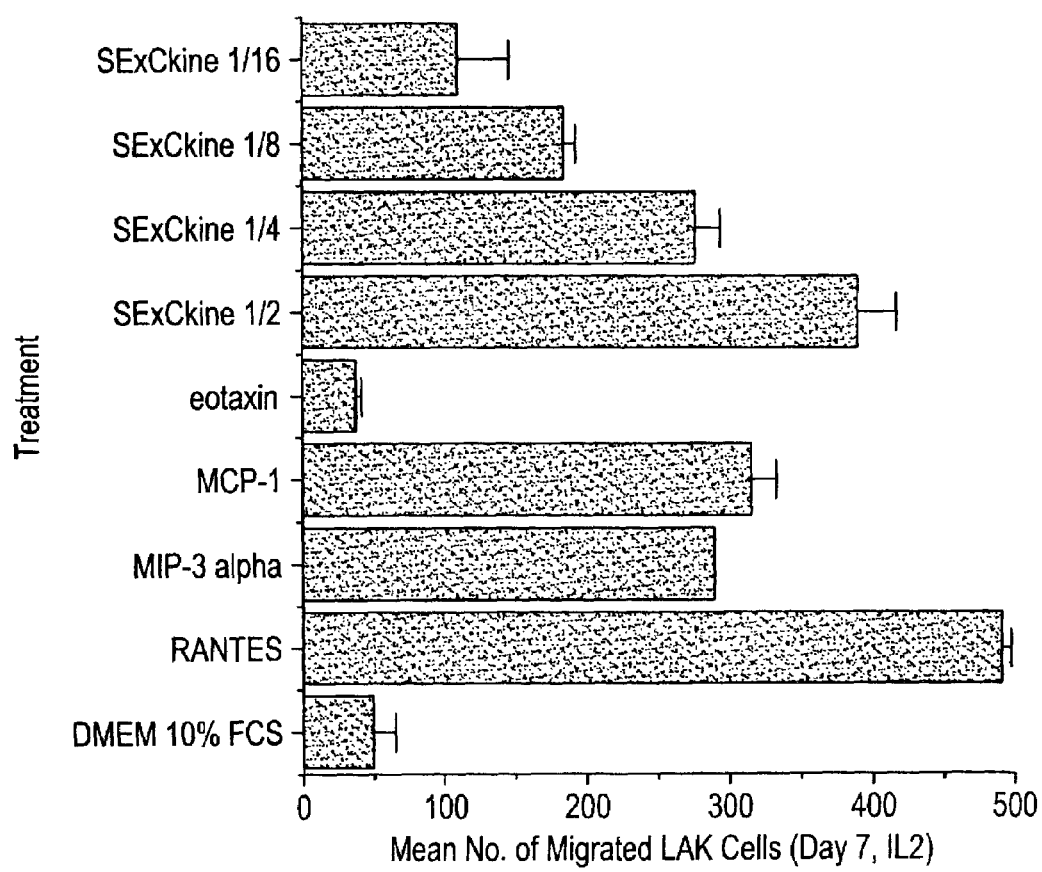
FIG. 18 is a histogram showing that chemotaxis of lymphokine-activated killer cells (LAK) was induced by SExCkine. Chemotaxis of LAK cells was also induced by RANTES, MIP-3 alpha and MCP-1. However, eotaxin did not induce chemotaxis of LAK cells, and no migration was seen in assays that did not contain chemokine.
Figure 19A:
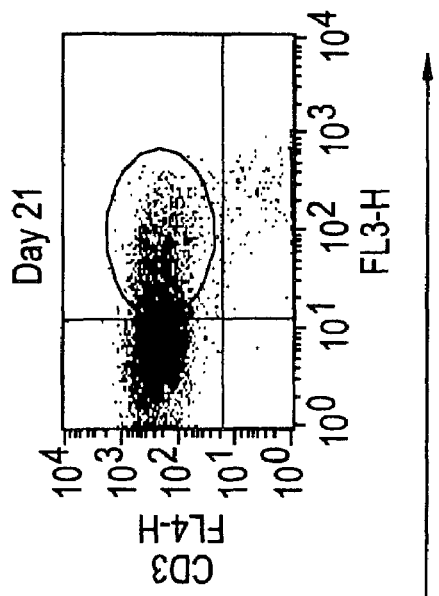
FIGS. 19A–19D are fluorescence plots showing up-regulation of Bonzo expression on in vitro-derived cytokine-induced killer (CIK) cells. Cells were removed from in vitro CIK cultures at day 1 (FIGS. 19A and 19C) and day 21 (FIGS. 19B and 19D) and analyzed for expression of Bonzo in a three-color study, gating on CD3$^+$CD56$^+$ cells.
Figure 19B:
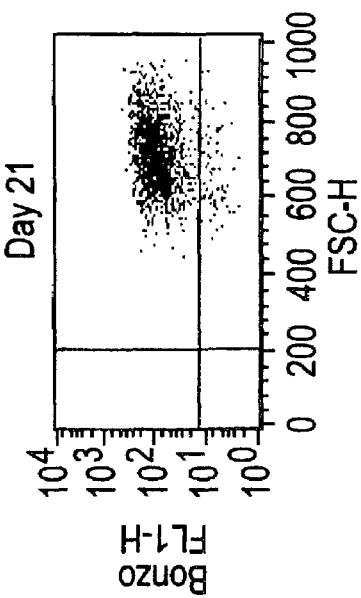
Figure 19C:
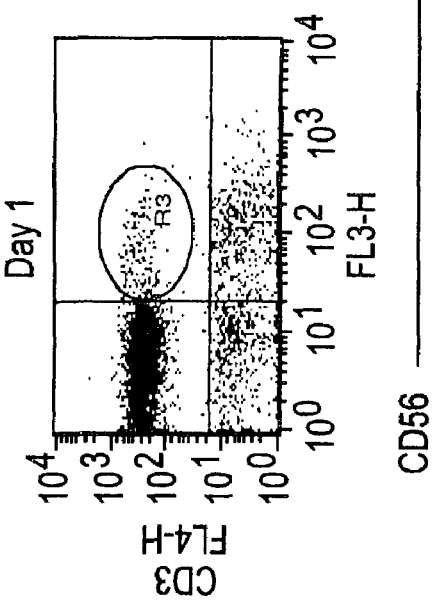
Figure 19D:
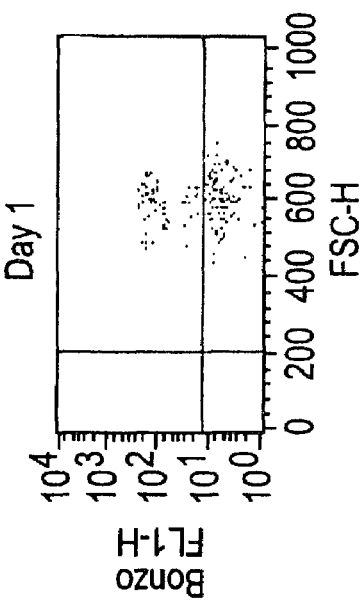
Figure 20:
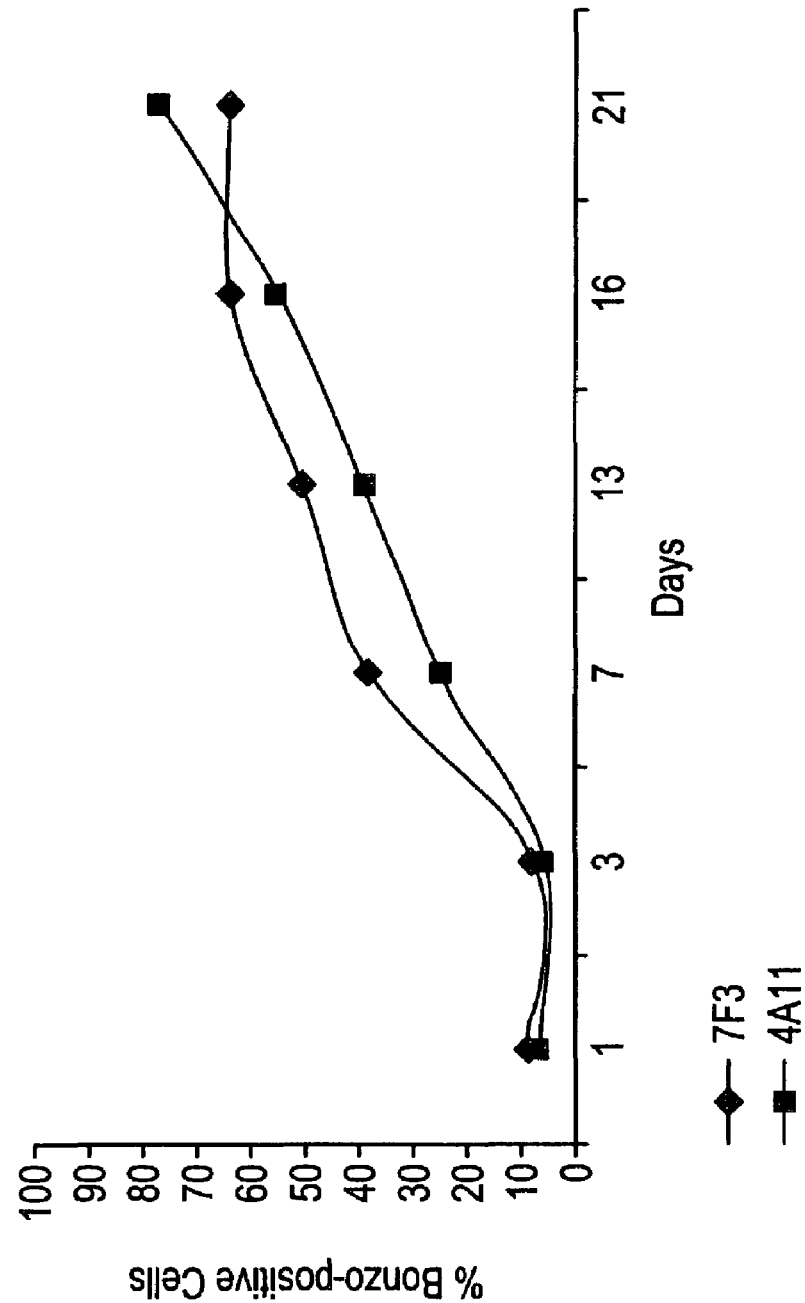
FIG. 20 is a graph showing that expression of Bonzo on in vitro-derived CIK cells increases over time. At selected time points, cells were analyzed for expression of Bonzo by staining with mAb 7F3 or mAb 4A11.
Figure 21:
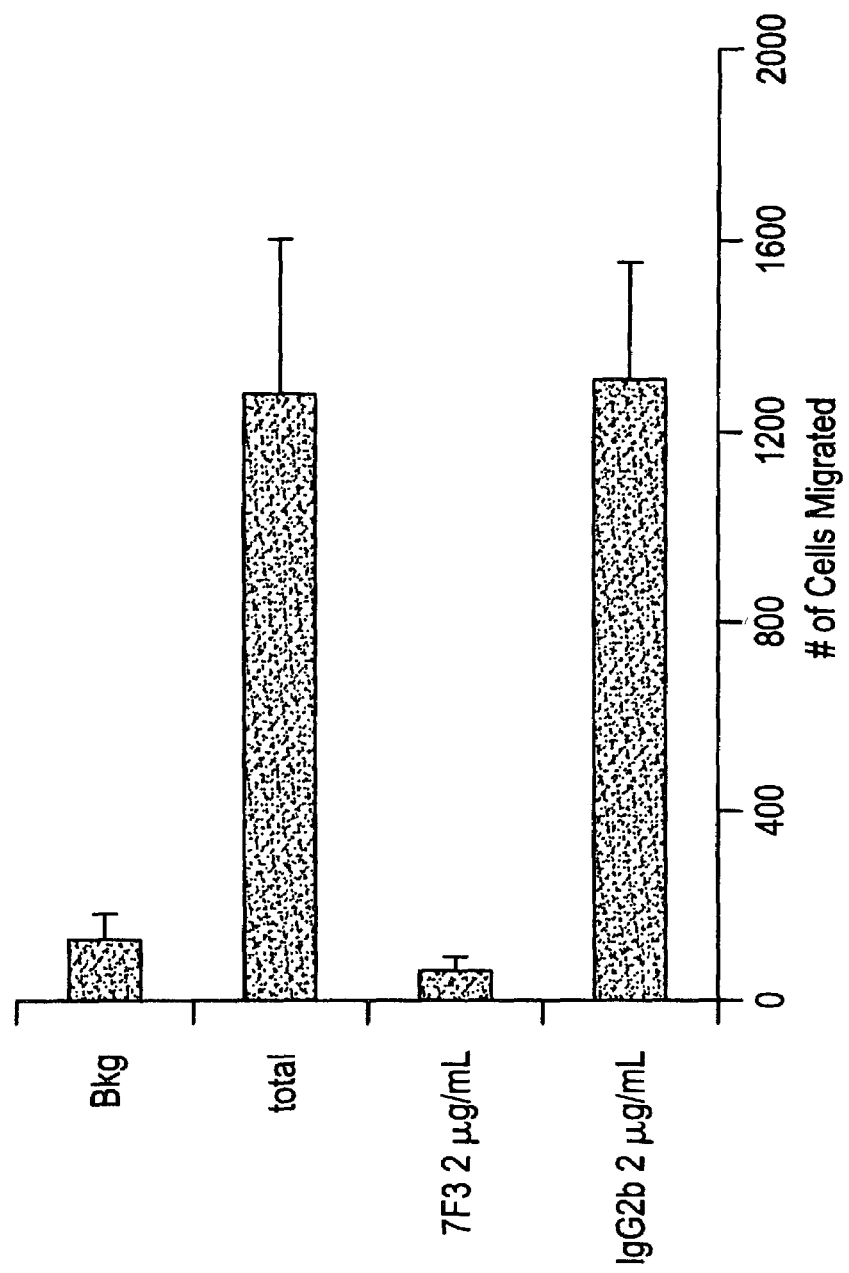
FIG. 21 is a graph showing that SExCkine-induced chemotaxis of CIK cells can be inhibited by mAb 7F3, but is not significantly inhibited by irrelevant control IgG2b. The in vitro-derived CIK cells used in the assay were prepared by 17 days of culture. Chemotaxis was measured in control wells that contained no SExCkine (Bkg) and control wells that contained culture supernatant of 293T cells transiently transfected with SExCkine (total). Antibody inhibition was assessed by incubating CIK cells with mAb 7F3 (2 μg/mL) or isotype control mAb IgG2b (2 μg/mL) for 20 minutes at 37° C. prior to exposure to SExCkine.
Figure 22:
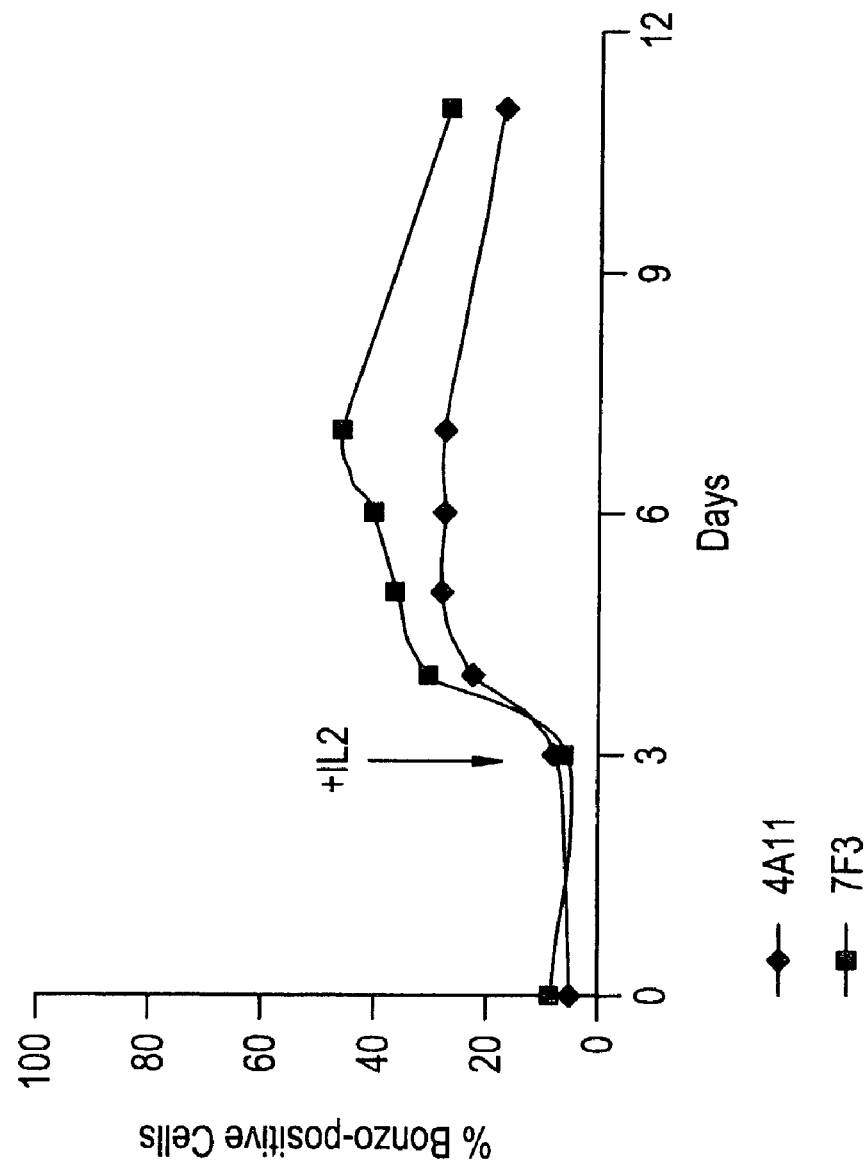
FIG. 22 is a graph showing the time course of activation-induced expression of Bonzo on activated human peripheral blood T cells. Human peripheral blood cells were activated by culture with immobilized anti-CD3 (OKT3, 5 μg/mL), on day three interleukin 2 (IL-2, 100 U/mL) was added to the cultures. Expression of Bonzo was assessed at selected times by staining with mAb 4A11 or mAb 7F3.
Figure 24A:
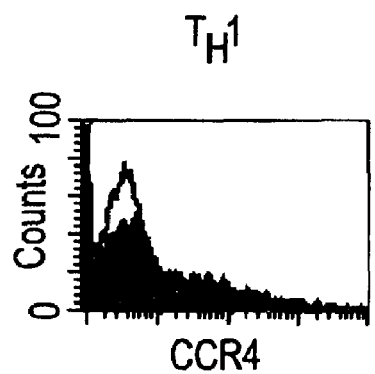
FIGS. 24A–24F are fluorescence histograms showing that Bonzo expression is augmented by repeated activation of in vitro-derived $T_H1$ cells. Cells which had been stimulated by one round of activation (FIGS. 24A-24C) or two rounds of activation (FIGS. 24D–24F) were stained with anti-Bonzo mAb 7F3 (FIGS. 24B and 24E), anti-CCR4 mAb mAb 1G1 (FIGS. 24A and 24D) or anti-CCR7 mAb 7H12 (FIGS. 24C and 24F). $T_H1$ cells expressed increased amounts of Bonzo after repeated activation (compare FIGS. 24B and 24E).
Figure 24D:
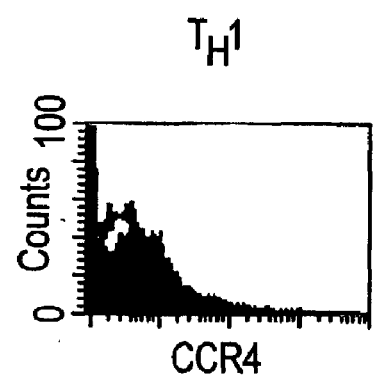
Figure 24B:
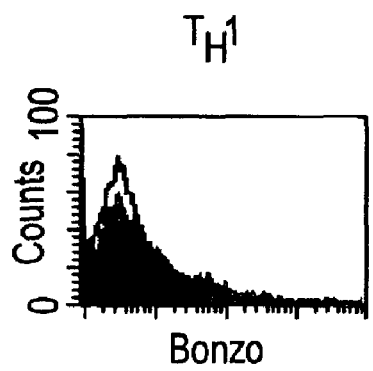
Figure 24E:
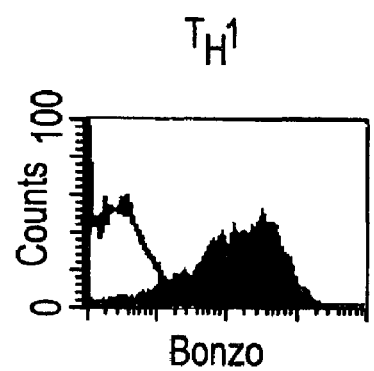
Figure 24C:
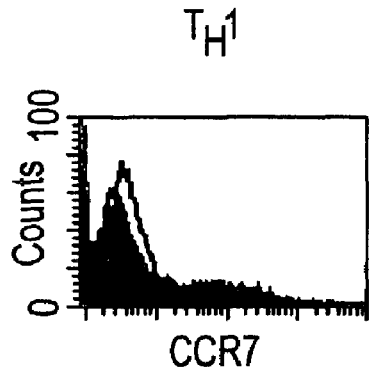
Figure 24F:
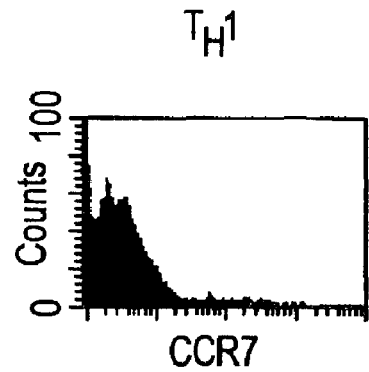
Figure 25A:
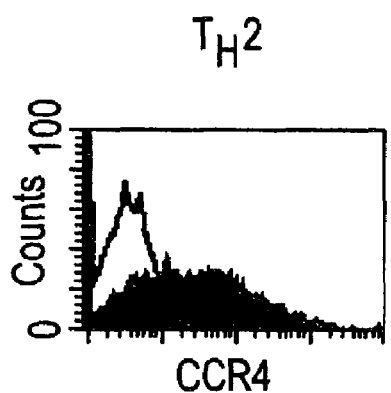
FIGS. 25A–25F are fluorescence histograms showing that Bonzo expression is augmented by repeated activation of in vitro-derived $T_H2$ cells. Cells which had been stimulated by one round of activation (FIGS. 25A–25C) or two rounds of activation (FIGS. 25D–25F) were stained with anti-Bonzo mAb 7F3 (FIGS. 25B and 25E), anti-CCR4 mAb mAb 1G1 (FIGS. 25A and 25D) or anti-CCR7 mAb 7H12 (FIGS. 25C and 25F). $T_H2$ cells expressed increased amounts of Bonzo after repeated activation (compare FIGS. 25B and 25E).
Figure 25D:
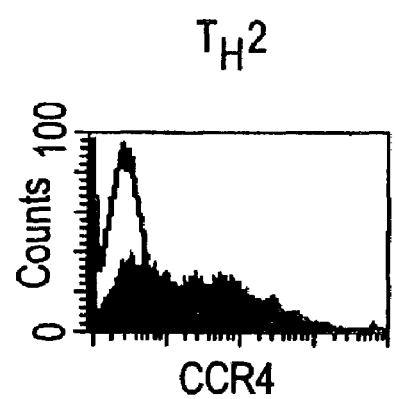
Figure 25B:
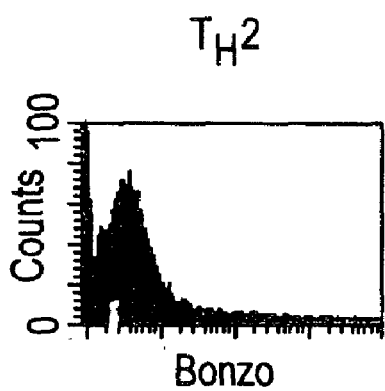
Figure 25E:
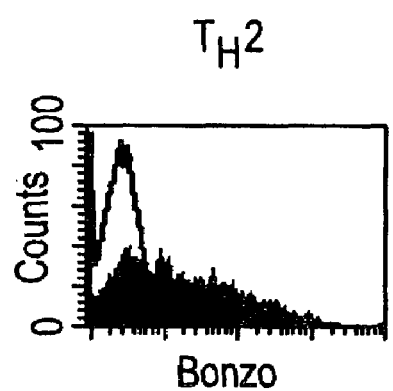
Figure 25C:
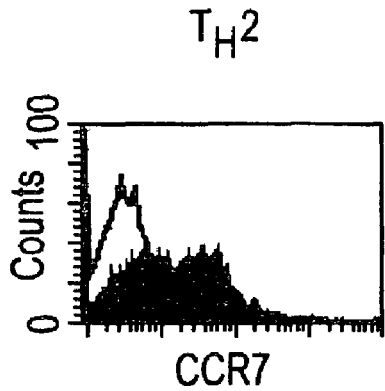
Figure 25F:
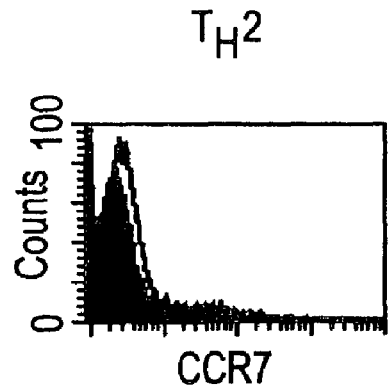
Figure 26A:
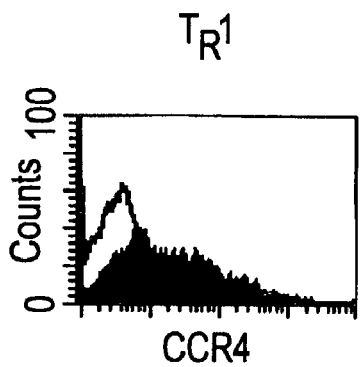
FIGS. 26A–26F are fluorescence histograms showing that Bonzo expression is augmented by repeated activation of in vitro-derived $T_R1$ cells. Cells which had been stimulated by one round of activation (FIGS. 26A–26C) or two rounds of activation (FIGS. 26D–26F) were stained with anti-Bonzo mAb 7F3 (FIGS. 26B and 26E), anti-CCR4 mAb 1G1 (FIGS. 26A and 26D) or anti-CCR7 mAb 7H12 (FIGS. 26C and 26F). $T_R1$ cells expressed increased amounts of Bonzo after repeated activation (compare FIGS. 26B and 26E).
Figure 26B:
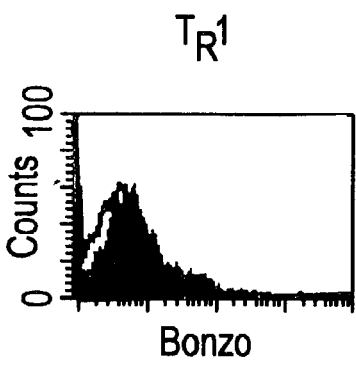
Figure 26C:
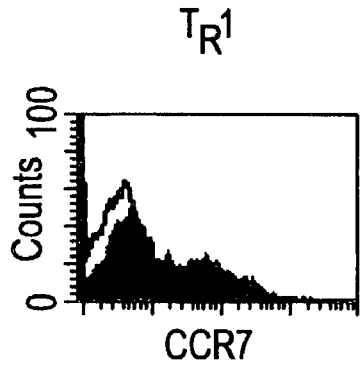
Figure 26D:
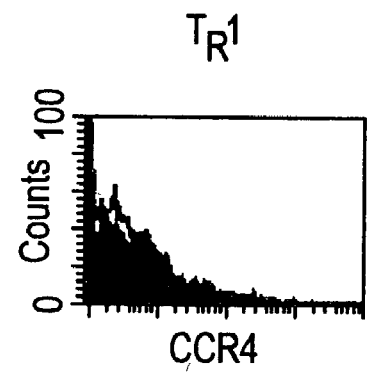
Figure 26E:
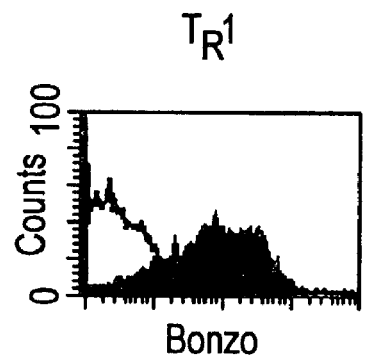
Figure 26F:
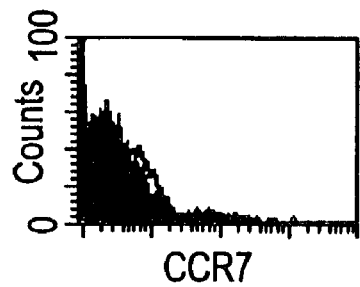

Bonzo expression was detected on the surface of a rare population of potent "anti-tumor" cytotoxic effector cells which are $CD3^+CD56^+CD8^+$ (FIGS. 16A–16D). These cells include lymphokine-activated killer cells (LAK) and cytokine-induced killer cells (CIK). Chemotaxis of both LAK ((FIG. 18) and CIK (FIG. 21) cells was induced by SExCkine, and in the case of CIK cells, the chemotaxis was completely inhibited by mAb 7F3 (FIG. 21). Further studies revealed that Bonzo is expressed on other subsets of chronically-activated lymphocytes. In fact, staining of CD3 blasts was characterized by an increase in cell surface Bonzo expression over time (FIG. 22). Similar activation-induced expression was observed on in vitro-derived $T_H1$, $T_H2$ and $T_R1$ lymphocytes (FIGS. 24B and 24E, 25B and 25E, 26B and 26E). The increase in Bonzo expression on these in vitro-derived cells paralleled their ability to exhibit chemotactic activity to conditioned supernatant from SExCkine-transfected 293T cells (FIGS. 27 and 28). Furthermore, SExCkine-induced chemotaxis of in vitro-derived $T_H2$ cells was inhibited by the anti-Bonzo mAb 7F3 (FIG. 28).

Figure 29:
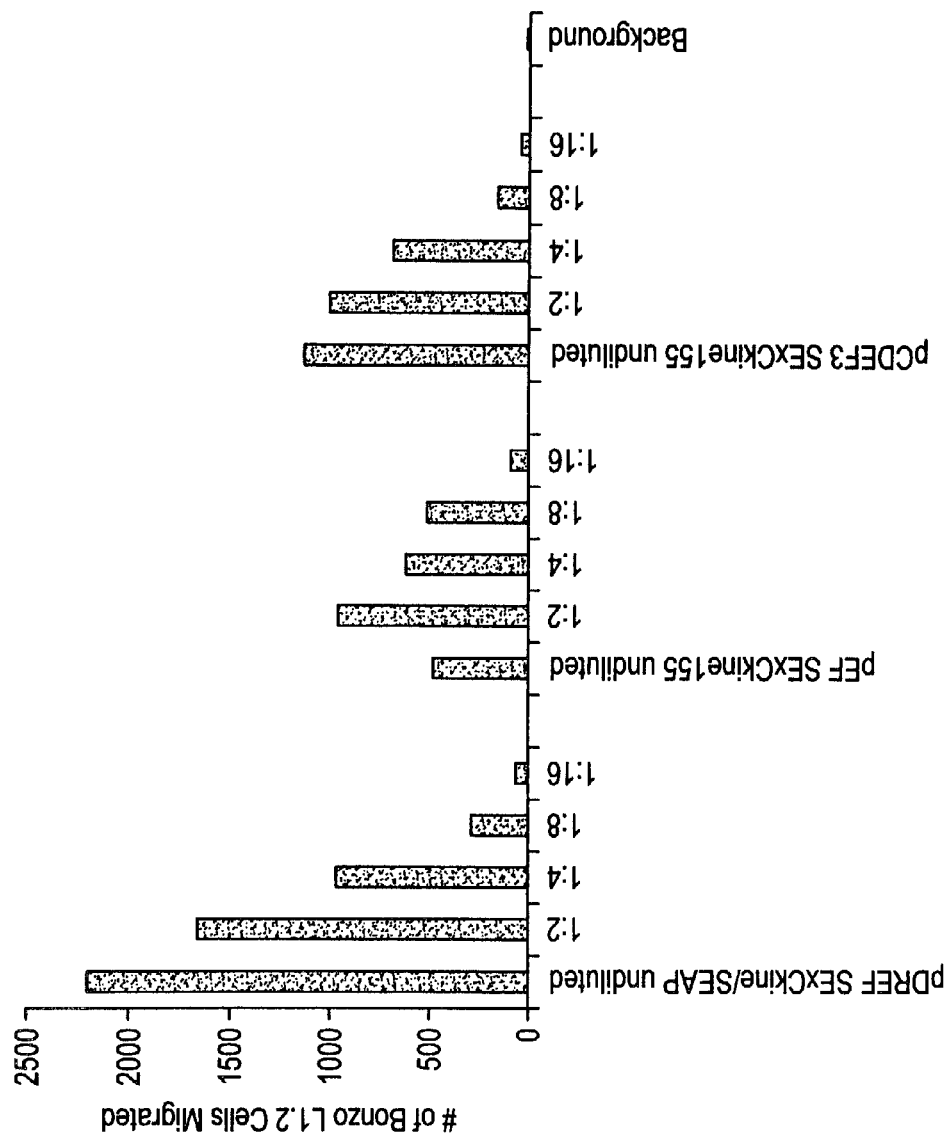
FIG. 29 is a histogram showing that chemotaxis of Bonzo/L1.2 cells is induced by amino-terminal fragments of human SExCkine. Chemotaxis was assessed in assays using Bonzo/L1.2 cells and conditioned culture supernatant from 293T cells transiently transfected with an expression vector encoding residues 1–199 of human SExCkine (SEQ ID NO:4) fused to human alkaline phosphatase (pDREF SExCkine/SEAP) or with a nucleic acid encoding residues 1–155 of human SExCkine (SEQ ID NO:4) cloned into expression vector pEF or pCDEF3. Bonzo/L1.2 cells were assayed for chemotactic response to undiluted culture supernatants of transiently transfected 293T cells or to various dilutions of the supernatants (1:2, 1:4, 1:8 and 1:16). Background migration was determined in cultures which contained assay media without chemokine.

Recombinant proteins consisting of the entire extracellular domain (or fragments thereof) of SExCkine fused to either a C-terminal His tag or to human placental alkaline phosphatase (i.e., carboxyl-terminal residue of SExCkine moiety bonded to amino-terminal residue of alkaline phosphatase moiety) were produced. One of the proteins contained the entire predicted extracellular domain of SExCkine (truncated after T202) fused to alkaline phosphates (pDEF SExCkine/SEAP), others consisted of the extracellular domain of SExCkine truncated in the middle of the mucin domain (after V155) and cloned into vector pEF or pCDEF3. These proteins were produced by transient expression in 293T cells and tested for chemoattractant activity in chemotaxis assays. The chemoattractant activity of the truncated recombinant proteins was about equivalent to that of SExCkine produced by expression of the full length cDNA (SEQ ID NO:3) (FIG. 29).

In a further study, a synthetic peptide consisting of amino acid residues 30 (Asn) to 95 (Ser) of SExCkine (SEQ ID NO:4) was produced. This peptide also induced chemotaxis of Bonzo/L1.2 cells. These data demonstrate that fragments of the amino-terminal region of SExCkine (e.g., peptides derived from the extracellular domain of SExCkine (SEQ ID NO:4)) can bind Bonzo and induce chemotaxis of Bonzo$^+$ cells.

This study demonstrates that recombinant SExCkine and recombinant proteins encoding parts of the amino-terminal portion of SExCkine can be used in conjunction with Bonzo (e.g., a cell expressing Bonzo) in receptor binding assays and functional assays to screen for potential agonists and antagonists of Bonzo. Considering that Bonzo is highly expressed on all classes of chronically-stimulated T cell subsets, antagonists of the receptor (e.g., mAbs 4A11, 7A2 and 7F3) can be administered to treat chronic inflammatory diseases. Furthermore, agonists of Bonzo (e.g., SExCkine) can be administered to recruit killer T cell subsets to, for example, solid tumors or sites of infection.

EXAMPLE 2

Generation and Characterization of Monoclonal Antibodies that Bind SExCkine (CXCL16).

Methods and Materials

Generation of Anti-SExCkine Hybridomas

MAbs reactive with SExCkine (CXCL16) were generated by fusing splenocytes to SP2/0 cells as described. The splenocytes were obtained from Balb/C mice that were immunized with a synthetic peptide consisting of amino acids residues 30 (Asn) to 95 (Ser) of human SExCkine (CXCL16) (SEQ ID NO:4).

Screening of SExCkine (CXCL16) Fusion Antibodies 96 well flat-bottom plates (Nunc-Immuno Plate MaxiSorp Surface) were coated with the chemokine domain of SExCkine (CXCL16) (3 µg/mL) in carbonate buffer and incubated overnight at 4° C. The plates were subsequently blocked in blocking buffer (PBS/1% BSA/0.05% sodium azide) for 2 hours at 37° C. or overnight at 4° C. The plates were washed four times with PBST (PBS/0.05% Tween 20 (polyoxyethylenesorbitan monolaurate)) and hybridoma supernatant (50 µL/well) was added and incubated at 37° C. for 1 hour. After the one-hour incubation period the plates were washed four times with PBST. The secondary antibody, horseradish peroxidase-conjugated goat anti-mouse antibody (Zymed Laboratories Inc., San Francisco, Calif.), was added at a dilution of 1:2000 and the plates were incubated for 30 minutes at 37° C. Plates were washed four times with PBST. The substrate (ABTS solution substrate kit for horseradish peroxidase, Zymed Laboratories Inc., San Francisco, Calif.) was added at 50 µL/well and the plates were read at 410 nm on an ELISA reader.

Positive clones were subcloned to 1.5 cells/well and 0.75 cells/well (2 plates each). Wells with a single colony were rescreened as described and the subcloning and screening process was repeated until a clonal antibody was obtained.

Isotyping SExCkine (CXCL16) Subclones 96 well flat-bottom plates (Nunc-Immuno Plate MaxiSorp Surface) were coated with murine IgM (10 µg/mL) in carbonate buffer and incubated overnight at 4° C. The plates were blocked in blocking buffer (PBS/1% BSA/0.05% sodium azide) and the plates were incubated for 2 hrs at 37° C. Hybridoma supernatant was added (50 µL/well) and incubated at 37° C. for 1 hour and then the plates were washed four time with PBST. The horseradish peroxidase-conjugated secondary antibodies (IgG1, IgG2a, IgG2b, IgG3, IgM, IgA, kappa, lambda (Mouse Standard Panel, Southern Biotechnology, Birmingham, Ala.)) were added to the wells at a dilution of 1:500 and then the plates were incubated for 30 minutes at 37° C. Plates were washed four times with PBST. The substrate (ABTS solution substrate kit for horseradish peroxidase, Zymed Laboratories Inc., San Francisco, Calif.) was added at 50 µL/well and the plates were read at 410 nm on the ELISA reader.

Results and Discussion

Monoclonal antibodies that were reactive with SExCkine (CXCL16) were generated by immunizing mice with a synthetic peptide consisting of amino acids residues 30 (Asn) to 95 (Ser) of human SExCkine (CXCL16) (SEQ ID NO:4). Three hybridomas that secreted anti-SExCkine mAbs were isolated and are presented in Table 3.

TABLE 3

| hybridoma | antibody | isotype | inhibited binding of SExCkine (CXCL16) to Bonzo |
|---|---|---|---|
| Murine hybridoma 9B10 | mAb 9B10 | IgG2 | no |
| Murine hybridoma 10B12 | mAb 10B12 | IgG2 | no |
| Murine hybridoma SD7 | mAb SD7 | IgG1 | yes |

EXAMPLE 3

SExCkine is Expressed on the Surface of Leukocyte Subsets and Functional SExCkine is Shed from Macrophages Methods and Materials Preparation of Peripheral Blood Mononuclear Cells (PBMCs)

Peripheral blood mononuclear cells (PBMCs) were isolated by Lymphoprep™ (Nycomed Pharma AS, Oslo Norway) density gradient centrifugation of venous blood collected from volunteer donors.

Preparation of Monocytes

Monocytes were seeded into T75 flasks, allowed to adhere, and cultured for 10 days in RPM1 1640 supplemented with 2.5 mM Hepes (N-(2-hydroxyethyl)piperazine-N'-(2-ethanesulfonic acid)), 20 µg/mL gentamycin, 2 mM L-glutamine, 1% penicillin/streptomycin, 2% nonessential amino acids and 1 mM sodium pyruvate (all from Gibco/BRL, Rockville, Md.). On the tenth day of culture, cells were incubated with either 50 ng/mL of LPS (Sigma, St. Louis, Mo.) or 10 ng/mL of TNF-α (R&D Systems, Minneapolis, Minn.) for 4 or 24 hours. Supernatants were drawn off the cells and were used in chemotaxis experiments with Bonzo/L1.2 transfectants. GusB/L1.2 transfectants were used as a negative control.

Fluorescence-Activated Cell Sorting (FACS) Analysis

PBMCs or tonsil cells were incubated in PBS with 5% True Clot human serum (Scantibodies Laboratories Inc., Santee, Calif.) and mouse IgG (Sigma, St. Louis, Mo.) in order to prevent non-specific staining. FITC-conjugated or Cy5-conjugated goat anti-mouse IgG antibodies (Jackson ImmunoResearch Lab, West Grove, Pa.) were used as the secondary antibodies at 1:200 dilutions. Antibodies directed against surface antigens, including CD4, CD14, and CD19, were directly conjugated to phycoerythrin (herein referred to as PE) and were obtained from Pharmingen (San Diego, Calif.).

Chemotaxis Assay

Chemotaxis assays were performed as described in Example 1, except that no endothelial cells were used.

Results and Discussion

As described in Example 1, northern blot analysis demonstrated high levels of expression of SExCkine in peripheral blood leukocytes. In order to examine whether certain subsets of leukocytes express cell-surface SExCkine, peripheral blood mononuclear cells (PBMCs) were stained with anti-SExCkine mAb SD7. Staining of PBMCs with mAb SD7 revealed that cell surface expression of SExCkine was observed on subsets of CD19$^+$ and CD14$^+$ peripheral blood leukocytes, indicating that primary antigen-presenting cells including B lymphocytes and monocyte/macrophages could present this chemokine as a cell-surface ligand (FIG. 33). Staining of subsets of CD19$^+$ and CD14$^+$ peripheral blood leukocytes from multiple donors revealed similar patterns, although there was some donor to donor variability (Table 4). These data indicate that novel interactions can occur between antigen-presenting cells which express SExCkine and activated T cell subsets which express Bonzo and that these interactions can result in subset-specific immune responses.

TABLE 4

| Donor Number | CD14$^+$ positive for mAb SD7 | CD19$^+$ positive for mAb SD7 |
|---|---|---|
| 96 | 70% | 25% |
| 170 | 5% | 46% |
| 184 | 25% | 39% |
| 185 | 43% | 32% |

Figure 34:
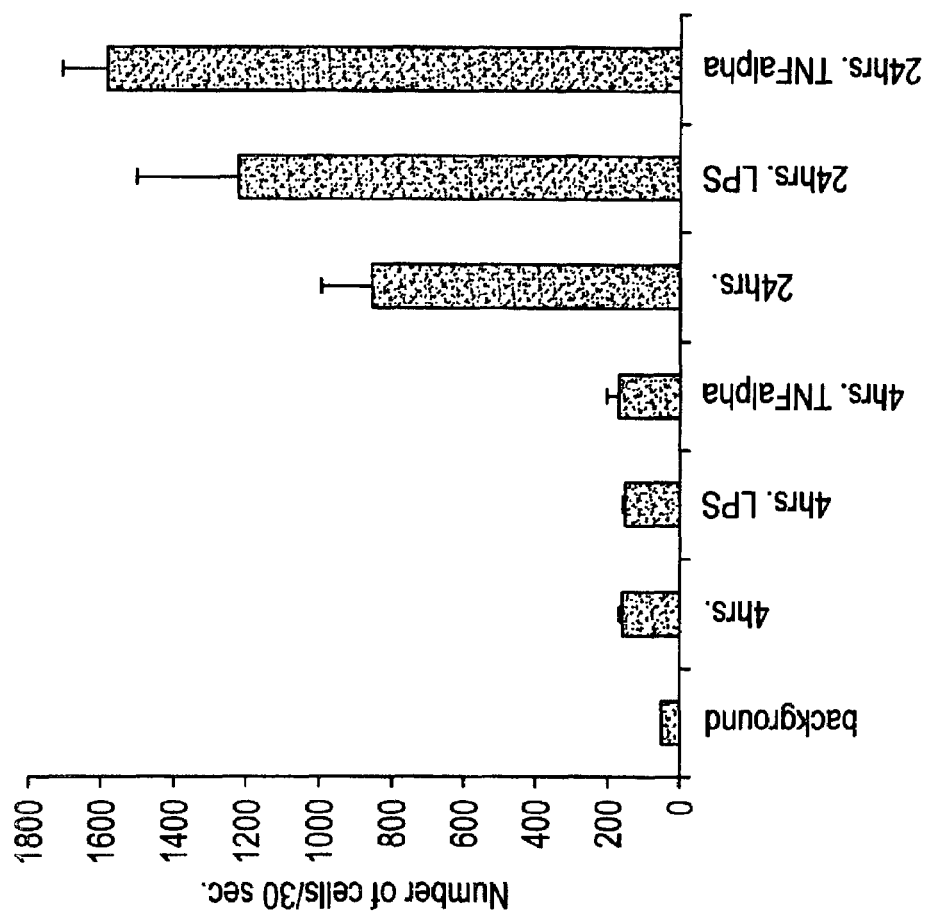
FIG. 34 is a histogram showing that SExCkine (CXCL16) is secreted from human macrophages and can induce chemotaxis. Monocyte-derived macrophages were cultured in media or media supplemented with LPS (50 ng/mL) or TNF-α (10 ng/mL) for 4 hours or 24 hours. Culture supernatants were assayed using a chemotaxis assay in which the migration of L1.2 cells that expressed Bonzo (Bonzo/L1.2 transfectants) was monitored. Levels of SExCkine (CXCL16) secreted by the monocyte-derived macrophages, measured by chemotactic activity, increased after stimulation with LPS or
TNF-α for 24 hours. Background is the amount of chemotaxis observed in assays that contained unconditioned media.

Studies also indicated that functional SExCkine could be shed from the cell surface of leukocyte subsets. Cultured monocyte/macrophages were propagated by adherence to plastic and SExCkine-induced chemotactic activity of supernatants isolated from the cultured monocyte/macrophages was examined. Examination of the expression of SExCkine on cultured monocyte/macrophages demonstrated that even after several days in culture, cell surface expression of SExCkine could be observed. The cultured monocyte/macrophages were then maintained in media or media supplemented with the inflammatory mediators LPS or TNF-α. After 4 or 24 hours, the culture supernatants were removed and assayed for chemotactic activity. There was no increase of cell-surface staining of SExCkine after a 4- or 24-hour incubation period with LPS or TNF-α. After four hours, chemotactic activity was only minimally higher than background, and there was no discernable difference between the chemotactic activity of supernatants from unstimulated and stimulated cells (FIG. 34). After 24 hours, however, a significant increase in chemotactic activity was observed and this increase was even greater in supernatants isolated from cells cultured in the presence of LPS, and greater still in supernatants isolated from cells cultured in the presence of TNF-α (FIG. 34). These results demonstrate that functional SExCkine chemokine was shed into the media over time and that the expression of soluble SExCkine was increased by inflammatory stimuli. These results also indicate that soluble SExCkine which is shed from the cell surface can participate in the recruitment of lymphocyte sub-populations to sites of immune and inflammatory responses.

EXAMPLE 4

SExCkine and Bonzo are Expressed in Tonsil-Derived CD4$^+$ Cells

Methods and Materials

Preparation of Tonsils

Tonsils were obtained from Massachusetts Eye and Ear Infirmary (Boston, Mass.). Tissue was macerated with surgical scissors, mixed with DMEM (Gibco/BRL, Rockville, Md.) and passed through a cell strainer (Becton Dickinson, Franklin Lakes, N.J.). Cells were washed three times with PBS prior to staining. For the chemotaxis experiments, CD4$^+$ T cells were isolated from tonsils by positive magnetic selection using CD4 microbeads (Milentyi Biotec, Auburn, Calif.) and the manufacturer's instructions. For the FACS analysis, mononuclear cells that were isolated from fresh tonsils were used.

Purification of Recombinant His-Tagged SExCkine Fusion Protein

Recombinant His-tagged SExCkine protein (consisting of the entire predicted extracellular domain of SExCkine, amino acid residues 1 to 202, SEQ ID NO:4) was generated as described in Example 1. Supernatant fractions that were isolated from the recombinant cells were run over a column containing 5 mL of Wheat germ agglutinin conjugated to agarose (Vector Labs, Burlingame, Calif.). The column was washed with PBS and the His-tagged SExCkine fusion protein was eluted with 10 mL of 100 mM acetic acid (pH 2.8). The 10 mL elution fraction was brought to pH neutrality with 5 mL of 1 M Tris-base (pH 10.5) and was run over a NiNTA agarose column (Qiagen, Valencia, Calif.). The column was washed with 50 mM $NaH_2PO_4$, pH 8; 300 mM NaCl; 20 mM imidazole and the His-tagged SExCkine fusion protein was subsequently eluted with 50 mM $NaH_2PO_4$, pH 8; 300 mM NaCl; 250 mM imidazole in five 1 mL aliquots. Samples were dialyzed overnight against PBS using a 3 mL 10,000 MW cutoff Slide-a-lyzer (Pierce, Rockford, Ill.). $OD_{280}$ readings were taken to determine the protein concentration.

Chemotaxis Assay

Chemotaxis assays were performed as described in Example 1, using endothelial-coated TRANSWELL inserts.

Results and Discussion

Figure 35B:
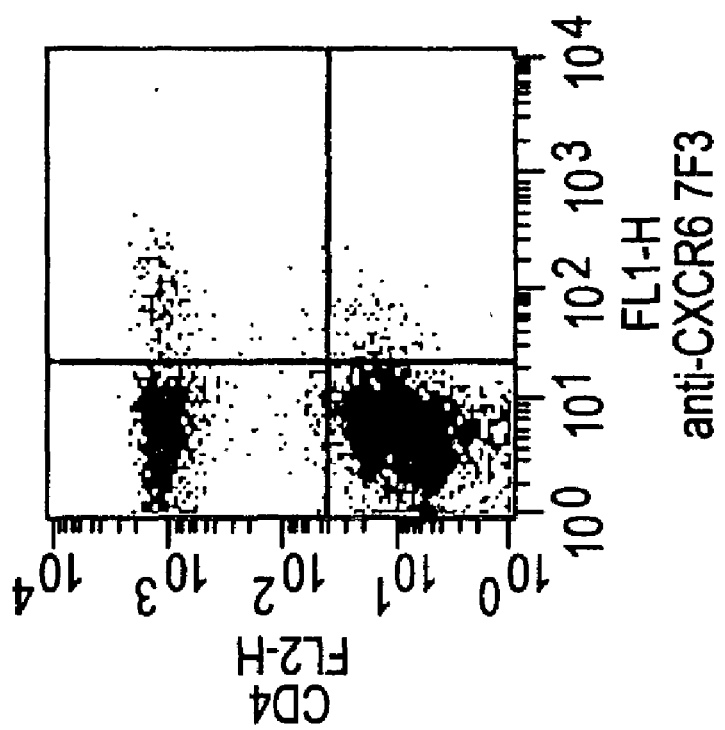
FIGS. 35A and 35B are fluorescence plots showing that Bonzo (CXCR6) is expressed on tonsil mononuclear cells. Mononuclear cells were isolated from fresh tonsils and were stained with FITC-conjugated anti-Bonzo mAb 7F3 (FIG. 35B) or a conjugated isotype control antibody (FIG. 35A).
Figure 35A:
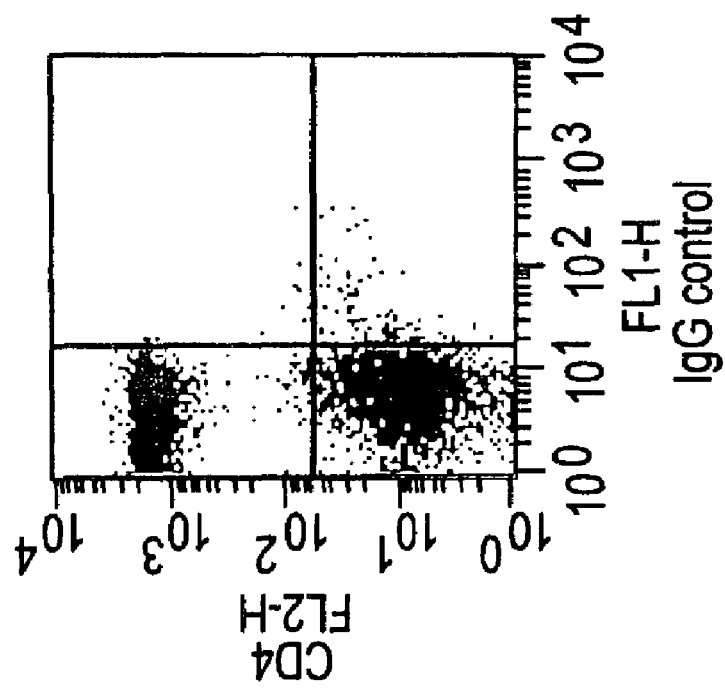
Figure 36B:
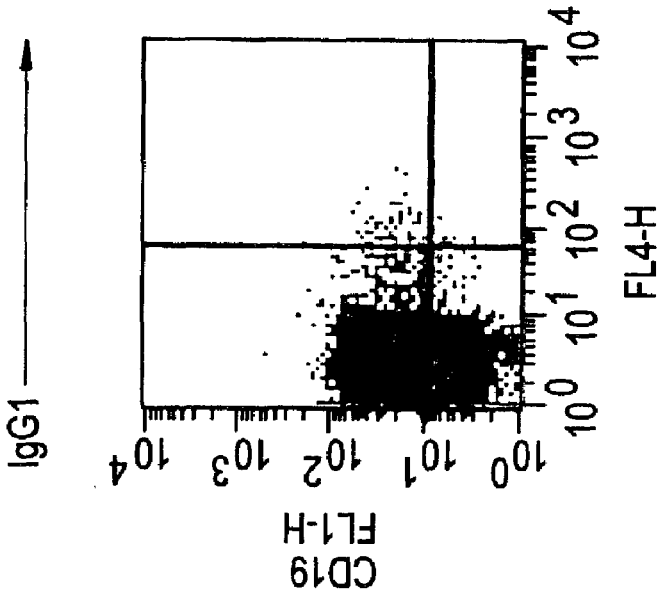
FIGS. 36A and 36B are fluorescence plots showing that SExCkine (CXCL16) is expressed on a subset of $CD19^+$ B lymphocytes isolated from tonsils. Freshly isolated tonsil cells were examined for expression of CD19 (y-axes) and SExCkine (CXCL 16), using anti-SExCkine monoclonal antibody mAb SD7 (FIG. 36A), or an IgG1 isotype control antibody (FIG. 36B).
Figure 36A:
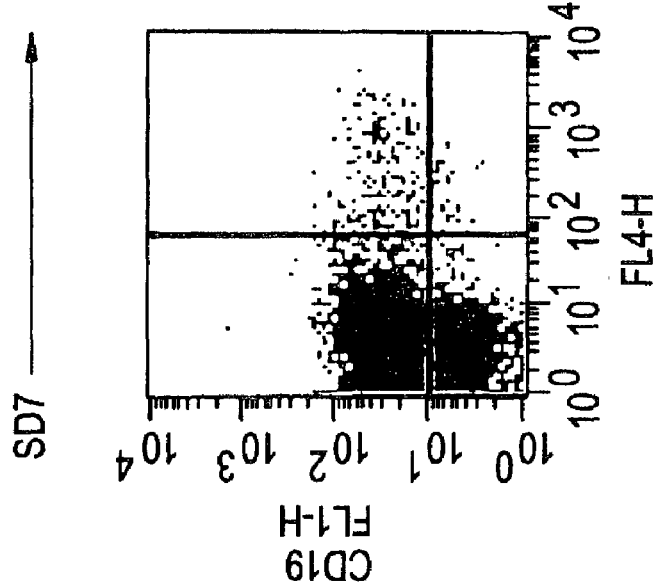

In order to determine if activated cells from a chronically-inflamed tissue express Bonzo (CXCR6), tonsil-derived mononuclear cells were stained with anti-Bonzo mAb 7F3. Staining of these tonsil-derived mononuclear cells demonstrated that a sub-population of $CD4^+$ T cells express Bonzo (compare FIGS. 35A and 35B). Staining experiments using anti-SExCkine mAb SD7 also showed cell surface expression of SExCkine in a subset of $CD19^+$ B cells that were isolated from tonsils (compare FIGS. 36A and 36B). These results indicate that, within secondary lymphoid tissue, B cells expressing SExCkine can be activated by a T cell-dependent process.

The data presented herein indicates that SExCkine which is expressed on B cells can bind to Bonzo expressed on T cells and can contribute to T cell activation. These B cell/T cell interactions can occur after $Bonzo^+$ T cell/dendritic cell interactions have been initiated, and SExCkine can play a role in both of these steps. Sequence analysis predicts that the cytoplasmic tail of SExCkine has a number of potential phosphorylation sites. Thus, the interactions of SExCkine with Bonzo may result in signals being transmitted through SExCkine and into the antigen-presenting cell.

Figure 37:
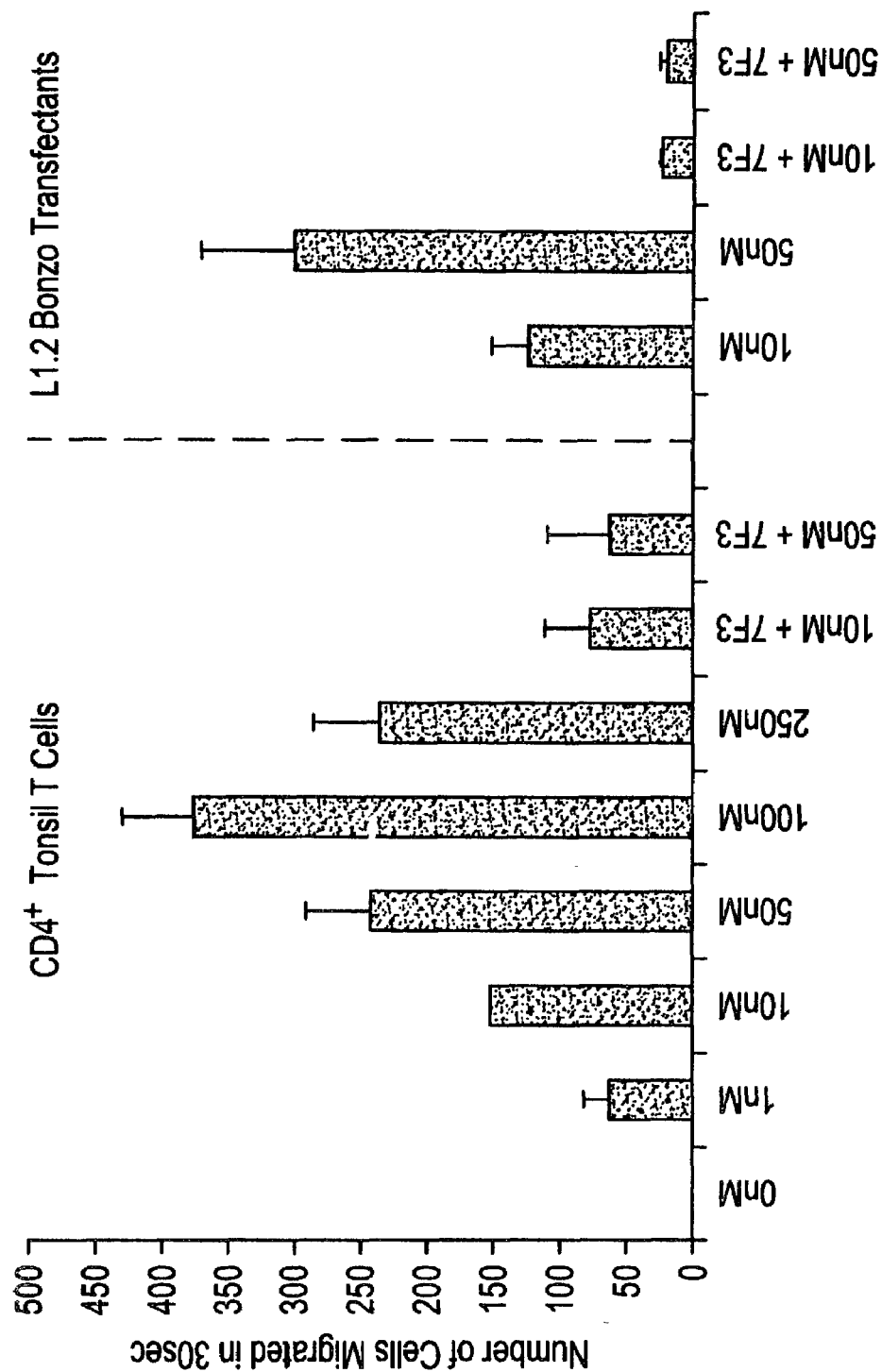
FIG. 37 is a histogram showing that purified recombinant SExCkine (CXCL16) induced dose-dependent chemotaxis of tonsil-derived $CD4^+$ T cells or of control L1.02 Bonzo transfectants. SExCkine (CXCL16)-induced chemotaxis of purified tonsil-derived $CD4^+$ T cells was assessed in in vitro chemotaxis assays using purified recombinant SExCkine (CXCL16) at the indicated concentrations. Control chemotaxis assays using L1.2 Bonzo transfectants were run simultaneously. Pre-incubation of the tonsil-derived $CD4^+$ T cells or L1.2 Bonzo transfectants with anti-Bonzo mAb 7F3 inhibited SExCkine (CXCL16)-induced chemotaxis.

In addition, purified recombinant SExCkine induced chemotaxis of isolated tonsil-derived $CD4^+$ T cells (FIG. 37). Preincubation of the tonsil-derived $CD4^+$ T cells with anti-Bonzo antibody mAb 7F3 blocked chemotaxis (FIG. 37), indicating that Bonzo is the receptor for SExCkine on these cells.

EXAMPLE 5

Anti-SExCkine mAb SD7 Inhibits Chemotaxis of Bonzo/L1.2 Cells

Methods and Materials

Reagents and Cells

Bonzo/L1.2 transfectants were generated as described in Example 1. Purified recombinant SExCkine (consisting of the entire predicted extracellular domain of SExCkine, amino acid residues 1 to 202, SEQ ID NO:4) was produced and purified as described in Examples 1 and 4.

Chemotaxis Assays

Chemotaxis assays were performed as described in Example 1, except that no endothelial cells were used.

Results and Discussion

Figure 38:
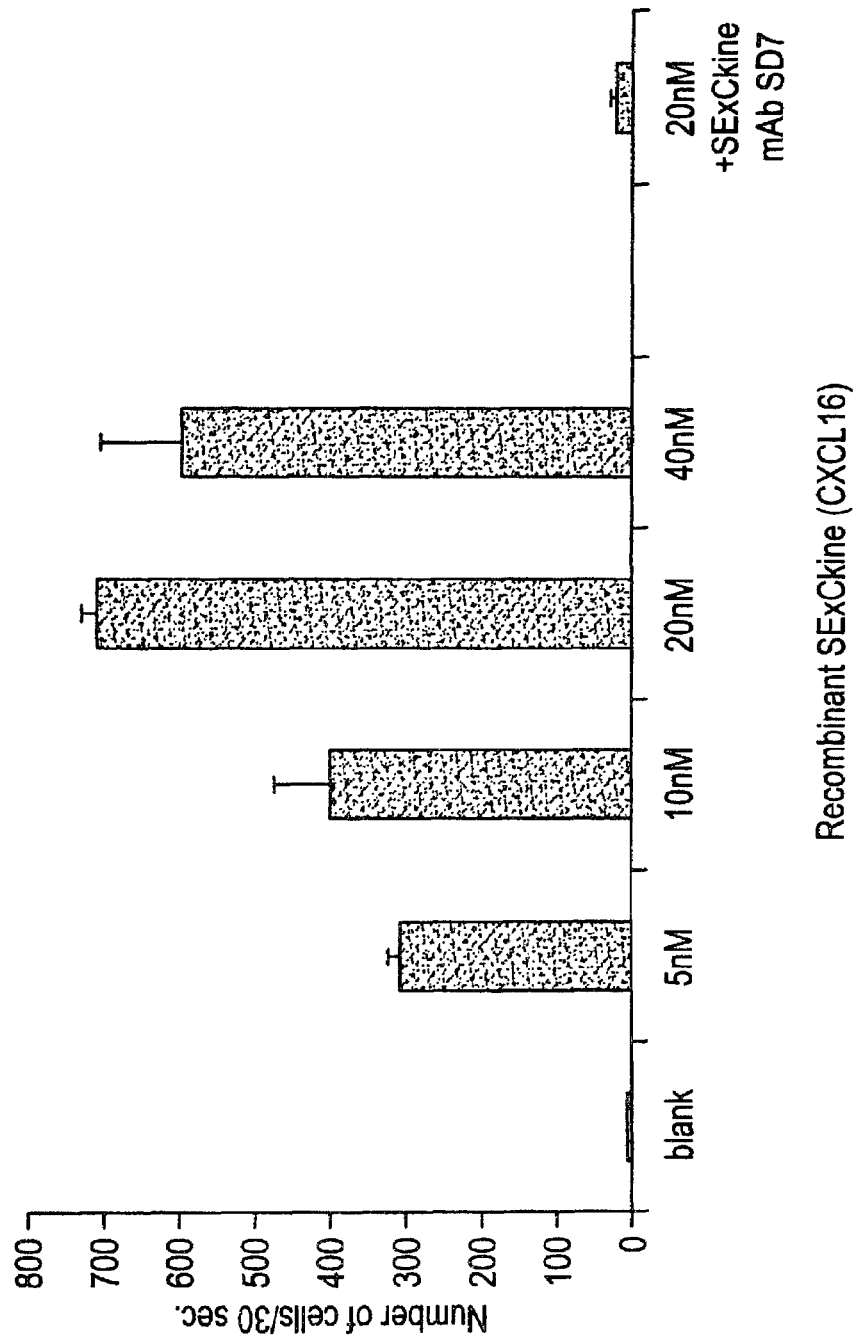
FIG. 38 is a histogram showing that purified recombinant SExCkine (CXCL16) induced dose-dependent chemotaxis of L1.2 cells that expressed Bonzo (L1.2 Bonzo transfectants). SExCkine (CXCL16)-induced chemotaxis of L1.2 Bonzo transfectants was assessed in in vitro chemotaxis assays using purified recombinant SExCkine (CXCL16) at the indicated concentrations. Pre-incubation of the L1.2/Bonzo cells with anti-SExCkine (CXCL16) mAb SD7 (20 μg/mL) inhibited SExCkine (CXCL16)-induced chemotaxis.

Chemotaxis assays also demonstrated that purified recombinant SExCkine induced chemotaxis of Bonzo/L1.2 transfectants (FIG. 38). L1.2 cells that were transfected with Bonzo (Bonzo/L1.2 transfectants) were tested for chemotactic activity to purified SExCkine. Preincubation of Bonzo/L1.2 transfectants with anti-SExCkine mAb SD7 inhibited chemotaxis of the Bonzo/L1.2 transfectants (FIG. 38). These results demonstrate that Bonzo-expressing cells undergo SExCkine-induced chemotaxis and that mAb SD7 blocks the binding of SExCkine to Bonzo.

EXAMPLE 6

SExCkine is Heavily Glycosylated

Methods and Materials

Deglycosylation of SExCkine

A Glycoprotein Deglycosylation Kit (Calbiochem, San Diego, Calif.) was used to deglycosylate 2 μg of SExCkine protein. The standard denaturing protocol was followed and 150 ng each of untreated and deglycosylase-treated protein was run on a 4–20% Tris-glycine gel (Novex, San Diego, Calif.). Protein was transferred onto a nitrocellulose membrane (Novex, San Diego, Calif.) and hybridized with a SExCkine (CXCL16) monoclonal antibody (mAb SD7). The NEN Renaissance system of chemiluminescence (NEN, Boston Mass.) was used for detection.

Results and Discussion

Figure 39:
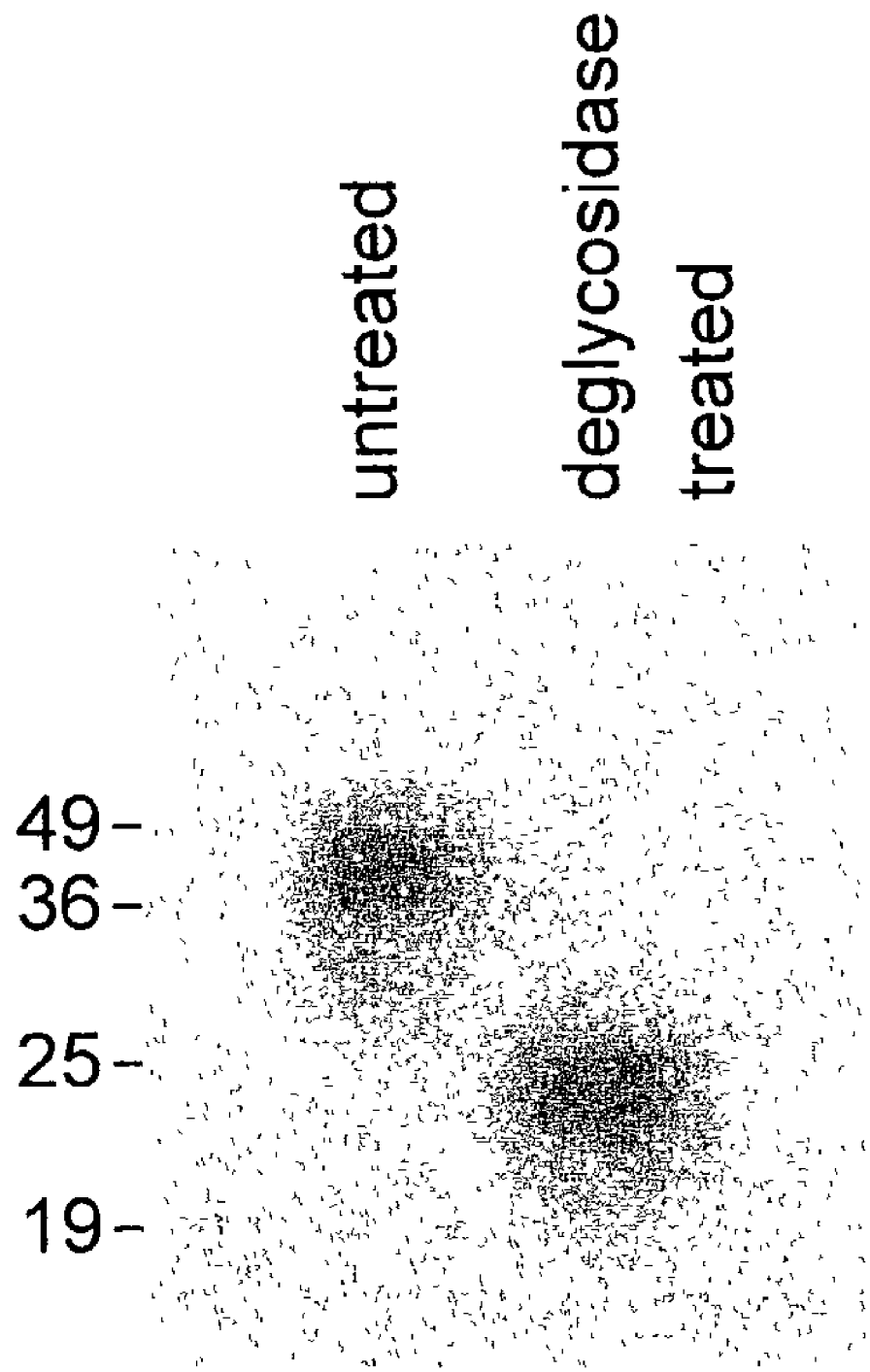
FIG. 39 is a photograph of a Western blot (produced by chemiluminescence) showing that purified recombinant SExCkine (CXCL16) is heavily glycosylated. 150 ng of purified recombinant SExCkine (CXCL16) was resolved on a 4–20% Tris-glycine electrophoresis gel, transferred to a nitrocellulose membrane and probed with a culture supernatant containing anti-SExCkine (CXCL16) nab SD7 (diluted 1:5). The mobility of the protein was increased to a size roughly corresponding to the protein backbone after incubation in a glycosidase mixture including N-Glycosidase F, Endo-α-N-acetylgalactosaminidase, α2–3,6,8,9-Neurominidase, β1,4-Galactosidase and β-N-Acetylglucosaminidase) (deglycosidase treated).

Although SExCkine has only one predicted N-linked glycosylation site (NETT at resides 168–171), the sequence of SExCkine indicated that the mucin domain was likely to be heavily glycosylated and rich in O-linked glycans. In order to test this, purified recombinant SExCkine was treated with a cocktail of deglycosylases including, N-Glycosidase F, Endo-α-N-acetylgalactosaminidase, α2-3,6,8,9-Neurominidase, β1,4-Galactosidase, and β-N-Acetylglucosaminidase and examined by Western blotting. Western blot analysis using anti-SExCkine mAb SD7 revealed that the untreated purified recombinant SExCkine has a relative molecular ($M_r$) mass of approximately 40 kD (approximately twice the size of the protein backbone of $M_r$ 19K) while the deglycosylase-treated recombinant SExCkine has a relative molecular mass of approximately 23 kD (FIG. 39). These results confirm that SExCkine is highly glycosylated.

EXAMPLE 7

Dose Response Curve of the Chemotactic Activity of Bonzo/L1.2 Transfectants for Purified Recombinant SExCkine Methods and Materials Reagents and Cells Bonzo/L1.2 transfectants were generated as described in Example 1. Purified recombinant SExCkine (consisting of the entire predicted extracellular domain of SExCkine, amino acid residues 1 to 202, SEQ ID NO:4) was produced and purified as described in Examples 1 and 4. L1.2 cell transfectants that expressed chemokine receptors CXCR-5, CCR1, CCR2, CCR3, CCR4, CCR5, CCR6, CCR7, CCR8, CCR9 or CX3CR1 were maintained in RPMI1649 media (Gibco/BRL, Rockville, Md.) with 0.88 g/L gentimycin (G418), 10% Hyclone serum, 10 nM HEPES, 1% penicillin/streptomycin, 1% L-glutamine, 1 mM sodium pyruvate and 55 nM β-mercaptoethanol.

Chemotaxis Assays

Chemotaxis assays were performed as described in Example 1, except that no endothelial cells were used.

Results and Discussion

Figure 40:
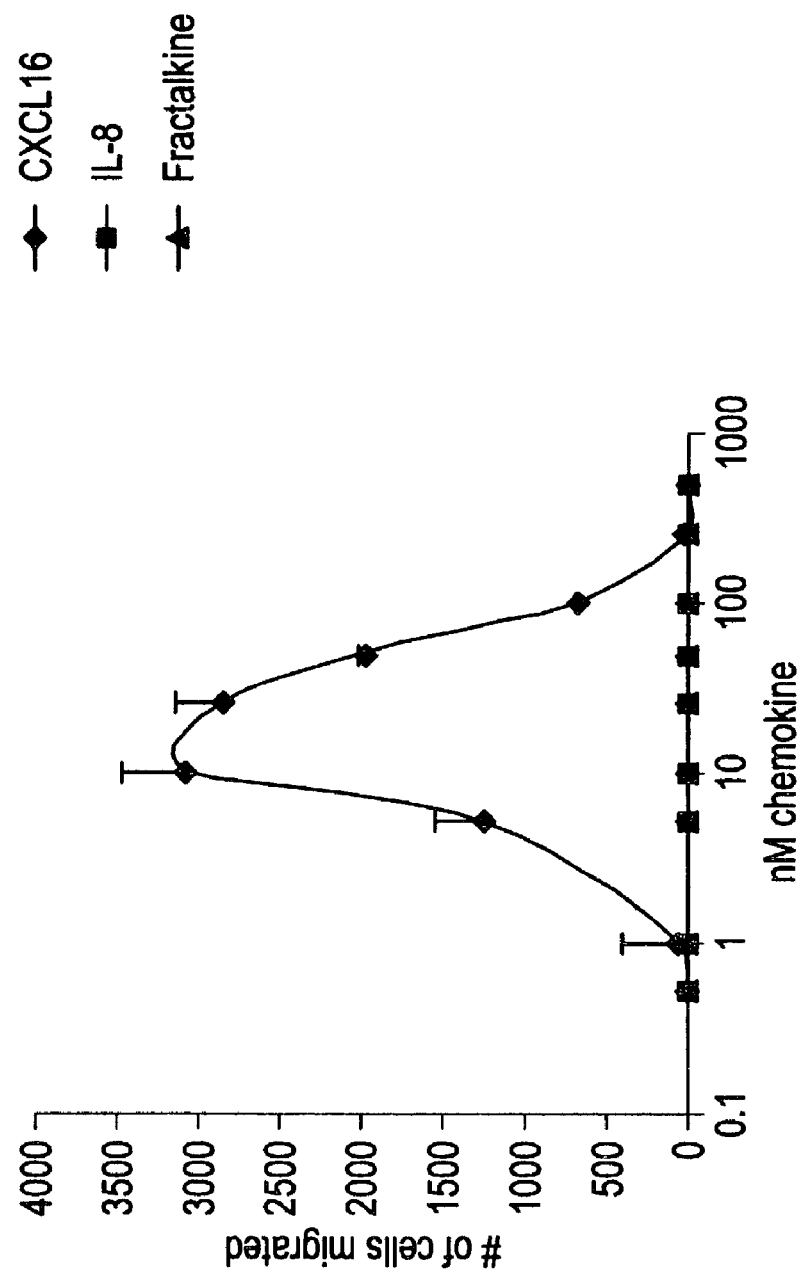
FIG. 40 is a graph showing that purified recombinant SExCkine (CXCL16) selectively induced dose-dependent chemotaxis of Bonzo/L1.2 transfectants. Chemotaxis of L1.2 Bonzo transfectants was assessed in in vitro chemotaxis assays using purified recombinant SExCkine (CXCL16) (-◆-), Interleukin 8 (IL-8; -■-) or Fractalkine (-▲-) at the indicated concentrations. Maximal chemotaxis occurred in response to stimulation with SExCkine (CXCL16) at a concentration of about 10 nM to about 50 nM.

Chemotactic activity of Bonzo/L1.2 transfectants was tested using purified recombinant SExCkine. L1.2 cells transfected with Bonzo exhibited a robust chemotactic response to purified recombinant SExCkine and displayed a typical bell-shaped dose response curve with peak activity ranging from 10–50 nM (FIG. 40). In contrast, Bonzo/L1.2 transfectants did not exhibit chemotactic activity to either IL-8 or fractalkine (FIG. 40)

Purified recombinant SExCkine was also tested in chemotaxis assays against a panel of cells expressing chemokine receptors CCR1, CCR2, CCR3, CCR4, CCR5, CCR6, CCR7, CCR8, CCR9, CXCR1, CXCR2, CXCR3, CXCR4, CXCR5 or CX3CR1. While known ligands for these receptors exhibited a robust response in this assay, purified recombinant SExCkine (CXCL16) failed to induce a chemotactic response in cells that expressed receptors other than CXCR6 at all concentrations tested (FIG. 41). These data illustrate that SExCkine is an exclusive ligand for Bonzo.

EXAMPLE 8

Calcium Flux Assays

Methods and Materials

Reagents and Cells

Bonzo/L1.2 transfectants were generated as described in Example 1. Purified recombinant SExCkine (consisting of the entire predicted extracellular domain of SExCkine, amino acid residues 1 to 202, SEQ ID NO:4) was produced and purified as described in Example 1 and 4. Chemokines were obtained from R and D Systems (Minneapolis, Minn.), Peprotech Inc. (Rocky Hill, N.J.) or were synthesized using an automated solid-phase peptide synthesizer using previously described methods (Topham, P. S. et al., *J. Clin. Invest.* 104:1549–1557 (1999)).

Calcium Flux Assays

Bonzo/ L1.2 transfectants or L1.2 parental cells were washed once in PBS and resuspended in load buffer (HBSS, 20 mM HEPES, 2.5 mM Probenecid, 0.1% BSA, 1% FBS). Fluo-3 (Molecular Probes, Inc., Eugene, Oreg.) was dissolved in 50% DMSO/50% Pluronic acid and added to the cells at a final concentration of 4 µM. Cells were incubated for 1 hour at 37° C. and then were washed twice in load buffer and plated into 96 well assay plates at $3\times10^5$ cells per well. The plates were spun for 5 minutes at 1200 rpm in order to pellet the cells on the bottom of the well. Chemokine (50 µL) was added to a separate 96 well plate at varying concentrations in order to achieve the indicated final concentrations. $Ca^{2+}$ mobilization was then measured on a 96 well FLIPR System (Molecular Devices, Sunnyvale, Calif.).

Results and Disscussion

SExCkine is able to specifically signal a rise in intracellular calcium in Bonzo/L1.2 cells. SExCkine (CXCL16) induced a dose-dependent rise in intracellular calcium of Bonzo/L1.2 cells which was similar to that seen for SDF-1α, the ligand for CXCR4 which is endogenously expressed on L1.2 cells (FIGS. 42A and 42B). As a negative control, both parental L1.2 cells and Bonzo-transfected L1.2 failed to respond to MIP 1β (FIGS. 42A and 42B).

EXAMPLE 9

Receptor Binding Assays

Methods and Materials

Reagents and Cells

Bonzo/L1.2 transfectants were generated as described in Example 1. Purified recombinant SExCkine (consisting of the entire predicted extracellular domain of SExCkine, amino acid residues 1 to 202, SEQ ID NO:4) was produced and purified as described in Examples 1 and 4.

Receptor Binding Assays

Exponentially-growing Bonzo/L1.2 transfectants were counted on the day of the assay and were resuspended in binding assay buffer (BAB) (10 mM HEPES/1 mM $CaCl_2$/5 mM $MgCl_2$/0.5% BSA/0.05% Na Azide) at a density of $2.5\times10^6$ cells/mL. Purified recombinant SExCkine (CXCL16) was labeled with $I^{125}$ using a sodium iodine method (Amersham, Arlington Heights, Ill.) and was diluted to 4 nM in BAB. Cold (unlabeled) SExCkine (in PBS at 5.3 µM) was diluted for competition in BAB to 0.4 nM, 2 nM, 4 nM, 20 nM, 40 nM, and 400 nM. Reactions were performed in triplicate and consisted of 50 µL of cells ($1.25\times10^5$ total cells), 25 µL of $I^{125}$-labeled SExCkine (at a final concentration of 1 nM) and 25 µL of cold (unlabeled) SExCkine which was serially diluted from 100 nM to 0 nM. The specific activity of the $I^{125}$-labeled SExCkine was $7.8\times10^{10}$ nmol/cpm, and the total counts, non-specific counts and specific counts were 813.67, 222.33, and 591.34 respectively. For calculation of total $I^{125}$ input, 50 µL of cells was added to 25 µL of $I^{125}$I-labeled SExCkine and 25 µL BAB. All tubes were incubated for 1 hour at room temperature, after which time the cells were spun down at 3500 rpm and washed five times in BAB+0.5 M NaCl. After the final wash, the cell pellet was resuspended in 100 µL of wash buffer and the $I^{125}$ counts were calculated using a Cobra II auto-gamma scintillation counter (Packard, Downers Grove, Ill.) along with the total input sample. Binding data was calculated using a program written in Excel.

Results and Disscussion

In order to directly examine binding of SExCkine to Bonzo/L1.2 cells, SExCkine was radiolabeled and used in competition receptor binding assays. Increasing concentrations of unlabeled (cold) SExCkine (CXCL16) competitively inhibited $^{125}$I-labeled SExCkine binding to Bonzo/L1.2 cells, with an $IC_{50}$ of 1 nM (FIG. 43A) while $^{125}$I-labeled SExCkine could not be inhibited by non-specific chemokines. In addition, SExCkine binding was not specific for control chemokine receptor transfectants, including CCR6 and CCR7. Scatchard analysis demonstrated that binding occurs with high affinity with an average Kd of 1 nM and with approximately 4,000 binding sites/transfectant. These results indicate that SExCkine is a high affinity, selective ligand for Bonzo (FIG. 43B).

EXAMPLE 10

Analysis of SExCkine and Bonzo Expression Using TaqMan® (Roche Molecular Systems, Inc., Basel, Switzerland) Quantitative PCR Methods and Materials RNA Isolation and Preparation Total RNA was isolated from various human cells, tissues and cell lines (Table 5) using Qiagen RNeasy Mini-kit (Qiagen, Valencia, Calif.) according to the manufacturer's protocol. Each RNA preparation was treated with DNase I (Qiagen, Valencia, Calif.) at room temperature for 15 minutes. DNase I treatment was determined to be complete if the sample required at least 38 PCR amplification cycles to reach a threshold level of fluorescence using β-2 microglobulin RNA as an internal amplicon reference. The integrity of the RNA samples following DNase I treatment was confirmed using agarose gel electrophoresis and ethidium bromide staining. The samples were then subjected to phenol extraction and cDNA was prepared using the Omniscript Reverse Transcriptase Kit (Qiagen, Valencia, Calif.) following the manufacturer's instructions. As a negative control, RNA was mock transcribed without reverse transcriptase. TaqMan® (Roche Molecular Systems, Inc., Basel, Switzerland) quantitative PCR SExCkine and Bonzo expression were measured using TaqMan® (Roche Molecular Systems, Inc., Basel, Switzerland) quantitative PCR on cDNA that was prepared from the various sources listed in Table 5.

TABLE 5

| Cell type | Source |
| --- | --- |
| CD4 | Isolated from human PBMCs using CD4 microbeads (Miltenyi Biotech, Auburn, CA) |
| CD8 | Isolated from human PBMCs using CD8 microbeads (Miltenyi Biotech, Auburn, CA) |
| CD14 | Isolated from human PBMCs using CD14 microbeads (Miltenyi Biotech, Auburn, CA) |
| CD19 | Isolated from human PBMCs using CD19 microbeads (Miltenyi Biotech, Auburn, CA) |
| Grans | Granulocytes that were isolated from whole blood using ficoll gradients |
| Macs (macrophages) | Macrophages that were isolated from human PBMCs using CD14 microbeads and plate binding (Miltenyi Biotech, Auburn, CA) |
| HMVEC | Human microvascular endothelial cells (Clonetics; San Diego, CA) |
| Eos (CD 16) | Eosinophils that were isolated from whole blood using ficoll gradients and negative selection on CD16 microbeads (Miltenyi Biotech, Auburn, CA) |
| NHBE | Normal human bronchial epithelial cells (Clonetics; San Diego, CA) |
| BSMC | Bronchial smooth muscle cells (Clonetics; San Diego, CA) |
| RL6 | T effector cells from M. Kapsenberg (Univ. of Amsterdam, Netherlands) |
| Kaps DCs | Dendritic cells from M. Kapsenberg (Univ. of Amsterdam, Netherlands) |
| NHLF | Normal human lung fibroblasts (Clonetics; San Diego, CA) |
| NHDF | Normal human dermal fibroblasts (Clonetics; San Diego, CA) |
| RA synovio type B | Rheumatoid arthritis synovial cells (Cell Applications) |
| Normal synoviums | Cells isolated from normal synoviums (Boston area hospitals) |
| Diseased synoviums | Cells isolated from diseased synoviums (Boston area hospitals) |
| Normal colon | Cells isolated form normal colons (Boston area hospitals) |
| Colitis colon | Cells isolated from colitic colons (Boston area hospitals) |
| Normal Brain | Cells isolated from normal brains (Boston area hospitals) |
| Normal Hearts | Cells isolated from normal hearts (Boston area hospitals) |
| Normal Kidneys | Cells isolated from normal kidneys (Boston area hospitals) |
| Normal Spleens | Cells isolated from normal spleens (Boston area hospitals) |
| Normal Tonsils | Cells isolated from normal tonsils (Boston area hospitals) |
| Normal Lymph nodes | Cells isolated from normal lymph nodes (Boston area hospitals) |
| Liver Pool Pit 260/CHT 339 | Cells isolated from normal livers (Boston area hospitals) |
| Lung CHT B11 | Cells isolated from normal lungs (Boston area hospitals) |
| COPD-1 | Lung cells isolated from patients with chronic obstructive pulmonary disease (Boston area hospitals) |
| COPD-2 | Lung cells isolated from patients with chronic obstructive pulmonary disease (Boston area hospitals) |
| IPF | Lung cells isolated from patients with interstitial pulmonary fibrosis (Boston area hospitals) |

Primers and Probes

PCR probes were designed using PrimerExpress software (Perkin Elmer Applied Biosystems, Foster City, Calif.). The primers and probes that were used to measure expression of SExCkine and β-2 microglobulin were as follows: SExCkine forward primer; 5' att gtg gta aaa gaa ttt ctt ccg a 3' (SEQ ID NO:19). SExCkine reverse primer; 5' cag gtg ttt ccg gag acg at 3' (SEQ ID NO:20), SExCkine probe; 5' tcc ccg cca tcg gtt cag ttc at 3' (SEQ ID NO:21), β-2 microglobulin forward primer; 5' cac ccc cac tga aaa aga tga 3' (SEQ ID NO:22), β-2 microglobulin reverse primer; 5' ctt aac tat ctt ggg ctg tga caa ag 5' (SEQ ID NO:23), and β-2 microglobulin probe; 5' atg cct gcc gtg tga acc acg tg 5' (SEQ ID NO:24). The primers and probe that were used to measure expression of Bonzo were as follows: Bonzo forward primer; 5' atg cca tga cca get ttc act a 3' (SEQ ID NO:25), Bonzo reverse primer; 5' tta agg cag gcc ctc agg t 3' (SEQ ID NO:26), and Bonzo probe; 5' tca tgg tga cag agg cca tcg ca 3' (SEQ ID NO:27).

Each gene probe was labeled using FAM (6-carboxyfluorescein) (Perkin Elmer Applied Biosystems, Foster City, Calif.) and the β-2 microglobulin reference probe was labeled with a different flourescent dye, VIC (Perkin Elmer Applied Biosystems, Foster City, Calif.). The differential labeling of the target gene and internal reference gene thus enabled measurement in the same well. Forward and reverse primers and the probes for both β-2 microglobulin and SExCkine were added to the TaqMan® (Roche Molecular Systems, Inc., Basel, Switzerland) Universal PCR Master Mix (Perkin Elmer Applied Biosystems, Foster City, Calif.). Each reaction contained 200 nM of forward and reverse primers plus 100 nM probe for β-2 microglobulin and 600 nM of forward and reverse primer plus 200 nM probe for SExCkine. TaqMan® (Roche Molecular Systems, Inc., Basel, Switzerland) experiments were carried out on an ABI PRISM 7700 Sequence Detection System (Perkin Elmer Applied Biosystems, Foster City, Calif.). The thermal cycler conditions were as follows: 2 minutes at 50° C.; followed by 10 minutes at 95° C.; followed by 40 cycles of 2-step PCR that consisted of 15 seconds at 95° C. and 1 minute at 60° C.

The following method was used to quantitatively calculate SExCkine gene expression in the various tissues relative to β-2 microglobulin expression in the same tissue. The threshold cycle (Ct) value was defined as the cycle at which a statistically-significant increase in fluorescence was detected. The Ct value of SExCkine was normalized by subtracting the Ct value of the β-2 microglobulin gene to obtain a ΔCt value using the following formula:

$$\Delta Ct = Ct_{SExCkine} - Ct_{beta-2\ microglobulin}$$

Expression was then calibrated against a cDNA sample showing a comparatively low level of expression of SExCkine, i.e., a no-template control reaction (NTC)

($\Delta Ct_{calibrator}$). The $\Delta Ct$ value for the calibrator sample was then subtracted from the $\Delta Ct$ value for each tissue sample according to the following formula:

$$\Delta\Delta Ct = \Delta Ct_{sample} - \Delta Ct_{calibrator}$$

Relative expression was then calculated using the following formula:

$$Rel\ EXP = 2^{-\Delta\Delta Ct}$$

Relative expression of the target gene in each of the tested tissues was then represented graphically.

Cell Isolations Using the Miltenyi Biotec (Auburn, Calif.) Magnetic Bead System

Peripheral blood mononuclear cells (PBMCs) were isolated from human blood using density gradient centrifugation. Cells were then isolated using the Miltenyi Biotec magnetic microbead system (Miltenyi Biotech, Auburn, Calif.) according to the manufacturer's instructions. After isolation of the appropriate cell type, the cells were stimulated with various agents at the following concentrations: Plate-bound anti-CD3 Ab (Pharmingen, San Diego, Calif.) at 10 μg/mL, soluble anti-CD28 Ab at 5 μg/mL (Pharmingen, San Diego, Calif.), LPS (Sigma Chemicals Co., St. Louis, Mo.), at 1 μg/mL, CD40L/TRAP (Peprotech Inc., Rocky Hill, N.J.) at 5 μg/mL, TNF-α at 100 ng/mL, IFN-γ at 100 ng/mL, L-4 at 100 ng/mL, IL-13 at 100 ng/mL and TGF-β at 10 ng/mL, IL-1 at 50 ng/mL (all from Endogen Inc. Woburn, Mass.).

Results and Discussion

Figure 44A:
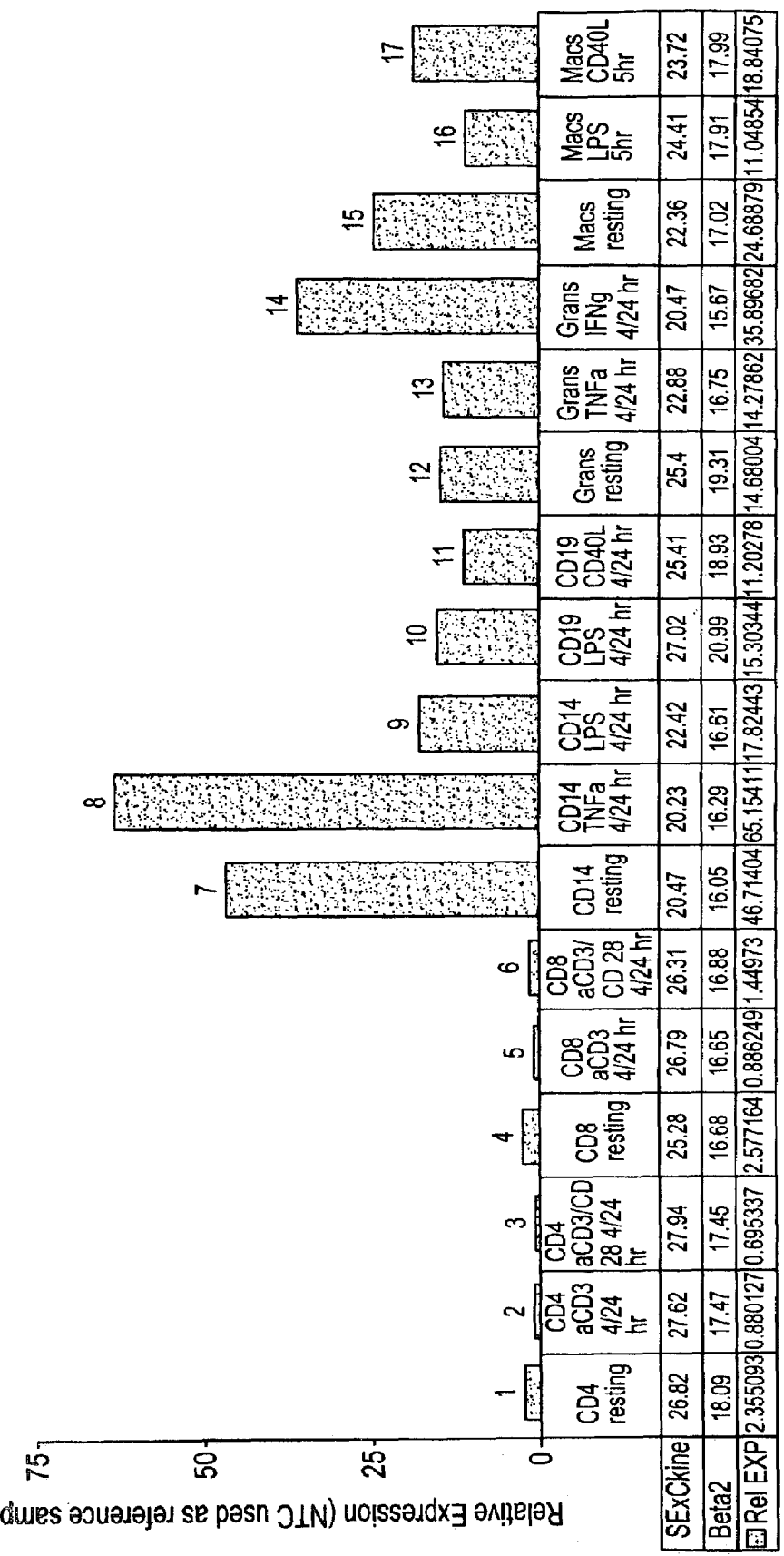
FIGS. 44A and 44B are histograms depicting the results of TaqMan® (Roche Molecular Systems, Inc., Basel, Switzerland) quantitative PCR analysis of the expression of SExCkine (CXCL16) in a variety of cell types. The values plotted correspond to the relative expression (REL EXP), which takes into consideration expression of a control gene, β-2 microglobulin, as well as a no-template control reaction (NTC). The cell types examined were CD4$^+$ T cells (bars 1–3), CD8$^+$ T cells (bars 4–6), CD14$^+$ monocytes (bars 7–9), CD19$^+$ B cells (bars 10–11), granulocytes (Grans) (bars 12–14), macrophages (Macs) (bars 15–20), human microvascular endothelial cells (HMVEC) (bars 12–24), eosinophils (Eos) (bars 25–26), normal human bronchial epithelial cells (NHBE) (bars 27–30) and bronchial smooth muscle cells (BSMC) (bars 31–33). In certain cases, the cell types were stimulated with one or more of the following agents: anti-CD3 (aCD3), anti-CD28 (CD28), TNF-α (TNFa), LPS, CD40L/TRAP (CD40L), IFNγ (IFNg), IL-4, IL-13, IL-1. Stimulated cell were produced by culturing the cells in media that contained the indicated agent(s) for 4 hours or for 24 hours. RNA was isolated from the cells, the isolated RNAs were pooled (4/24 hr), and cDNA was produced and used as template in the TaqMan® (Roche Molecular Systems, Inc., Basel, Switzerland) quantitative PCR reactions.
Figure 44B:
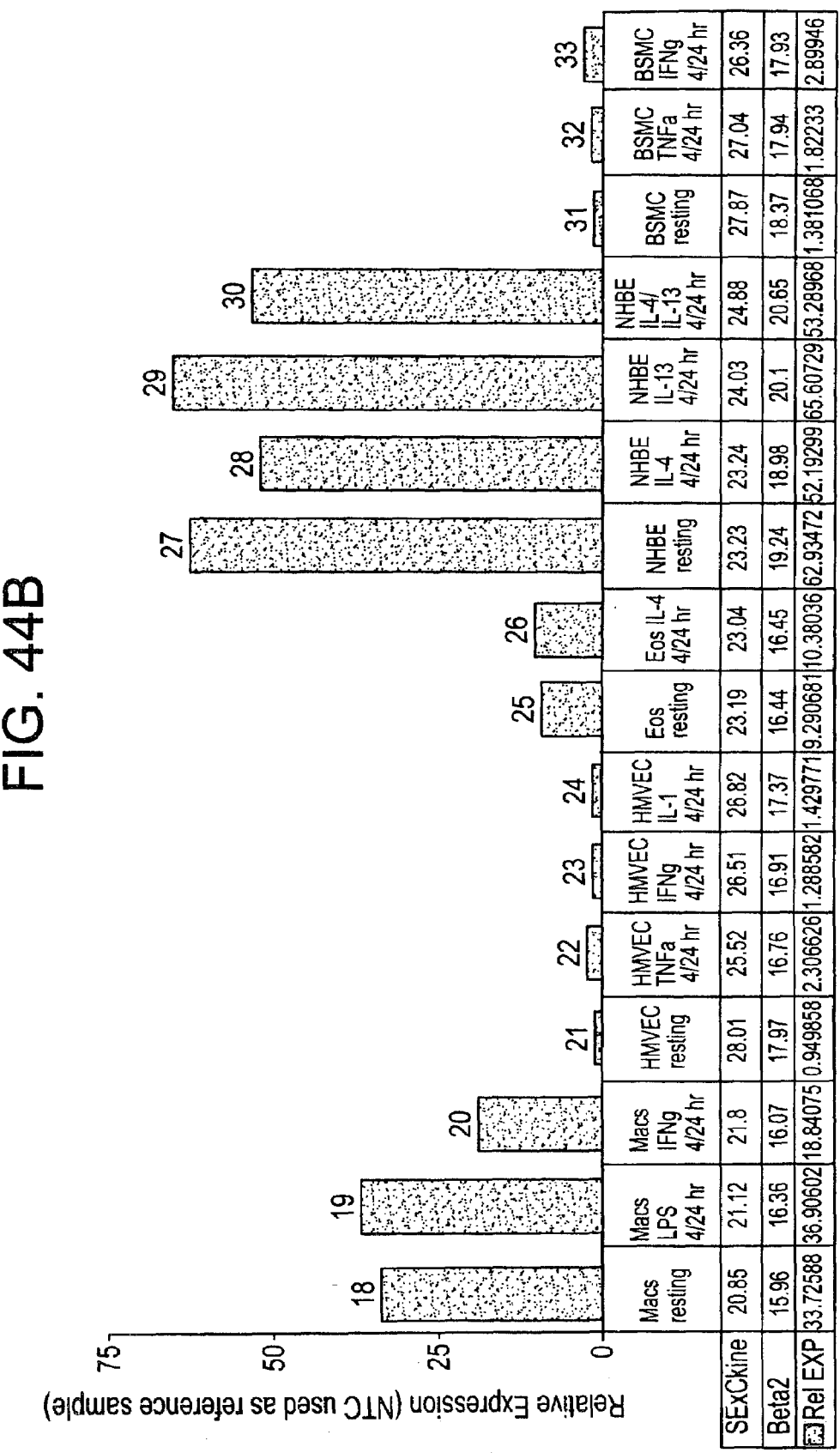
Figure 45:
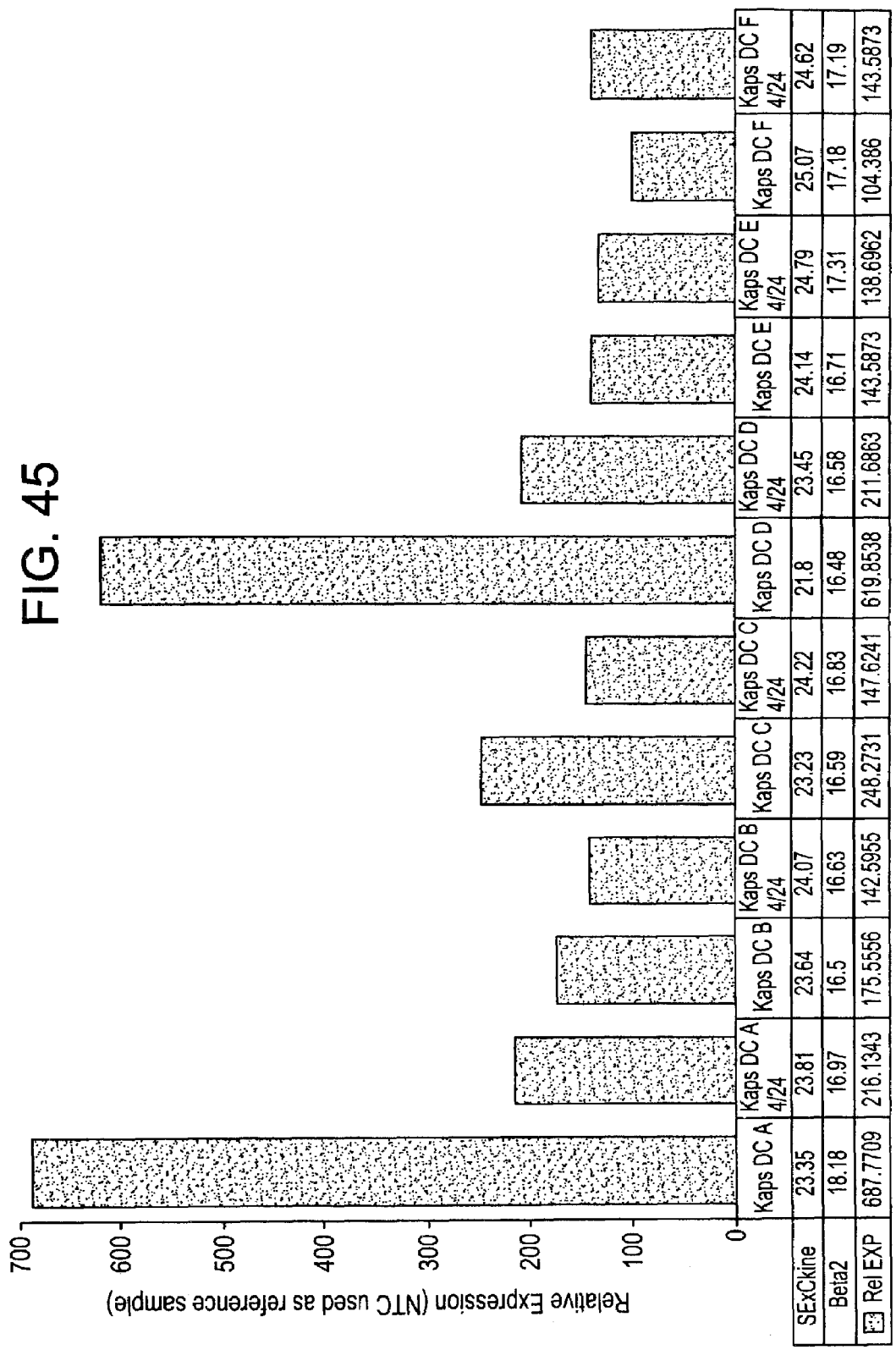
FIG. 45 is a histogram depicting the results of TaqMan® (Roche Molecular Systems, Inc., Basel, Switzerland) quantitative PCR analysis of the expression of SExCkine (CXCL16) in monocyte-derived dendritic cells (Kaps DC). Dendritic cells were obtained from M. Kapsenberg (University of Amsterdam, The Netherlands). The values plotted correspond to the relative expression (REL EXP), which takes into consideration expression of a control gene, β-2 microglobulin, as well as a no-template control reaction (NTC). The dendritic cells were subjected to seven different treatments. Stimulated cells were cultured in media that contained the following agents: Kaps DC A were immature unstimulated dendritic cells (no agent), Kaps DC B were cultured in LPS+IL-1β+TNF-α, Kaps DC C were cultured in LPS+IL-1β+TNF-α+IFN-γ, Kaps DC D were cultured in LPS+IL-1β+TNF-α+PGe2 (prostaglandin E2), Kaps DC E were cultured in poly I:C RNA (double stranded poly I (inosine):poly C (cytosine) RNA) and Kaps DC F were cultured in CD40L. Separate RNA pools were isolated from these dendritic cells prior to stimulation and after 4 hours of stimulation, and after 24 hours of stimulation. RNA that was isolated from the 4-hour and 24-hour time points was pooled (4/24 hr) and cDNA was produced and used as template in the TaqMan® (Roche Molecular Systems, Inc., Basel, Switzerland) quantitative PCR reactions.

SExCkine was expressed in several lymphocyte subsets and a variety of lymphatic and non-lymphatic human tissues. In cells isolated from human peripheral blood, expression of SExCkine was highest in cell types that act as antigen-presenting cells. The highest level of expression of SExCkine was observed in CD14+ cells monocytes (FIG. 44). Expression of SExCkine in CD14+ cells was increased upon TNF-α activation, but not LPS activation (FIG. 44). Macrophages also expressed SExCkine at moderate to high levels (FIG. 44). Monocyte-derived dendritic cells showed moderate to high levels of SExCkine expression and this expression decreased upon activation (FIG. 45). Moderate expression was also seen in CD19+ cells (B cells) and granulocytes (FIG. 44). Weak or no expression was found in T cell subsets (CD4+ and CD8+ cells) (FIG. 44) or T effector cells ($T_H0$, $T_H1$ and $T_H2$) (FIG. 45). In contrast, Bonzo (CXCR6), the receptor for SExCkine, displayed high expression in T cell subsets, indicating that Bonzo-SExCkine interactions can play a role in the interactions that occur between T cells and antigen presenting cells.

Figure 46A:
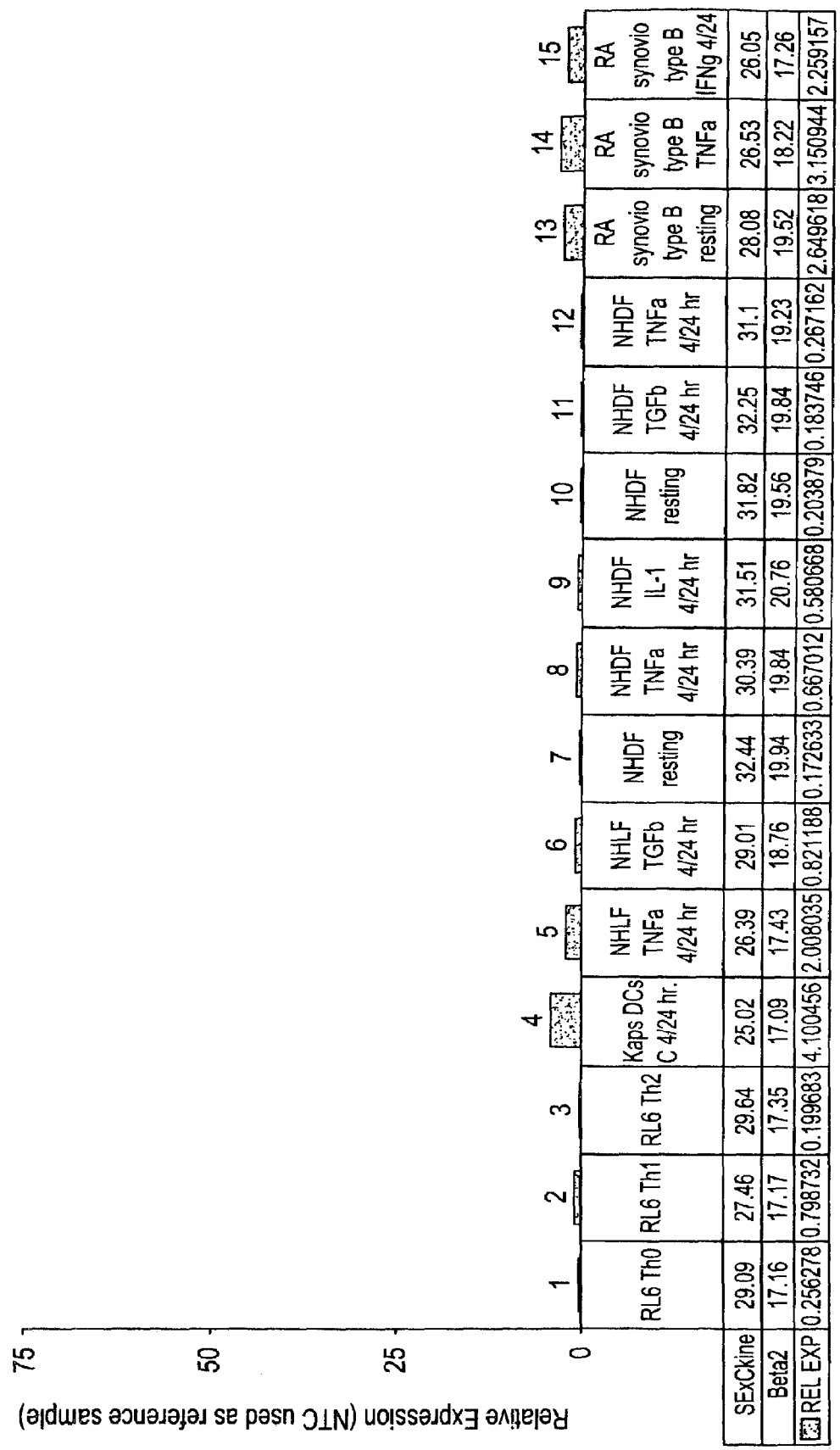
Figure 46B:
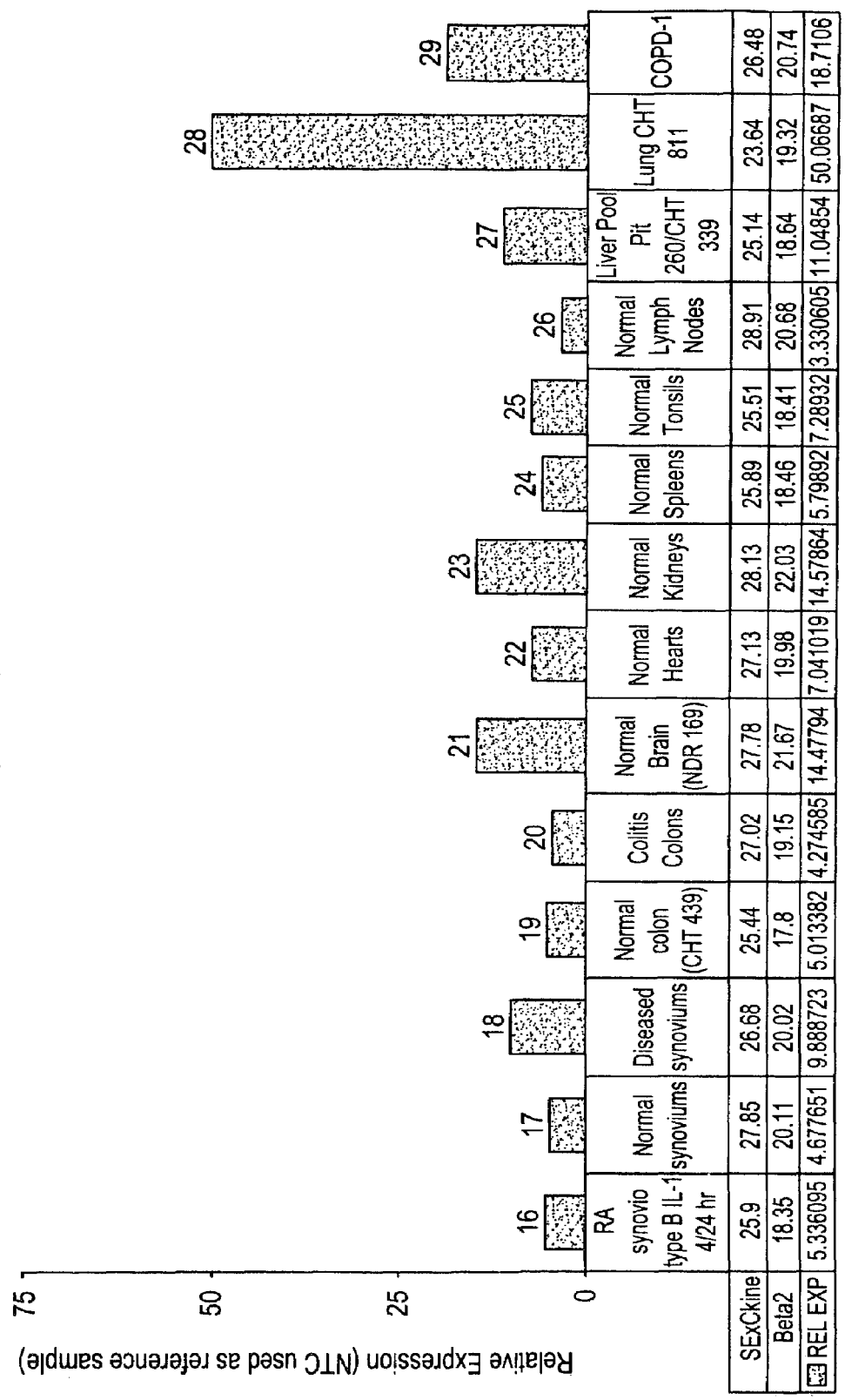

SExCkine expression is high in bulk lung tissue (FIG. 46) and normal human bronchial epithelium (FIG. 44), but was not observed in bronchial smooth muscle cells (FIG. 44) or normal lung fibroblasts (FIG. 46). Little or no SExCkine expression was seen in endothelial tissue (HMVEC) (FIG. 44). Expression of SExCkine was increased in diseased synoviums as compared to normal synoviums (FIG. 46), consistent with a role of SExCkine in inflammatory arthritis (e.g., rheumatoid arthritis). Low expression of SExCkine was also observed in normal brain, heart, kidney, spleen, tonsil and liver tissue (FIG. 46).

Figure 48A:
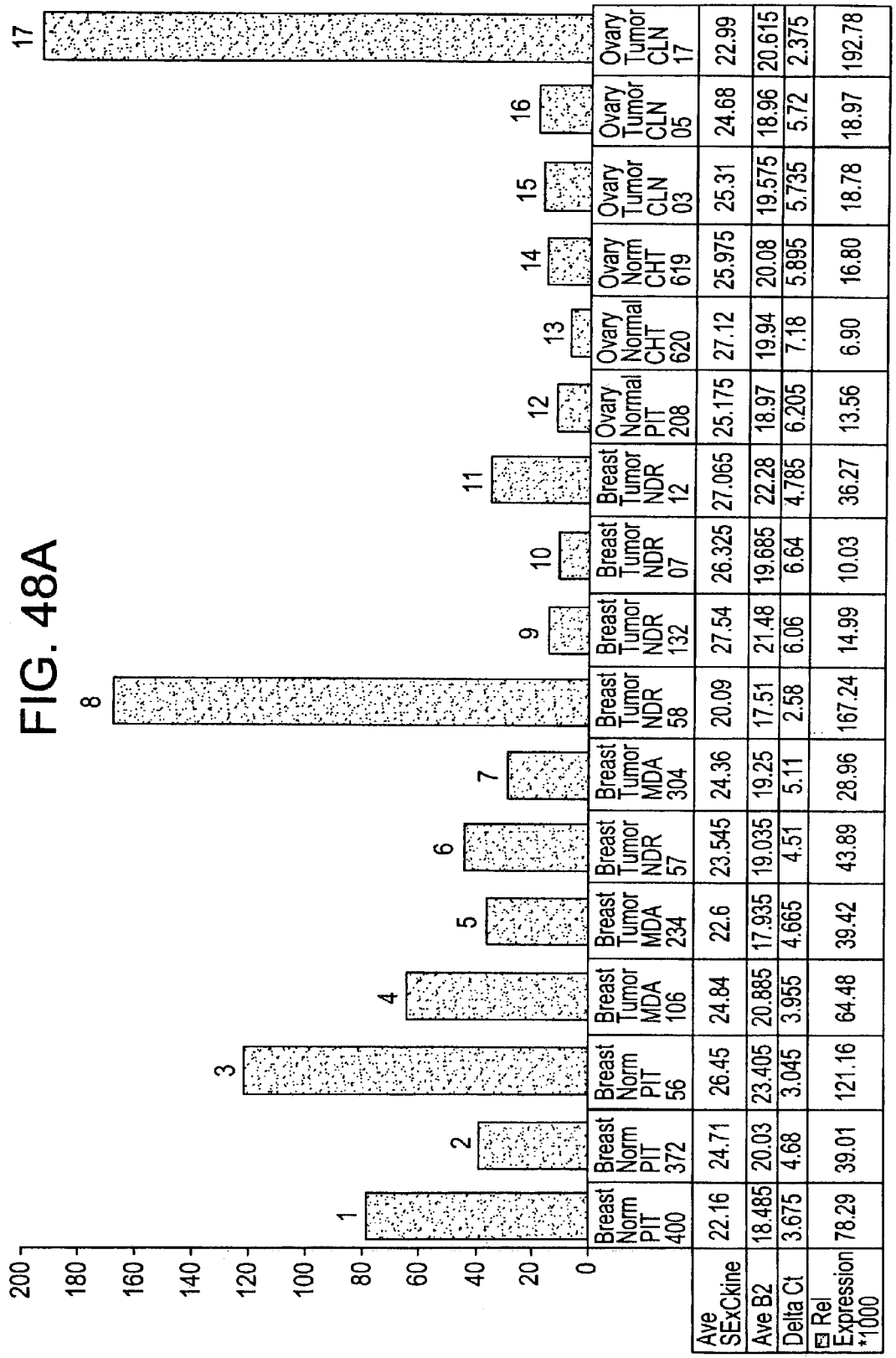
FIGS. 48A and 48B are histograms depicting the results of TaqMan® (Roche Molecular Systems, Inc., Basel, Switzerland) quantitative PCR analysis of the expression of SExCkine (CXCL16) in a variety of normal human tissue and human tumors. The values plotted correspond to the relative expression (REL EXP), which takes into consideration expression of a control gene, β-2 microglobulin, as well as a no-template control reaction (NTC). The tissues that were examined include normal breast tissue (bars 1–3), breast tumor tissue (bars 4–11), normal ovary tissue (bars 12–14), ovary tumor tissue (bars 15–22), normal lung tissue (bars 23–26) and lung tumor tissue (bars 27–34).
Figure 48B:
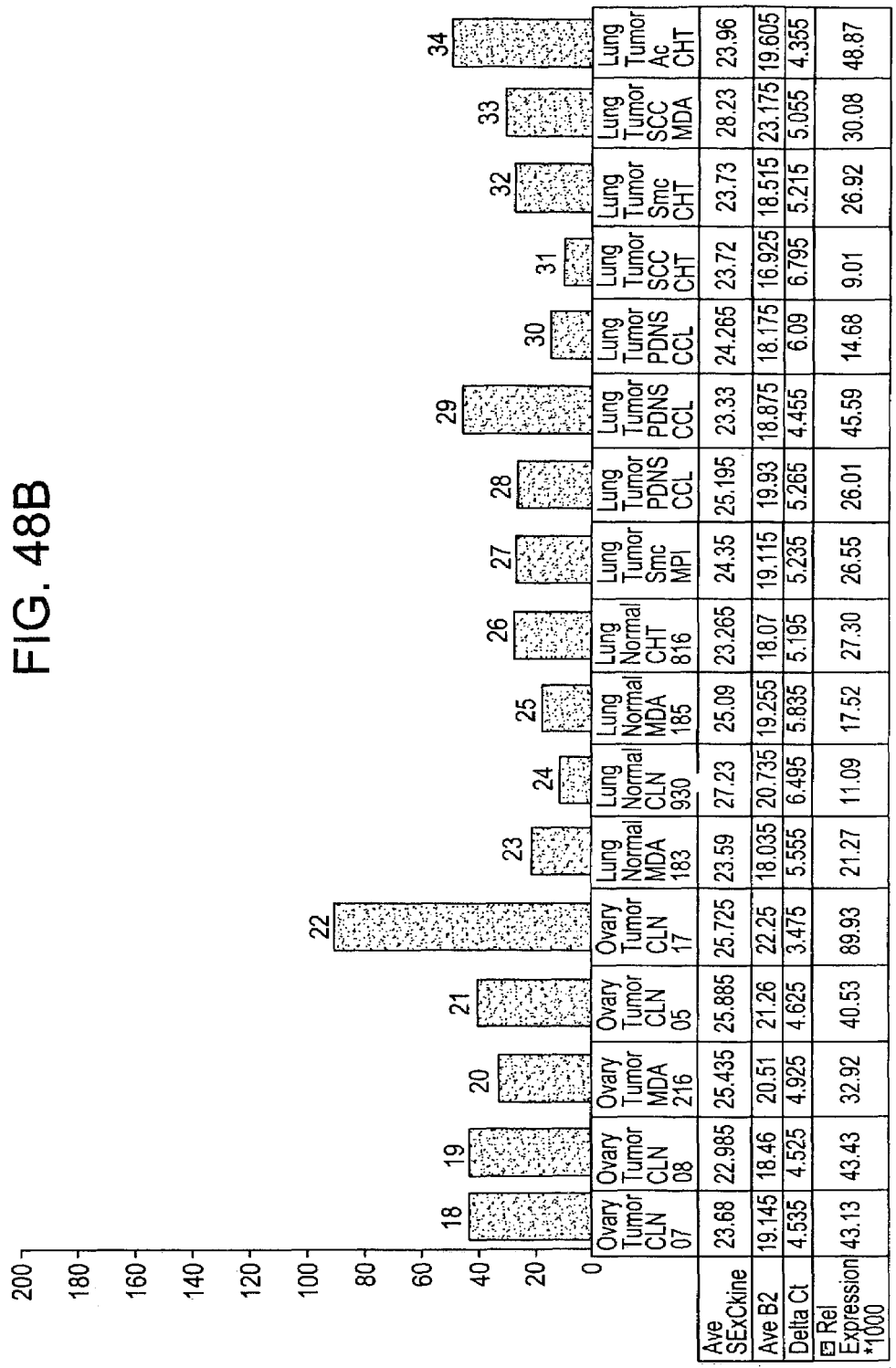
Figure 49A:
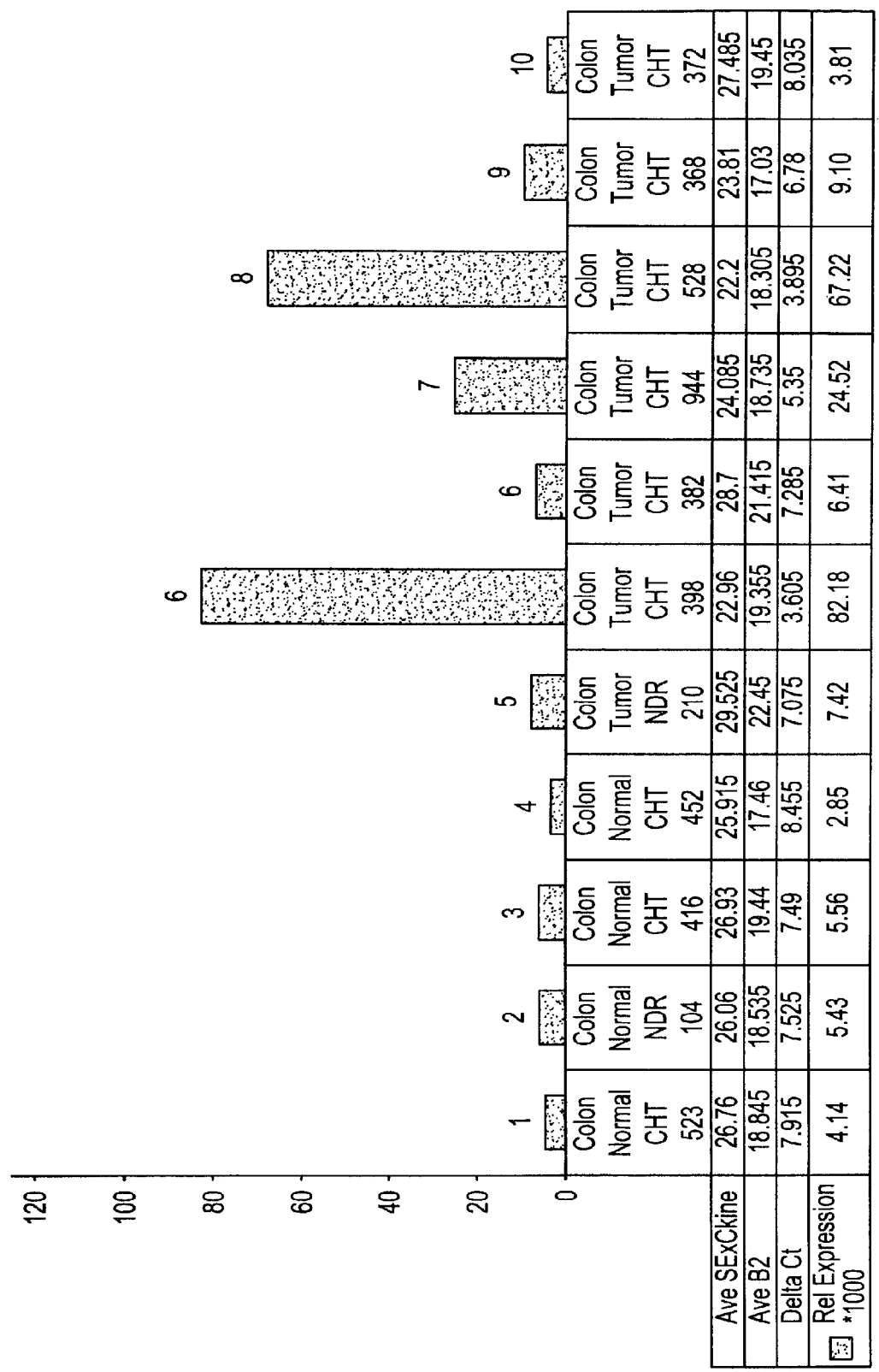
FIGS. 49A, 49B and 49C are histograms depicting the results of TaqMan® (Roche Molecular Systems, Inc., Basel, Switzerland) quantitative PCR analysis of the expression of SExCkine (CXCL16) in a variety of normal human tissue and human tumors. The values plotted correspond to the relative expression (REL EXP), which takes into consideration expression of a control gene, β-2 microglobulin, as well as a no-template control reaction (NTC). The tissues that were examined include normal colon tissue (bars 1–4), colon tumor tissue (bars 5–11), liver tissue that had metastasized (bars 12–14), normal liver tissue (bars 15–17), colon tumor tissue (bars 18–20), normal prostate tissue (bars 21–22), prostate tumor tissue (bars 23–25) and prostate tissue that had metastasized (bars 26–33).
Figure 49B:
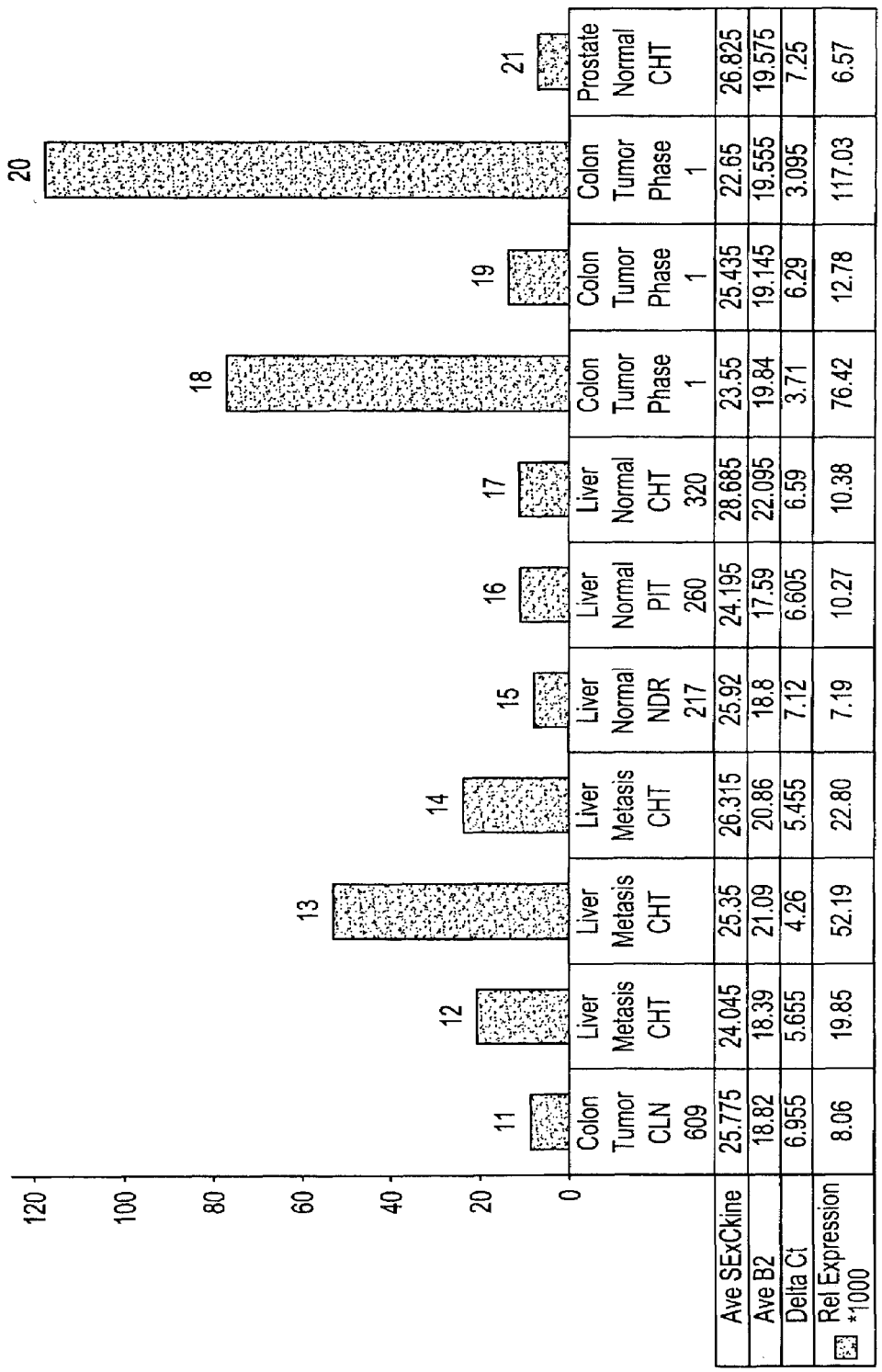
Figure 49C:
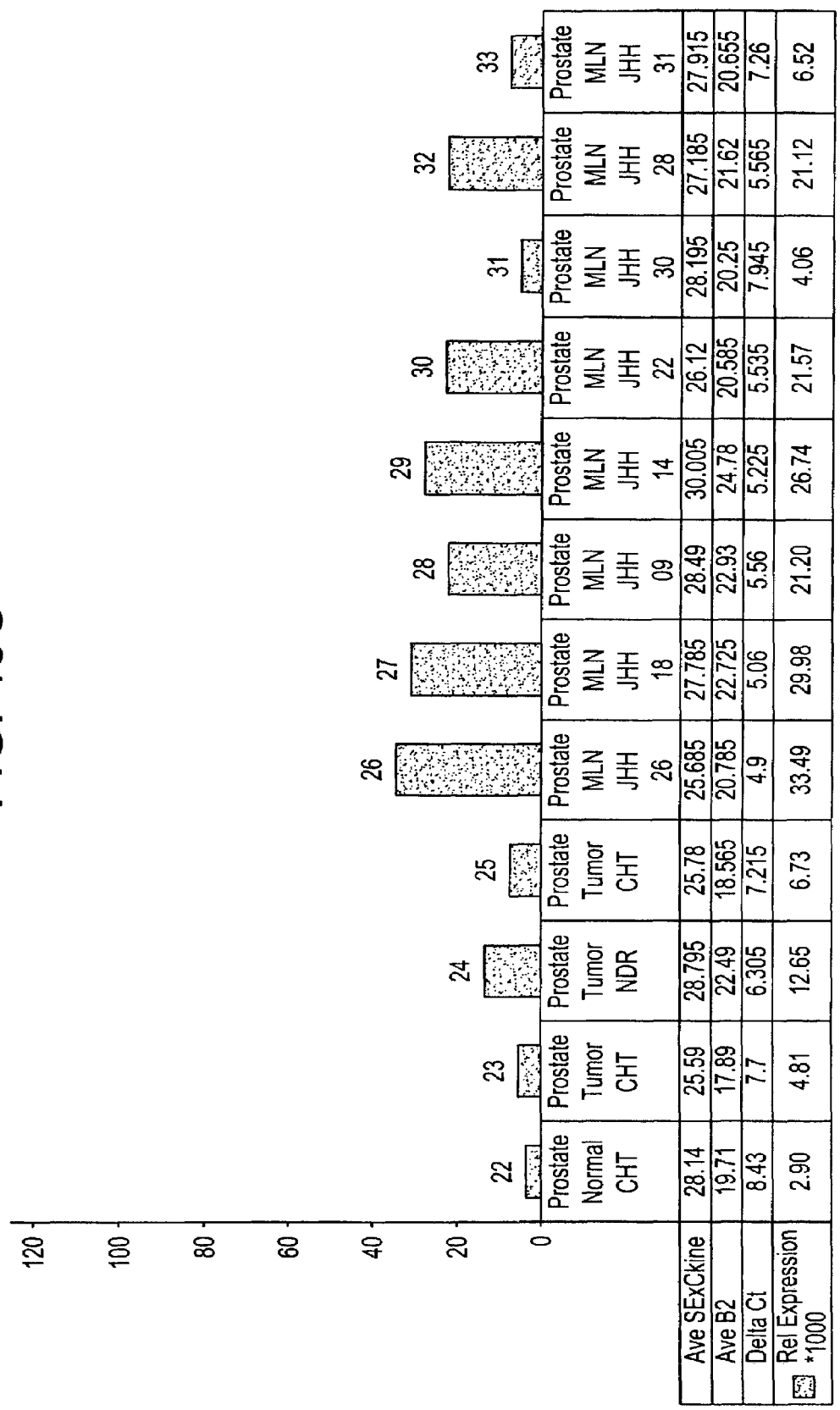
Figure 50A:
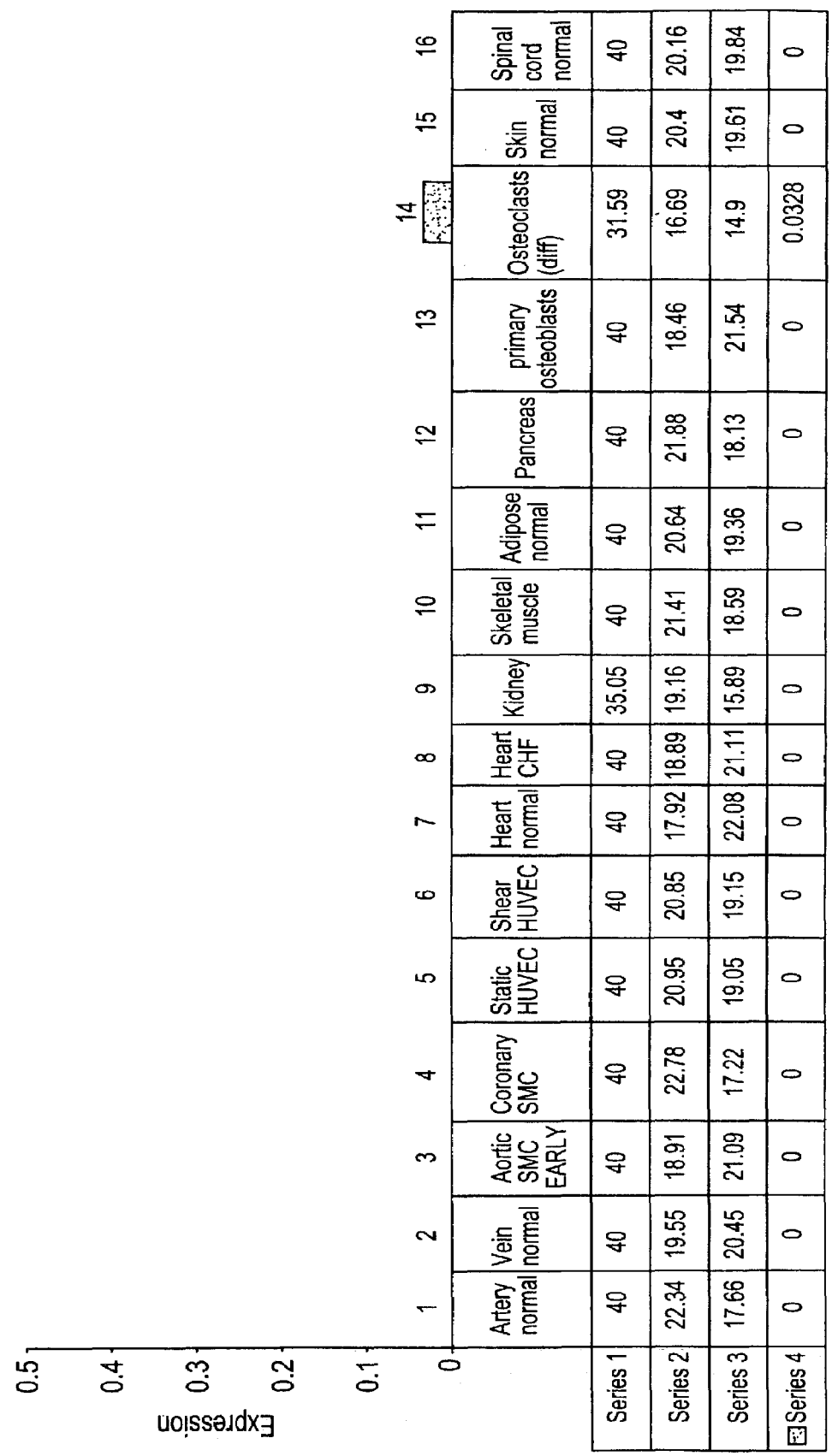
FIGS. 50A, 50B and 50C are histograms depicting the results of TaqMan® (Roche Molecular Systems, Inc., Basel, Switzerland) quantitative PCR analysis of the expression of SExCkine (CXCL16) in a variety of normal human tissue and diseased human tissues. The values plotted correspond to the relative expression (REL EXP), which takes into consideration expression of a control gene, β-2 microglobulin, as well as a no-template control reaction (NTC). The tissues that were examined include normal artery tissue (bar 1), normal vein tissue (bar 2), early aortic Smooth muscle cells (SMC) (bar 3), coronary smooth muscle cells (bar 4), static human umbilical vein endothelial cells (Static HUVEC) (bar 5), Shear human umbilical vein endothelial cells (Shear HUVEC) (bar 6), normal heart tissue (bar 7), heart tissue isolated from patients with congestive heart failure (Heart CHF) (bar 8), normal kidney tissue (bar 9), skeletal muscle tissue (bar 10), normal adipose tissue (bar 11), normal pancreas (bar 12), primary osteoblast tissue (bar 13), differentiated osteoclast tissue (bar 14), normal skin tissue (bar 15), normal spinal cord tissue (bar 16), normal brain cortex (bar 17), normal brain hypothalamus (bar 18), normal nerve tissue (bar 19), normal dorsal root ganglion tissue (bar 20), glial cells (astrocytes) (bar 21), glioblastoma tissue (bar 22), normal breast tissue (bar 23), breast tumor tissue (bar 24), normal ovary tissue (bar 25), ovary tumor tissue (bar 26), normal prostate tissue (bar 27), prostate tumor tissue (bar 28), prostate epithelial cells (bar 29), normal colon tissue (bar 30), colon tumor tissue (bar 31), lung tumor tissue (bar 32), lung tissue isolated from patients with chronic obstructive pulmonary disease (COPD) (bar 33), colon tissue isolated from patients with inflammatory bowel disease (IBD) (bar 35), normal liver tissue (bar 3S), fibrosis liver tissue (bar 36), dermal cell fibroblasts (bar 37), normal spleen tissue (bar 38), normal tonsils (bar 39), normal lymph nodes (bar 40), normal small intestine tissue (bar 41), decubitus skin tissue (bar 42), normal synoviums (bar 43), bone marrow mononuclear cells (BM-MNC) (bar 44) and anti-CD3 and PHA (phytohemagluttinin)-activated peripheral blood mononuclear cells (PBMC) (bar 45).
Figure 50B:
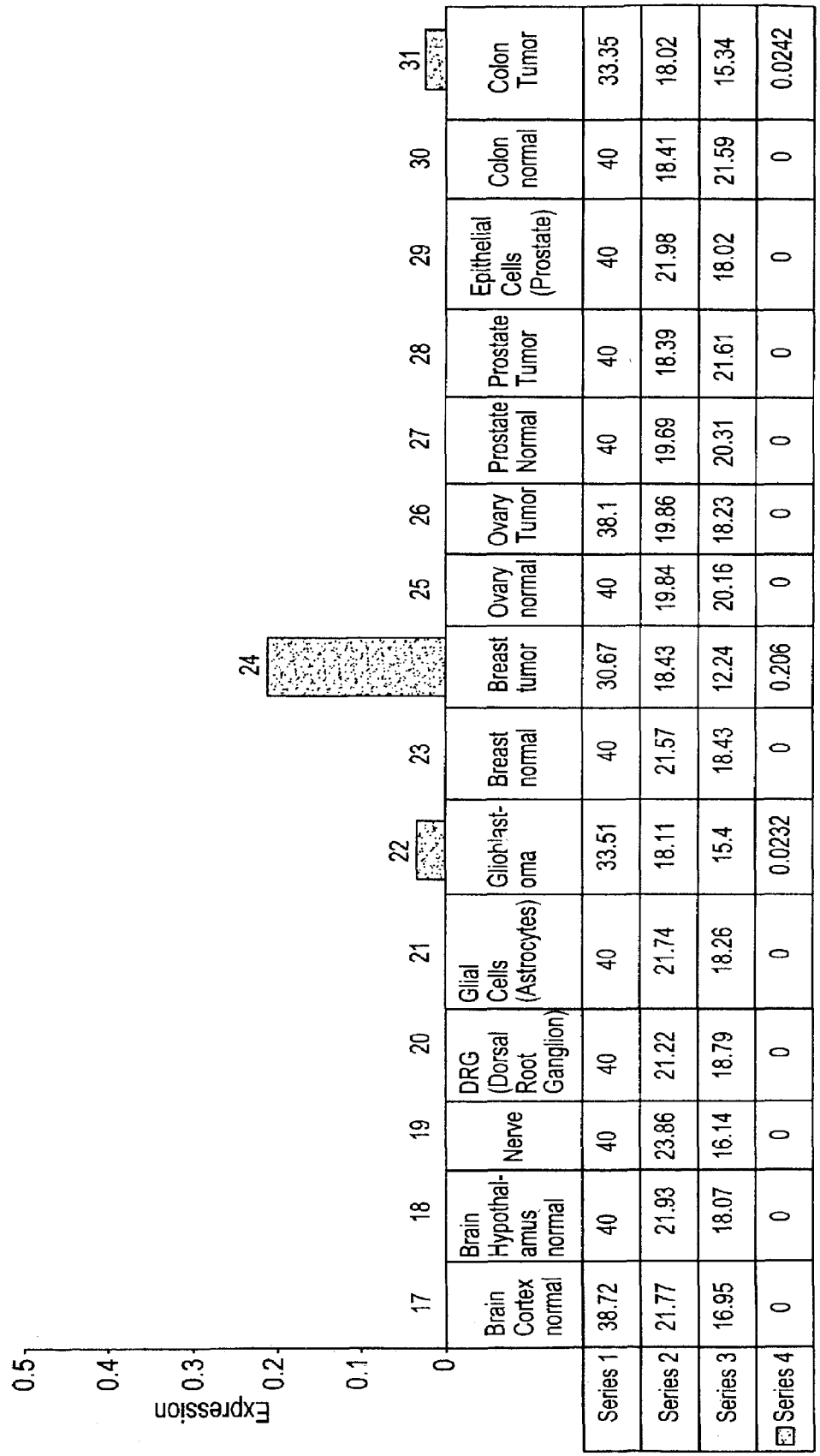
Figure 50C:
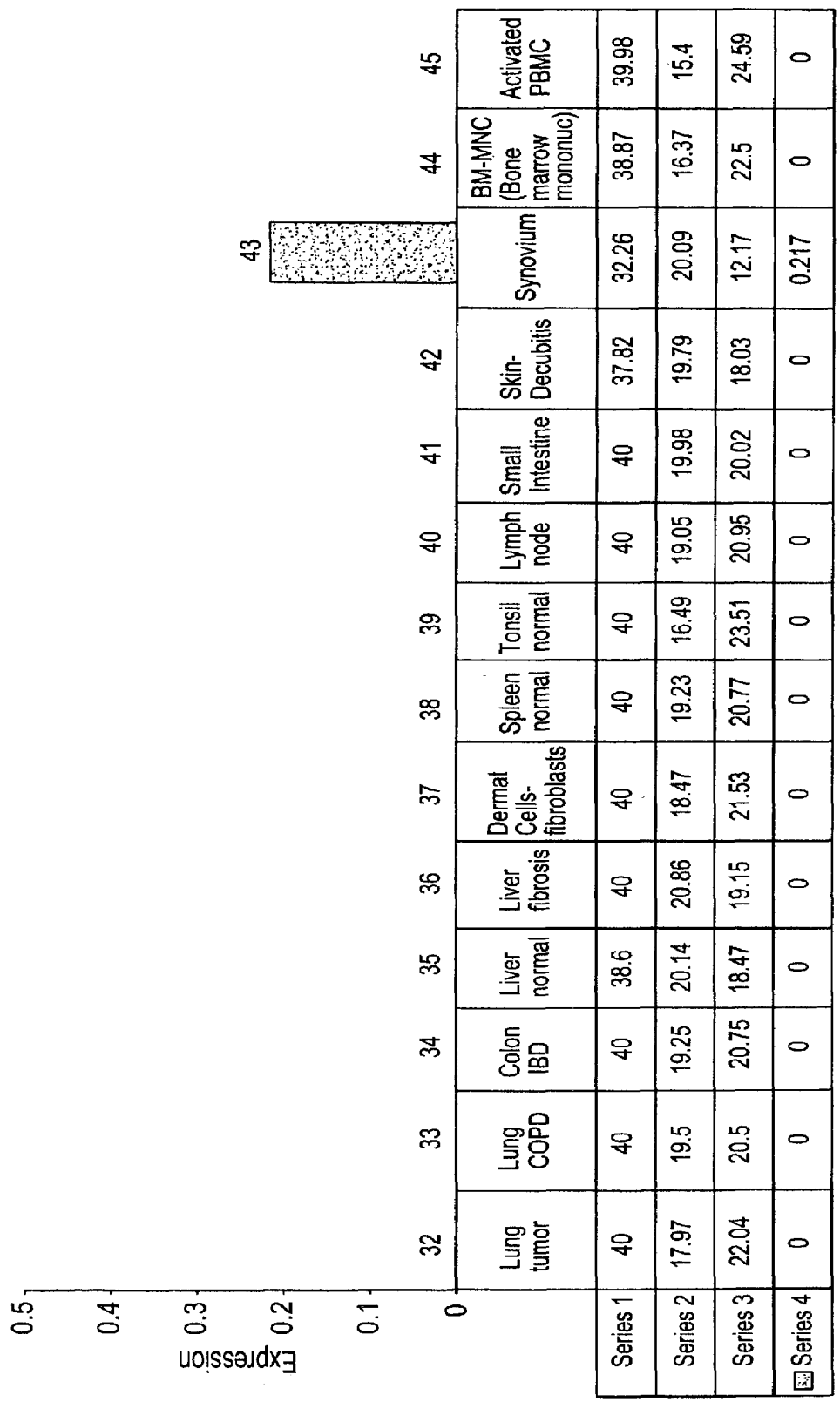

In additional studies, RNA was isolated from normal human tissue and various human tumors and expression of SExCkine was analyzed by TaqMan® (Roche Molecular Systems, Inc., Basel, Switzerland) quantitative PCR as described. The tissues and tumors analyzed include breast (normal and tumor), ovary (normal and tumor), lung (normal and tumor), colon (normal and tumor), liver (normal and metastasis), prostate (normal and tumor), normal artery, normal vein, aortic smooth muscle cells (SMC), coronary SMC, static human umbilical vein endothelial cells (HUVEC), shear HUVEC, heart, heart tissue isolated from patients with congestive heart failure, kidney, skeletal muscle, adipose (normal), pancreas, primary osteoclasts, skin (normal), spinal cord (normal), brain (normal), hypothalamus (normal), nerve, dorsal root ganglion (DRG), glial cells (astrocytes), glioblastoma, epithelial cells (prostate), lung (chronic obstructive pulmonary disease), colon (inflammatory bowel disease), liver (fibrosis), dermal cells (fibroblasts) tonsil, lymph node, small intestine, skin (decubitus), synovium, bone marrow mononuclear cells (BM-MNC) and activated PBMC (FIGS. 48, 49 and 50). These additional studies revealed expression of SExCkine in certain tumors (e.g., breast, ovary, colon, glioblastoma) and in synovium.

TaqMan® (Roche Molecular Systems, Inc., Basel, Switzerland) quantitative PCR studies were also used to examine expression of Bonzo on various cell types and tissues. The cell types that were examined include CD4+ cells (resting, stimulated with plate-bound anti-CD3 Ab and stimulated with plate-bound anti-CD3 Ab and soluble anti-CD28 Ab), CD8+ cells (resting, stimulated with plate-bound anti-CD3 Ab and stimulated with plate-bound anti-CD3 Ab and soluble anti-CD28), CD14+ monocytes (resting, stimulated with TNF-α and stimulated with LPS), CD19+ cells (resting, stimulated with LPS and stimulated with CD40L), tonsil-derived CD19+ cells (resting, stimulated with LPS and stimulated with CD40L), granulocytes (resting, stimulated with TNF-α and stimulated with IFN-γ), eosinophils (resting and stimulated with IL-4) and $T_H0$, $T_H1$ and $T_H2$ effector T cells. Cells were stimulated as described herein. Expression of Bonzo was detected on resting and stimulated CD4+ cells as well as resting and stimulated CD8+ cells. Bonzo was also highly expressed on $T_H0$, $T_H1$ and $T_H2$ effector T cells. In addition, expression of Bonzo was detected on LPS-stimulated CD19+ cells and lower levels of expression were observed on granulocytes and eosinophils.

Tissues that were examined for expression of Bonzo showed that Bonzo was expressed on normal synoviums, diseased synoviums, normal colon tissue, colitis colon tissue, normal spleen tissue, normal tonsil tissue, normal lung tissue and lung tissue isolated from patients with chronic pulmonary obstructive disease

EXAMPLE 11

Immunohistological Analysis of SExCkine

Methods and Materials

Immunohistology

Liver and spleen sections were embedded in OCT, cut at 6 μm, and were allowed to dry for 2 hours at room temperature. The sections were then fixed in 100% acetone for 10 minutes at 4° C., after which time they were washed with PBS/1% gelatin (PBS-G). The sections were blocked with PBS/10% normal goat serum/5% human AB serum (Vector Labs, Burlingame, Calif.) for 15 minutes at room temperature prior to addition of anti-SExCkine mAb SD7 or an isotype-matched control antibody (MOPC-21, Sigma Chemicals Co., St. Louis, Mo.). After an overnight incubation at 4° C., the slides were washed twice in PBS-G and biotinylated goat-anti-mouse antibody was added (diluted 1:100 in PBS/5% human AB serum; Vector Labs, Burlingame, Calif.). Following a 30-minute incubation at room temperature, the slides were washed in PBS-G and avidin-biotin-peroxidase complexes (Biogenex, San Ramon, Calif.) were added. After a final wash in PBS-G, the slides were developed with fast red (Biogenex, San Ramon, Calif.), counterstained with hematoxylin, and coverslipped.

Results and Discussion

Figure 47A:
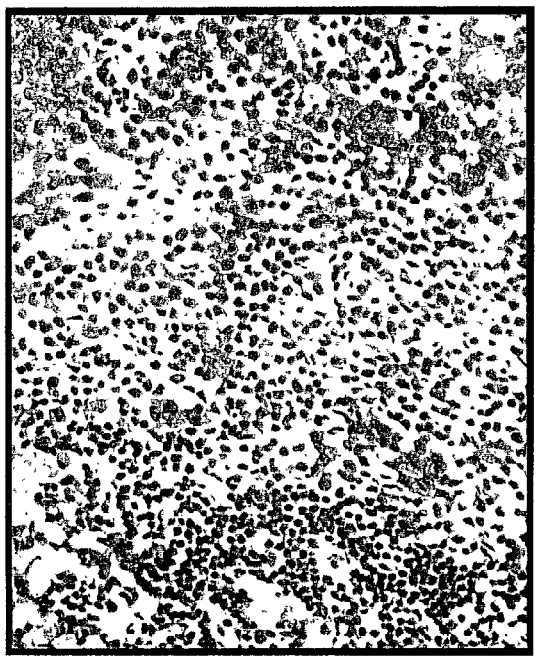
FIGS. 47A and 47B are photographs of sections of spleen stained with anti-SExCkine (CXCL16) mAb SD7 (FIG. 47A) or an isotype control antibody (FIG. 47B). The photographs show that cells with morphology characteristic of dendritic cells express cell surface SExCkine (CXCL16) (FIG. 47A). Sections were counterstained with hematoxylin.
Figure 47B:
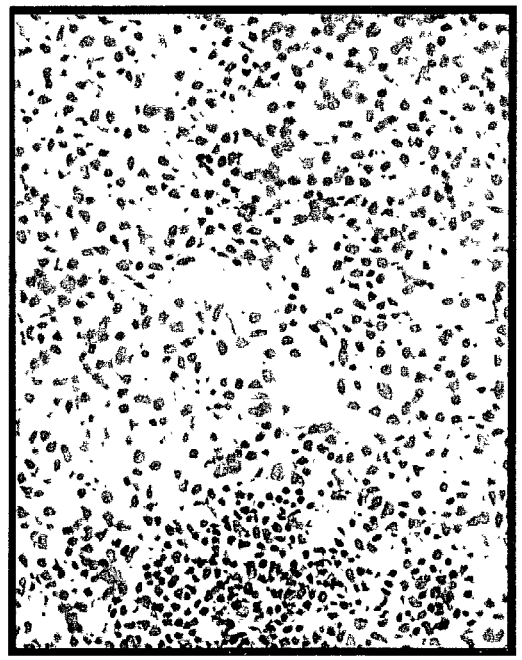

Immunohistological staining of spleen sections using anti-SExCkine mAb SD7 revealed that small numbers of mononuclear cells in the red pulp and rare mononuclear cells within B cell follicles were immunoreactive for SExCkine (FIG. 47). The immunoreactive cells included dendritic cells and were generally observed individually or in small clusters. In addition, many of the immunoreactive cells contained a large vesicular nucleus with little cytoplasm.

Immunohistological staining of liver sections using anti-SExCkine mAb SD7 demonstrated that Kupffer cells were immunoreactive for SExCkine.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of inhibiting a Bonzo (CXCR6) function selected from the group consisting of ligand-induced chemotaxis and ligand-induced $Ca^{2+}$ flux in a subject having an inflammatory disease, comprising administering to said subject an effective amount of an antibody or antigen-binding fragment thereof that binds to mammalian Bonzo (CXCR6) and inhibits the binding of a ligand to said Bonzo (CXCR6), wherein said ligand is selected from the group consisting of:
   i) a ligand having the amino acid sequence of SEQ ID NO:4;
   ii) a ligand having an amino acid sequence that is a fragment of SEQ ID NO:4, wherein said fragment is selected from the group consisting of:
      a) amino acid residues 30–254 of SEQ ID NO:4;
      b) amino acid residues 1–202 of SEQ ID NO:4;
      c) amino acid residues 30–202 of SEQ ID NO:4;
      d) amino acid residues 1–155 of SEQ ID NO:4;
      e) amino acid residues 30–155 of SEQ ID NO:4;
      f) amino acid residues 1–117 of SEQ ID NO:4;
      g) amino acid residues 30–117 of SEQ ID NO:4; and
      h) amino acid residues 30–95 of SEQ ID NO:4,
   iii) a ligand having the amino acid sequence of SEQ ID NO:6;
   iv) a ligand having the amino acid sequence of SEQ ID NO:8; and
   v) a ligand having the amino acid sequence of amino acid residues 32–101 of SEQ ID NO:8.

2. The method of claim 1 wherein said mammalian Bonzo (CXCR6) is human Bonzo (CXCR6).

3. The method of claim 1 wherein said antibody or antigen-binding fragment thereof is a monoclonal antibody or antigen-binding fragment thereof.

4. The method of claim 1 wherein said antibody or antigen-binding fragment thereof is selected from the group consisting of a single chain antibody, a chimeric antibody, a humanized antibody, a human antibody, a primatized antibody, a veneered antibody, a bispecific antibody and an antigen-binding fragment of any of the foregoing.

5. The method of claim 1 wherein said antibody or antigen-binding fragment thereof is a chimeric antibody or antigen-binding fragment thereof.

6. The method of claim 1 wherein said antibody or antigen-binding fragment thereof is a humanized antibody or antigen-binding fragment thereof.

7. The method of claim 1 wherein said antibody or antigen-binding fragment thereof is a human antibody or antigen-binding fragment thereof.

8. The method of claim 1 wherein said antibody or antigen-binding fragment thereof is an antigen-binding fragment.

9. The method of claim 8 wherein said antigen-binding fragment is selected from the group consisting of an Fv fragment, an Fab fragment, an Fab' fragment and an F(ab')$_2$ fragment.

10. The method of claim 1 wherein said antibody or antigen-binding fragment is an IgG or an antigen-binding fragment thereof.

11. The method of claim 1 wherein said inflammatory disease is a T cell-mediated disease.

12. The method of claim 1 wherein said inflammatory disease is inflammatory arthritis.

13. The method of claim 12 wherein said inflammatory arthritis is rheumatoid arthritis.

14. The method of claim 1 wherein said inflammatory disease is graft rejection.

15. The method of claim 14 wherein said graft rejection is selected from the group consisting of allograft rejection and graft-versus-host disease.

16. The method of claim 1 wherein said inflammatory disease is multiple sclerosis.

17. A method of inhibiting a cellular response to binding of a ligand to mammalian Bonzo (CXCR6) expressed on the surface of a leukocyte in a mammal, comprising administering to said mammal an effective amount of an antibody or antigen-binding fragment thereof that binds to said Bonzo (CXCR6) and inhibits the binding of a ligand to said Bonzo (CXCR6), wherein:
   a) said ligand is selected from the group consisting of:
      i) a ligand having the amino acid sequence of SEQ ID NO:4;
      ii) a ligand having an amino acid sequence that is a fragment of SEQ ID NO:4, wherein said fragment is selected from the group consisting of:
         a) amino acid residues 30–254 of SEQ ID NO:4;
         b) amino acid residues 1–202 of SEQ ID NO:4;
         c) amino acid residues 30–202 of SEQ ID NO:4;
         d) amino acid residues 1–155 of SEQ ID NO4;
         e) amino acid residues 30–155 of SEQ ID NO:4;
         f) amino acid residues 1–117 of SEQ ID NO:4,
         g) amino acid residues 30–117 of SEQ ID NO:4; and
         h) amino acid residues 30–95 of SEQ ID NO:4,
      iii) a ligand having the amino acid sequence of SEQ ID NO:6;

iv) a ligand having the amino acid sequence of SEQ ID NO:8; and
v) a ligand having the amino acid sequence of amino acid residues 32–101 of SEQ ID NO:8; and
b) said cellular response is selected from the group consisting of ligand-induced chemotaxis and ligand-induced $Ca^{2+}$ flux.

18. The method of claim 17 wherein said mammalian Bonzo (CXCR6) is human Bonzo (CXCR6).

19. The method of claim 17 wherein said antibody or antigen-binding fragment thereof is a monoclonal antibody or antigen-binding fragment thereof.

20. The method of claim 17 wherein said antibody or antigen-binding fragment thereof is selected from the group consisting of a single chain antibody, a, chimeric antibody, a humanized antibody, a human antibody, a primatized antibody, a veneered antibody, a bispecific antibody and an antigen-binding fragment of any of the foregoing.

21. The method of claim 17 wherein said antibody or antigen-binding fragment thereof is a chimeric antibody or antigen-binding fragment thereof.

22. The method of claim 17 wherein said antibody or antigen-binding fragment thereof is a humanized antibody or antigen-binding fragment thereof.

23. The method of claim 17 wherein said antibody or antigen-binding fragment thereof is a human antibody or antigen-binding fragment thereof.

24. The method of claim 17 wherein said antibody or antigen-binding fragment thereof is an antigen-binding fragment.

25. The method of claim 24 wherein said antigen-binding fragment is selected from the group consisting of an Fv fragment, an Fab fragment, an Fab' fragment and an F(ab')$_2$ fragment.

26. The method of claim 17 wherein said antibody or antigen-binding fragment is an IgG or an antigen-binding fragment thereof.

27. A method of inhibiting a Bonzo (CXCR6) function comprising contacting a cell that expresses mammalian Bonzo (CXCR6) with an antibody or antigen-binding fragment thereof that binds to said Bonzo (CXCR6) and inhibits the binding of a ligand to said Bonzo (CXCR6), thereby inhibiting the function of said Bonzo (CXCR6), wherein:
a) said ligand is selected from the group consisting of:
i) a ligand having the amino acid sequence of SEQ ID NO:4;
ii) a ligand having an amino acid sequence that is a fragment of SEQ ID NO:4, wherein said fragment is selected from the group consisting of:
a) amino acid residues 30–254 of SEQ ID NO:4;
b) amino acid residues 1–202 of SEQ ID NO:4;
c) amino acid residues 30–202 of SEQ ID NO:4;
d) amino acid residues 1–155 of SEQ ID NO:4;
e) amino acid residues 30–135 of SEQ ID NO:4;
f) amino acid residues 1–117 of SEQ ID NO:4;
g) amino acid residues 30–117 of SEQ ID NO:4; and
h) amino acid residues 30–95 of SEQ ID NO:4;
iii) a ligand having the amino acid sequence of SEQ ID NO:6;
iv) a ligand having the amino acid sequence of SEQ ID NO:8; and
v) a ligand having the amino acid sequence of amino acid residues 32–101 of SEQ ID NO:8; and
b) said Bonzo (CXCR6) function is selected from the group consisting of ligand-induced chemotaxis and ligand-induced $Ca^{2+}$ flux.

28. The method of claim 27 wherein said mammalian Bonzo (CXCR6) is human Bonzo (CXCR6).

29. The method of claim 27 wherein said antibody or antigen-binding fragment thereof is a monoclonal antibody or antigen-binding fragment thereof.

30. The method of claim 27 wherein said antibody or antigen-binding fragment thereof is selected front the group consisting of a single chain antibody, a chimeric antibody, a humanized antibody, a human antibody, a primaxized antibody, a veneered antibody, a bispecific antibody and an antigen-binding fragment of any of the foregoing.

31. The method of claim 27 wherein said antibody or antigen-binding fragment thereof is a chimeric antibody or antigen-binding fragment thereof.

32. The method of claim 27 wherein said antibody or antigen-binding fragment thereof is a humanized antibody or antigen-binding fragment thereof.

33. The method of claim 27 wherein said antibody or antigen-binding fragment thereof is a human antibody or antigen-binding fragment thereof.

34. The method of claim 27 wherein said antibody or antigen-binding fragment thereof is an antigen-binding fragment.

35. the method of claim 34 wherein said antigen-binding fragment is selected from the group consisting of an Fv fragment, an Fab fragment, an Fab' fragment and an F(ab')$_2$ fragment.

36. The method of claim 27 wherein said antibody or antigen-binding fragment is an IgG or an antigen-binding fragment thereof.

37. A method of inhibiting a Bonzo (CXCR6) function selected from the group consisting of ligand-induced chemotaxis and ligand-induced $Ca^{2+}$ flux in a subject having an inflammatory disease, comprising administering to said subject an effective amount of an antibody or antigen-binding fragment thereof, wherein said antibody or antigen-binding fragment has the epitopic specificity of an antibody selected from the group consisting of:
a) mAb 4A11, the antibody produced by the hybridoma cell line deposited at the American Type Culture Collection (ATCC) as Accession Number PTA-991;
b) mAb 7A2, the antibody produced by the hybridoma cell line deposited at the American Type Culture Collection (ATCC) as Accession Number PTA-992; and
c) mAb 7F3, the antibody produced by the hybridoma cell line deposited at the American Type Culture Collection (A FCC) as Accession Number PTA-990.

38. The method of claim 37 wherein said antibody or antigen-binding fragment thereof has the epitopic specificity of mAb 7F3.

39. A method of inhibiting a Bonzo (CXCR6) function selected from the group consisting of ligand-induced chemotaxis and ligand-induced $Ca^{2+}$ flux in a subject having an inflammatory disease, comprising administering to said subject an effective amount of an antibody or antigen-binding fragment thereof that binds to mammalian Bonzo (CXCR6), wherein the binding of said antibody or antigen-binding fragment to said mammalian Bonzo (CXCR6) is inhibited by an antibody selected from the group consisting of:
a) mAb 4A11, the antibody produced by the hybridoma cell line deposited at the American Type Culture Collection (ATCC) as Accession Number PTA-991;
b) mAb 7A2, the antibody produced by the hybridoma cell line deposited at the American Type Culture Collection (ATCC) as Accession Number PTA-992; and c) mAb 7F3, the antibody produced by the hybridoma cell line deposited at the American Type Culture Collection (ATCC) as Accession Number PTA-990.

40. The method of claim 39 wherein the binding of said antibody or said antigen-binding fragment to said mammalian Bonzo (CXCR6) is inhibited by mAb 7F3.

41. A method of inhibiting a Bonzo (CXCR6) function selected from the group consisting of ligand-induced chemotaxis and ligand-induced $Ca^{2+}$ flux in a subject having an inflammatory disease, comprising administering to said subject an effective amount of an antibody selected from the group consisting of:
   a) mAb 4A11, the antibody produced by the hybridoma cell line deposited at the American Type Culture Collection (ATCC) as Accession Number PTA-991;
   b) mAb 7A2, the antibody produced by the hybridoma cell line deposited at the American Type Culture Collection (ATCC) as Accession Number PTA-992;
   c) mAb 7F3, the antibody produced by the hybridoma cell line deposited at the American Type Culture Collection (ATCC) as Accession Number PTA-990; and
   d) an antigen-binding fragment of any of the foregoing.

42. The method of claim 41 wherein said antibody is mAb 7F3 or an antigen-binding fragment thereof.

43. A method of inhibiting a Bonzo (CXCR6) function selected from the group consisting of ligand-induced chemotaxis and ligand-induced $Ca^{2+}$ flux in a subject having an inflammatory disease, comprising administering to said subject an effective amount of an antibody or antigen-binding fragment thereof, wherein said antibody or antigen-binding fragment comprises the complementarity determining regions (CDRs) from an antibody selected from the group consisting of:
   a) mAb 4A11, the antibody produced by the hybridoma cell line deposited at the American Type Culture Collection (ATCC) as Accession Number PTA-991;
   b) mAb 7A2, the antibody produced by the hybridoma cell line deposited at the American Type Culture Collection (ATCC) as Accession Number PTA-992; and
   c) mAb 7F3, the antibody produced by the hybridoma cell line deposited at the American Type Culture Collection (ATCC) as Accession Number PTA-990.

44. The method of claim 43 wherein said antibody or antigen-binding fragment comprises the CDRs from mAb 7F3.

45. A method of inhibiting a cellular response to binding of a ligand to Bonzo (CXCR6) expressed on the surface of a leukocyte in a mammal, comprising administering to said mammal an effective amount of an antibody or antigen-binding fragment thereof, wherein:
   1) said antibody or antigen-binding fragment has the epitopic specificity of an antibody selected from the group consisting of:
      a) mAb 4A11, the antibody produced by the hybridoma cell line deposited at the American Type Culture Collection (ATCC) as Accession Number PTA-991,
      b) mAb 7A2, the antibody produced by the hybridoma cell line deposited at the American Type Culture Collection (ATCC) as Accession Number PTA-992; and
      c) mAb 7F3, the antibody produced by the hybridoma cell line deposited at the American Type Culture Collection (ATCC) as Accession Number PTA-990; and
   2) said cellular response is selected from the group consisting of ligand-induced chemotaxis and ligand-induced $Ca^{2+}$ flux and
   3) said ligand is selected from the group consisting of:
      i) a ligand having the amino acid sequence of SEQ ID NO:4;
      ii) a ligand having an amino acid sequence that is a fragment of SEQ ID NO:4, wherein said fragment is selected from the group consisting of:
         a) amino acid residues 30–254 of SEQ ID NO:4;
         b) amino acid residues 1–202 of SEQ ID NO;4;
         c) amino acid residues 30–202 of SEQ ID NO:4;
         d) amino acid residues 1–155 of SEQ ID NO:4;
         e) amino acid residues 30–155 of SEQ ID NO:4;
         f) amino acid residues 1–117 of SEQ ID NO:4,
         g) amino acid residues 30–117 of SEQ ID NO;4; and
         h) amino acid residues 30–95 of SEQ ID NO:4;
      iii) a ligand having the amino acid sequence of SEQ ID NO:6;
      iv) a ligand having the amino acid sequence of SEQ ID NO:8; and
      v) a ligand having the amino acid sequence of amino acid residues 32–101 of SEQ ID NO:8.

46. The method of claim 45 wherein said antibody or antigen-binding fragment thereof has the epitopic specificity of mAb 7F3.

47. A method of inhibiting a cellular response to binding of a ligand to Bonzo (CXCR6) expressed on the surface of a leukocyte in a mammal, comprising administering to said mammal an effective amount of an antibody or antigen-binding fragment thereof that binds to said Bonzo (CXCR6), wherein:
   1) the binding of said antibody or antigen-binding fragment to said Bonzo (CXCR6) is inhibited by an antibody selected from the group consisting of
      a) mAb 4A11, the antibody produced by the hybridoma cell line deposited at the American Type Culture Collection (ATCC) as Accession Number PTA-991;
      b) mAb 7A2, the antibody produced by the hybridoma cell line deposited at the American Type Culture Collection (ATCC) as Accession Number PTA-992; and
      c) mAb 7F3, the antibody produced by the hybridoma cell line deposited at the American Type Culture Collection (ATCC) as Accession Number PTA-990; and
   2) said cellular response is selected from the group consisting of ligand-induced chemotaxis and ligand-induced $C^{2+}$ flux; and
   3) said ligand is selected from the group consisting of:
      i) a ligand having the amino acid sequence of SEQ ID NO:4;
      ii) a ligand having an amino acid sequence that is a fragment of SEQ ID NO:4, wherein said fragment is selected from the group consisting of:
         a) amino acid residues 30–254 of SEQ ID NO:4;
         b) amino acid residues 1–202 of SEQ ID NO:4;
         c) amino acid residues 30–202 of SEQ ID NO:4;
         d) amino acid residues 1–155 of SEQ ID NO:4;
         e) amino acid residues 30–155 of SEQ ID NO:4;
         f) amino acid residues 1–117 of SEQ ID NO:4;
         g) amino acid residues 30–117 of SEQ ID NO:4; and
         h) amino acid residues 30–95 of SEQ ID NO:4;
      iii) a ligand having the amino acid sequence of SEQ ID NO:6;
      iv) a ligand having the amino acid sequence of SEQ ID NO:8; and
      v) a ligand having the amino acid sequence of amino acid residues 32–101 of SEQ ID NO:8.

48. The method of claim 47 wherein the binding of said antibody or said antigen-binding fragment to said Bonzo (CXCR6) is inhibited by mAb 7F3.

49. A method of inhibiting a cellular response to binding of a ligand to Bonzo (CXCR6) expressed on the surface of a leukocyte in a mammal, comprising administering to said mammal an effective amount of an antibody or antigen-binding fragment thereof, wherein:
1) said antibody or antigen-binding fragment is selected from the group consisting of:
   a) mAb 4A11, the antibody produced by the hybridoma cell line deposited at the American Type Culture Collection (ATCC) as Accession Number PTA-991;
   b) mAb 7A2, the antibody produced by the hybridoma cell line deposited at the American Type Culture Collection (ATCC) as Accession Number PTA-992;
   c) mAb 7F3, the antibody produced by the hybridoma cell line deposited at the American Type Culture Collection (ATCC) as Accession Number PTA-990; and
   d) an antigen-binding fragment of any of the foregoing; and
2) said cellular response is selected from the group consisting of ligand-induced chemotaxis and ligand-induced $C^{2+}$ flux; and
3) said ligand is selected from the group consisting of:
   i) a ligand having the amino acid sequence of SEQ ID NO:4;
   ii) a ligand having an amino acid sequence that is a fragment of SEQ ID NO:4, wherein said fragment is selected from the group consisting of:
      a) amino acid residues 30–254 of SEQ ID NO:4;
      b) amino acid residues 1–202 of SEQ ID NO:4;
      c) amino acid residues 30–202 of SEQ ID NO:4;
      d) amino acid residues 1–155 of SEQ ID NO:4;
      e) amino acid residues 30–155 of SEQ ID NO:4;
      f) amino acid residues 1–117 of SEQ ID NO:4;
      g) amino acid residues 30–117 of SEQ ID NO:4; and
      h) amino acid residues 30–95 of SEQ ID NO:4;
   iii) a ligand having the amino acid sequence of SEQ ID NO:6;
   iv) a ligand having the amino acid sequence of SEQ ID NO:8; and
   v) a ligand having the amino acid sequence of amino acid residues 32–101 of SEQ ID NO:8.

50. The method of claim 49 wherein said antibody or antigen-binding fragment is mAb 7F3 or an antigen-binding fragment thereof.

51. A method of inhibiting a cellular response to binding of a ligand to Bonzo (CXC R6) expressed on the surface of a leukocyte in a mammal, comprising administering to said mammal an effective amount of an antibody or antigen-binding fragment thereof, wherein:
1) said antibody or antigen-binding fragment comprises the complementarity determining regions (CDRs) from an antibody selected from the group consisting of:
   a) mAb 4A11, the antibody produced by the hybridoma cell line deposited at the American Type Culture Collection (ATCC) as Accession Number PTA-991;
   b) mAb 7A2, the antibody produced by the hybridoma cell line deposited at the American Type Culture Collection (ATCC) as Accession Number PTA-992; and
   c) mAb 7E3, the antibody produced by the hybridoma cell line deposited at the American Type Culture Collection (ATCC) as Accession Number PTA-990; and
2) said cellular response is selected from the group consisting of ligand-induced chemotaxis and ligand-induced $Ca^{2+}$ flux; and
3) said ligand is selected from the group consisting of:
   i) a ligand having the amino acid sequence of SEQ ID NO:4;
   ii) a tigand having an amino acid sequence that is a fragment of SEQ ID NO:4, wherein said fragment is selected from the group consisting of:
      a) amino acid residues 30–254 of SEQ ID NO:4;
      b) amino acid residues 1–202 of SEQ ID NO:4;
      c) amino acid residues 30–202 of SEQ ID NO:4;
      d) amino acid residues 1–155 of SEQ ID NO:4;
      e) amino acid residues 30–155 of SEQ ID NO:4;
      f) amino acid residues 1–117 of SEQ ID NO:4;
      g) amino acid residues 30–117 of SEQ ID NO:4; and
      h) amino acid residues 30–95 of SEQ ID NO:4;
   iii) a ligand having the amino acid sequence of SEQ ID NO:6,
   iv) a ligand having the amino acid sequence of SEQ ID NO:8; and
   v) a ligand having the amino acid sequence of amino acid residues 32–101 of SEQ ID NO:8.

52. The method of claim 51 wherein said antibody or antigen-binding fragment comprises the CDRs from mAb 7F3.

53. A method of inhibiting a Bonzo (CXCR6) function selected from the group consisting of ligand-induced chemotaxis and ligand-induced $Ca^{2+}$ flux comprising contacting a cell that expresses Bonzo (CXCR6) with an antibody or antigen-binding fragment thereof, wherein:
1) said antibody or antigen-binding fragment:
   a) binds to, and thereby inhibits the function of, said Bonzo (CXCR6); and
   b) has the epitopic specificity of an antibody selected from the group consisting of:
      i) mAb 4A11, the antibody produced by the hybridoma cell line deposited at the American Type Culture Collection (ATCC) as Accession Number PTA-991;
      ii) mAb 7A2, the antibody produced by the hybridoma cell line deposited at the American Type Culture Collection (ATCC) as Accession Number PTA-992; and
      iii) mAb 7E3, the antibody produced by the hybridoma cell line deposited at the American Type Culture Collection (ATCC) as Accession Number PTA-990; and
2) said ligand is selected from the group consisting of:
   i) a ligand having the amino acid sequence of SEQ ID NO:4,
   ii) a ligand having an amino acid sequence that is a fragment of SEQ ID NO:4, wherein said fragment is selected from the group consisting of:
      a) amino acid residues 30–254 of SEQ ID NO:4;
      b) amino acid residues 1–202 of SEQ ID NO:4;
      c) amino acid residues 30–202 of SEQ ID NO:4;
      d) amino acid residues 1–155 of SEQ ID NO:4;
      e) amino acid residues 30–155 of SEQ ID NO:4;
      f) amino acid residues 1–117 of SEQ ID NO:4;
      g) amino acid residues 30–117 of SEQ ID NO:4; and
      h) amino acid residues 30–95 of SEQ ID NO:4;
   iii) a ligand having the amino acid sequence of SEQ ID NO:6;
   iv) a ligand having the amino acid sequence of SEQ ID NO:8; and v) a ligand having the amino acid sequence of amino acid residues 32–101 of SEQ ID NO:8.

54. The method of claim 53 wherein said antibody or antigen-binding fragment has the epitopic specificity of mAb 7F3.

55. A method of inhibiting a Bonzo (CXCR6) function selected from the group consisting of ligand-induced chemotaxis and ligand-induced $Ca^{2+}$ flux comprising contacting a cell that expresses Bonzo (CXCR6) with an antibody or antigen-binding fragment thereof, wherein:
1) said antibody or antigen-binding fragment binds to, and thereby inhibits the function of, said Bonzo (CXCR6), and the binding of said antibody or antigen-binding fragment to said Bonzo (CXCR6) is inhibited by an antibody selected from the group consisting of:
   a) mAb 4A11, the antibody produced by the hybridoma cell line deposited at the American Type Culture Collection (ATCC) as Accession Number PTA-991;
   b) mAb 7A2, the antibody produced by the hybridoma cell line deposited at the American Type Culture Collection (ATCC) as Accession Number PTA-992; and
   c) mAb 7F3, the antibody produced by the hybridoma cell line deposited at the American Type Culture Collection (ATCC) as Accession Number PTA-990; and
2) said ligand is selected from the group consisting of:
   i) a ligand having the amino acid sequence of SEQ ID NO4;
   ii) a ligand having an amino acid sequence that is a fragment of SEQ ID NO:4, wherein said fragment is selected from the group consisting of:
      a) amino acid residues 30–254 of SEQ ID NO:4;
      b) amino acid residues 1–202 of SEQ ID NO:4;
      c) amino acid residues 30–202 of SEQ ID NO:4;
      d) amino acid residues 1–155 of SEQ ID NO:4;
      e) amino acid residues 30–155 of SEQ ID NO:4;
      f) amino acid residues 1–117 of SEQ ID NO:4;
      g) amino acid residues 30–117 of SEQ ID NO:4; and
      h) amino acid residues 30–95 of SEQ ID NO:4;
   iii) a ligand having the amino acid sequence of SEQ ID NO:6;
   iv) a ligand having the amino acid sequence of SEQ ID NO:8; and
   v) a ligand having the amino acid sequence of amino acid residues 32–101 of SEQ ID NO:8.

56. The method of claim 55 wherein the binding of said antibody or antigen-binding fragment to said Bonzo (CXCR6) is inhibited by mAb 7F3.

57. A method of inhibiting a Bonzo (CXCR6) function selected from the group consisting of ligand-induced chemotaxis and ligand-induced $Ca^{2+}$ flux comprising contacting a cell that expresses Bonzo (CXCR6) with an antibody or antigen-binding fragment thereof wherein:
1) said antibody or antigen-binding fragment binds to, and thereby inhibits the function of, said Bonzo (CXCR6), and is selected from the group consisting of:
   a) mAb 4A11, the antibody produced by the hybridoma cell line deposited at the American Type Culture Collection (ATCC) as Accession Number PTA-991;
   b) mAb 7A2, the antibody produced by the hybridoma cell line deposited at the American Type Culture Collection (ATCC) as Accession Number PTA-992;
   c) mAb 7A3, the antibody produced by the hybridoma cell line deposited at the American Type Culture Collection (ATCC) as Accession Number PTA-990; and
   d) an antigen-binding fragment of any of the foregoing; and
2) said ligand is selected from the group consisting of:
   i) a ligand having the amino acid sequence of SEQ ID NO:4;
   ii) a ligand having an amino acid sequence that is a fragment of SEQ ID NO:4, wherein said fragment is selected from the group consisting of:
      a) amino acid residues 30–254 of SEQ ID NO:4;
      b) amino acid residues 1–202 of SEQ ID NO:4;
      c) amino acid residues 30–202 of SEQ ID NO:4;
      d) amino acid residues 1–155 of SEQ ID NO:4;
      e) amino acid residues 30–155 of SEQ ID NO:4;
      f) amino acid residues 1–117 of SEQ ID NO:4;
      g) amino acid residues 30–117 of SEQ ID NO:4; and
      h) amino acid residues 30–95 of SEQ ID NO:4;
   iii) a ligand having the amino acid sequence of SEQ ID NO:6;
   iv) a ligand having the amino acid sequence of SEQ ID NO:8; and
   v) a ligand having the amino acid sequence of amino acid residues 32–101 of SEQ ID NO:8.

58. The method of claim 57 wherein said antibody or antigen-binding fragment is mAb 7F3 or an antigen-binding fragment thereof.

59. A method of inhibiting a Bonzo (CXCR6) function selected from the group consisting of ligand-induced chemotaxis and ligand-induced $Ca^{2+}$ flux comprising contacting a cell that expresses Bonzo (CXCR6) with an antibody or antigen-binding fragment thereof, wherein:
1) said antibody or antigen-binding fragment binds to, and thereby inhibits the function of, said Bonzo (CXCR6), and comprises the complementarity determining regions (CDRs) from an antibody selected from the group consisting of:
   a) mAb 4A11, the antibody produced by the hybridoma cell line deposited at the American Type Culture Collection (ATCC) as Accession Number PTA-991;
   b) mAb 7A2, the antibody produced by the hybridoma cell line deposited at the American Type Culture Collection (ATCC) as Accession Number PVA-992; and
   c) mAb 7F3, the antibody produced by the hybridoma cell line deposited at the American Type Culture Collection (ATCC) as Accession Number PTA-990; and
2) said ligand is selected from the group consisting of:
   i) a ligand having the amino acid sequence of SEQ ID NO:4;
   ii) a ligand having an amino acid sequence that is a fragment of SEQ ID NO:4, wherein said fragment is selected from the group consisting of:
      a) amino acid residues 30–254 of SEQ ID NO:4;
      b) amino acid residues 1–202 of SEQ ID NO:4;
      c) amino acid residues 30–202 of SEQ ID NO:4;
      d) amino acid residues 1–155 of SEQ ID NO:4;
      e) amino acid residues 30–155 of SEQ ID NO:4;
      f) amino acid residues 1–117 of SEQ ID NO:4;
      g) amino acid residues 30–117 of SEQ ID NO:4; and
      h) amino acid residues 30–95 of SEQ ID NO:4;
   iii) a ligand having the amino acid sequence of SEQ ID NO:6;
   iv) a ligand having the amino acid sequence of SEQ ID NO:8; and
   v) a ligand having the amino acid sequence of amino acid residues 32–101 of SEQ ID NO:8.

60. The method of claim 59 wherein said antibody or antigen-binding fragment comprises the CDRs from mAb 7F3.

61. A method of treating a subject having an inflammatory disease, comprising administering to said subject an effective amount of an antibody or antigen-binding fragment thereof that binds to mammalian Bonzo (CXCR6) and inhibits the binding of a ligand to said Bonzo (CXCR6),
  wherein said inflammatory disease is inflammatory arthritis, multiple sclerosis or graft rejection, and wherein said ligand is selected from the group consisting of
  i) a ligand having the amino acid sequence of SEQ ID NO: 4,
  ii) a ligand having an amino acid sequence that is a fragment of SEQ ID NO:4, wherein said fragment is selected from the group consisting of:
    a) amino acid residues 30–254 of SEQ ID NO:4;
    b) amino acid residues 1–202 of SEQ ID NO:4;
    c) amino acid residues 30–202 of SEQ ID NO:4;
    d) amino acid residues 1–155 of SEQ ID NO:4;
    e) amino acid residues 30–155 of SEQ ID NO:4;
    f) amino acid residues 1–117 of SEQ ID NO:4;
    g) amino acid residues 30–117 of SEQ ID NO:4; and
    h) amino acid residues 30–95 of SEQ ID NO:4;
  iii) a ligand having the amino acid sequence of SEQ ID NO:6;
  iv) a ligand having the amino acid sequence of SEQ ID NO:8; and
  v) a ligand having the amino acid sequence of amino acid residues 32–101 of SEQ ID NO:8.

62. The method of claim 61, wherein said inflammatory disease is inflammatory arthritis and said inflammatory arthritis is rheumatoid arthritis.

63. The method of claim 61, wherein said inflammatory disease is graft rejection, and said graft rejection is selected from the group consisting of allograft rejection and graft-versus-host disease.

64. The method of claim 61, wherein said inflammatory disease is multiple sclerosis.

65. The method of claim 61, wherein said antibody or antigen-binding fragment has the epitopic specificity of an antibody selected from the group consisting of:
  a) mAb 4A11, the antibody produced by the hybridoma cell line deposited at the American Type Culture Collection (ATCC) as Accession Number PTA-991;
  b) mAb 7A2, the antibody produced by the hybridoma cell line deposited at the American Type Culture Collection (ATCC) as Accession Number PTA-992; and
  c) mAb 7F3, the antibody produced by the hybridoma cell line deposited at the American Type Culture Collection (ATCC) as Accession Number PTA-990.

66. The method of claim 61, wherein the binding of said antibody or antigen-binding fragment to said mammalian Bonzo (CXCR6) is inhibited by an antibody selected from the group consisting of:
  a) mAb 4A11, the antibody produced by the hybridoma cell line deposited at the American Type Culture Collection (ATCC) as Accession Number PTA-991;
  b) mAb 7A2, the antibody produced by the hybridoma cell line deposited at the American Type Culture Collection (ATCC) as Accession Number PTA-992; and
  c) mAb 7F3, the antibody produced by the hybridoma cell line deposited at the American Type Culture Collection (ATCC) as Accession Number PTA-990.

67. The method of claim 61, wherein said antibody or antigen-binding fragment comprises the complementarity determining regions (CDRs) from an antibody selected from the group consisting of:
  a) mAb 4A11, the antibody produced by the hybridoma cell line deposited at the American Type Culture Collection (ATCC) as Accession Number PTA-991;
  b) mAb 7A2, the antibody produced by the hybridoma cell line deposited at the American Type Culture Collection (ATCC) as Accession Number PTA-992; and
  c) mAb 7F3, the antibody produced by the hybridoma cell line deposited at the American Type Culture Collection (ATCC) as Accession Number PTA-990.

68. The method of claim 61, wherein said antibody is selected from the group consisting of:
  a) mAb 4A11, the antibody produced by the hybridoma cell line deposited at the American Type Culture Collection (ATCC) as Accession Number PTA-991;
  b) mAb 7A2, the antibody produced by the hybridoma cell line deposited at the American Type Culture Collection (ATCC) as Accession Number PTA-992; and
  c) mAb 7F3, the antibody produced by the hybridoma cell line deposited at the American Type Culture Collection (ATCC) as Accession Number PTA-990.

* * * * *